(12) United States Patent
DiDonato et al.

(10) Patent No.: US 11,136,366 B2
(45) Date of Patent: Oct. 5, 2021

(54) METHODS OF TREATING IMMUNE RELATED DISORDERS USING ANTIBODY-CYTOKINE ENGRAFTED COMPOSITIONS

(71) Applicant: Novarts AG, Basel (CH)

(72) Inventors: Michael DiDonato, San Diego, CA (US); Bernhard Hubert Geierstanger, Solana Beach, CA (US); Tobias Junt, Liestal (CH); Mark Knuth, El Cajon, CA (US); Shelly Meeusen, San Diego, CA (US); Carolina Nicole Simpson, Chula Vista, CA (US); Glen Spraggon, San Diego, CA (US); John Trauger, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/163,857

(22) Filed: Oct. 18, 2018

(65) Prior Publication Data

US 2019/0241636 A1   Aug. 8, 2019

Related U.S. Application Data

(62) Division of application No. 15/367,003, filed on Dec. 1, 2016, now Pat. No. 10,144,768.

(60) Provisional application No. 62/263,008, filed on Dec. 4, 2015.

(51) Int. Cl.
| | |
|---|---|
| *A61K 39/395* | (2006.01) |
| *C07K 14/54* | (2006.01) |
| *A61K 38/20* | (2006.01) |
| *A61K 45/06* | (2006.01) |
| *C07K 16/00* | (2006.01) |
| *A61K 39/00* | (2006.01) |

(52) U.S. Cl.
CPC ...... *C07K 14/5428* (2013.01); *A61K 38/2066* (2013.01); *A61K 39/395* (2013.01); *A61K 45/06* (2013.01); *C07K 16/00* (2013.01); *A61K 2039/505* (2013.01); *C07K 2317/51* (2013.01); *C07K 2317/52* (2013.01); *C07K 2317/56* (2013.01); *C07K 2317/565* (2013.01); *C07K 2317/71* (2013.01); *C07K 2318/10* (2013.01); *C07K 2319/31* (2013.01)

(58) Field of Classification Search
CPC .................. A61K 38/2066; A61K 39/3955
See application file for complete search history.

(56) References Cited

U.S. PATENT DOCUMENTS

| | | |
|---|---|---|
| 5,112,946 A | 5/1992 | Maione |
| 5,336,603 A | 8/1994 | Capon |
| 5,349,053 A | 9/1994 | Landolfi |
| 5,359,046 A | 10/1994 | Capon |
| 5,447,851 A | 9/1995 | Beutler |
| 5,622,929 A | 4/1997 | Willner |
| 2003/0162261 A1 | 8/2003 | Oppmann et al. |
| 2007/0117774 A1 | 5/2007 | Zanetti |
| 2011/0091463 A1 | 4/2011 | Ghayur et al. |
| 2014/0099331 A1 | 4/2014 | Tzianabos et al. |
| 2015/0218244 A1 | 8/2015 | Emrich et al. |

FOREIGN PATENT DOCUMENTS

| | | |
|---|---|---|
| EP | 307434 | 3/1989 |
| EP | 367166 | 5/1990 |
| EP | 2882774 | 2/2014 |
| WO | WO 91/06570 | 5/1991 |
| WO | WO1996/018412 A1 | 12/1995 |
| WO | WO 91/06570 | 2/1996 |
| WO | 99/45110 A1 | 9/1999 |
| WO | WO1999/043713 A1 | 9/1999 |
| WO | WO2002/044197 A2 | 6/2002 |
| WO | WO2002/046238 A2 | 6/2002 |
| WO | 03/086296 A2 | 10/2003 |
| WO | WO2003/085086 A3 | 10/2003 |
| WO | WO2004/050017 A2 | 7/2004 |
| WO | WO2004/108078 A2 | 12/2004 |
| WO | WO2005/060642 A2 | 7/2005 |
| WO | 2007/149875 A2 | 12/2007 |
| WO | WO2009/088805 A2 | 7/2009 |
| WO | WO2010/099019 A1 | 9/2010 |
| WO | WO2011/020783 A2 | 2/2011 |
| WO | 2011064398 A1 | 6/2011 |
| WO | 2011064399 A1 | 6/2011 |

(Continued)

OTHER PUBLICATIONS

Peng et al.,"A General Method for Insertion of Functional Proteins within Proteins via Combinatorial Selection of Permissive Junctions", Chemistry & Biology, vol. 22, Aug. 20, 2015, pages 1134-1143.

(Continued)

*Primary Examiner* — Prema M Mertz
(74) *Attorney, Agent, or Firm* — Kun Wang

(57) ABSTRACT

The present disclosure provides antibody cytokine engrafted proteins that bind to and stimulate intracellular signaling through interleukin 10 receptor. Provided antibody cytokine engrafted proteins find use in enhancing anti-inflammatory cell responses, and reducing pro-inflammatory effects in the treatment, amelioration and prophylaxis of immune related disorders. Additionally provided are polynucleotides and vectors that encode antibody cytokine engrafted proteins and host cells capable of producing antibody cytokine engrafted proteins, as well as methods of combining antibody cytokine engrafted proteins with other therapeutics in treating immune related disorder.

12 Claims, 17 Drawing Sheets

Specification includes a Sequence Listing.

(56) References Cited

FOREIGN PATENT DOCUMENTS

| | | |
|---|---|---|
| WO | WO2012/009705 | 1/2012 |
| WO | WO2012/045334 A1 | 4/2012 |
| WO | 2012078878 A2 | 6/2012 |
| WO | WO2012/107416 A2 | 8/2012 |
| WO | WO2012/107417 A1 | 8/2012 |
| WO | WO2012/146628 A1 | 11/2012 |
| WO | WO2013/106485 A2 | 7/2013 |
| WO | WO2013/106489 A1 | 7/2013 |
| WO | WO2014/023673 A1 | 2/2014 |
| WO | WO2014/023679 A1 | 2/2014 |
| WO | WO2014/023752 A1 | 2/2014 |
| WO | WO2014/110368 A1 | 7/2014 |
| WO | WO2014/138725 A1 | 9/2014 |
| WO | 2014/158528 A1 | 10/2014 |
| WO | WO2015/006736 A2 | 1/2015 |
| WO | WO2015/006744 A1 | 1/2015 |
| WO | WO2015/010100 A2 | 1/2015 |
| WO | WO2015/017146 A2 | 2/2015 |
| WO | 2015/117930 A1 | 8/2015 |
| WO | WO2015/118016 A1 | 8/2015 |

OTHER PUBLICATIONS

Metheringham et al., "Antibodies designed as effective cancer vaccines", MABS, vol. 1, No. 1, Jan./Feb. 2009, pp. 71-85.

Xiong et al., "Engineering Vaccines With Heterologous B and T Cell Epitopes Using Immunoglobulin Genes", Nature Biotechnology, vol. 15, Sep. 1, 1997, pp. 882-886.

U.S. Appl. No. 15/367,003.

U.S. Appl. No. 62/263,008.

Zhang, et al., "Functional Antibody CDR3 fusion Proteins with Enhanced Pharmacological Properties", Angewandte Chemie International Edition, Aug. 5, 2013, pp. 8295-8298, vol. 52, No. 32, Wiley-VCH Verlag GmbH & Co. KGaA, Weinheim.

Zhang, et al., "An Antibody CDR3-Erythropoietin Fusion Protein", ACS Chemical Biology, Oct. 18, 2013, pp. 2117-2121, vol. 8, No. 10, American Chemical Society.

Liu, et al., "Rational Design of CXCR4 Specific Antibodies with Elongated CDRs", Journal of the American Chemical Society, Jul. 30, 2014, pp. 10557-10560, vol. 136, No. 30, American Chemical Society.

Liu, et al., "Functional human antibody CDR fusions as long-activing therapeutic endocrine agonists", Proceedings of the National Academy of Sciences, Jan. 20, 2015, pp. 1356-1361, vol. 112, No. 5.

Wang, et al., "Reshaping Antibody Diversity", Cell, Jun. 6, 2013, pp. 1379-1393, vol. 153, Elsevier Inc.

Zhang, et al., "Rational Design of Humanized Dual-Agonist Antibodies", Journal of the American Chemical Society, 2015, pp. 38-41, vol. 137, American Chemical Society.

Ashkenazi et al., "Protection against endotoxic shock by a tumor necrosis factor receptor immunoadhesin" Proc. Natl. Acad. Sci. USA 88(23):10535-10539, Dec. 1991.

Glocker et al., "Inflammatory Bowel Disease and Mutations Affecting the Interleukin-10 Receptor" The New England Journal of Medicine 361(21):2033-2045, Nov. 19, 2009.

Herfarth et al., "IL-10 therapy in Crohn's disease: at the crossroads" Gut 50(2):146-147, 2002.

Josephson et al., "Design and Analysis of an Engineered Human Interleukin-10" The Journal of Biological Chemistry 275(18):13552-13557, May 5, 2000.

Lauw et al., "Proinflammatory Effects of IL-10 During Human Endotoxemia" Journal of Immunology 165(5):2783-2789, 2000.

Lindsay and Hodgson, "Review Article: The Immunoregulatory Cytokine Interleukin-10-a Therapy for Crohn's Disease?" Aliment Pharmacol. Ther. 15:1709-1716, 2001.

Moore et al., "Interleukin-10 and the Interleukin-10 Receptor" Annu. Rev. Immunol 19:683-765, 2001.

Mosmann et al., "Properties and Functions of Interleukin-10" Advances in Immunology 56:1-26, 1994.

Szkaradkiewicz et al., "Proinflammatory cytokines and IL-10 in inflammatory bowel disease and colorectal cancer patients" Arch. Immunol. Ther Exp 57(4):291-294, 2009.

Tilg et al., "Treatment of Crohn's disease with recombinant human interleukin 10 induces the proinflammatory cytokine interferon gamma" Gut 50(2):191-195, 2002.

Vie et al., "Human fusion proteins between interleukin 2 and IgM heavy chain are cytotoxic for cells expressing the interleukin 2 receptor" Proc. Natl. Acad. Sci. USA 89(23):11337-11341, 1992.

Zheng et al., "Administration of noncytolytic IL-10/Fc in murine models of lipopolysaccharide-induced septic shock and allogeneic islet transplantation" Journal of Immunology 154:5590-5600, 1995.

Simmons et al., "Shark IgNAR antibody mimotopes target a murine immunoglobulin through extended CDR3 loop structures", Proteins: Structure, Function, and Bioinformatics, Oct. 11, 2007, vol. 71, No. 1, pp. 119-130.

Streltsov et al., "Supplemental Material Crystal Structure of the Amyloid-β p3 Fragment Provides a Model for Oligomer Formation in Alzheimer's Disease", The Journal of Neuroscience, Jan. 26, 2011, 31(4), pp. 1419-1426.

Josephson et al., "Noncompetitive Antibody Neutralization of IL-10 Revealed by Protein Engineering and X-Ray Crystallography", Structure, vol. 10, Jul. 2002, pp. 981-987.

Structure of an IL10 antibody cytokine engrafted protein

Figure 3A-3B
IgGIL10M13 demonstrates decreased pro-inflammatory activity, with similar anti-inflammatory activity
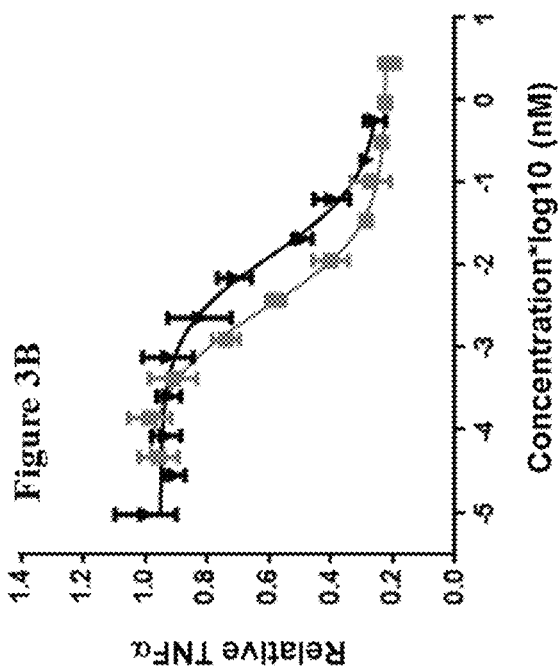
Figure 3B
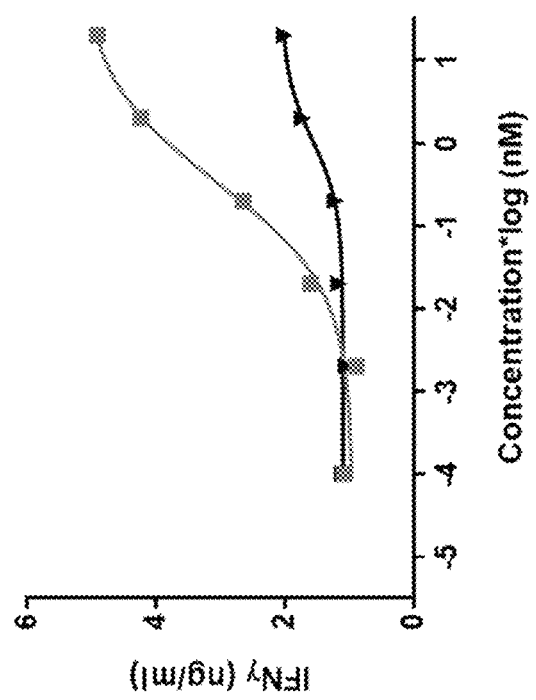
Figure 3A CyTOF analysis of IL10 dependent pSTAT3 signaling in human whole blood stimulated with rhuIL10 (left panel) or IgGIL10M13 (right panel)

Figure 5A-5D
Pharmacokinetic studies of rhuIL10 and IgGIL10M13
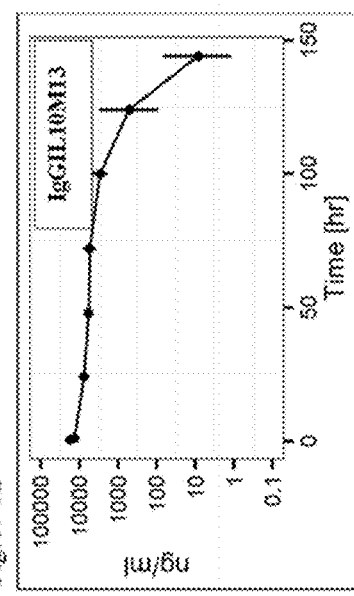
Figure 5A
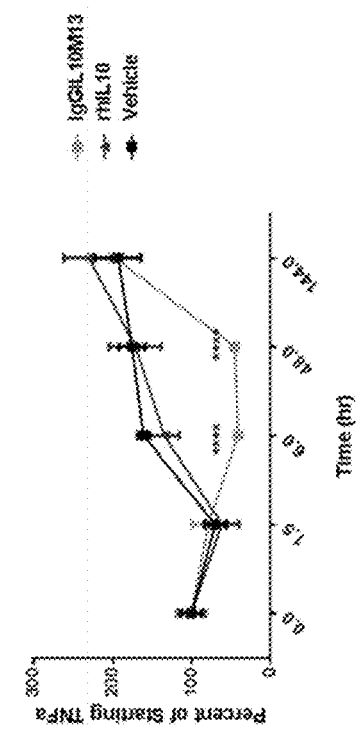
Figure 5B
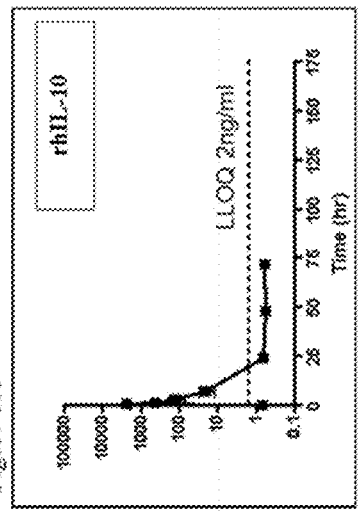
Figure 5C
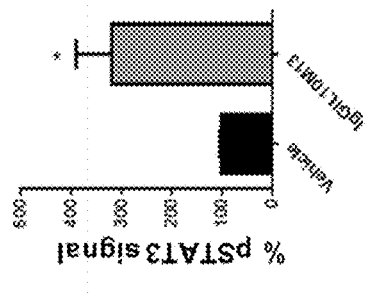
Figure 5D IgGIL10M13 has improved Cmax CyTOF data of pSTAT3 activity in immune cells from healthy subjects and patients IgGIL10M13 has reduced pro-inflammatory activity in PHA stimulated human whole blood compared to rhIL-10

IgGIL10M13 has reduced pro-inflammatory activity in PHA stimulated human whole blood compared to rhIL-10

IgGIL10M13 has reduced pro-inflammatory activity in PHA stimulated human whole blood compared to rhIL-10

IgGIL10M13 can compete rhIL10

Figure 11

| | | | | |
|---|---|---|---|---|
| RSV coat in PBS | a | 2.74 | 0.99 | 1.10 |
| | b | 2.46 | 0.74 | 0.84 |
| RSV coat in Carb/Bi pH9.6 | c | 2.41 | 1.11 | 0.78 |
| | d | 2.66 | 1.20 | 0.93 |
| neg coat in PBS | e | 0.04 | 0.04 | 0.04 |
| | f | 0.04 | 0.04 | 0.04 |
| | | | | |
| Primary detector | | un-grafted Ab backbone | IL10M in CDR-L1 | IL10M in CDR-L1 DAPA |

Representation of the mechanism of action of an antibody cytokine engrafted protein Crystal structure of IL10 engrafted into a CDR

SEQUENCE LISTING

```
<160> NUMBER OF SEQ ID NOS: 253

<210> SEQ ID NO 1
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Tyr
1               5

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Gly Ser Gly Gly Ser
1               5

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 3

Thr Arg Thr Lys Arg Phe
1               5

<210> SEQ ID NO 4
<211> LENGTH: 174
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ser Gln Ser Val Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
            20                  25                  30

Ala Phe Ser Arg Val Lys Thr Phe Phe Gln Met Lys Asp Gln Leu Asp
        35                  40                  45

Asn Leu Leu Leu Lys Glu Ser Leu Leu Glu Asp Phe Lys Gly Tyr Leu
    50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
        115                 120                 125

Lys Ala Val Glu Gln Val Lys Asn Ala Phe Asn Lys Leu Gln Glu Lys
    130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Ser Ser Ser Tyr
                165                 170

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Ser
1

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Tyr Gly Ser Ser Pro Leu

```
<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser Tyr Ala Met Ser
1               5

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Ile Ser Gly Ser Gly Gly Ser Thr Tyr Tyr Gly Asp Ser Val Lys
1               5                   10                  15

Gly

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Thr Arg Thr Lys Arg Phe
1               5

<210> SEQ ID NO 10
<211> LENGTH: 178
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Arg Ala Ser Gln Ser Val Ser Pro Gly Gln Gly Thr Gln Ser Glu Asn
1               5                   10                  15

Ser Cys Thr His Phe Pro Gly Asn Leu Pro Asn Met Leu Arg Asp Leu
                20                  25                  30

Arg Asp Ala Phe Ser Arg Val Lys Thr Phe Phe Gln Met Lys Asp Gln
                    35                  40                  45

Leu Asp Asn Leu Leu Leu Lys Glu Ser Leu Leu Glu Asp Phe Lys Gly
        50                  55                  60

Tyr Leu Gly Cys Gln Ala Leu Ser Glu Met Ile Gln Phe Tyr Leu Glu
65                  70                  75                  80

Glu Val Met Pro Gln Ala Glu Asn Gln Asp Pro Asp Ile Lys Ala His
                85                  90                  95
```

```
Val Asn Ser Leu Gly Glu Asn Leu Lys Thr Leu Arg Leu Arg Leu Arg
            100                 105                 110

Arg Cys His Arg Phe Leu Pro Cys Glu Gly Gly Ser Gly Gly Asn
        115                 120                 125

Lys Ser Lys Ala Val Glu Gln Val Lys Asn Ala Phe Asn Lys Leu Gln
    130                 135                 140

Glu Lys Gly Ile Tyr Lys Ala Met Ser Glu Phe Asp Ile Phe Ile Asn
145                 150                 155                 160

Tyr Ile Glu Ala Tyr Met Thr Met Lys Ile Arg Asn Ser Ser Tyr
                165                 170                 175

Leu Ala

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Ala Ser Ser Arg Ala Thr
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Tyr Gly Ser Ser Pro Leu Thr
1               5

<210> SEQ ID NO 13
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Thr Lys Arg Phe Trp Gly Gln Gly Thr Leu Val Thr
            100                 105                 110
```

Val Ser Ser
        115

<210> SEQ ID NO 14
<211> LENGTH: 274
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Gly
            20                  25                  30

Gln Gly Thr Gln Ser Glu Asn Ser Cys Thr His Phe Pro Gly Asn Leu
        35                  40                  45

Pro Asn Met Leu Arg Asp Leu Arg Asp Ala Phe Ser Arg Val Lys Thr
    50                  55                  60

Phe Phe Gln Met Lys Asp Gln Leu Asp Asn Leu Leu Leu Lys Glu Ser
65                  70                  75                  80

Leu Leu Glu Asp Phe Lys Gly Tyr Leu Gly Cys Gln Ala Leu Ser Glu
                85                  90                  95

Met Ile Gln Phe Tyr Leu Glu Glu Val Met Pro Gln Ala Glu Asn Gln
            100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
    130                 135                 140

Asn Gly Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
                165                 170                 175

Glu Phe Asp Ile Phe Ile Asn Tyr Ile Glu Ala Tyr Met Thr Met Lys
            180                 185                 190

Ile Arg Asn Ser Ser Ser Tyr Leu Ala Trp Tyr Gln Gln Lys Pro Gly
        195                 200                 205

Gln Ala Pro Arg Leu Leu Ile Tyr Gly Ala Ser Ser Arg Ala Thr Gly
    210                 215                 220

Ile Pro Asp Arg Phe Ser Gly Ser Gly Ser Gly Thr Asp Phe Thr Leu
225                 230                 235                 240

Thr Ile Ser Arg Leu Glu Pro Glu Asp Phe Ala Val Tyr Tyr Cys Gln
                245                 250                 255

Gln Tyr Gly Ser Ser Pro Leu Thr Phe Gly Gly Gly Thr Lys Val Glu
            260                 265                 270

Ile Lys

<210> SEQ ID NO 15
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Gly Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
            85                  90                  95
Ala Arg Thr Arg Thr Lys Arg Phe Trp Gly Gln Gly Thr Leu Val Thr
        100                 105                 110
Val Ser Ser Ala Ser Thr Lys Gly Pro Ser Val Phe Pro Leu Ala Pro
    115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
            165                 170                 175
Leu Tyr Ser Leu Ser Ser Val Val Thr Val Pro Ser Ser Ser Leu Gly
        180                 185                 190
Thr Gln Thr Tyr Ile Cys Asn Val Asn His Lys Pro Ser Asn Thr Lys
    195                 200                 205
Val Asp Lys Arg Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
            245                 250                 255
Val Thr Cys Val Val Val Asp Val Ser His Glu Asp Pro Glu Val Lys
        260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
            325                 330                 335
Ala Lys Gly Gln Pro Arg Glu Pro Gln Val Tyr Thr Leu Pro Pro Ser
        340                 345                 350
Arg Glu Glu Met Thr Lys Asn Gln Val Ser Leu Thr Cys Leu Val Lys
    355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
            405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 16
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Gly
            20                  25                  30

Gln Gly Thr Gln Ser Glu Asn Ser Cys Thr His Phe Pro Gly Asn Leu
            35                  40                  45

Pro Asn Met Leu Arg Asp Leu Arg Asp Ala Phe Ser Arg Val Lys Thr
        50                  55                  60

Phe Phe Gln Met Lys Asp Gln Leu Asp Asn Leu Leu Leu Lys Glu Ser
65                  70                  75                  80

Leu Leu Glu Asp Phe Lys Gly Tyr Leu Gly Cys Gln Ala Leu Ser Glu
                85                  90                  95

Met Ile Gln Phe Tyr Leu Glu Glu Val Met Pro Gln Ala Glu Asn Gln
            100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
    130                 135                 140

Asn Gly Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
                165                 170                 175

Glu Phe Asp Ile Phe Ile Asn Tyr Ile Glu Ala Tyr Met Thr Met Lys
            180                 185                 190

Ile Arg Asn Ser Ser Ser Tyr Leu Ala Trp Tyr Gln Gln Lys Pro Gly
        195                 200                 205

Gln Ala Pro Arg Leu Leu Ile Tyr Gly Ala Ser Ser Arg Ala Thr Gly
    210                 215                 220

Ile Pro Asp Arg Phe Ser Gly Ser Gly Ser Gly Thr Asp Phe Thr Leu
225                 230                 235                 240

Thr Ile Ser Arg Leu Glu Pro Glu Asp Phe Ala Val Tyr Tyr Cys Gln
                245                 250                 255

Gln Tyr Gly Ser Ser Pro Leu Thr Phe Gly Gly Gly Thr Lys Val Glu
            260                 265                 270

Ile Lys Arg Thr Val Ala Ala Pro Ser Val Phe Ile Phe Pro Pro Ser
        275                 280                 285

Asp Glu Gln Leu Lys Ser Gly Thr Ala Ser Val Val Cys Leu Leu Asn
    290                 295                 300

Asn Phe Tyr Pro Arg Glu Ala Lys Val Gln Trp Lys Val Asp Asn Ala
305                 310                 315                 320
```

Leu Gln Ser Gly Asn Ser Gln Glu Ser Val Thr Glu Gln Asp Ser Lys
            325                 330                 335

Asp Ser Thr Tyr Ser Leu Ser Ser Thr Leu Thr Leu Ser Lys Ala Asp
        340                 345                 350

Tyr Glu Lys His Lys Val Tyr Ala Cys Glu Val Thr His Gln Gly Leu
            355                 360                 365

Ser Ser Pro Val Thr Lys Ser Phe Asn Arg Gly Glu Cys
        370                 375                 380

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Phe Thr Phe Ser Ser Tyr
1               5

<210> SEQ ID NO 18
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Gly Ser Gly Gly Ser
1               5

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Thr Arg Thr Lys Arg Phe
1               5

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Gln Ser Val Ser Ser Ser Tyr
1               5

<210> SEQ ID NO 21
<211> LENGTH: 170
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gly Ala Ser Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
            20                  25                  30

Ala Phe Ser Arg Val Lys Thr Phe Phe Gln Met Lys Asp Gln Leu Asp
            35                  40                  45

Asn Leu Leu Leu Lys Glu Ser Leu Leu Glu Asp Phe Lys Gly Tyr Leu
        50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
            115                 120                 125

Lys Ala Val Glu Gln Val Lys Asn Ala Phe Asn Lys Leu Gln Glu Lys
        130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn
                165                 170

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Tyr Gly Ser Ser Pro Leu
1               5

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Tyr Ala Met Ser
1               5

<210> SEQ ID NO 24
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Ala Ile Ser Gly Ser Gly Gly Ser Thr Tyr Tyr Gly Asp Ser Val Lys
1               5                   10                  15

Gly
```

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

```
Thr Arg Thr Lys Arg Phe
1               5
```

<210> SEQ ID NO 26
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

```
Arg Ala Ser Gln Ser Val Ser Ser Ser Tyr Leu Ala
1               5                   10
```

<210> SEQ ID NO 27
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Gly Ala Ser Ser Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
                20                  25                  30

Ala Phe Ser Arg Val Lys Thr Phe Phe Gln Met Lys Asp Gln Leu Asp
            35                  40                  45

Asn Leu Leu Leu Lys Glu Ser Leu Leu Glu Asp Phe Lys Gly Tyr Leu
50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
        115                 120                 125

Lys Ala Val Glu Gln Val Lys Asn Ala Phe Asn Lys Leu Gln Glu Lys
    130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Arg Ala Thr
```

```
                165                 170

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln Gln Tyr Gly Ser Ser Pro Leu Thr
1               5

<210> SEQ ID NO 29
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Thr Lys Arg Phe Trp Gly Gln Gly Thr Leu Val Thr
            100                 105                 110

Val Ser Ser
        115

<210> SEQ ID NO 30
<211> LENGTH: 274
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Pro Gly Gln Thr Gln Ser Glu Asn
    50                  55                  60

Ser Cys Thr His Phe Pro Gly Asn Leu Pro Asn Met Leu Arg Asp Leu
65                  70                  75                  80
```

Arg Asp Ala Phe Ser Arg Val Lys Thr Phe Phe Gln Met Lys Asp Gln
                85                  90                  95

Leu Asp Asn Leu Leu Leu Lys Glu Ser Leu Leu Glu Asp Phe Lys Gly
            100                 105                 110

Tyr Leu Gly Cys Gln Ala Leu Ser Glu Met Ile Gln Phe Tyr Leu Glu
        115                 120                 125

Glu Val Met Pro Gln Ala Glu Asn Gln Asp Pro Asp Ile Lys Ala His
    130                 135                 140

Val Asn Ser Leu Gly Glu Asn Leu Lys Thr Leu Arg Leu Arg Leu Arg
145                 150                 155                 160

Arg Cys His Arg Phe Leu Pro Cys Glu Asn Gly Gly Ser Gly Gly
                165                 170                 175

Lys Ser Lys Ala Val Glu Gln Val Lys Asn Ala Phe Asn Lys Leu Gln
            180                 185                 190

Glu Lys Gly Ile Tyr Lys Ala Met Ser Glu Phe Asp Ile Phe Ile Asn
        195                 200                 205

Tyr Ile Glu Ala Tyr Met Thr Met Lys Ile Arg Asn Arg Ala Thr Gly
    210                 215                 220

Ile Pro Asp Arg Phe Ser Gly Ser Gly Ser Gly Thr Asp Phe Thr Leu
225                 230                 235                 240

Thr Ile Ser Arg Leu Glu Pro Glu Asp Phe Ala Val Tyr Tyr Cys Gln
            245                 250                 255

Gln Tyr Gly Ser Ser Pro Leu Thr Phe Gly Gly Gly Thr Lys Val Glu
        260                 265                 270

Ile Lys

<210> SEQ ID NO 31
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Thr Arg Thr Lys Arg Phe Trp Gly Gln Gly Thr Leu Val Thr
        100                 105                 110

Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala

```
                145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Arg Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
                435                 440                 445

<210> SEQ ID NO 32
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Pro Gly Gln Gly Thr Gln Ser Glu Asn
        50                  55                  60
```

```
Ser Cys Thr His Phe Pro Gly Asn Leu Pro Asn Met Leu Arg Asp Leu
 65                  70                  75                  80

Arg Asp Ala Phe Ser Arg Val Lys Thr Phe Gln Met Lys Asp Gln
             85                  90                  95

Leu Asp Asn Leu Leu Leu Lys Glu Ser Leu Leu Glu Asp Phe Lys Gly
            100                 105                 110

Tyr Leu Gly Cys Gln Ala Leu Ser Glu Met Ile Gln Phe Tyr Leu Glu
            115                 120                 125

Glu Val Met Pro Gln Ala Glu Asn Gln Asp Pro Asp Ile Lys Ala His
            130                 135                 140

Val Asn Ser Leu Gly Glu Asn Leu Lys Thr Leu Arg Leu Arg Leu Arg
145                 150                 155                 160

Arg Cys His Arg Phe Leu Pro Cys Glu Asn Gly Gly Ser Gly Gly
                165                 170                 175

Lys Ser Lys Ala Val Glu Gln Val Lys Asn Ala Phe Asn Lys Leu Gln
            180                 185                 190

Glu Lys Gly Ile Tyr Lys Ala Met Ser Glu Phe Asp Ile Phe Ile Asn
            195                 200                 205

Tyr Ile Glu Ala Tyr Met Thr Met Lys Ile Arg Asn Arg Ala Thr Gly
210                 215                 220

Ile Pro Asp Arg Phe Ser Gly Ser Gly Ser Gly Thr Asp Phe Thr Leu
225                 230                 235                 240

Thr Ile Ser Arg Leu Glu Pro Glu Asp Phe Ala Val Tyr Tyr Cys Gln
                245                 250                 255

Gln Tyr Gly Ser Ser Pro Leu Thr Phe Gly Gly Gly Thr Lys Val Glu
            260                 265                 270

Ile Lys Arg Thr Val Ala Ala Pro Ser Val Phe Ile Phe Pro Pro Ser
            275                 280                 285

Asp Glu Gln Leu Lys Ser Gly Thr Ala Ser Val Val Cys Leu Leu Asn
            290                 295                 300

Asn Phe Tyr Pro Arg Glu Ala Lys Val Gln Trp Lys Val Asp Asn Ala
305                 310                 315                 320

Leu Gln Ser Gly Asn Ser Gln Glu Ser Val Thr Glu Gln Asp Ser Lys
            325                 330                 335

Asp Ser Thr Tyr Ser Leu Ser Ser Thr Leu Thr Leu Ser Lys Ala Asp
            340                 345                 350

Tyr Glu Lys His Lys Val Tyr Ala Cys Glu Val Thr His Gln Gly Leu
            355                 360                 365

Ser Ser Pro Val Thr Lys Ser Phe Asn Arg Gly Glu Cys
            370                 375                 380

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Phe Thr Phe Ser Ser Tyr
1               5

<210> SEQ ID NO 34
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Gly Ser Gly Gly Ser
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Thr Arg Thr Lys Arg Phe
1               5

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ser Gln Ser Val Ser Ser Ser Tyr
1               5

<210> SEQ ID NO 37
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Ala Ser
1

<210> SEQ ID NO 38
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Tyr Gly Ser Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
                20                  25                  30

Phe Ser Arg Val Lys Thr Phe Phe Gln Met Lys Asp Gln Leu Asp Asn
            35                  40                  45

Leu Leu Leu Lys Glu Ser Leu Leu Glu Asp Phe Lys Gly Tyr Leu Gly
```

```
                50                  55                  60
Cys Gln Ala Leu Ser Glu Met Ile Gln Phe Tyr Leu Glu Glu Val Met
 65                  70                  75                  80

Pro Gln Ala Glu Asn Gln Asp Pro Asp Ile Lys Ala His Val Asn Ser
                 85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Gly Lys Ser Lys
        115                 120                 125

Ala Val Glu Gln Val Lys Asn Ala Phe Asn Lys Leu Gln Glu Lys Gly
        130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Ser Pro Leu
            165                 170
```

<210> SEQ ID NO 39
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

```
Ser Tyr Ala Met Ser
 1               5
```

<210> SEQ ID NO 40
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

```
Ala Ile Ser Gly Ser Gly Gly Ser Thr Tyr Tyr Gly Asp Ser Val Lys
 1               5                  10                  15

Gly
```

<210> SEQ ID NO 41
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

```
Thr Arg Thr Lys Arg Phe
 1               5
```

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 42

Arg Ala Ser Gln Ser Val Ser Ser Ser Tyr Leu Ala
1               5                   10

<210> SEQ ID NO 43
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Ala Ser Ser Arg Ala Thr
1               5

<210> SEQ ID NO 44
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Gln Tyr Gly Ser Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
                20                  25                  30

Asp Ala Phe Ser Arg Val Lys Thr Phe Phe Gln Met Lys Asp Gln Leu
            35                  40                  45

Asp Asn Leu Leu Leu Lys Glu Ser Leu Leu Glu Asp Phe Lys Gly Tyr
        50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Ser Gly Gly Lys
        115                 120                 125

Ser Lys Ala Val Glu Gln Val Lys Asn Ala Phe Asn Lys Leu Gln Glu
        130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Ser Pro Leu Thr
                165                 170                 175

<210> SEQ ID NO 45
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Leu Glu Ser Gly Gly Gly Leu Val Gln Pro Gly Gly
```

```
                 1               5                  10                    15
Ser Leu Arg Leu Ser Cys Ala Ala Ser Gly Phe Thr Phe Ser Ser Tyr
                20                  25                 30

Ala Met Ser Trp Val Arg Gln Ala Pro Gly Lys Gly Leu Glu Trp Val
                35                  40                 45

Ser Ala Ile Ser Gly Ser Gly Gly Ser Thr Tyr Tyr Gly Asp Ser Val
                50                  55                 60

Lys Gly Arg Phe Thr Ile Ser Arg Asp Asn Ser Lys Asn Thr Leu Tyr
65                              70              75                  80

Leu Gln Met Asn Ser Leu Arg Ala Glu Asp Thr Ala Val Tyr Tyr Cys
                85                  90                 95

Ala Arg Thr Arg Thr Lys Arg Phe Trp Gly Gln Gly Thr Leu Val Thr
                100                 105                110

Val Ser Ser
        115

<210> SEQ ID NO 46
<211> LENGTH: 274
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                 30

Tyr Leu Ala Trp Tyr Gln Gln Lys Pro Gly Gln Ala Pro Arg Leu Leu
                35                  40                 45

Ile Tyr Gly Ala Ser Ser Arg Ala Thr Gly Ile Pro Asp Arg Phe Ser
                50                  55                 60

Gly Ser Gly Ser Gly Thr Asp Phe Thr Leu Thr Ile Ser Arg Leu Glu
65                              70              75                  80

Pro Glu Asp Phe Ala Val Tyr Tyr Cys Gln Gln Tyr Gly Ser Ser Pro
                85                  90                 95

Gly Gln Gly Thr Gln Ser Glu Asn Ser Cys Thr His Phe Pro Gly Asn
                100                 105                110

Leu Pro Asn Met Leu Arg Asp Leu Arg Asp Ala Phe Ser Arg Val Lys
                115                 120                125

Thr Phe Phe Gln Met Lys Asp Gln Leu Asp Asn Leu Leu Leu Lys Glu
                130                 135                140

Ser Leu Leu Glu Asp Phe Lys Gly Tyr Leu Gly Cys Gln Ala Leu Ser
145                             150                 155                 160

Glu Met Ile Gln Phe Tyr Leu Glu Glu Val Met Pro Gln Ala Glu Asn
                165                 170                175

Gln Asp Pro Asp Ile Lys Ala His Val Asn Ser Leu Gly Glu Asn Leu
                180                 185                190

Lys Thr Leu Arg Leu Arg Leu Arg Arg Cys His Arg Phe Leu Pro Cys
                195                 200                205

Glu Asn Gly Gly Gly Ser Gly Gly Lys Ser Ala Val Glu Gln Val
                210                 215                220

Lys Asn Ala Phe Asn Lys Leu Gln Glu Lys Gly Ile Tyr Lys Ala Met
225                             230                 235                 240
```

```
Ser Glu Phe Asp Ile Phe Ile Asn Tyr Ile Glu Ala Tyr Met Thr Met
                245                 250                 255

Lys Ile Arg Asn Ser Pro Leu Thr Phe Gly Gly Gly Thr Lys Val Glu
            260                 265                 270

Ile Lys

<210> SEQ ID NO 47
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Arg Thr Lys Arg Phe Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
            305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 48
<211> LENGTH: 381
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Gly Gln Gly Thr Gln Ser Glu Asn Ser Cys Thr His Phe Pro Gly Asn
            100                 105                 110

Leu Pro Asn Met Leu Arg Asp Leu Arg Asp Ala Phe Ser Arg Val Lys
        115                 120                 125

Thr Phe Phe Gln Met Lys Asp Gln Leu Asp Asn Leu Leu Leu Lys Glu
    130                 135                 140

Ser Leu Leu Glu Asp Phe Lys Gly Tyr Leu Gly Cys Gln Ala Leu Ser
145                 150                 155                 160

Glu Met Ile Gln Phe Tyr Leu Glu Glu Val Met Pro Gln Ala Glu Asn
                165                 170                 175

Gln Asp Pro Asp Ile Lys Ala His Val Asn Ser Leu Gly Glu Asn Leu
            180                 185                 190

Lys Thr Leu Arg Leu Arg Leu Arg Arg Cys His Arg Phe Leu Pro Cys
        195                 200                 205

Glu Asn Gly Gly Gly Ser Gly Gly Lys Ser Lys Ala Val Glu Gln Val
    210                 215                 220
```

```
Lys Asn Ala Phe Asn Lys Leu Gln Glu Lys Gly Ile Tyr Lys Ala Met
225                 230                 235                 240

Ser Glu Phe Asp Ile Phe Ile Asn Tyr Ile Glu Ala Tyr Met Thr Met
                245                 250                 255

Lys Ile Arg Asn Ser Pro Leu Thr Phe Gly Gly Gly Thr Lys Val Glu
            260                 265                 270

Ile Lys Arg Thr Val Ala Ala Pro Ser Val Phe Ile Phe Pro Pro Ser
        275                 280                 285

Asp Glu Gln Leu Lys Ser Gly Thr Ala Ser Val Val Cys Leu Leu Asn
290                 295                 300

Asn Phe Tyr Pro Arg Glu Ala Lys Val Gln Trp Lys Val Asp Asn Ala
305                 310                 315                 320

Leu Gln Ser Gly Asn Ser Gln Glu Ser Val Thr Glu Gln Asp Ser Lys
                325                 330                 335

Asp Ser Thr Tyr Ser Leu Ser Ser Thr Leu Thr Leu Ser Lys Ala Asp
            340                 345                 350

Tyr Glu Lys His Lys Val Tyr Ala Cys Glu Val Thr His Gln Gly Leu
        355                 360                 365

Ser Ser Pro Val Thr Lys Ser Phe Asn Arg Gly Glu Cys
370                 375                 380
```

```
<210> SEQ ID NO 49
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gly Phe Thr Phe Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
                20                  25                  30

Ala Phe Ser Arg Val Lys Thr Phe Phe Gln Met Lys Asp Gln Leu Asp
            35                  40                  45

Asn Leu Leu Leu Lys Glu Ser Leu Leu Glu Asp Phe Lys Gly Tyr Leu
50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Gly Ser Gly Gly Lys Ser
        115                 120                 125

Lys Ala Val Glu Gln Val Lys Asn Ala Phe Asn Lys Leu Gln Glu Lys
130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Ser Ser Tyr
                165                 170
```

```
<210> SEQ ID NO 50
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ser Gly Ser Gly Gly Ser
1               5

<210> SEQ ID NO 51
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Thr Arg Thr Lys Arg Phe
1               5

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ser Gln Ser Val Ser Ser Ser Tyr
1               5

<210> SEQ ID NO 53
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Ala Ser
1

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Gly Ser Ser Pro Leu
1               5

<210> SEQ ID NO 55
<211> LENGTH: 172
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 55

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
130                 135                 140

Ala Met Ser Glu Phe Asp Ile Phe Ile Asn Tyr Ile Glu Ala Tyr Met
145                 150                 155                 160

Thr Met Lys Ile Arg Asn Ser Ser Tyr Ala Met Ser
                165                 170

<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ala Ile Ser Gly Ser Gly Gly Ser Thr Tyr Tyr Gly Asp Ser Val Lys
1               5                   10                  15

Gly

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Thr Arg Thr Lys Arg Phe
1               5

<210> SEQ ID NO 58
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 58

Arg Ala Ser Gln Ser Val Ser Ser Ser Tyr Leu Ala
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Ala Ser Ser Arg Ala Thr
1               5

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gln Gln Tyr Gly Ser Ser Pro Leu Thr
1               5

<210> SEQ ID NO 61
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Gly
            20                  25                  30

Gln Gly Thr Gln Ser Glu Asn Ser Cys Thr His Phe Pro Gly Asn Leu
        35                  40                  45

Pro Asn Met Leu Arg Asp Leu Arg Asp Ala Phe Ser Arg Val Lys Thr
    50                  55                  60

Phe Phe Gln Met Lys Asp Gln Leu Asp Asn Leu Leu Leu Lys Glu Ser
65                  70                  75                  80

Leu Leu Glu Asp Phe Lys Gly Tyr Leu Gly Cys Gln Ala Leu Ser Glu
                85                  90                  95

Met Ile Gln Phe Tyr Leu Glu Glu Val Met Pro Gln Ala Glu Asn Gln
            100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
    130                 135                 140

Asn Gly Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
```

```
                    165                 170                 175

Glu Phe Asp Ile Phe Ile Asn Tyr Ile Glu Ala Tyr Met Thr Met Lys
                180                 185                 190

Ile Arg Asn Ser Ser Tyr Ala Met Ser Trp Val Arg Gln Ala Pro Gly
            195                 200                 205

Lys Gly Leu Glu Trp Val Ser Ala Ile Ser Gly Ser Gly Gly Ser Thr
        210                 215                 220

Tyr Tyr Gly Asp Ser Val Lys Gly Arg Phe Thr Ile Ser Arg Asp Asn
225                 230                 235                 240

Ser Lys Asn Thr Leu Tyr Leu Gln Met Asn Ser Leu Arg Ala Glu Asp
                245                 250                 255

Thr Ala Val Tyr Tyr Cys Ala Arg Thr Arg Thr Lys Arg Phe Trp Gly
            260                 265                 270

Gln Gly Thr Leu Val Thr Val Ser Ser
        275                 280

<210> SEQ ID NO 62
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 63
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Gly
            20                  25                  30

Gln Gly Thr Gln Ser Glu Asn Ser Cys Thr His Phe Pro Gly Asn Leu
        35                  40                  45

Pro Asn Met Leu Arg Asp Leu Arg Asp Ala Phe Ser Arg Val Lys Thr
    50                  55                  60
```

-continued

```
Phe Phe Gln Met Lys Asp Gln Leu Asp Asn Leu Leu Leu Lys Glu Ser
 65                  70                  75                  80

Leu Leu Glu Asp Phe Lys Gly Tyr Leu Gly Cys Gln Ala Leu Ser Glu
             85                  90                  95

Met Ile Gln Phe Tyr Leu Glu Glu Val Met Pro Gln Ala Glu Asn Gln
        100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
130                 135                 140

Asn Gly Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
                165                 170                 175

Glu Phe Asp Ile Phe Ile Asn Tyr Ile Glu Ala Tyr Met Thr Met Lys
            180                 185                 190

Ile Arg Asn Ser Ser Tyr Ala Met Ser Trp Val Arg Gln Ala Pro Gly
        195                 200                 205

Lys Gly Leu Glu Trp Val Ser Ala Ile Ser Gly Ser Gly Gly Ser Thr
210                 215                 220

Tyr Tyr Gly Asp Ser Val Lys Gly Arg Phe Thr Ile Ser Arg Asp Asn
225                 230                 235                 240

Ser Lys Asn Thr Leu Tyr Leu Gln Met Asn Ser Leu Arg Ala Glu Asp
                245                 250                 255

Thr Ala Val Tyr Tyr Cys Ala Arg Thr Arg Thr Lys Arg Phe Trp Gly
            260                 265                 270

Gln Gly Thr Leu Val Thr Val Ser Ser Ala Ser Thr Lys Gly Pro Ser
        275                 280                 285

Val Phe Pro Leu Ala Pro Ser Ser Lys Ser Thr Ser Gly Gly Thr Ala
    290                 295                 300

Ala Leu Gly Cys Leu Val Lys Asp Tyr Phe Pro Glu Pro Val Thr Val
305                 310                 315                 320

Ser Trp Asn Ser Gly Ala Leu Thr Ser Gly Val His Thr Phe Pro Ala
                325                 330                 335

Val Leu Gln Ser Ser Gly Leu Tyr Ser Leu Ser Ser Val Val Thr Val
            340                 345                 350

Pro Ser Ser Ser Leu Gly Thr Gln Thr Tyr Ile Cys Asn Val Asn His
        355                 360                 365

Lys Pro Ser Asn Thr Lys Val Asp Lys Arg Val Glu Pro Lys Ser Cys
    370                 375                 380

Asp Lys Thr His Thr Cys Pro Pro Cys Pro Ala Pro Glu Leu Leu Gly
385                 390                 395                 400

Gly Pro Ser Val Phe Leu Phe Pro Pro Lys Pro Lys Asp Thr Leu Met
                405                 410                 415

Ile Ser Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
        435                 440                 445

His Asn Ala Lys Thr Lys Pro Arg Glu Glu Gln Tyr Asn Ser Thr Tyr
    450                 455                 460

Arg Val Val Ser Val Leu Thr Val Leu His Gln Asp Trp Leu Asn Gly
465                 470                 475                 480
```

```
Lys Glu Tyr Lys Cys Lys Val Ser Asn Lys Ala Leu Pro Ala Pro Ile
                485                 490                 495

Glu Lys Thr Ile Ser Lys Ala Lys Gly Gln Pro Arg Glu Pro Gln Val
            500                 505                 510

Tyr Thr Leu Pro Pro Ser Arg Glu Glu Met Thr Lys Asn Gln Val Ser
            515                 520                 525

Leu Thr Cys Leu Val Lys Gly Phe Tyr Pro Ser Asp Ile Ala Val Glu
            530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
                580                 585                 590

His Glu Ala Leu His Asn His Tyr Thr Gln Lys Ser Leu Ser Leu Ser
                595                 600                 605

Pro Gly Lys
        610

<210> SEQ ID NO 64
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Gly Phe Thr Phe Ser Ser Tyr
1               5

<210> SEQ ID NO 66
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

Ser Gly Ser Gly Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
                20                  25                  30

Ala Phe Ser Arg Val Lys Thr Phe Phe Gln Met Lys Asp Gln Leu Asp
            35                  40                  45

Asn Leu Leu Leu Lys Glu Ser Leu Leu Glu Asp Phe Lys Gly Tyr Leu
        50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
        115                 120                 125

Lys Ala Val Glu Gln Val Lys Asn Ala Phe Asn Lys Leu Gln Glu Lys
    130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Gly Ser
                165                 170

<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 67

Thr Arg Thr Lys Arg Phe
1               5

<210> SEQ ID NO 68

-continued

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ser Gln Ser Val Ser Ser Ser Tyr
1               5

<210> SEQ ID NO 69
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Ala Ser
1

<210> SEQ ID NO 70
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Tyr Gly Ser Ser Pro Leu
1               5

<210> SEQ ID NO 71
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ser Tyr Ala Met Ser
1               5

<210> SEQ ID NO 72
<211> LENGTH: 183
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Ala Ile Ser Gly Ser Gly Ser Pro Gly Gln Gly Thr Gln Ser Glu Asn
1               5                   10                  15

Ser Cys Thr His Phe Pro Gly Asn Leu Pro Asn Met Leu Arg Asp Leu
                20                  25                  30

Arg Asp Ala Phe Ser Arg Val Lys Thr Phe Phe Gln Met Lys Asp Gln
            35                  40                  45
```

Leu Asp Asn Leu Leu Leu Lys Glu Ser Leu Leu Glu Asp Phe Lys Gly
        50                  55                  60

Tyr Leu Gly Cys Gln Ala Leu Ser Glu Met Ile Gln Phe Tyr Leu Glu
 65                  70                  75                  80

Glu Val Met Pro Gln Ala Glu Asn Gln Asp Pro Asp Ile Lys Ala His
                85                  90                  95

Val Asn Ser Leu Gly Glu Asn Leu Lys Thr Leu Arg Leu Arg Leu Arg
            100                 105                 110

Arg Cys His Arg Phe Leu Pro Cys Glu Asn Gly Gly Ser Gly Gly
        115                 120                 125

Lys Ser Lys Ala Val Glu Gln Val Lys Asn Ala Phe Asn Lys Leu Gln
    130                 135                 140

Glu Lys Gly Ile Tyr Lys Ala Met Ser Glu Phe Asp Ile Phe Ile Asn
145                 150                 155                 160

Tyr Ile Glu Ala Tyr Met Thr Met Lys Ile Arg Asn Gly Ser Thr Tyr
                165                 170                 175

Tyr Gly Asp Ser Val Lys Gly
            180

<210> SEQ ID NO 73
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Thr Arg Thr Lys Arg Phe
1               5

<210> SEQ ID NO 74
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Arg Ala Ser Gln Ser Val Ser Ser Ser Tyr Leu Ala
1               5                   10

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Ala Ser Ser Arg Ala Thr
1               5

<210> SEQ ID NO 76
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gln Gln Tyr Gly Ser Ser Pro Leu Thr
1               5

<210> SEQ ID NO 77
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Pro Gly Gln Gly Thr Gln Ser Glu
    50                  55                  60

Asn Ser Cys Thr His Phe Pro Gly Asn Leu Pro Asn Met Leu Arg Asp
65                  70                  75                  80

Leu Arg Asp Ala Phe Ser Arg Val Lys Thr Phe Phe Gln Met Lys Asp
                85                  90                  95

Gln Leu Asp Asn Leu Leu Leu Lys Glu Ser Leu Leu Glu Asp Phe Lys
            100                 105                 110

Gly Tyr Leu Gly Cys Gln Ala Leu Ser Glu Met Ile Gln Phe Tyr Leu
        115                 120                 125

Glu Glu Val Met Pro Gln Ala Glu Asn Gln Asp Pro Asp Ile Lys Ala
    130                 135                 140

His Val Asn Ser Leu Gly Glu Asn Leu Lys Thr Leu Arg Leu Arg Leu
145                 150                 155                 160

Arg Arg Cys His Arg Phe Leu Pro Cys Glu Asn Gly Gly Gly Ser Gly
                165                 170                 175

Gly Lys Ser Lys Ala Val Glu Gln Val Lys Asn Ala Phe Asn Lys Leu
            180                 185                 190

Gln Glu Lys Gly Ile Tyr Lys Ala Met Ser Glu Phe Asp Ile Phe Ile
        195                 200                 205

Asn Tyr Ile Glu Ala Tyr Met Thr Met Lys Ile Arg Asn Gly Ser Thr
    210                 215                 220

Tyr Tyr Gly Asp Ser Val Lys Gly Arg Phe Thr Ile Ser Arg Asp Asn
225                 230                 235                 240

Ser Lys Asn Thr Leu Tyr Leu Gln Met Asn Ser Leu Arg Ala Glu Asp
                245                 250                 255

Thr Ala Val Tyr Tyr Cys Ala Arg Thr Arg Thr Lys Arg Phe Trp Gly
            260                 265                 270

Gln Gly Thr Leu Val Thr Val Ser Ser
        275                 280

<210> SEQ ID NO 78
<211> LENGTH: 108
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 78
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

```
<210> SEQ ID NO 79
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Pro Gly Gln Gly Thr Gln Ser Glu
50                  55                  60

Asn Ser Cys Thr His Phe Pro Gly Asn Leu Pro Asn Met Leu Arg Asp
65                  70                  75                  80

Leu Arg Asp Ala Phe Ser Arg Val Lys Thr Phe Phe Gln Met Lys Asp
                85                  90                  95

Gln Leu Asp Asn Leu Leu Leu Lys Glu Ser Leu Leu Glu Asp Phe Lys
            100                 105                 110

Gly Tyr Leu Gly Cys Gln Ala Leu Ser Glu Met Ile Gln Phe Tyr Leu
        115                 120                 125

Glu Glu Val Met Pro Gln Ala Glu Asn Gln Asp Pro Asp Ile Lys Ala
130                 135                 140

His Val Asn Ser Leu Gly Glu Asn Leu Lys Thr Leu Arg Leu Arg Leu
145                 150                 155                 160

Arg Arg Cys His Arg Phe Leu Pro Cys Glu Asn Gly Gly Ser Gly
                165                 170                 175

Gly Lys Ser Lys Ala Val Glu Gln Val Lys Asn Ala Phe Asn Lys Leu
            180                 185                 190

Gln Glu Lys Gly Ile Tyr Lys Ala Met Ser Glu Phe Asp Ile Phe Ile
        195                 200                 205

-continued

```
Asn Tyr Ile Glu Ala Tyr Met Thr Met Lys Ile Arg Asn Gly Ser Thr
    210                 215                 220
Tyr Tyr Gly Asp Ser Val Lys Gly Arg Phe Thr Ile Ser Arg Asp Asn
225                 230                 235                 240
Ser Lys Asn Thr Leu Tyr Leu Gln Met Asn Ser Leu Arg Ala Glu Asp
                245                 250                 255
Thr Ala Val Tyr Tyr Cys Ala Arg Thr Arg Thr Lys Arg Phe Trp Gly
            260                 265                 270
Gln Gly Thr Leu Val Thr Val Ser Ala Ser Thr Lys Gly Pro Ser
        275                 280                 285
Val Phe Pro Leu Ala Pro Ser Ser Lys Ser Thr Ser Gly Gly Thr Ala
    290                 295                 300
Ala Leu Gly Cys Leu Val Lys Asp Tyr Phe Pro Glu Pro Val Thr Val
305                 310                 315                 320
Ser Trp Asn Ser Gly Ala Leu Thr Ser Gly Val His Thr Phe Pro Ala
                325                 330                 335
Val Leu Gln Ser Ser Gly Leu Tyr Ser Leu Ser Ser Val Val Thr Val
            340                 345                 350
Pro Ser Ser Ser Leu Gly Thr Gln Thr Tyr Ile Cys Asn Val Asn His
        355                 360                 365
Lys Pro Ser Asn Thr Lys Val Asp Lys Arg Val Glu Pro Lys Ser Cys
    370                 375                 380
Asp Lys Thr His Thr Cys Pro Pro Cys Pro Ala Pro Glu Leu Leu Gly
385                 390                 395                 400
Gly Pro Ser Val Phe Leu Phe Pro Pro Lys Pro Lys Asp Thr Leu Met
                405                 410                 415
Ile Ser Arg Thr Pro Glu Val Thr Cys Val Val Val Asp Val Ser His
            420                 425                 430
Glu Asp Pro Glu Val Lys Phe Asn Trp Tyr Val Asp Gly Val Glu Val
        435                 440                 445
His Asn Ala Lys Thr Lys Pro Arg Glu Glu Gln Tyr Asn Ser Thr Tyr
    450                 455                 460
Arg Val Val Ser Val Leu Thr Val Leu His Gln Asp Trp Leu Asn Gly
465                 470                 475                 480
Lys Glu Tyr Lys Cys Lys Val Ser Asn Lys Ala Leu Pro Ala Pro Ile
                485                 490                 495
Glu Lys Thr Ile Ser Lys Ala Lys Gly Gln Pro Arg Glu Pro Gln Val
            500                 505                 510
Tyr Thr Leu Pro Pro Ser Arg Glu Glu Met Thr Lys Asn Gln Val Ser
        515                 520                 525
Leu Thr Cys Leu Val Lys Gly Phe Tyr Pro Ser Asp Ile Ala Val Glu
    530                 535                 540
Trp Glu Ser Asn Gly Gln Pro Glu Asn Asn Tyr Lys Thr Thr Pro Pro
545                 550                 555                 560
Val Leu Asp Ser Asp Gly Ser Phe Phe Leu Tyr Ser Lys Leu Thr Val
                565                 570                 575
Asp Lys Ser Arg Trp Gln Gln Gly Asn Val Phe Ser Cys Ser Val Met
            580                 585                 590
His Glu Ala Leu His Asn His Tyr Thr Gln Lys Ser Leu Ser Leu Ser
        595                 600                 605
Pro Gly Lys
    610
```

```
<210> SEQ ID NO 80
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

```
<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81
```

Gly Phe Thr Phe Ser Ser Tyr
1               5

```
<210> SEQ ID NO 82
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82
```

```
Ser Gly Ser Gly Gly Ser
1               5
```

<210> SEQ ID NO 83
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

```
Thr Arg Thr Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
            20                  25                  30

Phe Ser Arg Val Lys Thr Phe Phe Gln Met Lys Asp Gln Leu Asp Asn
        35                  40                  45

Leu Leu Leu Lys Glu Ser Leu Leu Glu Asp Phe Lys Gly Tyr Leu Gly
    50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Gly Lys Ser Lys
        115                 120                 125

Ala Val Glu Gln Val Lys Asn Ala Phe Asn Lys Leu Gln Glu Lys Gly
    130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Lys Arg Phe
                165                 170
```

<210> SEQ ID NO 84
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

```
Ser Gln Ser Val Ser Ser Ser Tyr
1               5
```

<210> SEQ ID NO 85
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

```
Gly Ala Ser
1
```

-continued

<210> SEQ ID NO 86
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Tyr Gly Ser Ser Pro Leu
1               5

<210> SEQ ID NO 87
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Ser Tyr Ala Met Ser
1               5

<210> SEQ ID NO 88
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Ala Ile Ser Gly Ser Gly Gly Ser Thr Tyr Tyr Gly Asp Ser Val Lys
1               5                   10                  15

Gly

<210> SEQ ID NO 89
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Thr Arg Thr Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
                20                  25                  30

Phe Ser Arg Val Lys Thr Phe Phe Gln Met Lys Asp Gln Leu Asp Asn
            35                  40                  45

Leu Leu Leu Lys Glu Ser Leu Leu Glu Asp Phe Lys Gly Tyr Leu Gly
        50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

```
Arg Phe Leu Pro Cys Glu Asn Gly Gly Gly Ser Gly Gly Lys Ser Lys
            115                 120                 125

Ala Val Glu Gln Val Lys Asn Ala Phe Asn Lys Leu Gln Glu Lys Gly
        130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Lys Arg Phe
                165                 170
```

<210> SEQ ID NO 90
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

```
Arg Ala Ser Gln Ser Val Ser Ser Ser Tyr Leu Ala
1               5                   10
```

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

```
Gly Ala Ser Ser Arg Ala Thr
1               5
```

<210> SEQ ID NO 92
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

```
Gln Gln Tyr Gly Ser Ser Pro Leu Thr
1               5
```

<210> SEQ ID NO 93
<211> LENGTH: 281
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Gly Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Arg Thr Ser Pro Gly Gln Gly Thr Gln Ser Glu Asn Ser
            100                 105                 110

Cys Thr His Phe Pro Gly Asn Leu Pro Asn Met Leu Arg Asp Leu Arg
            115                 120                 125

Asp Ala Phe Ser Arg Val Lys Thr Phe Phe Gln Met Lys Asp Gln Leu
130                 135                 140

Asp Asn Leu Leu Leu Lys Glu Ser Leu Leu Glu Asp Phe Lys Gly Tyr
145                 150                 155                 160

Leu Gly Cys Gln Ala Leu Ser Glu Met Ile Gln Phe Tyr Leu Glu Glu
                165                 170                 175

Val Met Pro Gln Ala Glu Asn Gln Asp Pro Asp Ile Lys Ala His Val
            180                 185                 190

Asn Ser Leu Gly Glu Asn Leu Lys Thr Leu Arg Leu Arg Leu Arg Arg
            195                 200                 205

Cys His Arg Phe Leu Pro Cys Glu Asn Gly Gly Ser Gly Gly Lys
210                 215                 220

Ser Lys Ala Val Glu Gln Val Lys Asn Ala Phe Asn Lys Leu Gln Glu
225                 230                 235                 240

Lys Gly Ile Tyr Lys Ala Met Ser Glu Phe Asp Ile Phe Ile Asn Tyr
                245                 250                 255

Ile Glu Ala Tyr Met Thr Met Lys Ile Arg Asn Lys Arg Phe Trp Gly
            260                 265                 270

Gln Gly Thr Leu Val Thr Val Ser Ser
            275                 280

<210> SEQ ID NO 94
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105
```

```
<210> SEQ ID NO 95
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Arg | Leu | Ser | Cys | Ala | Ala | Ser | Gly | Phe | Thr | Phe | Ser | Ser |
| | | | 20 | | | | | 25 | | | | | 30 | |
| Tyr | | | | | | | | | | | | | | |
| Ala | Met | Ser | Trp | Val | Arg | Gln | Ala | Pro | Gly | Lys | Gly | Leu | Glu | Trp |
| | | 35 | | | | | 40 | | | | | 45 | | |
| Val | | | | | | | | | | | | | | |
| Ser | Ala | Ile | Ser | Gly | Ser | Gly | Gly | Ser | Thr | Tyr | Tyr | Gly | Asp | Ser |
| 50 | | | | | 55 | | | | | 60 | | | | |
| Val | | | | | | | | | | | | | | |
| Lys | Gly | Arg | Phe | Thr | Ile | Ser | Arg | Asp | Asn | Ser | Lys | Asn | Thr | Leu |
| 65 | | | | 70 | | | | | 75 | | | | | 80 |
| Tyr | | | | | | | | | | | | | | |
| Leu | Gln | Met | Asn | Ser | Leu | Arg | Ala | Glu | Asp | Thr | Ala | Val | Tyr | Tyr |
| | | | | 85 | | | | | 90 | | | | | 95 |
| Cys | | | | | | | | | | | | | | |
| Ala | Arg | Thr | Arg | Thr | Ser | Pro | Gly | Gln | Gly | Thr | Gln | Ser | Glu | Asn |
| | | | 100 | | | | | 105 | | | | | 110 | |
| Ser | | | | | | | | | | | | | | |
| Cys | Thr | His | Phe | Pro | Gly | Asn | Leu | Pro | Asn | Met | Leu | Arg | Asp | Leu |
| | | 115 | | | | | 120 | | | | | 125 | | |
| Arg | | | | | | | | | | | | | | |
| Asp | Ala | Phe | Ser | Arg | Val | Lys | Thr | Phe | Phe | Gln | Met | Lys | Asp | Gln |
| | 130 | | | | | 135 | | | | | 140 | | | |
| Leu | | | | | | | | | | | | | | |
| Asp | Asn | Leu | Leu | Leu | Lys | Glu | Ser | Leu | Leu | Glu | Asp | Phe | Lys | Gly |
| 145 | | | | | 150 | | | | | 155 | | | | 160 |
| Tyr | | | | | | | | | | | | | | |
| Leu | Gly | Cys | Gln | Ala | Leu | Ser | Glu | Met | Ile | Gln | Phe | Tyr | Leu | Glu |
| | | | | 165 | | | | | 170 | | | | | 175 |
| Glu | | | | | | | | | | | | | | |
| Val | Met | Pro | Gln | Ala | Glu | Asn | Gln | Asp | Pro | Asp | Ile | Lys | Ala | His |
| | | | 180 | | | | | 185 | | | | | 190 | |
| Val | | | | | | | | | | | | | | |
| Asn | Ser | Leu | Gly | Glu | Asn | Leu | Lys | Thr | Leu | Arg | Leu | Arg | Leu | Arg |
| | | 195 | | | | | 200 | | | | | 205 | | |
| Arg | | | | | | | | | | | | | | |
| Cys | His | Arg | Phe | Leu | Pro | Cys | Glu | Asn | Gly | Gly | Ser | Gly | Gly | Lys |
| | 210 | | | | | 215 | | | | | 220 | | | |
| Ser | Lys | Ala | Val | Glu | Gln | Val | Lys | Asn | Ala | Phe | Asn | Lys | Leu | Gln |
| 225 | | | | | 230 | | | | | 235 | | | | | 240 |
| Glu | | | | | | | | | | | | | | |
| Lys | Gly | Ile | Tyr | Lys | Ala | Met | Ser | Glu | Phe | Asp | Ile | Phe | Ile | Asn |
| | | | | 245 | | | | | 250 | | | | | 255 |
| Tyr | | | | | | | | | | | | | | |
| Ile | Glu | Ala | Tyr | Met | Thr | Met | Lys | Ile | Arg | Asn | Lys | Arg | Phe | Trp |
| | | | 260 | | | | | 265 | | | | | 270 | |
| Gly | | | | | | | | | | | | | | |
| Gln | Gly | Thr | Leu | Val | Thr | Val | Ser | Ala | Ser | Thr | Lys | Gly | Pro | Ser |
| | | 275 | | | | | 280 | | | | | 285 | | |
| Val | Phe | Pro | Leu | Ala | Pro | Ser | Ser | Lys | Ser | Thr | Ser | Gly | Gly | Thr |
| | 290 | | | | | 295 | | | | | 300 | | | |
| Ala | | | | | | | | | | | | | | |
| Ala | Leu | Gly | Cys | Leu | Val | Lys | Asp | Tyr | Phe | Pro | Glu | Pro | Val | Thr |
| 305 | | | | | 310 | | | | | 315 | | | | | 320 |
| Val | | | | | | | | | | | | | | |
| Ser | Trp | Asn | Ser | Gly | Ala | Leu | Thr | Ser | Gly | Val | His | Thr | Phe | Pro |
| | | | | 325 | | | | | 330 | | | | | 335 |
| Ala | | | | | | | | | | | | | | |
| Val | Leu | Gln | Ser | Ser | Gly | Leu | Tyr | Ser | Leu | Ser | Ser | Val | Val | Thr |
| | | | | 340 | | | | | 345 | | | | | 350 |
| Val | | | | | | | | | | | | | | |
| Pro | Ser | Ser | Ser | Leu | Gly | Thr | Gln | Thr | Tyr | Ile | Cys | Asn | Val | Asn |
| | | | | 355 | | | | | 360 | | | | | 365 |
| His | | | | | | | | | | | | | | |

Lys Pro Ser Asn Thr Lys Val Asp Lys Arg Val Glu Pro Lys Ser Cys
            370                 375                 380

Asp Lys Thr His Thr Cys Pro Pro Cys Pro Ala Pro Glu Leu Leu Gly
385                 390                 395                 400

Gly Pro Ser Val Phe Leu Phe Pro Pro Lys Pro Lys Asp Thr Leu Met
                405                 410                 415

Ile Ser Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
        435                 440                 445

His Asn Ala Lys Thr Lys Pro Arg Glu Glu Gln Tyr Asn Ser Thr Tyr
    450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile
                485                 490                 495

Glu Lys Thr Ile Ser Lys Ala Lys Gly Gln Pro Arg Glu Pro Gln Val
            500                 505                 510

Tyr Thr Leu Pro Pro Ser Arg Glu Glu Met Thr Lys Asn Gln Val Ser
        515                 520                 525

Leu Thr Cys Leu Val Lys Gly Phe Tyr Pro Ser Asp Ile Ala Val Glu
    530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
            580                 585                 590

His Glu Ala Leu His Asn His Tyr Thr Gln Lys Ser Leu Ser Leu Ser
        595                 600                 605

Pro Gly Lys
    610

<210> SEQ ID NO 96
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Leu Thr Phe Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 97
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Phe Ser Leu Ser Thr Ser Gly Met
1               5

<210> SEQ ID NO 98
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Trp Trp Asp Asp Lys
1               5

<210> SEQ ID NO 99
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Ser Met Ile Thr Asn Trp Tyr Phe Asp Val
1               5                   10

<210> SEQ ID NO 100
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 100

Gln Leu Ser Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
            20                  25                  30

Phe Ser Arg Val Lys Thr Phe Phe Gln Met Lys Asp Gln Leu Asp Asn
        35                  40                  45

Leu Leu Leu Lys Glu Ser Leu Leu Glu Asp Phe Lys Gly Tyr Leu Gly
    50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Gly Lys Ser Lys
        115                 120                 125

Ala Val Glu Gln Val Lys Asn Ala Phe Asn Lys Leu Gln Glu Lys Gly
    130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Val Gly Tyr
                165                 170

<210> SEQ ID NO 101
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Asp Thr Ser
1

<210> SEQ ID NO 102
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Ser Gly Tyr Pro Phe
1               5

<210> SEQ ID NO 103
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Thr Ser Gly Met Ser Val Gly
1               5

<210> SEQ ID NO 104
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Asp Ile Trp Trp Asp Asp Lys Lys Asp Tyr Asn Pro Ser Leu Lys Ser
1               5                   10                  15

<210> SEQ ID NO 105
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ser Met Ile Thr Asn Trp Tyr Phe Asp Val
1               5                   10

<210> SEQ ID NO 106
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Lys Ala Gln Leu Ser Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
                20                  25                  30

Asp Ala Phe Ser Arg Val Lys Thr Phe Phe Gln Met Lys Asp Gln Leu
            35                  40                  45

Asp Asn Leu Leu Leu Lys Glu Ser Leu Leu Glu Asp Phe Lys Gly Tyr
        50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Gly Ser Gly Gly Lys
        115                 120                 125

Ser Lys Ala Val Glu Gln Val Lys Asn Ala Phe Asn Lys Leu Gln Glu
130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Val Gly Tyr Met His
                165                 170                 175

<210> SEQ ID NO 107
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Asp Thr Ser Lys Leu Ala Ser
1               5

<210> SEQ ID NO 108
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Phe Gln Gly Ser Gly Tyr Pro Phe Thr
1               5

<210> SEQ ID NO 109
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 110
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
```

```
                20                  25                  30
Gly Thr Gln Ser Glu Asn Ser Cys Thr His Phe Pro Gly Asn Leu Pro
            35                  40                  45
Asn Met Leu Arg Asp Leu Arg Asp Ala Phe Ser Arg Val Lys Thr Phe
 50                  55                  60
Phe Gln Met Lys Asp Gln Leu Asp Asn Leu Leu Lys Glu Ser Leu
 65                  70                  75                  80
Leu Glu Asp Phe Lys Gly Tyr Leu Gly Cys Gln Ala Leu Ser Glu Met
                85                  90                  95
Ile Gln Phe Tyr Leu Glu Glu Val Met Pro Gln Ala Glu Asn Gln Asp
            100                 105                 110
Pro Asp Ile Lys Ala His Val Asn Ser Leu Gly Glu Asn Leu Lys Thr
        115                 120                 125
Leu Arg Leu Arg Leu Arg Arg Cys His Arg Phe Leu Pro Cys Glu Asn
    130                 135                 140
Gly Gly Gly Ser Gly Gly Lys Ser Lys Ala Val Glu Gln Val Lys Asn
145                 150                 155                 160
Ala Phe Asn Lys Leu Gln Glu Lys Gly Ile Tyr Lys Ala Met Ser Glu
                165                 170                 175
Phe Asp Ile Phe Ile Asn Tyr Ile Glu Ala Tyr Met Thr Met Lys Ile
            180                 185                 190
Arg Asn Val Gly Tyr Met His Trp Tyr Gln Gln Lys Pro Gly Lys Ala
        195                 200                 205
Pro Lys Leu Leu Ile Tyr Asp Thr Ser Lys Leu Ala Ser Gly Val Pro
    210                 215                 220
Ser Arg Phe Ser Gly Ser Gly Ser Gly Thr Ala Phe Thr Leu Thr Ile
225                 230                 235                 240
Ser Ser Leu Gln Pro Asp Asp Phe Ala Thr Tyr Tyr Cys Phe Gln Gly
                245                 250                 255
Ser Gly Tyr Pro Phe Thr Phe Gly Gly Gly Thr Lys Leu Glu Ile Lys
            260                 265                 270

<210> SEQ ID NO 111
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Gln Val Thr Leu Arg Glu Ser Gly Pro Ala Leu Val Lys Pro Thr Gln
 1                5                  10                  15
Thr Leu Thr Leu Thr Cys Thr Phe Ser Gly Phe Ser Leu Ser Thr Ser
                20                  25                  30
Gly Met Ser Val Gly Trp Ile Arg Gln Pro Pro Gly Lys Ala Leu Glu
            35                  40                  45
Trp Leu Ala Asp Ile Trp Trp Asp Asp Lys Lys Asp Tyr Asn Pro Ser
 50                  55                  60
Leu Lys Ser Arg Leu Thr Ile Ser Lys Asp Thr Ser Asn Gln Val
 65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Trp Tyr Phe Asp Val Trp Gly Ala
            100                 105                 110
```

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 112
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
50                  55                  60

Phe Gln Met Lys Asp Gln Leu Asp Asn Leu Leu Lys Glu Ser Leu
65              70                  75                  80

Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
                100                 105                 110

Pro Asp Ile Lys Ala His Val Asn Ser Leu Gly Glu Asn Leu Lys Thr
            115                 120                 125

Leu Arg Leu Arg Leu Arg Arg Cys His Arg Phe Leu Pro Cys Glu Asn
130                 135                 140

Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
                180                 185                 190

Arg Asn Val Gly Tyr Met His Trp Tyr Gln Gln Lys Pro Gly Lys Ala
                195                 200                 205

Pro Lys Leu Leu Ile Tyr Asp Thr Ser Lys Leu Ala Ser Gly Val Pro
210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
                260                 265                 270

Arg Thr Val Ala Ala Pro Ser Val Phe Ile Phe Pro Pro Ser Asp Glu
            275                 280                 285

Gln Leu Lys Ser Gly Thr Ala Ser Val Val Cys Leu Leu Asn Asn Phe
                290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
                340                 345                 350

Lys His Lys Val Tyr Ala Cys Glu Val Thr His Gln Gly Leu Ser Ser
                355                 360                 365

Pro Val Thr Lys Ser Phe Asn Arg Gly Glu Cys
            370                 375

<210> SEQ ID NO 113
<211> LENGTH: 9
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 113

Gly Phe Ser Leu Ser Thr Ser Gly Met
1               5

<210> SEQ ID NO 114
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Trp Trp Asp Asp Lys
1               5

<210> SEQ ID NO 115
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ser Met Ile Thr Asn Trp Tyr Phe Asp Val
1               5                   10

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Gln Leu Ser Val Gly Tyr
1               5

<210> SEQ ID NO 117
<211> LENGTH: 169
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Asp Thr Ser Pro Gly Gln Gly Thr Gln Ser Glu Asn Ser Cys Thr His
1               5                   10                  15

Phe Pro Gly Asn Leu Pro Asn Met Leu Arg Asp Leu Arg Asp Ala Phe
            20                  25                  30

Ser Arg Val Lys Thr Phe Phe Gln Met Lys Asp Gln Leu Asp Asn Leu
        35                  40                  45

Leu Leu Lys Glu Ser Leu Leu Glu Asp Phe Lys Gly Tyr Leu Gly Cys
    50                  55                  60

Gln Ala Leu Ser Glu Met Ile Gln Phe Tyr Leu Glu Glu Val Met Pro
65                  70                  75                  80
```

```
Gln Ala Glu Asn Gln Asp Pro Asp Ile Lys Ala His Val Asn Ser Leu
                85                  90                  95
Gly Glu Asn Leu Lys Thr Leu Arg Leu Arg Leu Arg Cys His Arg
            100                 105                 110
Phe Leu Pro Cys Glu Asn Gly Gly Ser Gly Gly Lys Ser Lys Ala
        115                 120                 125
Val Glu Gln Val Lys Asn Ala Phe Asn Lys Leu Gln Glu Lys Gly Ile
    130                 135                 140
Tyr Lys Ala Met Ser Glu Phe Asp Ile Phe Ile Asn Tyr Ile Glu Ala
145                 150                 155                 160
Tyr Met Thr Met Lys Ile Arg Asn Ser
                165

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gly Ser Gly Tyr Pro Phe
1               5

<210> SEQ ID NO 119
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Thr Ser Gly Met Ser Val Gly
1               5

<210> SEQ ID NO 120
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Asp Ile Trp Trp Asp Asp Lys Lys Asp Tyr Asn Pro Ser Leu Lys Ser
1               5                   10                  15

<210> SEQ ID NO 121
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ser Met Ile Thr Asn Trp Tyr Phe Asp Val
1               5                   10
```

<210> SEQ ID NO 122
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 122

Lys Ala Gln Leu Ser Val Gly Tyr Met His
1               5                   10

<210> SEQ ID NO 123
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Asp Thr Ser Pro Gly Gln Gly Thr Gln Ser Glu Asn Ser Cys Thr His
1               5                   10                  15

Phe Pro Gly Asn Leu Pro Asn Met Leu Arg Asp Leu Arg Asp Ala Phe
            20                  25                  30

Ser Arg Val Lys Thr Phe Phe Gln Met Lys Asp Gln Leu Asp Asn Leu
        35                  40                  45

Leu Leu Lys Glu Ser Leu Leu Glu Asp Phe Lys Gly Tyr Leu Gly Cys
    50                  55                  60

Gln Ala Leu Ser Glu Met Ile Gln Phe Tyr Leu Glu Glu Val Met Pro
65                  70                  75                  80

Gln Ala Glu Asn Gln Asp Pro Asp Ile Lys Ala His Val Asn Ser Leu
                85                  90                  95

Gly Glu Asn Leu Lys Thr Leu Arg Leu Arg Leu Arg Arg Cys His Arg
            100                 105                 110

Phe Leu Pro Cys Glu Asn Gly Gly Gly Ser Gly Gly Lys Ser Lys Ala
        115                 120                 125

Val Glu Gln Val Lys Asn Ala Phe Asn Lys Leu Gln Glu Lys Gly Ile
    130                 135                 140

Tyr Lys Ala Met Ser Glu Phe Asp Ile Phe Ile Asn Tyr Ile Glu Ala
145                 150                 155                 160

Tyr Met Thr Met Lys Ile Arg Asn Ser Lys Leu Ala Ser
                165                 170

<210> SEQ ID NO 124
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 124

Phe Gln Gly Ser Gly Tyr Pro Phe Thr
1               5

<210> SEQ ID NO 125
<211> LENGTH: 120
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
            115                 120

<210> SEQ ID NO 126
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Pro Gly Gln Gly Thr Gln Ser Glu Asn Ser Cys Thr His
    50                  55                  60

Phe Pro Gly Asn Leu Pro Asn Met Leu Arg Asp Leu Arg Asp Ala Phe
65                  70                  75                  80

Ser Arg Val Lys Thr Phe Phe Gln Met Lys Asp Gln Leu Asp Asn Leu
                85                  90                  95

Leu Leu Lys Glu Ser Leu Leu Glu Asp Phe Lys Gly Tyr Leu Gly Cys
            100                 105                 110

Gln Ala Leu Ser Glu Met Ile Gln Phe Tyr Leu Glu Glu Val Met Pro
            115                 120                 125

Gln Ala Glu Asn Gln Asp Pro Asp Ile Lys Ala His Val Asn Ser Leu
        130                 135                 140

Gly Glu Asn Leu Lys Thr Leu Arg Leu Arg Leu Arg Arg Cys His Arg
145                 150                 155                 160

Phe Leu Pro Cys Glu Asn Gly Gly Ser Gly Gly Lys Ser Lys Ala
                165                 170                 175

Val Glu Gln Val Lys Asn Ala Phe Asn Lys Leu Gln Glu Lys Gly Ile
            180                 185                 190
```

```
Tyr Lys Ala Met Ser Glu Phe Asp Ile Phe Ile Asn Tyr Ile Glu Ala
        195                 200                 205

Tyr Met Thr Met Lys Ile Arg Asn Ser Lys Leu Ala Ser Gly Val Pro
    210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
                260                 265                 270

<210> SEQ ID NO 127
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 128
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Pro Gly Gln Gly Thr Gln Ser Glu Asn Ser Cys Thr His
    50                  55                  60

Phe Pro Gly Asn Leu Pro Asn Met Leu Arg Asp Leu Arg Asp Ala Phe
65                  70                  75                  80

Ser Arg Val Lys Thr Phe Phe Gln Met Lys Asp Gln Leu Asp Asn Leu
                85                  90                  95

Leu Leu Lys Glu Ser Leu Leu Glu Asp Phe Lys Gly Tyr Leu Gly Cys
            100                 105                 110

Gln Ala Leu Ser Glu Met Ile Gln Phe Tyr Leu Glu Glu Val Met Pro
        115                 120                 125

Gln Ala Glu Asn Gln Asp Pro Asp Ile Lys Ala His Val Asn Ser Leu
    130                 135                 140

Gly Glu Asn Leu Lys Thr Leu Arg Leu Arg Leu Arg Arg Cys His Arg
145                 150                 155                 160

Phe Leu Pro Cys Glu Asn Gly Gly Gly Ser Gly Gly Lys Ser Lys Ala

```
                    165                 170                 175
Val Glu Gln Val Lys Asn Ala Phe Asn Lys Leu Gln Glu Lys Gly Ile
            180                 185                 190

Tyr Lys Ala Met Ser Glu Phe Asp Ile Phe Ile Asn Tyr Ile Glu Ala
            195                 200                 205

Tyr Met Thr Met Lys Ile Arg Asn Ser Lys Leu Ala Ser Gly Val Pro
            210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
                260                 265                 270

Arg Thr Val Ala Ala Pro Ser Val Phe Ile Phe Pro Pro Ser Asp Glu
            275                 280                 285

Gln Leu Lys Ser Gly Thr Ala Ser Val Val Cys Leu Leu Asn Asn Phe
            290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
                340                 345                 350

Lys His Lys Val Tyr Ala Cys Glu Val Thr His Gln Gly Leu Ser Ser
            355                 360                 365

Pro Val Thr Lys Ser Phe Asn Arg Gly Glu Cys
            370                 375
```

```
<210> SEQ ID NO 129
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Phe Ser Leu Ser Thr Ser Gly Met
1               5

<210> SEQ ID NO 130
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Trp Trp Asp Asp Lys
1               5

<210> SEQ ID NO 131
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 131

Ser Met Ile Thr Asn Trp Tyr Phe Asp Val
1               5                   10

<210> SEQ ID NO 132
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Gln Leu Ser Val Gly Tyr
1               5

<210> SEQ ID NO 133
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Asp Thr Ser
1

<210> SEQ ID NO 134
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Gly Ser Gly Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
            20                  25                  30

Phe Ser Arg Val Lys Thr Phe Phe Gln Met Lys Asp Gln Leu Asp Asn
        35                  40                  45

Leu Leu Leu Lys Glu Ser Leu Leu Glu Asp Phe Lys Gly Tyr Leu Gly
    50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Gly Ser Gly Gly Lys Ser Lys
        115                 120                 125

Ala Val Glu Gln Val Lys Asn Ala Phe Asn Lys Leu Gln Glu Lys Gly
    130                 135                 140

Ile Tyr Lys Ala Met Ser Glu Phe Asp Ile Phe Ile Asn Tyr Ile Glu
145                 150                 155                 160

```
Ala Tyr Met Thr Met Lys Ile Arg Asn Tyr Pro Phe
            165                 170
```

<210> SEQ ID NO 135
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

```
Thr Ser Gly Met Ser Val Gly
1               5
```

<210> SEQ ID NO 136
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

```
Asp Ile Trp Trp Asp Asp Lys Lys Asp Tyr Asn Pro Ser Leu Lys Ser
1               5                   10                  15
```

<210> SEQ ID NO 137
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

```
Ser Met Ile Thr Asn Trp Tyr Phe Asp Val
1               5                   10
```

<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

```
Lys Ala Gln Leu Ser Val Gly Tyr Met His
1               5                   10
```

<210> SEQ ID NO 139
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

```
Asp Thr Ser Lys Leu Ala Ser
1               5
```

```
<210> SEQ ID NO 140
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140
```

Phe Gln Gly Ser Gly Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
            20                  25                  30

Asp Ala Phe Ser Arg Val Lys Thr Phe Phe Gln Met Lys Asp Gln Leu
        35                  40                  45

Asp Asn Leu Leu Leu Lys Glu Ser Leu Leu Glu Asp Phe Lys Gly Tyr
    50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Gly Ser Gly Gly Lys
        115                 120                 125

Ser Lys Ala Val Glu Gln Val Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Tyr Pro Phe Thr
                165                 170                 175

```
<210> SEQ ID NO 141
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141
```

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 142
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 142

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Ser Pro Gly Gln
                85                  90                  95

Gly Thr Gln Ser Glu Asn Ser Cys Thr His Phe Pro Gly Asn Leu Pro
            100                 105                 110

Asn Met Leu Arg Asp Leu Arg Asp Ala Phe Ser Arg Val Lys Thr Phe
        115                 120                 125

Phe Gln Met Lys Asp Gln Leu Asp Asn Leu Leu Leu Lys Glu Ser Leu
    130                 135                 140

Leu Glu Asp Phe Lys Gly Tyr Leu Gly Cys Gln Ala Leu Ser Glu Met
145                 150                 155                 160

Ile Gln Phe Tyr Leu Glu Glu Val Met Pro Gln Ala Glu Asn Gln Asp
                165                 170                 175

Pro Asp Ile Lys Ala His Val Asn Ser Leu Gly Glu Asn Leu Lys Thr
            180                 185                 190

Leu Arg Leu Arg Leu Arg Arg Cys His Arg Phe Leu Pro Cys Glu Asn
        195                 200                 205

Gly Gly Gly Ser Gly Gly Lys Ser Lys Ala Val Glu Gln Val Lys Asn
    210                 215                 220

Ala Phe Asn Lys Leu Gln Glu Lys Gly Ile Tyr Lys Ala Met Ser Glu
225                 230                 235                 240

Phe Asp Ile Phe Ile Asn Tyr Ile Glu Ala Tyr Met Thr Met Lys Ile
                245                 250                 255

Arg Asn Tyr Pro Phe Thr Phe Gly Gly Gly Thr Lys Leu Glu Ile Lys
            260                 265                 270

<210> SEQ ID NO 143
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 143

Gln Val Thr Leu Arg Glu Ser Gly Pro Ala Leu Val Lys Pro Thr Gln
1               5                   10                  15

```
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Asp Lys Asp Tyr Asn Pro Ser
    50                  55                  60
Leu Lys Ser Arg Leu Thr Ile Ser Lys Asp Thr Ser Ala Asn Gln Val
65                  70                  75                  80
Val Leu Lys Val Thr Asn Met Asp Pro Ala Asp Thr Ala Thr Tyr Tyr
                85                  90                  95
Cys Ala Arg Ser Met Ile Thr Asn Trp Tyr Phe Asp Val Trp Gly Ala
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
```

```
                    435                 440                 445

Gly Lys
    450

<210> SEQ ID NO 144
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Ser Pro Gly Gln
                85                  90                  95

Gly Thr Gln Ser Glu Asn Ser Cys Thr His Phe Pro Gly Asn Leu Pro
            100                 105                 110

Asn Met Leu Arg Asp Leu Arg Asp Ala Phe Ser Arg Val Lys Thr Phe
        115                 120                 125

Phe Gln Met Lys Asp Gln Leu Asp Asn Leu Leu Leu Lys Glu Ser Leu
    130                 135                 140

Leu Glu Asp Phe Lys Gly Tyr Leu Gly Cys Gln Ala Leu Ser Glu Met
145                 150                 155                 160

Ile Gln Phe Tyr Leu Glu Glu Val Met Pro Gln Ala Glu Asn Gln Asp
                165                 170                 175

Pro Asp Ile Lys Ala His Val Asn Ser Leu Gly Glu Asn Leu Lys Thr
            180                 185                 190

Leu Arg Leu Arg Leu Arg Arg Cys His Arg Phe Leu Pro Cys Glu Asn
        195                 200                 205

Gly Gly Gly Ser Gly Gly Lys Ser Lys Ala Val Glu Gln Val Lys Asn
    210                 215                 220

Ala Phe Asn Lys Leu Gln Glu Lys Gly Ile Tyr Lys Ala Met Ser Glu
225                 230                 235                 240

Phe Asp Ile Phe Ile Asn Tyr Ile Glu Ala Tyr Met Thr Met Lys Ile
                245                 250                 255

Arg Asn Tyr Pro Phe Thr Phe Gly Gly Gly Thr Lys Leu Glu Ile Lys
            260                 265                 270

Arg Thr Val Ala Ala Pro Ser Val Phe Ile Phe Pro Pro Ser Asp Glu
        275                 280                 285

Gln Leu Lys Ser Gly Thr Ala Ser Val Val Cys Leu Leu Asn Asn Phe
    290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335
```

Thr Tyr Ser Leu Ser Ser Thr Leu Thr Leu Ser Lys Ala Asp Tyr Glu
            340                 345                 350

Lys His Lys Val Tyr Ala Cys Glu Val Thr His Gln Gly Leu Ser Ser
        355                 360                 365

Pro Val Thr Lys Ser Phe Asn Arg Gly Glu Cys
    370                 375

<210> SEQ ID NO 145
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Gly Phe Ser Leu Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
            20                  25                  30

Ala Phe Ser Arg Val Lys Thr Phe Phe Gln Met Lys Asp Gln Leu Asp
        35                  40                  45

Asn Leu Leu Leu Lys Glu Ser Leu Leu Glu Asp Phe Lys Gly Tyr Leu
    50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
        115                 120                 125

Lys Ala Val Glu Gln Val Lys Asn Ala Phe Asn Lys Leu Gln Glu Lys
    130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Ser Thr Ser Gly Met
                165                 170                 175

<210> SEQ ID NO 146
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Trp Trp Asp Asp Lys
1               5

<210> SEQ ID NO 147
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 147

Ser Met Ile Thr Asn Trp Tyr Phe Asp Val
1               5                   10

<210> SEQ ID NO 148
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Gln Leu Ser Val Gly Tyr
1               5

<210> SEQ ID NO 149
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Asp Thr Ser
1

<210> SEQ ID NO 150
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gly Ser Gly Tyr Pro Phe
1               5

<210> SEQ ID NO 151
<211> LENGTH: 174
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
```

```
                    85                  90                  95
Asn Leu Lys Thr Leu Arg Leu Arg Leu Arg Arg Cys His Arg Phe Leu
                100                 105                 110

Pro Cys Glu Asn Gly Gly Ser Gly Gly Lys Ser Lys Ala Val Glu
            115                 120                 125

Gln Val Lys Asn Ala Phe Asn Lys Leu Gln Glu Lys Gly Ile Tyr Lys
    130                 135                 140

Ala Met Ser Glu Phe Asp Ile Phe Ile Asn Tyr Ile Glu Ala Tyr Met
145                 150                 155                 160

Thr Met Lys Ile Arg Asn Ser Thr Ser Gly Met Ser Val Gly
                165                 170

<210> SEQ ID NO 152
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Asp Ile Trp Trp Asp Asp Lys Lys Asp Tyr Asn Pro Ser Leu Lys Ser
1               5                   10                  15

<210> SEQ ID NO 153
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ser Met Ile Thr Asn Trp Tyr Phe Asp Val
1               5                   10

<210> SEQ ID NO 154
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Lys Ala Gln Leu Ser Val Gly Tyr Met His
1               5                   10

<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Asp Thr Ser Lys Leu Ala Ser
1               5

<210> SEQ ID NO 156
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Phe Gln Gly Ser Gly Tyr Pro Phe Thr
1               5

<210> SEQ ID NO 157
<211> LENGTH: 286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Pro Gly
            20                  25                  30

Gln Gly Thr Gln Ser Glu Asn Ser Cys Thr His Phe Pro Gly Asn Leu
        35                  40                  45

Pro Asn Met Leu Arg Asp Leu Arg Asp Ala Phe Ser Arg Val Lys Thr
    50                  55                  60

Phe Phe Gln Met Lys Asp Gln Leu Asp Asn Leu Leu Leu Lys Glu Ser
65                  70                  75                  80

Leu Leu Glu Asp Phe Lys Gly Tyr Leu Gly Cys Gln Ala Leu Ser Glu
                85                  90                  95

Met Ile Gln Phe Tyr Leu Glu Glu Val Met Pro Gln Ala Glu Asn Gln
            100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
    130                 135                 140

Asn Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
                165                 170                 175

Glu Phe Asp Ile Phe Ile Asn Tyr Ile Glu Ala Tyr Met Thr Met Lys
            180                 185                 190

Ile Arg Asn Ser Thr Ser Gly Met Ser Val Gly Trp Ile Arg Gln Pro
        195                 200                 205

Pro Gly Lys Ala Leu Glu Trp Leu Ala Asp Ile Trp Trp Asp Asp Lys
    210                 215                 220

Lys Asp Tyr Asn Pro Ser Leu Lys Ser Arg Leu Thr Ile Ser Lys Asp
225                 230                 235                 240

Thr Ser Ala Asn Gln Val Val Leu Lys Val Thr Asn Met Asp Pro Ala
                245                 250                 255

Asp Thr Ala Thr Tyr Tyr Cys Ala Arg Ser Met Ile Thr Asn Trp Tyr
            260                 265                 270

Phe Asp Val Trp Gly Ala Gly Thr Thr Val Thr Val Ser Ser
        275                 280                 285
```

<210> SEQ ID NO 158
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 158

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 159
<211> LENGTH: 616
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Pro Gly
            20                  25                  30

Gln Gly Thr Gln Ser Glu Asn Ser Cys Thr His Phe Pro Gly Asn Leu
        35                  40                  45

Pro Asn Met Leu Arg Asp Leu Arg Asp Ala Phe Ser Arg Val Lys Thr
    50                  55                  60

Phe Phe Gln Met Lys Asp Gln Leu Asp Asn Leu Leu Leu Lys Glu Ser
65                  70                  75                  80

Leu Leu Glu Asp Phe Lys Gly Tyr Leu Gly Cys Gln Ala Leu Ser Glu
                85                  90                  95

Met Ile Gln Phe Tyr Leu Glu Glu Val Met Pro Gln Ala Glu Asn Gln
            100                 105                 110

Asp Pro Asp Ile Lys Ala His Val Asn Ser Leu Gly Glu Asn Leu Lys
        115                 120                 125

Thr Leu Arg Leu Arg Leu Arg Arg Cys His Arg Phe Leu Pro Cys Glu
    130                 135                 140

Asn Gly Gly Gly Ser Gly Gly Lys Ser Lys Ala Val Glu Gln Val Lys
145                 150                 155                 160

Asn Ala Phe Asn Lys Leu Gln Glu Lys Gly Ile Tyr Lys Ala Met Ser
                165                 170                 175

Glu Phe Asp Ile Phe Ile Asn Tyr Ile Glu Ala Tyr Met Thr Met Lys

```
            180                 185                 190
Ile Arg Asn Ser Thr Ser Gly Met Ser Val Gly Trp Ile Arg Gln Pro
            195                 200                 205
Pro Gly Lys Ala Leu Glu Trp Leu Ala Asp Ile Trp Trp Asp Asp Lys
        210                 215                 220
Lys Asp Tyr Asn Pro Ser Leu Lys Ser Arg Leu Thr Ile Ser Lys Asp
225                 230                 235                 240
Thr Ser Ala Asn Gln Val Val Leu Lys Val Thr Asn Met Asp Pro Ala
                245                 250                 255
Asp Thr Ala Thr Tyr Tyr Cys Ala Arg Ser Met Ile Thr Asn Trp Tyr
            260                 265                 270
Phe Asp Val Trp Gly Ala Gly Thr Thr Val Thr Val Ser Ser Ala Ser
        275                 280                 285
Thr Lys Gly Pro Ser Val Phe Pro Leu Ala Pro Ser Ser Lys Ser Thr
    290                 295                 300
Ser Gly Gly Thr Ala Ala Leu Gly Cys Leu Val Lys Asp Tyr Phe Pro
305                 310                 315                 320
Glu Pro Val Thr Val Ser Trp Asn Ser Gly Ala Leu Thr Ser Gly Val
                325                 330                 335
His Thr Phe Pro Ala Val Leu Gln Ser Ser Gly Leu Tyr Ser Leu Ser
            340                 345                 350
Ser Val Val Thr Val Pro Ser Ser Ser Leu Gly Thr Gln Thr Tyr Ile
        355                 360                 365
Cys Asn Val Asn His Lys Pro Ser Asn Thr Lys Val Asp Lys Arg Val
    370                 375                 380
Glu Pro Lys Ser Cys Asp Lys Thr His Thr Cys Pro Pro Cys Pro Ala
385                 390                 395                 400
Pro Glu Leu Leu Gly Gly Pro Ser Val Phe Leu Phe Pro Pro Lys Pro
                405                 410                 415
Lys Asp Thr Leu Met Ile Ser Arg Thr Pro Glu Val Thr Cys Val Val
            420                 425                 430
Val Asp Val Ser His Glu Asp Pro Glu Val Lys Phe Asn Trp Tyr Val
        435                 440                 445
Asp Gly Val Glu Val His Asn Ala Lys Thr Lys Pro Arg Glu Glu Gln
    450                 455                 460
Tyr Asn Ser Thr Tyr Arg Val Val Ser Val Leu Thr Val Leu His Gln
465                 470                 475                 480
Asp Trp Leu Asn Gly Lys Glu Tyr Lys Cys Lys Val Ser Asn Lys Ala
                485                 490                 495
Leu Pro Ala Pro Ile Glu Lys Thr Ile Ser Lys Ala Lys Gly Gln Pro
            500                 505                 510
Arg Glu Pro Gln Val Tyr Thr Leu Pro Pro Ser Arg Glu Glu Met Thr
        515                 520                 525
Lys Asn Gln Val Ser Leu Thr Cys Leu Val Lys Gly Phe Tyr Pro Ser
    530                 535                 540
Asp Ile Ala Val Glu Trp Glu Ser Asn Gly Gln Pro Glu Asn Asn Tyr
545                 550                 555                 560
Lys Thr Thr Pro Pro Val Leu Asp Ser Asp Gly Ser Phe Phe Leu Tyr
                565                 570                 575
Ser Lys Leu Thr Val Asp Lys Ser Arg Trp Gln Gln Gly Asn Val Phe
            580                 585                 590
Ser Cys Ser Val Met His Glu Ala Leu His Asn His Tyr Thr Gln Lys
        595                 600                 605
```

```
Ser Leu Ser Leu Ser Pro Gly Lys
    610                 615
```

<210> SEQ ID NO 160
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 161
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

```
Gly Phe Ser Leu Ser Thr Ser Gly Met
1               5
```

<210> SEQ ID NO 162
<211> LENGTH: 171
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 162

```
Trp Trp Asp Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
            20                  25                  30

Phe Ser Arg Val Lys Thr Phe Phe Gln Met Lys Asp Gln Leu Asp Asn
        35                  40                  45

Leu Leu Leu Lys Glu Ser Leu Leu Glu Asp Phe Lys Gly Tyr Leu Gly
50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Gly Lys Ser Lys
            115                 120                 125

Ala Val Glu Gln Val Lys Asn Ala Phe Asn Lys Leu Gln Glu Lys Gly
130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Asp Lys
                165                 170
```

<210> SEQ ID NO 163
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

```
Ser Met Ile Thr Asn Trp Tyr Phe Asp Val
1               5                   10
```

<210> SEQ ID NO 164
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

```
Gln Leu Ser Val Gly Tyr
1               5
```

<210> SEQ ID NO 165
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Asp Thr Ser
1

<210> SEQ ID NO 166
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Ser Gly Tyr Pro Phe
1               5

<210> SEQ ID NO 167
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Thr Ser Gly Met Ser Val Gly
1               5

<210> SEQ ID NO 168
<211> LENGTH: 182
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Asp Ile Trp Trp Asp Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
                20                  25                  30

Asp Ala Phe Ser Arg Val Lys Thr Phe Phe Gln Met Lys Asp Gln Leu
            35                  40                  45

Asp Asn Leu Leu Leu Lys Glu Ser Leu Leu Glu Asp Phe Lys Gly Tyr
        50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Ser Gly Gly Lys
        115                 120                 125

Ser Lys Ala Val Glu Gln Val Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Asp Lys Lys Asp Tyr
                165                 170                 175

Asn Pro Ser Leu Lys Ser
            180

<210> SEQ ID NO 169
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Ser Met Ile Thr Asn Trp Tyr Phe Asp Val
1               5                   10

<210> SEQ ID NO 170
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Lys Ala Gln Leu Ser Val Gly Tyr Met His
1               5                   10

<210> SEQ ID NO 171
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Asp Thr Ser Lys Leu Ala Ser
1               5

<210> SEQ ID NO 172
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Phe Gln Gly Ser Gly Tyr Pro Phe Thr
1               5

<210> SEQ ID NO 173
<211> LENGTH: 286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Ser Pro Gly Gln Gly Thr Gln Ser
 50                  55                  60

Glu Asn Ser Cys Thr His Phe Pro Gly Asn Leu Pro Asn Met Leu Arg
65                  70                  75                  80

Asp Leu Arg Asp Ala Phe Ser Arg Val Lys Thr Phe Phe Gln Met Lys
                85                  90                  95

Asp Gln Leu Asp Asn Leu Leu Leu Lys Glu Ser Leu Leu Glu Asp Phe
            100                 105                 110

Lys Gly Tyr Leu Gly Cys Gln Ala Leu Ser Glu Met Ile Gln Phe Tyr
        115                 120                 125

Leu Glu Glu Val Met Pro Gln Ala Glu Asn Gln Asp Pro Asp Ile Lys
130                 135                 140

Ala His Val Asn Ser Leu Gly Glu Asn Leu Lys Thr Leu Arg Leu Arg
145                 150                 155                 160

Leu Arg Arg Cys His Arg Phe Leu Pro Cys Glu Asn Gly Gly Gly Ser
                165                 170                 175

Gly Gly Lys Ser Lys Ala Val Glu Gln Val Lys Asn Ala Phe Asn Lys
            180                 185                 190

Leu Gln Glu Lys Gly Ile Tyr Lys Ala Met Ser Glu Phe Asp Ile Phe
        195                 200                 205

Ile Asn Tyr Ile Glu Ala Tyr Met Thr Met Lys Ile Arg Asn Asp Lys
210                 215                 220

Lys Asp Tyr Asn Pro Ser Leu Lys Ser Arg Leu Thr Ile Ser Lys Asp
225                 230                 235                 240

Thr Ser Ala Asn Gln Val Val Leu Lys Val Thr Asn Met Asp Pro Ala
                245                 250                 255

Asp Thr Ala Thr Tyr Tyr Cys Ala Arg Ser Met Ile Thr Asn Trp Tyr
            260                 265                 270

Phe Asp Val Trp Gly Ala Gly Thr Thr Val Thr Val Ser Ser
        275                 280                 285

<210> SEQ ID NO 174
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr

```
                        85                  90                  95
Phe Gly Gly Gly Thr Lys Leu Glu Ile Lys
                100                 105

<210> SEQ ID NO 175
<211> LENGTH: 616
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Ser Pro Gly Gln Gly Thr Gln Ser
    50                  55                  60

Glu Asn Ser Cys Thr His Phe Pro Gly Asn Leu Pro Asn Met Leu Arg
65                  70                  75                  80

Asp Leu Arg Asp Ala Phe Ser Arg Val Lys Thr Phe Phe Gln Met Lys
                85                  90                  95

Asp Gln Leu Asp Asn Leu Leu Leu Lys Glu Ser Leu Leu Glu Asp Phe
            100                 105                 110

Lys Gly Tyr Leu Gly Cys Gln Ala Leu Ser Glu Met Ile Gln Phe Tyr
        115                 120                 125

Leu Glu Glu Val Met Pro Gln Ala Glu Asn Gln Asp Pro Asp Ile Lys
    130                 135                 140

Ala His Val Asn Ser Leu Gly Glu Asn Leu Lys Thr Leu Arg Leu Arg
145                 150                 155                 160

Leu Arg Arg Cys His Arg Phe Leu Pro Cys Glu Asn Gly Gly Gly Ser
                165                 170                 175

Gly Gly Lys Ser Lys Ala Val Glu Gln Val Lys Asn Ala Phe Asn Lys
            180                 185                 190

Leu Gln Glu Lys Gly Ile Tyr Lys Ala Met Ser Glu Phe Asp Ile Phe
        195                 200                 205

Ile Asn Tyr Ile Glu Ala Tyr Met Thr Met Lys Ile Arg Asn Asp Lys
    210                 215                 220

Lys Asp Tyr Asn Pro Ser Leu Lys Ser Arg Leu Thr Ile Ser Lys Asp
225                 230                 235                 240

Thr Ser Ala Asn Gln Val Val Leu Lys Val Thr Asn Met Asp Pro Ala
                245                 250                 255

Asp Thr Ala Thr Tyr Tyr Cys Ala Arg Ser Met Ile Thr Asn Trp Tyr
            260                 265                 270

Phe Asp Val Trp Gly Ala Gly Thr Thr Val Thr Val Ser Ser Ala Ser
        275                 280                 285

Thr Lys Gly Pro Ser Val Phe Pro Leu Ala Pro Ser Ser Lys Ser Thr
    290                 295                 300

Ser Gly Gly Thr Ala Ala Leu Gly Cys Leu Val Lys Asp Tyr Phe Pro
305                 310                 315                 320

Glu Pro Val Thr Val Ser Trp Asn Ser Gly Ala Leu Thr Ser Gly Val
                325                 330                 335
```

```
His Thr Phe Pro Ala Val Leu Gln Ser Ser Gly Leu Tyr Ser Leu Ser
            340                 345                 350

Ser Val Val Thr Val Pro Ser Ser Leu Gly Thr Gln Thr Tyr Ile
        355                 360                 365

Cys Asn Val Asn His Lys Pro Ser Asn Thr Lys Val Asp Lys Arg Val
        370                 375                 380

Glu Pro Lys Ser Cys Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
        420                 425                 430

Val Asp Val Ser His Glu Asp Pro Glu Val Lys Phe Asn Trp Tyr Val
        435                 440                 445

Asp Gly Val Glu Val His Asn Ala Lys Thr Lys Pro Arg Glu Glu Gln
    450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
                500                 505                 510

Arg Glu Pro Gln Val Tyr Thr Leu Pro Pro Ser Arg Glu Glu Met Thr
            515                 520                 525

Lys Asn Gln Val Ser Leu Thr Cys Leu Val Lys Gly Phe Tyr Pro Ser
        530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys
    610                 615

<210> SEQ ID NO 176
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60
```

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
            85                  90                  95

Phe Gly Gly Gly Thr Lys Leu Glu Ile Lys Arg Thr Val Ala Ala Pro
        100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 177
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Phe Ser Leu Ser Thr Ser Gly Met
1               5

<210> SEQ ID NO 178
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Trp Trp Asp Asp Lys
1               5

<210> SEQ ID NO 179
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Ser Met Ile Thr Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
            20                  25                  30

Ala Phe Ser Arg Val Lys Thr Phe Phe Gln Met Lys Asp Gln Leu Asp

```
                35                  40                  45
Asn Leu Leu Leu Lys Glu Ser Leu Leu Glu Asp Phe Lys Gly Tyr Leu
 50                  55                  60

Gly Cys Gln Ala Leu Ser Glu Met Ile Gln Phe Tyr Leu Glu Glu Val
 65                  70                  75                  80

Met Pro Gln Ala Glu Asn Gln Asp Pro Asp Ile Lys Ala His Val Asn
                 85                  90                  95

Ser Leu Gly Glu Asn Leu Lys Thr Leu Arg Leu Arg Leu Arg Arg Cys
                100                 105                 110

His Arg Phe Leu Pro Cys Glu Asn Gly Gly Ser Gly Gly Lys Ser
                115                 120                 125

Lys Ala Val Glu Gln Val Lys Asn Ala Phe Asn Lys Leu Gln Glu Lys
                130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Asn Trp Tyr Phe Asp Val
                165                 170                 175

<210> SEQ ID NO 180
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Gln Leu Ser Val Gly Tyr
 1               5

<210> SEQ ID NO 181
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Asp Thr Ser
 1

<210> SEQ ID NO 182
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Gly Ser Gly Tyr Pro Phe
 1               5

<210> SEQ ID NO 183
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 183

Thr Ser Gly Met Ser Val Gly
1               5

<210> SEQ ID NO 184
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Asp Ile Trp Trp Asp Asp Lys Lys Asp Tyr Asn Pro Ser Leu Lys Ser
1               5                   10                  15

<210> SEQ ID NO 185
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Ser Met Ile Thr Ser Pro Gly Gln Gly Thr Gln Ser Glu Asn Ser Cys
1               5                   10                  15

Thr His Phe Pro Gly Asn Leu Pro Asn Met Leu Arg Asp Leu Arg Asp
            20                  25                  30

Ala Phe Ser Arg Val Lys Thr Phe Phe Gln Met Lys Asp Gln Leu Asp
        35                  40                  45

Asn Leu Leu Leu Lys Glu Ser Leu Leu Glu Asp Phe Lys Gly Tyr Leu
    50                  55                  60

Gly Cys Gln Ala Leu Ser Glu Met Ile Gln Phe Tyr Leu Glu Glu Val
65                  70                  75                  80

Met Pro Gln Ala Glu Asn Gln Asp Pro Asp Ile Lys Ala His Val Asn
                85                  90                  95

Ser Leu Gly Glu Asn Leu Lys Thr Leu Arg Leu Arg Leu Arg Arg Cys
            100                 105                 110

His Arg Phe Leu Pro Cys Glu Asn Gly Gly Ser Gly Gly Lys Ser
        115                 120                 125

Lys Ala Val Glu Gln Val Lys Asn Ala Phe Asn Lys Leu Gln Glu Lys
    130                 135                 140

Gly Ile Tyr Lys Ala Met Ser Glu Phe Asp Ile Phe Ile Asn Tyr Ile
145                 150                 155                 160

Glu Ala Tyr Met Thr Met Lys Ile Arg Asn Asn Trp Tyr Phe Asp Val
                165                 170                 175

<210> SEQ ID NO 186
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Lys Ala Gln Leu Ser Val Gly Tyr Met His
1               5                   10

<210> SEQ ID NO 187
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Asp Thr Ser Lys Leu Ala Ser
1               5

<210> SEQ ID NO 188
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Phe Gln Gly Ser Gly Tyr Pro Phe Thr
1               5

<210> SEQ ID NO 189
<211> LENGTH: 286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Ser Pro Gly Gln Gly Thr Gln Ser Glu
            100                 105                 110

Asn Ser Cys Thr His Phe Pro Gly Asn Leu Pro Asn Met Leu Arg Asp
        115                 120                 125

Leu Arg Asp Ala Phe Ser Arg Val Lys Thr Phe Phe Gln Met Lys Asp
    130                 135                 140

Gln Leu Asp Asn Leu Leu Leu Lys Glu Ser Leu Leu Glu Asp Phe Lys
145                 150                 155                 160

Gly Tyr Leu Gly Cys Gln Ala Leu Ser Glu Met Ile Gln Phe Tyr Leu
                165                 170                 175

Glu Glu Val Met Pro Gln Ala Glu Asn Gln Asp Pro Asp Ile Lys Ala

```
              180                 185                 190
His Val Asn Ser Leu Gly Glu Asn Leu Lys Thr Leu Arg Leu Arg Leu
                195                 200                 205

Arg Arg Cys His Arg Phe Leu Pro Cys Glu Asn Gly Gly Ser Gly
    210                 215                 220

Gly Lys Ser Lys Ala Val Glu Gln Val Lys Asn Ala Phe Asn Lys Leu
225                 230                 235                 240

Gln Glu Lys Gly Ile Tyr Lys Ala Met Ser Glu Phe Asp Ile Phe Ile
                245                 250                 255

Asn Tyr Ile Glu Ala Tyr Met Thr Met Lys Ile Arg Asn Asn Trp Tyr
            260                 265                 270

Phe Asp Val Trp Gly Ala Gly Thr Thr Val Thr Val Ser Ser
            275                 280                 285

<210> SEQ ID NO 190
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 191
<211> LENGTH: 616
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Ala Asn Gln Val
65                  70                  75                  80
```

```
Val Leu Lys Val Thr Asn Met Asp Pro Ala Asp Thr Ala Thr Tyr Tyr
                85                  90                  95

Cys Ala Arg Ser Met Ile Thr Ser Pro Gly Gln Gly Thr Gln Ser Glu
            100                 105                 110

Asn Ser Cys Thr His Phe Pro Gly Asn Leu Pro Asn Met Leu Arg Asp
        115                 120                 125

Leu Arg Asp Ala Phe Ser Arg Val Lys Thr Phe Phe Gln Met Lys Asp
    130                 135                 140

Gln Leu Asp Asn Leu Leu Leu Lys Glu Ser Leu Leu Glu Asp Phe Lys
145                 150                 155                 160

Gly Tyr Leu Gly Cys Gln Ala Leu Ser Glu Met Ile Gln Phe Tyr Leu
                165                 170                 175

Glu Glu Val Met Pro Gln Ala Glu Asn Gln Asp Pro Asp Ile Lys Ala
            180                 185                 190

His Val Asn Ser Leu Gly Glu Asn Leu Lys Thr Leu Arg Leu Arg Leu
        195                 200                 205

Arg Arg Cys His Arg Phe Leu Pro Cys Glu Asn Gly Gly Gly Ser Gly
    210                 215                 220

Gly Lys Ser Lys Ala Val Glu Gln Val Lys Asn Ala Phe Asn Lys Leu
225                 230                 235                 240

Gln Glu Lys Gly Ile Tyr Lys Ala Met Ser Glu Phe Asp Ile Phe Ile
                245                 250                 255

Asn Tyr Ile Glu Ala Tyr Met Thr Met Lys Ile Arg Asn Asn Trp Tyr
            260                 265                 270

Phe Asp Val Trp Gly Ala Gly Thr Thr Val Thr Val Ser Ser Ala Ser
        275                 280                 285

Thr Lys Gly Pro Ser Val Phe Pro Leu Ala Pro Ser Ser Lys Ser Thr
    290                 295                 300

Ser Gly Gly Thr Ala Ala Leu Gly Cys Leu Val Lys Asp Tyr Phe Pro
305                 310                 315                 320

Glu Pro Val Thr Val Ser Trp Asn Ser Gly Ala Leu Thr Ser Gly Val
                325                 330                 335

His Thr Phe Pro Ala Val Leu Gln Ser Ser Gly Leu Tyr Ser Leu Ser
            340                 345                 350

Ser Val Val Thr Val Pro Ser Ser Ser Leu Gly Thr Gln Thr Tyr Ile
        355                 360                 365

Cys Asn Val Asn His Lys Pro Ser Asn Thr Lys Val Asp Lys Arg Val
    370                 375                 380

Glu Pro Lys Ser Cys Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
            420                 425                 430

Val Asp Val Ser His Glu Asp Pro Glu Val Lys Phe Asn Trp Tyr Val
        435                 440                 445

Asp Gly Val Glu Val His Asn Ala Lys Thr Lys Pro Arg Glu Glu Gln
    450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495
```

```
Leu Pro Ala Pro Ile Glu Lys Thr Ile Ser Lys Ala Lys Gly Gln Pro
                500                 505                 510

Arg Glu Pro Gln Val Tyr Thr Leu Pro Pro Ser Arg Glu Glu Met Thr
            515                 520                 525

Lys Asn Gln Val Ser Leu Thr Cys Leu Val Lys Gly Phe Tyr Pro Ser
        530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys
    610                 615

<210> SEQ ID NO 192
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Ala Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 193
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gly Phe Ser Leu Ser Thr Ser Gly Met
1               5

<210> SEQ ID NO 194
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Trp Trp Asp Asp Lys
1               5

<210> SEQ ID NO 195
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ser Met Ile Thr Asn Trp Tyr Phe Asp Val
1               5                   10

<210> SEQ ID NO 196
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Gln Leu Ser Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
                20                  25                  30

Phe Ser Arg Val Lys Thr Phe Phe Gln Met Lys Asp Gln Leu Asp Asn
            35                  40                  45

Leu Leu Leu Lys Glu Ser Leu Leu Glu Asp Phe Lys Gly Tyr Leu Gly
        50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Lys Ser Lys
            115                 120                 125
```

Ala Val Glu Gln Val Lys Asn Ala Phe Asn Lys Leu Gln Glu Lys Gly
            130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Val Gly Tyr
                165                 170

<210> SEQ ID NO 197
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Asp Thr Ser
1

<210> SEQ ID NO 198
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Gly Ser Gly Tyr Pro Phe
1               5

<210> SEQ ID NO 199
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Thr Ser Gly Met Ser Val Gly
1               5

<210> SEQ ID NO 200
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Asp Ile Trp Trp Asp Asp Lys Lys Asp Tyr Asn Pro Ser Leu Lys Ser
1               5                   10                  15

<210> SEQ ID NO 201
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ser Met Ile Thr Asn Trp Tyr Phe Asp Val
1               5                   10

<210> SEQ ID NO 202
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Lys Ala Gln Leu Ser Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
                20                  25                  30

Asp Ala Phe Ser Arg Val Lys Thr Phe Phe Gln Met Lys Asp Gln Leu
            35                  40                  45

Asp Asn Leu Leu Leu Lys Glu Ser Leu Leu Glu Asp Phe Lys Gly Tyr
        50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Ser Gly Gly Lys
        115                 120                 125

Ser Lys Ala Val Glu Gln Val Lys Asn Ala Phe Asn Lys Leu Gln Glu
        130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Val Gly Tyr Met His
                165                 170                 175

<210> SEQ ID NO 203
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Asp Thr Ser Lys Leu Ala Ser
1               5

<210> SEQ ID NO 204
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Phe Gln Gly Ser Gly Tyr Pro Phe Thr

<210> SEQ ID NO 205
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 205

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120
```

<210> SEQ ID NO 206
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 206

```
Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
    50                  55                  60

Phe Gln Met Lys Asp Gln Leu Asp Asn Leu Leu Leu Lys Glu Ser Leu
65                  70                  75                  80

Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
            100                 105                 110

Pro Asp Ile Lys Ala His Val Asn Ser Leu Gly Glu Asn Leu Lys Thr
        115                 120                 125

Leu Arg Leu Arg Leu Arg Arg Cys His Arg Phe Leu Pro Cys Glu Asn
    130                 135                 140

Gly Gly Gly Ser Gly Gly Lys Ser Lys Ala Val Glu Gln Val Lys Asn
145                 150                 155                 160
```

```
Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
            180                 185                 190

Arg Asn Val Gly Tyr Met His Trp Tyr Gln Gln Lys Pro Gly Lys Ala
        195                 200                 205

Pro Lys Leu Leu Ile Tyr Asp Thr Ser Lys Leu Ala Ser Gly Val Pro
    210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
            260                 265                 270

<210> SEQ ID NO 207
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Ala Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 208
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
50                  55                  60

Phe Gln Met Lys Asp Gln Leu Asp Asn Leu Leu Leu Lys Glu Ser Leu
65                  70                  75                  80

Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
            100                 105                 110

Pro Asp Ile Lys Ala His Val Asn Ser Leu Gly Glu Asn Leu Lys Thr
        115                 120                 125

Leu Arg Leu Arg Leu Arg Arg Cys His Arg Phe Leu Pro Cys Glu Asn
```

```
                  130                 135                 140
Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
            180                 185                 190

Arg Asn Val Gly Tyr Met His Trp Tyr Gln Gln Lys Pro Gly Lys Ala
        195                 200                 205

Pro Lys Leu Leu Ile Tyr Asp Thr Ser Lys Leu Ala Ser Gly Val Pro
    210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
            260                 265                 270

Arg Thr Val Ala Ala Pro Ser Val Phe Ile Phe Pro Pro Ser Asp Glu
        275                 280                 285

Gln Leu Lys Ser Gly Thr Ala Ser Val Val Cys Leu Leu Asn Asn Phe
    290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
            340                 345                 350

Lys His Lys Val Tyr Ala Cys Glu Val Thr His Gln Gly Leu Ser Ser
        355                 360                 365

Pro Val Thr Lys Ser Phe Asn Arg Gly Glu Cys
    370                 375

<210> SEQ ID NO 209
<211> LENGTH: 166
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110
```

```
Pro Cys Glu Asn Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
    130                 135                 140

Ala Met Ser Glu Phe Asp Ile Phe Ile Asn Tyr Ile Glu Ala Tyr Met
145                 150                 155                 160

Thr Met Lys Ile Arg Asn
                165

<210> SEQ ID NO 210
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Phe Ser Leu Ser Thr Ser Gly Met
1               5

<210> SEQ ID NO 211
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Trp Trp Asp Asp Lys
1               5

<210> SEQ ID NO 212
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 212

Ser Met Ile Thr Asn Trp Tyr Phe Asp Val
1               5                   10

<210> SEQ ID NO 213
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Gln Leu Ser Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
                20                  25                  30

Phe Ser Arg Val Lys Thr Phe Phe Gln Met Lys Asp Gln Leu Asp Asn
            35                  40                  45
```

Leu Leu Leu Lys Glu Ser Leu Leu Glu Asp Phe Lys Gly Tyr Leu Gly
     50                  55                  60

Cys Gln Ala Leu Ser Glu Met Ile Gln Phe Tyr Leu Glu Glu Val Met
 65                  70                  75                  80

Pro Gln Ala Glu Asn Gln Asp Pro Asp Ile Lys Ala His Val Asn Ser
                 85                  90                  95

Leu Gly Glu Asn Leu Lys Thr Leu Arg Leu Arg Leu Arg Arg Cys His
            100                 105                 110

Arg Phe Leu Pro Cys Glu Asn Gly Gly Ser Gly Gly Lys Ser Lys
        115                 120                 125

Ala Val Glu Gln Val Lys Asn Ala Phe Asn Lys Leu Gln Glu Lys Gly
        130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Val Gly Tyr
                165                 170

<210> SEQ ID NO 214
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Asp Thr Ser
1

<210> SEQ ID NO 215
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Gly Ser Gly Tyr Pro Phe
1               5

<210> SEQ ID NO 216
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Thr Ser Gly Met Ser Val Gly
1               5

<210> SEQ ID NO 217
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Asp Ile Trp Trp Asp Asp Lys Lys Asp Tyr Asn Pro Ser Leu Lys Ser
1               5                   10                  15

<210> SEQ ID NO 218
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Ser Met Ile Thr Asn Trp Tyr Phe Asp Val
1               5                   10

<210> SEQ ID NO 219
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Lys Ala Gln Leu Ser Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
            20                  25                  30

Asp Ala Phe Ser Arg Val Lys Thr Phe Phe Gln Met Lys Asp Gln Leu
        35                  40                  45

Asp Asn Leu Leu Leu Lys Glu Ser Leu Leu Glu Asp Phe Lys Gly Tyr
    50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
            100                 105                 110

Cys His Arg Phe Leu Pro Cys Glu Asn Gly Gly Gly Ser Gly Gly Lys
        115                 120                 125

Ser Lys Ala Val Glu Gln Val Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Val Gly Tyr Met His
                165                 170                 175

<210> SEQ ID NO 220
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Asp Thr Ser Lys Leu Ala Ser
1               5

<210> SEQ ID NO 221
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Phe Gln Gly Ser Gly Tyr Pro Phe Thr
1               5

<210> SEQ ID NO 222
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 223
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
50                  55                  60

Phe Gln Met Lys Asp Gln Leu Asp Asn Leu Leu Leu Lys Glu Ser Leu
65                  70                  75                  80

```
Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
            100                 105                 110

Pro Asp Ile Lys Ala His Val Asn Ser Leu Gly Glu Asn Leu Lys Thr
        115                 120                 125

Leu Arg Leu Arg Leu Arg Arg Cys His Arg Phe Leu Pro Cys Glu Asn
    130                 135                 140

Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
            180                 185                 190

Arg Asn Val Gly Tyr Met His Trp Tyr Gln Gln Lys Pro Gly Lys Ala
        195                 200                 205

Pro Lys Leu Leu Ile Tyr Asp Thr Ser Lys Leu Ala Ser Gly Val Pro
    210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
            260                 265                 270

<210> SEQ ID NO 224
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 225
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 225

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
    50                  55                  60

```
Phe Gln Met Lys Asp Gln Leu Asp Asn Leu Leu Lys Glu Ser Leu
 65                  70                  75                  80

Leu Glu Asp Phe Lys Gly Tyr Leu Gly Cys Gln Ala Leu Ser Glu Met
                 85                  90                  95

Ile Gln Phe Tyr Leu Glu Glu Val Met Pro Gln Ala Glu Asn Gln Asp
            100                 105                 110

Pro Asp Ile Lys Ala His Val Asn Ser Leu Gly Glu Asn Leu Lys Thr
            115                 120                 125

Leu Arg Leu Arg Leu Arg Arg Cys His Arg Phe Leu Pro Cys Glu Asn
130                 135                 140

Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
            180                 185                 190

Arg Asn Val Gly Tyr Met His Trp Tyr Gln Gln Lys Pro Gly Lys Ala
            195                 200                 205

Pro Lys Leu Leu Ile Tyr Asp Thr Ser Lys Leu Ala Ser Gly Val Pro
210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
                245                 250                 255

Ser Gly Tyr Pro Phe Thr Phe Gly Gly Gly Thr Lys Leu Glu Ile Lys
            260                 265                 270

Arg Thr Val Ala Ala Pro Ser Val Phe Ile Phe Pro Pro Ser Asp Glu
            275                 280                 285

Gln Leu Lys Ser Gly Thr Ala Ser Val Val Cys Leu Leu Asn Asn Phe
290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
                325                 330                 335

Thr Tyr Ser Leu Ser Ser Thr Leu Thr Leu Ser Lys Ala Asp Tyr Glu
            340                 345                 350

Lys His Lys Val Tyr Ala Cys Glu Val Thr His Gln Gly Leu Ser Ser
            355                 360                 365

Pro Val Thr Lys Ser Phe Asn Arg Gly Glu Cys
370                 375

<210> SEQ ID NO 226
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Gly Phe Ser Leu Ser Thr Ser Gly Met
1               5

<210> SEQ ID NO 227
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Trp Trp Asp Asp Lys
1               5

<210> SEQ ID NO 228
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ser Met Ile Thr Asn Trp Tyr Phe Asp Val
1               5                   10

<210> SEQ ID NO 229
<211> LENGTH: 172
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 229

Gln Leu Ser Ser Pro Gly Gln Gly Thr Gln Ser Glu Asn Ser Cys Thr
1               5                   10                  15

His Phe Pro Gly Asn Leu Pro Asn Met Leu Arg Asp Leu Arg Asp Ala
                20                  25                  30

Phe Ser Arg Val Lys Thr Phe Phe Gln Met Lys Asp Gln Leu Asp Asn
            35                  40                  45

Leu Leu Leu Lys Glu Ser Leu Leu Glu Asp Phe Lys Gly Tyr Leu Gly
        50                  55                  60

Cys Gln Ala Leu Ser Glu Met Ile Gln Phe Tyr Leu Glu Glu Val Met
65                  70                  75                  80

Pro Gln Ala Glu Asn Gln Asp Pro Asp Ile Lys Ala His Val Asn Ser
                85                  90                  95

Leu Gly Glu Asn Leu Lys Thr Leu Arg Leu Arg Leu Arg Arg Cys His
                100                 105                 110

Arg Phe Leu Pro Cys Glu Asn Gly Gly Gly Ser Gly Gly Lys Ser Lys
            115                 120                 125

Ala Val Glu Gln Val Lys Asn Ala Phe Asn Lys Leu Gln Glu Lys Gly
        130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn Val Gly Tyr
                165                 170

<210> SEQ ID NO 230
<211> LENGTH: 3
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 230

Asp Thr Ser
1

<210> SEQ ID NO 231
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gly Ser Gly Tyr Pro Phe
1               5

<210> SEQ ID NO 232
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Thr Ser Gly Met Ser Val Gly
1               5

<210> SEQ ID NO 233
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Asp Ile Trp Trp Asp Asp Lys Lys Asp Tyr Asn Pro Ser Leu Lys Ser
1               5                   10                  15

<210> SEQ ID NO 234
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Ser Met Ile Thr Asn Trp Tyr Phe Asp Val
1               5                   10

<210> SEQ ID NO 235
<211> LENGTH: 176
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235
```

Lys Ala Gln Leu Ser Ser Pro Gly Gln Gly Thr Gln Ser Glu Asn Ser
1               5                   10                  15

Cys Thr His Phe Pro Gly Asn Leu Pro Asn Met Leu Arg Asp Leu Arg
                20                  25                  30

Asp Ala Phe Ser Arg Val Lys Thr Phe Phe Gln Met Lys Asp Gln Leu
                35                  40                  45

Asp Asn Leu Leu Leu Lys Glu Ser Leu Leu Glu Asp Phe Lys Gly Tyr
            50                  55                  60

Leu Gly Cys Gln Ala Leu Ser Glu Met Ile Gln Phe Tyr Leu Glu Glu
65                  70                  75                  80

Val Met Pro Gln Ala Glu Asn Gln Asp Pro Asp Ile Lys Ala His Val
                85                  90                  95

Asn Ser Leu Gly Glu Asn Leu Lys Thr Leu Arg Leu Arg Leu Arg Arg
                100                 105                 110

Cys His Arg Phe Leu Pro Cys Glu Asn Gly Gly Ser Gly Gly Lys
                115                 120                 125

Ser Lys Ala Val Glu Gln Val Lys Asn Ala Phe Asn Lys Leu Gln Glu
        130                 135                 140

Lys Gly Ile Tyr Lys Ala Met Ser Glu Phe Asp Ile Phe Ile Asn Tyr
145                 150                 155                 160

Ile Glu Ala Tyr Met Thr Met Lys Ile Arg Asn Val Gly Tyr Met His
                165                 170                 175

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Asp Thr Ser Lys Leu Ala Ser
1               5

<210> SEQ ID NO 237
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Phe Gln Gly Ser Gly Tyr Pro Phe Thr
1               5

<210> SEQ ID NO 238
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 238

Gln Val Thr Leu Arg Glu Ser Gly Pro Ala Leu Val Lys Pro Thr Gln
1               5                   10                  15

```
Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
        50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser
                115                 120

<210> SEQ ID NO 239
<211> LENGTH: 272
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 239

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
                20                  25                  30

Gly Thr Gln Ser Glu Asn Ser Cys Thr His Phe Pro Gly Asn Leu Pro
            35                  40                  45

Asn Met Leu Arg Asp Leu Arg Asp Ala Phe Ser Arg Val Lys Thr Phe
        50                  55                  60

Phe Gln Met Lys Asp Gln Leu Asp Asn Leu Leu Leu Lys Glu Ser Leu
65                  70                  75                  80

Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
                100                 105                 110

Pro Asp Ile Lys Ala His Val Asn Ser Leu Gly Glu Asn Leu Lys Thr
                115                 120                 125

Leu Arg Leu Arg Leu Arg Arg Cys His Arg Phe Leu Pro Cys Glu Asn
            130                 135                 140

Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
                180                 185                 190

Arg Asn Val Gly Tyr Met His Trp Tyr Gln Gln Lys Pro Gly Lys Ala
            195                 200                 205

Pro Lys Leu Leu Ile Tyr Asp Thr Ser Lys Leu Ala Ser Gly Val Pro
        210                 215                 220

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
```

```
                        245                 250                 255

Ser Gly Tyr Pro Phe Thr Phe Gly Gly Gly Thr Lys Leu Glu Ile Lys
            260                 265                 270

<210> SEQ ID NO 240
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 240

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Ala Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Val Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Ile His
            420                 425                 430

Glu Ala Leu His Asn His Tyr Thr Gln Lys Ser Leu Ser Leu Ser Pro
            435                 440                 445

Gly Lys
    450

<210> SEQ ID NO 241
<211> LENGTH: 379
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Ser Pro Gly Gln
            20                  25                  30

Gly Thr Gln Ser Glu Asn Ser Cys Thr His Phe Pro Gly Asn Leu Pro
        35                  40                  45

Asn Met Leu Arg Asp Leu Arg Asp Ala Phe Ser Arg Val Lys Thr Phe
    50                  55                  60

Phe Gln Met Lys Asp Gln Leu Asp Asn Leu Leu Leu Lys Glu Ser Leu
65                  70                  75                  80

Leu Glu Asp Phe Lys Gly Tyr Leu Gly Cys Gln Ala Leu Ser Glu Met
                85                  90                  95

Ile Gln Phe Tyr Leu Glu Glu Val Met Pro Gln Ala Glu Asn Gln Asp
            100                 105                 110

Pro Asp Ile Lys Ala His Val Asn Ser Leu Gly Glu Asn Leu Lys Thr
        115                 120                 125

Leu Arg Leu Arg Leu Arg Arg Cys His Arg Phe Leu Pro Cys Glu Asn
    130                 135                 140

Gly Gly Gly Ser Gly Gly Lys Ser Lys Ala Val Glu Gln Val Lys Asn
145                 150                 155                 160

Ala Phe Asn Lys Leu Gln Glu Lys Gly Ile Tyr Lys Ala Met Ser Glu
                165                 170                 175

Phe Asp Ile Phe Ile Asn Tyr Ile Glu Ala Tyr Met Thr Met Lys Ile
            180                 185                 190

Arg Asn Val Gly Tyr Met His Trp Tyr Gln Gln Lys Pro Gly Lys Ala
        195                 200                 205

Pro Lys Leu Leu Ile Tyr Asp Thr Ser Lys Leu Ala Ser Gly Val Pro
    210                 215                 220
```

Ser Arg Phe Ser Gly Ser Gly Ser Gly Thr Ala Phe Thr Leu Thr Ile
225                 230                 235                 240

Ser Ser Leu Gln Pro Asp Asp Phe Ala Thr Tyr Tyr Cys Phe Gln Gly
            245                 250                 255

Ser Gly Tyr Pro Phe Thr Phe Gly Gly Gly Thr Lys Leu Glu Ile Lys
                260                 265                 270

Arg Thr Val Ala Ala Pro Ser Val Phe Ile Phe Pro Pro Ser Asp Glu
        275                 280                 285

Gln Leu Lys Ser Gly Thr Ala Ser Val Val Cys Leu Leu Asn Asn Phe
    290                 295                 300

Tyr Pro Arg Glu Ala Lys Val Gln Trp Lys Val Asp Asn Ala Leu Gln
305                 310                 315                 320

Ser Gly Asn Ser Gln Glu Ser Val Thr Glu Gln Asp Ser Lys Asp Ser
            325                 330                 335

Thr Tyr Ser Leu Ser Ser Thr Leu Thr Leu Ser Lys Ala Asp Tyr Glu
                340                 345                 350

Lys His Lys Val Tyr Ala Cys Glu Val Thr His Gln Gly Leu Ser Ser
        355                 360                 365

Pro Val Thr Lys Ser Phe Asn Arg Gly Glu Cys
    370                 375

<210> SEQ ID NO 242
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
caggtcacac tgagagagtc aggccctgcc ctggtcaagc ctactcagac cctgaccctg      60
acctgcacct ttagcggctt tagcctgagc actagcggaa tgagcgtggg ctggattaga     120 cagcccctg gtaaagccct ggagtggctg gccgatattt ggtgggacga taagaaggac     180 tataaccta gcctgaagtc taggctgact atctctaagg acactagcgc taatcaggtg     240
gtgctgaaag tgactaatat ggaccccgcc gacaccgcta cctactactg cgctagatct     300
atgatcacta actggtactt cgacgtgtgg ggcgctggca ctaccgtgac cgtgtctagc     360

<210> SEQ ID NO 243
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
gatattcaga tgactcagtc acctagcacc ctgagcgcta gtgtgggcga tagagtgact      60
atcacctgta aagctcagct gtctagccca ggtcagggaa ctcagtcaga gaatagctgc     120
actcacttcc ccggtaacct gcctaatatg ctgagagatc tgaggacgc cttctctagg     180 gtcaagacct tctttcagat gaaggatcag ctggataacc tgctgctgaa agagtcactg     240
ctggaggact taagggcta cctgggctgt caggccctga gcgagatgat tcagttctac     300
ctggaagaag tgatgcccca ggccgagaat caggaccccg atattaaggc tcacgtgaac     360
tcactgggcg agaacctgaa aaccctgaga ctgaggctga ggcggtgtca ccggtttctg     420

```
ccctgcgaga acggcggagg tagcggcggt aaatctaagg ccgtggaaca ggtcaaaaac    480
gcctttaaca agctgcagga aaagggaatc tataaggcta tgagcgagtt cgacatcttt    540
attaactata tcgaggccta tatgactatg aagattagga acgtgggcta tatgcactgg    600
tatcagcaga agcccggtaa agcccctaag ctgctgatct acgacacctc taagctggct    660
agtggcgtgc cctctaggtt tagcggtagc ggtagtggca ccgccttcac cctgactatc    720
tctagcctgc agcccgacga cttcgctacc tactactgtt ttcagggtag cggctacccc    780
ttcaccttcg gcggaggcac taagctggag attaag                             816
```

<210> SEQ ID NO 244
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 244

```
caggtcacac tgagagagtc aggccctgcc ctggtcaagc ctactcagac cctgaccctg     60
acctgcacct ttagcggctt tagcctgagc actagcggaa tgagcgtggg ctggattaga    120 cagcccctg gtaaagccct ggagtggctg gccgatattt ggtgggacga taagaaggac    180 tatacccta gcctgaagtc taggctgact atctctaagg acactagcgc taatcaggtg    240
gtgctgaaag tgactaatat ggaccccgcc gacaccgcta cctactactg cgctagatct    300
atgatcacta actggtactt cgacgtgtgg ggcgctggca ctaccgtgac cgtgtctagc    360
gctagcacta agggcccaag tgtgtttccc ctggccccca gcagcaagtc tacttccggc    420
ggaactgctg ccctgggttg cctggtgaag gactacttcc ccgagcccgt gacagtgtcc    480
tggaactctg gggctctgac ttccggcgtg cacaccttcc ccgccgtgct gcagagcagc    540
ggcctgtaca gcctgagcag cgtggtgaca gtgccctcca gctctctggg aacccagacc    600
tatatctgca acgtgaacca caagcccagc aacaccaagg tggacaagag agtggagccc    660
aagagctgcg acaagaccca cacctgcccc cctgcccag ctccagaact gctgggaggg    720
ccttccgtgt tcctgttccc ccccaagccc aaggacaccc tgatgatcag caggaccccc    780
gaggtgacct gcgtggtggt ggacgtgtcc acgaggacc cagaggtgaa gttcaactgg    840
tacgtggacg gcgtggaggt gcacaacgcc aagaccaagc ccagagagga gcagtacaac    900
agcacctaca gggtggtgtc cgtgctgacc gtgctgcacc aggactggct gaacggcaaa    960
gaatacaagt gcaaagtctc caacaaggcc ctgccagccc caatcgaaaa gacaatcagc   1020
aaggccaagg gccagccacg ggagcccag gtgtacaccc tgccccccag ccgggaggag   1080
atgaccaaga accaggtgtc cctgacctgt ctggtgaagg gcttctaccc cagcgatatc   1140
gccgtggagt gggagagcaa cggccagccc gagaacaact acaagaccac ccccccagtg   1200
ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagtccc tgagcctgag ccccggcaag                                   1350
```

<210> SEQ ID NO 245
<211> LENGTH: 1137
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 245

| gatattcaga tgactcagtc acctagcacc ctgagcgcta gtgtgggcga tagagtgact | 60 |
| atcacctgta aagctcagct gtctagccca ggtcagggaa ctcagtcaga gaatagctgc | 120 |
| actcacttcc ccggtaacct gcctaatatg ctgagagatc tgagggacgc cttctctagg | 180 |
| gtcaagacct tctttcagat gaaggatcag ctggataacc tgctgctgaa agagtcactg | 240 |
| ctggaggact ttaagggcta cctgggctgt caggccctga gcgagatgat tcagttctac | 300 |
| ctggaagaag tgatgcccca ggccgagaat caggaccccg atattaaggc tcacgtgaac | 360 |
| tcactgggcg agaacctgaa aaccctgaga ctgaggctga ggcggtgtca ccggtttctg | 420 |
| ccctgcgaga acggcggagg tagcggcggt aaatctaagg ccgtggaaca ggtcaaaaac | 480 |
| gcctttaaca agctgcagga aaagggaatc tataaggcta tgagcgagtt cgacatcttt | 540 |
| attaactata tcgaggccta tatgactatg aagattagga acgtgggcta tatgcactgg | 600 |
| tatcagcaga agcccggtaa agcccctaag ctgctgatct acgacacctc taagctggct | 660 |
| agtggcgtgc cctctaggtt tagcggtagc ggtagtggca ccgccttcac cctgactatc | 720 |
| tctagcctgc agcccgacga cttcgctacc tactactgtt ttcagggtag cggctacccc | 780 |
| ttcaccttcg gcggaggcac taagctggag attaagcgta cggtggccgc tcccagcgtg | 840 |
| ttcatcttcc cccccagcga cgagcagctg aagagcggca ccgccagcgt ggtgtgcctg | 900 |
| ctgaacaact ctaccccccg ggaggccaag gtgcagtgga aggtggacaa cgccctgcag | 960 |
| agcggcaaca gccaggagag cgtcaccgag caggacagca aggactccac ctacagcctg | 1020 |
| agcagcaccc tgaccctgag caaggccgac tacgagaagc ataaggtgta cgcctgcgag | 1080 |
| gtgacccacc agggcctgtc cagccccgtg accaagagct caacaggggg cgagtgc | 1137 |

<210> SEQ ID NO 246
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 246

| caggtcacac tgagagagtc aggccctgcc ctggtcaagc ctactcagac cctgaccctg | 60 |
| acctgcacct ttagcggctt tagcctgagc actagcggaa tgagcgtggg ctggattaga | 120 |
| cagcccctg gtaaagccct ggagtggctg gccgatattt ggtgggacga taagaaggac | 180 |
| tataacccta gcctgaagtc taggctgact atctctaagg acactagcgc taatcaggtg | 240 |
| gtgctgaaag tgactaatat ggaccccgcc gacaccgcta cctactactg cgctagatct | 300 |
| atgatcacta actggtactt cgacgtgtgg ggcgctggca ctaccgtgac cgtgtctagc | 360 |

<210> SEQ ID NO 247
<211> LENGTH: 816
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 247

```
gatattcaga tgactcagtc acctagcacc ctgagcgcta gtgtgggcga tagagtgact      60
atcacctgta aagctcagct gtctagccca ggtcagggaa ctcagtcaga gaatagctgc     120
actcacttcc ccggtaacct gcctaatatg ctgagagatc tgagggacgc cttctctagg     180
gtcaagacct tctttcagat gaaggatcag ctggataacc tgctgctgaa agagtcactg     240
ctggaggact ttaagggcta cctgggctgt caggccctga gcgagatgat tcagttctac     300
ctggaagaag tgatgcccca ggccgagaat caggaccccg atattaaggc tcacgtgaac     360
tcactgggcg agaacctgaa aaccctgaga ctgaggctga ggcggtgtca ccggtttctg     420
ccctgcgaga acggcggagg tagccggcgg aaatctaagg ccgtggaaca ggtcaaaaac     480
gcctttaaca agctgcagga aaagggaatc tataaggcta tgagcgagtt cgacatcttt     540
attaactata tcgaggccta tatgactatg aagattagga acgtgggcta tatgcactgg     600
tatcagcaga agcccggtaa agcccctaag ctgctgatct acgacacctc taagctggct     660
agtggcgtgc cctctaggtt tagcggtagc ggtagtggca ccgccttcac cctgactatc     720
tctagcctgc agcccgacga cttcgctacc tactactgtt ttcagggtag cggctacccc     780
ttcaccttcg gcggaggcac taagctggag attaag                               816
```

<210> SEQ ID NO 248
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248

```
caggtcacac tgagagagtc aggccctgcc ctggtcaagc ctactcagac cctgaccctg      60
acctgcacct ttagcggctt tagcctgagc actagcggaa tgagcgtggg ctggattaga     120 cagcccctg gtaaagccct ggagtggctg gccgatattt ggtgggacga taagaaggac     180
tataacccta gcctgaagtc taggctgact atctctaagg acactagcgc taatcaggtg     240
gtgctgaaag tgactaatat ggaccccgcc gacaccgcta cctactactg cgctagatct     300
atgatcacta actggtactt cgacgtgtgg ggcgctggca ctaccgtgac cgtgtctagc     360
gctagcacta agggccccct cgtgttccct ctggccccct tccagcaagtc tacctccggc     420 ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc     540
ggcctgtact ccctgtcctc cgtggtcaca gtgccttcaa gcagcctggg cacccagacc     600
tatatctgca acgtgaacca caagccttcc aacaccaagg tggacaagcg ggtggagcct     660
aagtcctgcg acaagaccca cacctgtcct ccctgccctg ctcctgaact gctgggcggc     720
ccttctgtgt tcctgttccc tccaaagccc aaggacaccc tgatgatctc ccggacccct     780
gaagtgacct gcgtggtggt ggccgtgtcc cacgaggatc ctgaagtgaa gttcaattgg     840
tacgtggacg gcgtggaggt gcacaacgcc aagaccaagc ctcgggagga acagtacaac     900
tccacctacc gggtggtgtc cgtgctgacc gtgctgcacc aggactggct gaacggcaaa     960
gagtacaagt gcaaagtctc caacaaggcc ctggccgccc ctatcgaaaa gacaatctcc    1020
aaggccaagg gccagcctag ggaacccag gtgtacaccc tgccacccag ccgggaggaa     1080
atgaccaaga accaggtgtc cctgacctgt ctggtcaagg gcttctaccc ttccgatatc    1140
```

```
gccgtggagt gggagtctaa cggccagcct gagaacaact acaagaccac ccctcctgtg      1200
ctggactccg acggctcctt cttcctgtac tccaaactga ccgtggacaa gtcccggtgg      1260
cagcagggca acgtgttctc ctgctccgtg atgcacgagg ccctgcacaa ccactacacc      1320
cagaagtccc tgtccctgtc tcccggcaag                                       1350
```

<210> SEQ ID NO 249
<211> LENGTH: 1137
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 249

```
gatattcaga tgactcagtc acctagcacc ctgagcgcta gtgtgggcga tagagtgact        60
atcacctgta aagctcagct gtctagccca ggtcagggaa ctcagtcaga aatagctgc       120 actcacttcc ccgtaaccct gcctaatatg ctgagagatc tgaggacgc cttctctagg       180 gtcaagacct tctttcagat gaaggatcag ctggataacc tgctgctgaa agagtcactg      240
ctggaggact ttaagggcta cctgggctgt caggccctga gcgagatgat tcagttctac      300
ctggaagaag tgatgcccca ggccgagaat caggaccccg atattaaggc tcacgtgaac      360
tcactgggcg agaacctgaa aaccctgaga ctgaggctga ggcggtgtca ccggtttctg      420
ccctgcgaga acggcggagg tagcggcggt aaatctaagg ccgtgaaca ggtcaaaaac       480 gcctttaaca agctgcagga aaagggaatc tataaggcta tgagcgagtt cgacatcttt     540
attaactata tcgaggccta tatgactatg aagattagga acgtgggcta tatgcactgg     600
tatcagcaga agcccggtaa agcccctaag ctgctgatct acgacacctc taagctggct    660
agtggcgtgc cctctaggtt tagcggtagc ggtagtggca ccgccttcac cctgactatc    720
tctagcctgc agcccgacga cttcgctacc tactactgtt ttcagggtag cggctacccc    780
ttcaccttcg gcggaggcac taagctggag attaagcgta cggtggccgc tcccagcgtg    840
ttcatcttcc cccccagcga cgagcagctg aagagcggca ccgccagcgt ggtgtgcctg    900
ctgaacaact tctacccccg ggaggccaag gtgcagtgga aggtggacaa cgccctgcag    960
agcggcaaca gccaggagag cgtcaccgag caggacagca aggactccac ctacagcctg   1020
agcagcaccc tgaccctgag caaggccgac tacgagaagc ataaggtgta cgcctgcgag    1080
gtgacccacc agggcctgtc cagccccgtg accaagagct caacagggg cgagtgc         1137
```

<210> SEQ ID NO 250
<211> LENGTH: 498
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 250

```
agtcccggtc agggaactca gtcagagaat agctgcactc acttcccgg taacctgcct        60 aatatgctga gagatctgag ggacgccttc tctagggtca gaccttctt tcagatgaag      120 gatcagctgg ataacctgct gctgaaagag tcactgctgg aggactttaa gggctacctg     180
ggctgtcagg ccctgagcga gatgattcag ttctacctgg aagaagtgat gccccaggcc    240
gagaatcagg accccgatat taaggctcac gtgaactcac tgggcgagaa cctgaaaacc    300
```

```
ctgagactga ggctgaggcg gtgtcaccgg tttctgccct gcgagaacgg cggaggtagc    360
ggcggtaaat ctaaggccgt ggaacaggtc aaaaacgcct ttaacaagct gcaggaaaag    420
ggaatctata aggctatgag cgagttcgac atctttatta actatatcga ggcctatatg    480
actatgaaga ttaggaac                                                  498

<210> SEQ ID NO 251
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gly Gly Gly Ser Gly Gly
1               5

<210> SEQ ID NO 252
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Gly Gly Gly Gly Ser
1               5

<210> SEQ ID NO 253
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Gly Gly Gly Gly Ala
1               5
```

METHODS OF TREATING IMMUNE RELATED DISORDERS USING ANTIBODY-CYTOKINE ENGRAFTED COMPOSITIONS

RELATED APPLICATIONS

This application is a divisional of U.S. patent application Ser. No. 15/367,003, filed on Dec. 1, 2016, now U.S. Pat. No. 10,144,768, which claims priority to U.S. Provisional Application No. 62/263,008, filed on Dec. 5, 2015, the contents of which are incorporated herein by reference in their entireties.

FIELD

The present disclosure relates to antibody-cytokine engrafted compositions that bind to interleukin-ten receptor (IL10R), and stimulate signaling through this receptor.

BACKGROUND

Interleukin 10 (IL10) was identified as a cytokine synthesis inhibition factor, exerting effects on Th1 helper cells and antigen presenting cells (APC's). IL10, a 161 amino acid protein that exists as a domain-swapped non-covalent homodimer, binds to the high affinity IL-10 receptor I (IL-10RI) with a stoichiometry of one homodimer to four IL-10RI subunits that recruits IL-10R2 and activates signal transduction through JAKI/TYK2 pathway. IL10 inhibits monocyte and macrophage synthesis of pro-inflammatory cytokines, e.g., IL-1, IL-6, IL-8, IL-12, TNF-alpha, GM-CSF, and reactive oxygen and nitrogen intermediates, and has shown strong efficacy in numerous preclinical models of autoimmunity. IL10 efficacy is thought to result from its ability to inhibit activation and effector function of monocytes, macrophages, and T cells. However, IL10 is a pleiotropic immunoregulatory cytokine with a very broad spectrum of biological activities. IL10 has also been shown to promote growth and differentiation of B cells, NK cells, cytotoxic and helper T cells, mast cells, granulocytes, dendritic cells, keratinocytes, and even endothelial cells, indicating it also possesses pro-inflammatory functions (Moore et al., Annu Rev Immunol. 2001; 19:683-765).

IL10 as a therapeutic for the treatment of autoimmune and inflammatory conditions, specifically inflammatory bowel disease (IBD), is supported in animal model systems as well as genetics. For example, knockout of IL10 in mice and mice with a defect in the IL-10R develop a spontaneous onset of colitis. In humans, 9-16% of Crohn's Disease patients have a NOD2 mutation that is associated with defective or reduced IL10 production, and 20% of ulcerative colitis (UC) patients carry a disease-associated IL10 SNP in the 3'UTR. Lastly, certain mutations in IL-10R1 in humans cause a rare, severe form of Crohn's Disease (Glocker at al., N Engl J Med. 2009; 361(21):2033-45).

Despite the strong genetic linkage data, recombinant human IL10 demonstrated tolerability and safety in healthy volunteers and specific patient populations up to 25 µg/kg, and mild effects in a subset of recipients up to 100 µg/kg; however only mild clinical efficacy was found for the specific patient populations and clinical development was discontinued for lack of efficacy. Reviews of the studies have been undertaken and several possibilities for the results have been identified, for example, limited efficacy is due to poor exposure of the target organ (colon) due to short half-life of IL10; the pro-inflammatory effects of IL10 that manifested at high doses and counterbalanced the anti-inflammatory efficacy of low dose IL10. (Lindsay and Hodgson, Aliment Pharmacol Ther. 2001; 15(11) 1709-1716) Consistent with this possibility, high doses of IL10 were associated with elevated systemic IFNγ, granzyme and neopterin levels, which are associated with increased inflammation (Tilg et al., Gut 2002; 50(2)191-5).

Antibody cytokine engrafted proteins have been developed to generate a more effective IL10 therapeutic that confers an improved profile that address the clinical failings of recombinant human IL10. This improved therapeutic profile includes strong anti-inflammatory IL10 potency with a marked reduction in pro-inflammatory activity, extended half-life, ease of administration and stability. Thus, the disclosure provides improved IL10 antibody cytokine engrafted proteins and methods of treating immune related disorders.

SUMMARY

The disclosure provides for antibody-cytokine engrafted proteins having preferred therapeutic profiles over recombinant IL10 and IL10 constructs known and used in the clinic. In particular, provided are antibody cytokine engrafted proteins that maintain the desired anti-inflammatory activity of native or recombinant human IL10; however, a marked reduction in pro-inflammatory activity is retained. Additionally, the antibody cytokine engrafted proteins convey improved half-life, stability and ease of administration over recombinant human IL10 protein (rhIL10). The preferred properties of these compositions result in preferable therapeutic compositions over those previously used in the clinic or described in the literature. The present disclosure thus provides antibody cytokine engrafted proteins that bind to and promote signalling through IL10 receptors and stimulate certain cell types. Provided are antibody cytokine engrafted proteins comprising: (i) an immunoglobulin heavy chain sequence comprising a heavy chain variable region (VH) and a heavy chain constant region comprising CH1, CH2 and CH3 regions, and (ii) an immunoglobulin light chain sequence comprising a light chain variable region (VL), and a light chain constant region (CL); wherein a monomeric IL10 molecule is engrafted into a complementarity determining region (CDR) of the VH or the VL.

In some embodiments, the antibody cytokine engrafted protein includes a variable heavy chain comprising SEQ ID NO: 13 and a variable light chain comprising SEQ ID NO: 14. In some embodiments, the antibody cytokine engrafted protein includes a variable heavy chain comprising SEQ ID NO: 29 and a variable light chain comprising SEQ ID NO: 30. In some embodiments, the antibody cytokine engrafted protein includes a variable heavy chain comprising SEQ ID NO: 45 and a variable light chain comprising SEQ ID NO: 46. In some embodiments, the antibody cytokine engrafted protein includes a variable heavy chain comprising SEQ ID NO: 61 and a variable light chain comprising SEQ ID NO: 62. In some embodiments, the antibody cytokine engrafted protein includes a variable heavy chain comprising SEQ ID NO: 77 and a variable light chain comprising SEQ ID NO: 78. In some embodiments, the antibody cytokine engrafted protein a variable heavy chain comprising SEQ ID NO: 93 and a variable light chain comprising SEQ ID NO: 94. In some embodiments, the antibody cytokine engrafted protein includes a variable heavy chain comprising SEQ ID NO: 109 and a variable light chain comprising SEQ ID NO: 110. In some embodiments, the antibody cytokine engrafted protein includes a variable heavy chain comprising SEQ ID NO: 125 and a variable light chain comprising SEQ ID NO: 126. In some embodiments, the antibody cytokine engrafted protein includes a variable heavy chain comprising SEQ ID NO: 141 and a variable light chain comprising SEQ ID NO: 142. In some embodiments, the antibody cytokine engrafted protein includes a variable heavy chain comprising SEQ ID NO: 157 and a variable light chain comprising SEQ ID NO: 158. In some embodiments, the antibody cytokine engrafted protein includes a variable heavy chain comprising SEQ ID NO: 173 and a variable light chain comprising SEQ ID NO: 174. In some embodiments, the antibody cytokine engrafted protein includes a variable heavy chain comprising SEQ ID NO: 189 and a variable light chain comprising SEQ ID NO: 190. In some embodiments, the antibody cytokine engrafted protein includes a variable heavy chain comprising SEQ ID NO: 205 and a variable light chain comprising SEQ ID NO: 206. In some embodiments, the antibody cytokine engrafted protein includes a variable heavy chain comprising SEQ ID NO: 222 and a variable light chain comprising SEQ ID NO: 223. In some embodiments, the antibody cytokine engrafted protein includes a variable heavy chain comprising SEQ ID NO: 238 and a variable light chain comprising SEQ ID NO: 239.

In certain embodiments, the antibody cytokine engrafted protein comprises an IgG class antibody Fc region. In particular embodiments, the immunoglobulin is selected from IgG1, IgG2, or IgG4 subclass Fc region. In some embodiments, the antibody cytokine engrafted protein optionally contains at least one modification that modulates (i.e., increases or decreases) binding of the antibody or antibody fragment to an Fc receptor. The immunoglobulin heavy chain of the antibody cytokine engrafted protein optionally comprises a modification conferring modified effector function. In particular embodiments the immunoglobulin heavy chain comprises a mutation conferring reduced effector function selected from any of D265A, P329A, P329G, N297A, D265A/P329A, D265A/N297A, L234A/L235A, P329A/L234A/L235A, and P329G/L234A/L235A.

In a related aspect, the disclosure further provides polynucleotides encoding at least a heavy chain and/or a light chain protein of an antibody cytokine engrafted protein as described herein. In another related aspect, the disclosure further provides host cells suitable for the production of an antibody cytokine engrafted protein as described herein. In particular embodiments, host cells comprise nucleic acids encoding a heavy chain and/or light chain polypeptide of the antibody cytokine engrafted protein. In still another aspect, methods for producing antibody cytokine engrafted proteins of the disclosure are provided, comprising culturing provided host cells as described herein under conditions suitable for expression, formation, and secretion of the antibody cytokine engrafted protein and recovering the antibody cytokine engrafted protein from the culture. In a further aspect, the disclosure further provides kits comprising an antibody cytokine engrafted protein, as described herein.

In another related aspect, the disclosure further provides compositions comprising an antibody cytokine engrafted protein, as described herein, and a pharmaceutically acceptable carrier. In some embodiments, the disclosure provides pharmaceutical compositions comprising an antibody cytokine engrafted protein of the disclosure for administering to an individual.

In another aspect, the disclosure provides methods of treating an immune related disorder in an individual in need thereof, comprising administering to the individual a therapeutically effective amount of an antibody cytokine engrafted protein of the disclosure, as described herein. In a further aspect, the disclosure provides an antibody cytokine engrafted protein for use in treatment or prophylaxis of an immune related disorder in an individual.

In some embodiments, the patient has an immune related disorder, for example, inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD). In particular embodiments the inflammatory bowel disease is Crohn's disease or ulcerative colitis.

In some embodiments the disclosure provides an antibody cytokine engrafted protein comprising:
  (a) a heavy chain variable region (VH), comprising Complementarity Determining Regions (CDR) HCDR1, HCDR2, HCDR3; and
  (b) a light chain variable region (VL), comprising LCDR1, LCDR2, LCDR3; and
  (c) an Interleukin 10 (IL10) monomeric molecule engrafted into a CDR of the VH or the VL.

The antibody cytokine engrafted protein wherein the IL10 monomeric molecule is engrafted into a heavy chain CDR.

The antibody cytokine engrafted protein wherein the heavy chain CDR is selected from HCDR1, HCDR2 or HCDR3.

The antibody cytokine engrafted protein wherein the IL10 monomeric molecule is engrafted into HCDR1.

The antibody cytokine engrafted protein wherein the IL10 monomeric molecule is engrafted into a light chain CDR.

The antibody cytokine engrafted protein wherein the light chain CDR is selected from LCDR1, LCDR2 or LCDR3.

The antibody cytokine engrafted protein wherein the IL10 monomeric molecule is engrafted into a LCDR1.

The antibody cytokine engrafted protein wherein the antibody cytokine engrafted protein has less activation of T cells or NK cells when compared to IL10.

The antibody cytokine engrafted protein wherein the antibody cytokine engrafted protein has a longer half-life than rhIL10.

The antibody cytokine engrafted protein wherein the IL10 monomeric molecule consists of SEQ ID NO:209.

The antibody cytokine engrafted protein further comprising an IgG class antibody heavy chain.

The antibody cytokine engrafted protein wherein the IgG class heavy chain is selected from IgG1, IgG2, or IgG4.

The antibody cytokine engrafted protein wherein the binding specificity of the CDRs to a target protein is reduced by the presence of the engrafted IL10 monomeric molecule.

The antibody cytokine engrafted protein wherein the binding specificity of the CDRs to a target protein is retained in the presence of the engrafted IL10 monomeric molecule.

The antibody cytokine engrafted protein wherein the binding specificity of the CDRs is to a target protein distinct from the cytokine-receptor binding specificity of the IL10 monomeric molecule.

The antibody cytokine engrafted protein wherein the binding specificity of the CDRs is to a non-human target.

The antibody cytokine engrafted protein wherein the antibody cytokine engrafted protein is humanized or human.

An antibody cytokine engrafted protein comprising:
  (i) a heavy chain variable region that comprises (a) a HCDR1 of SEQ ID NO: 193, (b) a HCDR2 of SEQ ID NO:194, (c) a HCDR3 of SEQ ID NO:195 and a light chain variable region that comprises: (d) a LCDR1 of SEQ ID NO:196, (e) a LCDR2 of SEQ ID NO:197, and (f) a LCDR3 of SEQ ID NO:198;

(ii) a heavy chain variable region that comprises (a) a HCDR1 of SEQ ID NO:97, (b) a HCDR2 of SEQ ID NO:98, (c) a HCDR3 of SEQ ID NO:99; and a light chain variable region that comprises: (d) a LCDR1 of SEQ ID NO:100, (e) a LCDR2 of SEQ ID NO:101, and (f) a LCDR3 of SEQ ID NO:102;

(iii) a heavy chain variable region that comprises (a) a HCDR1 of SEQ ID NO:1, (b) a HCDR2 of SEQ ID NO:2, (c) a HCDR3 of SEQ ID NO:3; and a light chain variable region that comprises: (d) a LCDR1 of SEQ ID NO:4, (e) a LCDR2 of SEQ ID NO:5, and (f) a LCDR3 of SEQ ID NO:6;

(iv) a heavy chain variable region that comprises (a) a HCDR1 of SEQ ID NO:17, (b) a HCDR2 of SEQ ID NO:18, (c) a HCDR3 of SEQ ID NO:19; and a light chain variable region that comprises: (d) a LCDR1 of SEQ ID NO:20, (e) a LCDR2 of SEQ ID NO:21, and (f) a LCDR3 of SEQ ID NO:22;

(v) a heavy chain variable region that comprises (a) a HCDR1 of SEQ ID NO:33, (b) a HCDR2 of SEQ ID NO:34, (c) a HCDR3 of SEQ ID NO:35; and a light chain variable region that comprises: (d) a LCDR1 of SEQ ID NO:36, (e) a LCDR2 of SEQ ID NO:37, and (f) a LCDR3 of SEQ ID NO:38;

(vi) a heavy chain variable region that comprises (a) a HCDR1 of SEQ ID NO:49, (b) a HCDR2 of SEQ ID NO:50, (c) a HCDR3 of SEQ ID NO:51; and a light chain variable region that comprises: (d) a LCDR1 of SEQ ID NO:52, (e) a LCDR2 of SEQ ID NO:53, and (f) a LCDR3 of SEQ ID NO:54;

(vii) a heavy chain variable region that comprises (a) a HCDR1 of SEQ ID NO:65, (b) a HCDR2 of SEQ ID NO:66, (c) a HCDR3 of SEQ ID NO:67; and a light chain variable region that comprises: (d) a LCDR1 of SEQ ID NO:68, (e) a LCDR2 of SEQ ID NO:69, and (f) a LCDR3 of SEQ ID NO:70;

(viii) a heavy chain variable region that comprises (a) a HCDR1 of SEQ ID NO:81, (b) a HCDR2 of SEQ ID NO:82, (c) a HCDR3 of SEQ ID NO:83; and a light chain variable region that comprises: (d) a LCDR1 of SEQ ID NO:84, (e) a LCDR2 of SEQ ID NO:85, and (f) a LCDR3 of SEQ ID NO:86;

(ix) a heavy chain variable region that comprises (a) a HCDR1 of SEQ ID NO:113, (b) a HCDR2 of SEQ ID NO:114, (c) a HCDR3 of SEQ ID NO:115; and a light chain variable region that comprises: (d) a LCDR1 of SEQ ID NO:116, (e) a LCDR2 of SEQ ID NO:117, and (f) a LCDR3 of SEQ ID NO:118;

(x) a heavy chain variable region that comprises (a) a HCDR1 of SEQ ID NO:129, (b) a HCDR2 of SEQ ID NO:130, (c) a HCDR3 of SEQ ID NO:131; and a light chain variable region that comprises: (d) a LCDR1 of SEQ ID NO:132, (e) a LCDR2 of SEQ ID NO:133, and (f) a LCDR3 of SEQ ID NO:134;

(xi) a heavy chain variable region that comprises (a) a HCDR1 of SEQ ID NO:145, (b) a HCDR2 of SEQ ID NO:146, (c) a HCDR3 of SEQ ID NO:147; and a light chain variable region that comprises: (d) a LCDR1 of SEQ ID NO:148, (e) a LCDR2 of SEQ ID NO:149, and (f) a LCDR3 of SEQ ID NO:150;

(xii) a heavy chain variable region that comprises (a) a HCDR1 of SEQ ID NO:161, (b) a HCDR2 of SEQ ID NO:162, (c) a HCDR3 of SEQ ID NO:163; and a light chain variable region that comprises: (d) a LCDR1 of SEQ ID NO:164, (e) a LCDR2 of SEQ ID NO:165, and (f) a LCDR3 of SEQ ID NO:166;

(xiii) a heavy chain variable region that comprises (a) a HCDR1 of SEQ ID NO:177, (b) a HCDR2 of SEQ ID NO:178, (c) a HCDR3 of SEQ ID NO:179; and a light chain variable region that comprises: (d) a LCDR1 of SEQ ID NO:180, (e) a LCDR2 of SEQ ID NO:181, and (f) a LCDR3 of SEQ ID NO:182;

(xiv) a heavy chain variable region that comprises (a) a HCDR1 of SEQ ID NO:210, (b) a HCDR2 of SEQ ID NO:211, (c) a HCDR3 of SEQ ID NO:212; and a light chain variable region that comprises: (d) a LCDR1 of SEQ ID NO:213, (e) a LCDR2 of SEQ ID NO:214, and (f) a LCDR3 of SEQ ID NO:215; and (xv) a heavy chain variable region that comprises (a) a HCDR1 of SEQ ID NO:226, (b) a HCDR2 of SEQ ID NO:227, (c) a HCDR3 of SEQ ID NO:228; and a light chain variable region that comprises: (d) a LCDR1 of SEQ ID NO:229, (e) a LCDR2 of SEQ ID NO:230, and (f) a LCDR3 of SEQ ID NO:231.

An antibody cytokine engrafted protein comprising:

(i) a heavy chain variable region (VH) that comprises SEQ ID NO:205, and a light chain variable region (VL) that comprises SEQ ID NO:206;

(ii) a heavy chain variable region (VH) that comprises SEQ ID NO: 109, and a light chain variable region (VL) that comprises SEQ ID NO: 110;

(iii) a heavy chain variable region (VH) that comprises SEQ ID NO:13, and a light chain variable region (VL) that comprises SEQ ID NO:14;

(iv) a heavy chain variable region (VH) that comprises SEQ ID NO:29, and a light chain variable region (VL) that comprises SEQ ID NO:30;

(v) a heavy chain variable region (VH) that comprises SEQ ID NO:45, and a light chain variable region (VL) that comprises SEQ ID NO:46;

(vi) a heavy chain variable region (VH) that comprises SEQ ID NO:61, and a light chain variable region (VL) that comprises SEQ ID NO:62;

(vii) a heavy chain variable region (VH) that comprises SEQ ID NO:77, and a light chain variable region (VL) that comprises SEQ ID NO:78;

(viii) a heavy chain variable region (VH) that comprises SEQ ID NO:93, and a light chain variable region (VL) that comprises SEQ ID NO:94;

(ix) a heavy chain variable region (VH) that comprises SEQ ID NO:125, and a light chain variable region (VL) that comprises SEQ ID NO:126;

(x) a heavy chain variable region (VH) that comprises SEQ ID NO:141, and a light chain variable region (VL) that comprises SEQ ID NO:142;

(xi) a heavy chain variable region (VH) that comprises SEQ ID NO:157, and a light chain variable region (VL) that comprises SEQ ID NO:158;

(xii) a heavy chain variable region (VH) that comprises SEQ ID NO:173, and a light chain variable region (VL) that comprises SEQ ID NO:174;

(xiii) a heavy chain variable region (VH) that comprises SEQ ID NO:189, and a light chain variable region (VL) that comprises SEQ ID NO:190;

(xiv) a heavy chain variable region (VH) that comprises SEQ ID NO:222, and a light chain variable region (VL) that comprises SEQ ID NO:223; and (xv) a heavy chain variable region (VH) that comprises SEQ ID NO:238, and a light chain variable region (VL) that comprises SEQ ID NO:239.

The antibody cytokine engrafted protein further comprising a modified Fc region corresponding with reduced effector function.

The antibody cytokine engrafted protein wherein the modified Fc region comprises a mutation selected from one or more of D265A, P329A, P329G, N297A, L234A, and L235A.

The antibody cytokine engrafted protein wherein the modified Fc region is selected from the group consisting of D265A/P329A, D265A/N297A, L234A/L235A, P329A/L234A/L235A, and P329G/L234A/L235A.

An antibody cytokine engrafted protein consisting of a HCDR1 of SEQ ID NO: 193, a HCDR2 of SEQ ID NO:194, a HCDR3 of SEQ ID NO:195, a LCDR1 of SEQ ID NO:196, a LCDR2 of SEQ ID NO:197, a LCDR3 of SEQ ID NO:198, a modified Fc region containing the mutation D265A/P329A, and wherein the antibody cytokine engrafted protein has less activation of T cells or NK cells when compared to IL10.

The antibody cytokine engrafted protein wherein the binding specificity of the CDRs is to a non-human target.

The antibody cytokine engrafted protein wherein the antibody cytokine engrafted protein has a longer half-life than rhIL10.

An isolated nucleic acid comprising:
(i) a heavy chain variable region encoding polynucleotide sequence of SEQ ID NO: 246 and a light chain variable region encoding polynucleotide sequence of SEQ ID NO:247;
(ii) a heavy chain encoding polynucleotide sequence of SEQ ID NO:248 and a light chain encoding polynucleotide sequence of SEQ ID NO:249;
(iii) a heavy chain variable region encoding polynucleotide sequence of SEQ ID NO: 242 and a light chain variable region encoding polynucleotide sequence of SEQ ID NO:243; or
(iv) a heavy chain encoding polynucleotide sequence of SEQ ID NO:244 and a light chain encoding polynucleotide sequence of SEQ ID NO:245.

A recombinant host cell suitable for the production of an antibody cytokine engrafted protein, comprising the nucleic acids encoding the heavy and light chain polypeptides of the antibody cytokine engrafted protein, and optionally, secretion signals.

The host cell wherein the cell is mammalian.

A pharmaceutical composition comprising the antibody cytokine engrafted protein and a pharmaceutically acceptable carrier.

A method of treatment or prophylaxis of an immune related disorder in an individual in need thereof, comprising administering to the individual a therapeutically effective amount of the antibody cytokine engrafted protein.

The method wherein the immune related disorder is selected from the group consisting of: inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD).

The method wherein the antibody cytokine engrafted protein is administered in combination with another therapeutic agent.

The method wherein the therapeutic agent is an anti-TNF agent selected from the group consisting of: infliximab, adalimumab, certolizumab, golimumab, natalizumab, and vedolizumab.

The method wherein the therapeutic agent is an aminosalicylate agent selected from the group consisting of: sulfasalazine, mesalamine, balsalazide, olsalazine and other derivatives of 5-aminosalicylic acid.

The method wherein the therapeutic agent is a corticosteroid selected from the group consisting of: methylprednisolone, hydrocortisone, prednisone, budenisonide, mesalamine, and dexamethasone.

The method wherein the therapeutic agent is an antibacterial agent.

A method of activating monocytes in a patient in need thereof, comprising administering an antibody cytokine engrafted protein.

The method wherein monocytes are activated and T cells or NK cells are not activated.

The method wherein administration of the antibody cytokine engrafted protein reduces TNFα production.

The use of an antibody cytokine engrafted protein comprising:
(i) a heavy chain variable region that comprises (a) a HCDR1 of SEQ ID NO: 193, (b) a HCDR2 of SEQ ID NO:194, (c) a HCDR3 of SEQ ID NO:195 and a light chain variable region that comprises: (d) a LCDR1 of SEQ ID NO:196, (e) a LCDR2 of SEQ ID NO:197, and (f) a LCDR3 of SEQ ID NO:198; and
(ii) a heavy chain variable region that comprises (a) a HCDR1 of SEQ ID NO:97, (b) a HCDR2 of SEQ ID NO:98, (c) a HCDR3 of SEQ ID NO:99; and a light chain variable region that comprises: (d) a LCDR1 of SEQ ID NO:100, (e) a LCDR2 of SEQ ID NO:101, and (f) a LCDR3 of SEQ ID NO:102 in the treatment of immune related disorders.

The antibody cytokine engrafted protein for use as a therapeutic in treatment of an immune related disorder selected from the group consisting of: inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD).

The use wherein the antibody cytokine engrafted protein is administered in combination with another therapeutic agent.

The use wherein the therapeutic agent is an anti-TNF agent selected from the group consisting of: infliximab, adalimumab, certolizumab, golimumab, natalizumab, and vedolizumab.

The use wherein the therapeutic agent is an aminosalicylate agent selected from the group consisting of: sulfasalazine, mesalamine, balsalazide, olsalazine and other derivatives of 5-aminosalicylic acid.

The use wherein the therapeutic agent is a corticosteroid selected from the group consisting of: methylprednisolone, hydrocortisone, prednisone, budenisonide, mesalamine, and dexamethasone.

The use wherein the therapeutic agent is an antibacterial agent.

BRIEF DESCRIPTION OF THE DRAWINGS

FIGS. 3A-3B depicts results of in vitro biological assays of recombinant human IL10 (rhIL10, gray square) and the IgGIL10M13 antibody cytokine engrafted protein (black triangle). FIG. 3A illustrates that IgGIL10M13 demonstrated decreased pro-inflammatory activity as compared to rhIL10 as measured by IFN gamma induction in CD8 T cell assays. Similar differential activity was found on human primary NK cells, B cells, and mast cells, as well as using granzyme-B as a readout measurement. FIG. 3B illustrates that rhIL10 and IgGIL10M13 demonstrate similar anti-inflammatory activity as measured by inhibition of TNFα in whole blood assays.

FIGS. 5A-5D illustrates improved characteristics of antibody cytokine engrafted protein IgGIL10M13 in in vivo assays. FIGS. 5A-B depicts results of pharmacokinetic studies of rhIL10 and IgGIL10M13. Following intravenous administration, IgGIL10M13 demonstrates prolonged pharmacokinetics (half-life) as antibody cytokine engrafted protein is still detectable after 4.4 days (FIG. 5B), while rhIL10 had a half-life of approximately 1 hour (FIG. 5A). FIGS. 5C and 5D depict results of pharmacodynamic assays of in vivo activity of antibody cytokine engrafted proteins. FIG. 5C depicts in vivo activity in colon tissue as measured by pSTAT3 signaling seventy-two (72) hours post dosing. FIG. 5D depicts improved duration of in vivo response of IgGIL10M13 as compared to rhIL10 as measured by inhibition of TNFα in response to LPS challenge following administration of IgGIL10M13.

FIG. 11 is ELISA data showing that the IL10 antibody cytokine engrafted protein still binds to RSV.

DEFINITIONS

Figure 1:
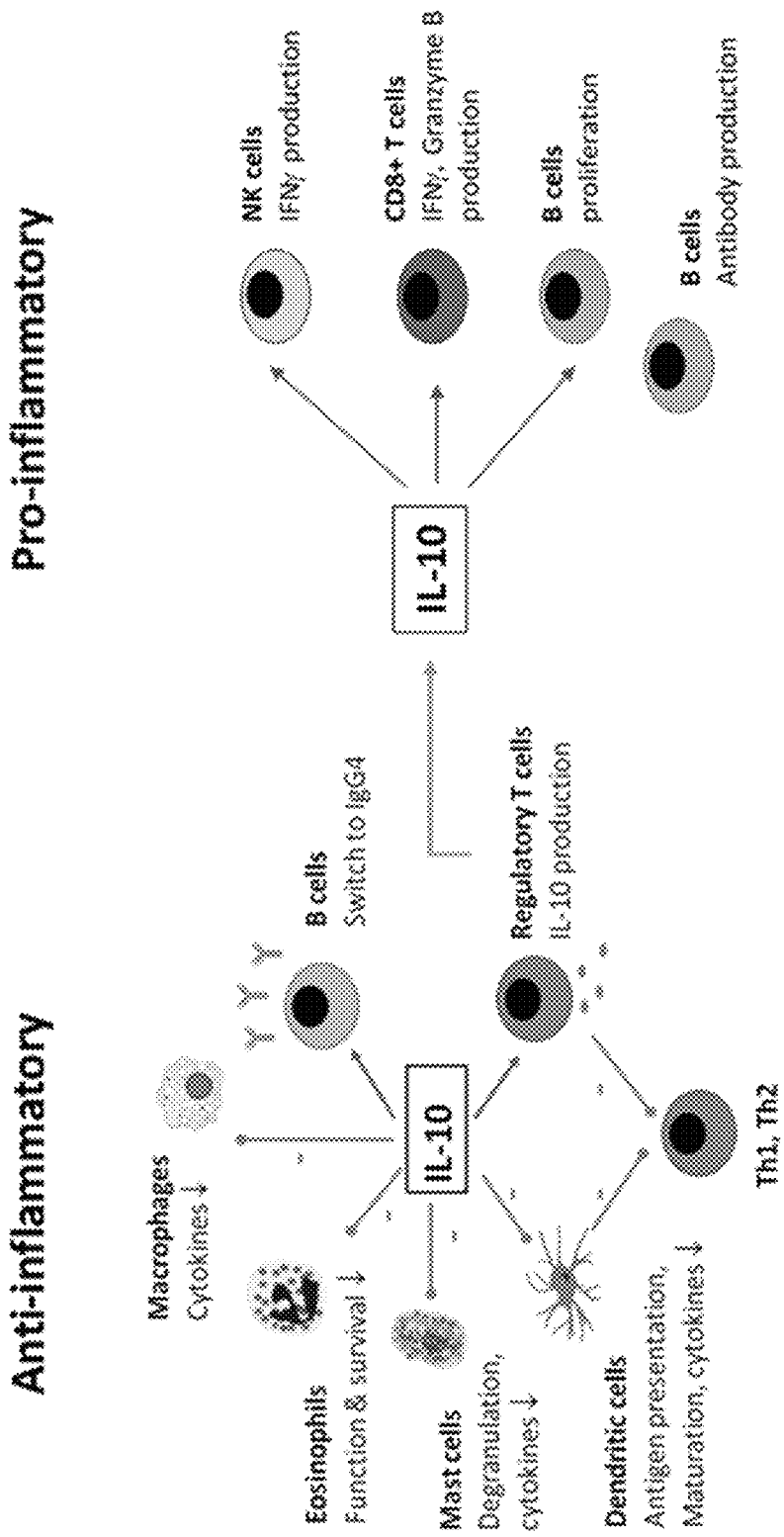
FIG. 1 illustrates the biological effects of IL10, the cell types it acts on, and whether those biological effects are anti-inflammatory or pro-inflammatory. Antibody cytokine engrafted proteins reduce the pro-inflammatory biological effects depicted on the right side of the diagram.

An "antibody" refers to a molecule of the immunoglobulin family comprising a tetrameric structural unit. Each tetramer is composed of two identical pairs of polypeptide chains, each pair having one "light" chain (about 25 kD) and one "heavy" chain (about 50-70 kD), connected through a disulfide bond. Recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. Antibodies can be of any isotype/class (e.g., IgG, IgM, IgA, IgD, and IgE), or any subclass (e.g., IgG1, IgG2, IgG3, IgG4, IgA1, IgA2).

Both the light and heavy chains are divided into regions of structural and functional homology. The terms "constant" and "variable" are used structurally and functionally. The N-terminus of each chain defines a variable (V) region or domain of about 100 to 110 or more amino acids primarily responsible for antigen recognition. The terms variable light chain ($V_L$) and variable heavy chain ($V_H$) refer to these regions of light and heavy chains respectively. The pairing of a $V_H$ and $V_L$ together forms a single antigen-binding site. In addition to V regions, both heavy chains and light chains contain a constant (C) region or domain. A secreted form of a immunoglobulin C region is made up of three C domains, CH1, CH2, CH3, optionally CH4 (Cμ), and a hinge region. A membrane-bound form of an immunoglobulin C region also has membrane and intracellular domains. Each light chain has a $V_L$ at the N-terminus followed by a constant domain (C) at its other end. The constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively. The VL is aligned with the VH and the CL is aligned with the first constant domain of the heavy chain. As used herein, an "antibody" encompasses conventional antibody structures and variations of antibodies. Thus, within the scope of this concept are full length antibodies, chimeric antibodies, humanized antibodies, human antibodies, and antibody fragments thereof.

Antibodies exist as intact immunoglobulin chains or as a number of well-characterized antibody fragments produced by digestion with various peptidases. The term "antibody fragment," as used herein, refers to one or more portions of an antibody that retain the ability to specifically interact with (e.g., by binding, steric hindrance, stabilizing/destabilizing, spatial distribution) an epitope of an antigen. Thus, for example, pepsin digests an antibody below the disulfide linkages in the hinge region to produce F(ab)'$_2$, a dimer of Fab' which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer.

The Fab' monomer is essentially Fab with part of the hinge region. Paul, *Fundamental Immunology* 3d ed. (1993). While various antibody fragments are defined in terms of the digestion of an intact antibody, one of skill will appreciate that such fragments may be synthesized de novo either chemically or by using recombinant DNA methodology. As used herein, an "antibody fragment" refers to one or more portions of an antibody, either produced by the modification of whole antibodies, or those synthesized de novo using recombinant DNA methodologies, that retain binding specificity and functional activity. Examples of antibody fragments include Fv fragments, single chain antibodies (ScFv), Fab, Fab', Fd (Vh and CH1 domains), dAb (Vh and an isolated CDR); and multimeric versions of these fragments (e.g., F(ab')$_2$,) with the same binding specificity. Antibody fragments can also be incorporated into cytokine engrafted proteins to achieve the binding specificity and activity provided in the present disclosure.

A "Fab" domain as used herein comprises a heavy chain variable domain, a constant region CH1 domain, a light chain variable domain, and a light chain constant region CL domain. The interaction of the domains is stabilized by a disulfide bond between the CH1 and CL domains. In some embodiments, the heavy chain domains of the Fab are in the order, from N-terminus to C-terminus, VH-CH and the light chain domains of a Fab are in the order, from N-terminus to C-terminus, VL-CL. In some embodiments, the heavy chain domains of the Fab are in the order, from N-terminus to C-terminus, CH-VH and the light chain domains of the Fab are in the order CL-VL. Although Fabs were historically identified by papain digestion of an intact immunoglobulin, in the context of this disclosure, a "Fab" is typically produced recombinantly by any method. Each Fab fragment is monovalent with respect to antigen binding, i.e., it has a single antigen-binding site.

"Complementarity-determining domains" or "complementarity-determining regions" ("CDRs") interchangeably refer to the hypervariable regions of $V_L$ and $V_H$. CDRs are the target protein-binding site of antibody chains that harbors specificity for such target protein. There are three CDRs (CDR1-3, numbered sequentially from the N-terminus) in each human $V_L$ or $V_H$, constituting about 15-20% of the variable domains. CDRs are structurally complementary to the epitope of the target protein and are thus directly responsible for the binding specificity. The remaining stretches of the $V_L$ or $V_H$, the so-called framework regions (FR), exhibit less variation in amino acid sequence (Kuby, Immunology, 4th ed., Chapter 4. W.H. Freeman & Co., New York, 2000).

Positions of CDRs and framework regions can be determined using various well known definitions in the art, e.g., Kabat, Chothia, international ImMunoGeneTics database (IMGT) and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, CDR amino acid residues in the $V_H$ are numbered 31-35 (HCDR1), 50-65 (HCDR2), and 95-102 (HCDR3); and the CDR amino acid residues in the $V_L$ are numbered 24-34 (LCDR1), 50-56 (LCDR2), and 89-97 (LCDR3). Under Chothia, CDR amino acids in the $V_H$ are numbered 26-32 (HCDR1), 52-56 (HCDR2), and 95-102 (HCDR3); and the amino acid residues in $V_L$ are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions (FR). The term "variable region" or "V-region" interchangeably refer to a heavy or light chain comprising FR1-CDR1-FR2-CDR2-FR3-CDR3-FR4. A V-region can be naturally occurring, recombinant or synthetic. In this application, antibody light chains and/or antibody heavy chains may, from time to time, be collectively referred to as "antibody chains." As provided and further described herein, an "antibody variable light chain" or an "antibody variable heavy chain" and/or a "variable region" and/or an "antibody chain" optionally comprises a cytokine polypeptide sequence engrafted into a CDR.

The C-terminal portion of an immunoglobulin heavy chain as disclosed herein, comprising, e.g., CH2 and CH3 domains, is the "Fc" domain. An "Fc region" as used herein refers to the constant region of an antibody excluding the first constant region (CH1) immunoglobulin domain. Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). "Fc region" may refer to this region in isolation or this region in the context of an antibody or antibody fragment. "Fc region" includes naturally occurring allelic variants of the Fc region, e.g., in the CH2 and CH3 region, including, e.g., modifications that modulate effector function. Fc regions also include variants that don't result in alterations to biological function. For example, one or more amino acids are deleted from the N-terminus or C-terminus of the Fc region of an immunoglobulin without substantial loss of biological function. For example, in certain embodiments a C-terminal lysine is modified replaced or removed. In particular embodiments one or more C-terminal residues in the Fc region is altered or removed. In certain embodiments one or more C-terminal residues in the Fc (e.g., a terminal lysine) is deleted. In certain other embodiments one or more C-terminal residues in the Fc is substituted with an alternate amino acid (e.g., a terminal lysine is replaced). Such variants are selected according to general rules known in the art so as to have minimal effect on activity (see, e.g., Bowie, et al., Science 247:306-1310, 1990). The Fc domain is the portion of the immunoglobulin (Ig) recognized by cell receptors, such as the FcR, and to which the complement-activating protein, C1 q, binds. The lower hinge region, which is encoded in the 5' portion of the CH2 exon, provides flexibility within the antibody for binding to FcR receptors.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

A "humanized" antibody is an antibody that retains the reactivity (e.g., binding specificity, activity) of a non-human antibody while being less immunogenic in humans. This can be achieved, for instance, by retaining non-human CDR regions and replacing remaining parts of an antibody with human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

A "human antibody" includes antibodies having variable regions in which both the framework and CDR regions are derived from sequences of human origin. Furthermore, if an antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Human antibodies may include amino acid residues not encoded by human sequences (e.g., mutations introduced by random or site-specific mutagenesis in vitro or by somatic mutation in vivo, or a conservative substitution to promote stability or manufacturing).

The term "corresponding human germline sequence" refers to a nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. A corresponding human germline sequence can also refer to the human variable region amino acid sequence or subsequence with the highest amino acid sequence identity with a reference variable region amino acid sequence or subsequence in comparison to all other evaluated variable region amino acid sequences. A corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) and V-base.

The term "valency" as used herein refers to the number of potential target binding sites in a polypeptide. Each target binding site specifically binds one target molecule or a specific site on a target molecule. When a polypeptide comprises more than one target binding site, each target binding site may specifically bind the same or different molecules (e.g., may bind to different molecules, e.g., different antigens, or different epitopes on the same molecule). A conventional antibody, for example, has two binding sites and is bivalent; "trivalent" and "tetravalent" refer to the presence of three binding sites and four binding sites, respectively, in an antibody molecule. The antibody cytokine engrafted protein can be monovalent (i.e., bind one target molecule), bivalent, or multivalent (i.e., bind more than one target molecule).

The phrase "specifically binds" or "binding specificity," when used in the context of describing the interaction between the original antibody target (e.g., an antigen) and an antibody cytokine engrafted protein before and after the cytokine engrafting. Under certain designated conditions, an antibody cytokine engrafted protein with a particular binding specificity binds to its original target at least two times the background and does not substantially bind in a significant amount to other targets present in a sample. In one embodiment, under designated conditions, an antibody cytokine engrafted protein with a particular binding specificity binds to its original target at least ten (10) times the background and does not substantially bind in a significant amount to other targets present in the sample. Specific binding of an antibody cytokine engrafted protein under such conditions can require an antibody cytokine engrafted protein to have been selected for its specificity to a particular target. Methods for determining binding specific are, for example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity).

As used herein, "cytokine-receptor binding specificity" or "cytokine-receptor specificity" includes antibody cytokine engrafted proteins that selectively bind to IL10 receptor and does not include antibody cytokine engrafted proteins that cross-react with other cytokine receptor superfamily members. In some embodiments, antibody cytokine engrafted proteins are selected that selectively bind to human IL10R and cross-react with non-human primate IL10R (e.g., cynomolgus IL10R). In some embodiments, antibody engrafted proteins are selected that selectively bind to human IL10R1.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibody cytokine engrafted proteins of the present disclosure generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "IL10" or "interleukin 10" or "interleukin-10 (IL-10)", interchangeably, refer to a potent anti-inflammatory cytokine, capable of down regulating activation of macrophages as well as reducing antigen presentation and maturation of dendritic cells. IL10 comprising residues 19-178 of the full length native human is utilized in construction of the agonist antibody cytokine engrafted proteins. The human IL10 as disclosed herein has over its full length at least about 90%, 91%, 92%, 93%, 94%, 95%, 96%, 97%, 98%, 99%, or 100% sequence identity with the amino acid sequence published as GenBank Accession No: NP_000563. The human IL10 nucleic acid encoding for the IL10 protein has over its full length at least about 90%, 91%, 92%, 93%, 94%, 95%, 96%, 97%, 98%, 99%, or 100% sequence identity with the nucleic acid sequence published under GenBank Accession No: NM_000572.

"Monomeric IL10" or "IL10M" refers to a molecule has at least 85%, 86%, 87%, 88%, 89%, 90%, 91%, 92%, 93%, 94% 95%, 96%, 97%, 98%, 99% or 100% sequence identity to the amino acid sequence of SEQ ID NO: 209. In some embodiments, the monomeric IL10 molecule comprises the sequence of SEQ ID NO: 209. In some embodiments, the monomeric IL10 molecule consists of the sequence of SEQ ID NO: 209.

The term "agonist" refers to an antibody cytokine engrafted protein capable of activating a receptor to induce a full or partial receptor-mediated response. For example, an agonist of IL10R binds to IL10R and induces IL10R-mediated intracellular signaling and/or cell activation. The antibody cytokine engrafted protein stimulates signaling through IL10R similar in some respects to the native ligand, human IL10. Binding of hIL10 to IL10R induces NFκB activation due to degradation of IκB. In some embodiments, an antibody cytokine engrafted protein agonist can be identified by its ability to bind IL10R and induce STAT3 phosphorylation, suppress production of pro-inflammatory cytokines (e.g. TNFα, IL1, IL6, IL12, IFNγ) and/or differentiation and proliferation in macrophages; induce T cell (e.g., CD8+ CTLs or CD4+ Th cells) proliferation, survival, cytolytic activity and/or cytokine production (e.g., IFNγ, IL10, IL-13, TNFα), or as otherwise described herein.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The disclosure provides polypeptides or polynucleotides that are substantially identical to the polypeptides or polynucleotides, respectively, exemplified herein (e.g., the variable regions exemplified in any one of SEQ ID NO:13, SEQ ID NO:14, SEQ ID NO:29, SEQ ID NO:30, SEQ ID NO:45, SEQ ID NO:46, SEQ ID NO:61, SEQ ID NO:62, SEQ ID NO:77, SEQ ID NO:78, SEQ ID NO:93, SEQ ID NO:94, SEQ ID NO:109, SEQ ID NO:110, SEQ ID NO:125, SEQ ID NO:126, SEQ ID NO:141, SEQ ID NO:142, SEQ ID NO:157, SEQ ID NO:158, SEQ ID NO:173, SEQ ID NO:174, SEQ ID NO:189, SEQ ID NO:190, SEQ ID NO:205, SEQ ID NO:206; SEQ ID NO:222, SEQ ID NO:223, SEQ ID NO:238 SEQ ID NO:239; the variable regions exemplified in any one of SEQ ID NO:15, SEQ ID NO:16, SEQ ID NO:31, SEQ ID NO:32, SEQ ID NO:47, SEQ ID NO:48, SEQ ID NO:63, SEQ ID NO:64, SEQ ID NO:79, SEQ ID NO:80, SEQ ID NO:95, SEQ ID NO:96, SEQ ID NO:111, SEQ ID NO:112, SEQ ID NO:127, SEQ ID NO:128, SEQ ID NO:143, SEQ ID NO:144, SEQ ID NO:159, SEQ ID NO:160, SEQ ID NO:175, SEQ ID NO:176, SEQ ID NO:191, SEQ ID NO:192, SEQ ID NO:207, SEQ ID NO:208, SEQ ID NO:224, SEQ ID NO:225, SEQ ID NO:240, SEQ ID NO:241; the CDRs exemplified in any one of SEQ ID NO:13, SEQ ID NO:14, SEQ ID NO:29, SEQ ID NO:30, SEQ ID NO:45, SEQ ID NO:46, SEQ ID NO:61, SEQ ID NO:62, SEQ ID NO:77, SEQ ID NO:78, SEQ ID NO:93, SEQ ID NO:94, SEQ ID NO:109, SEQ ID NO:110, SEQ ID NO:125, SEQ ID NO:126, SEQ ID NO:141, SEQ ID NO:142, SEQ ID NO:157, SEQ ID NO:158, SEQ ID NO:173, SEQ ID NO:174, SEQ ID NO:189, SEQ ID NO:190, SEQ ID NO:205, SEQ ID NO:206, SEQ ID NO:222, SEQ ID NO:223, SEQ ID NO:238 and SEQ ID NO:239. Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "antibody cytokine engrafted protein" or "antibody cytokine graft" or "engrafted" means that at least one cytokine is incorporated directly within a CDR of the antibody, interrupting the sequence of the CDR. The cytokine can be incorporated within HCDR1, HCDR2, HCDR3, LCDR1, LCDR2 or LCDR3. The cytokine can be incorporated within HCDR1, HCDR2, HCDR3, LCDR1, LCDR2 or LCDR3 and incorporated toward the N-terminal sequence of the CDR or toward the C-terminal sequence of the CDR. The cytokine incorporated within a CDR can reduce the specific binding of the antibody portion to its target protein or the antibody cytokine engrafted protein can retain its specific binding to its target protein.

An "immune related disorder" or "immune disease" refers to a dysfunction of the immune system, in which the body's own immune system attacks healthy tissue. The dysfunction can be in components of the immune cells, and includes both overactive and underactive immune systems.

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" or "prophylaxis" refers to preventing or delaying the onset or development or progression of a disease or disorder.

The term "therapeutically acceptable amount" or "therapeutically effective dose" interchangeably refer to an amount sufficient to effect the desired result (i.e., a reduction in inflammation, inhibition of pain, prevention of inflammation, inhibition or prevention of inflammatory response). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of an IL10 antibody cytokine engrafted protein can prevent the onset of, or result in a decrease in severity of, respectively, disease symptoms, including symptoms associated with immune related disorder.

The term "co-administer" refers to the simultaneous presence of two (or more) active agents in an individual. Active agents that are co-administered can be concurrently or sequentially delivered.

As used herein, the phrase "consisting essentially of" refers to the genera or species of active pharmaceutical agents included in a method or composition, as well as any inactive carrier or excipients for the intended purpose of the methods or compositions. In some embodiments, the phrase "consisting essentially of" expressly excludes the inclusion of one or more additional active agents other than an IL10 antibody cytokine engrafted protein. In some embodiments, the phrase "consisting essentially of" expressly excludes the inclusion of more additional active agents other than an IL10 antibody cytokine engrafted protein and a second co-administered agent.

The terms "a," "an," and "the" include plural referents, unless the context clearly indicates otherwise.

DETAILED DESCRIPTION

IL10 Antibody Cytokine Engrafted Proteins

Interleukin-10 (IL10) is a multifunctional, homodimeric immunomodulatory cytokine that has both immunostimulatory and immunosuppressive activities. IL10 inhibits the induction of a number of proinflammatory cytokines in activated monocytes and macrophages but is a costimulator for immature and mature lymphocytes, mast cells and B cells (reviewed in Mosmann, Adv. Immunol. 1994; 56:1-26; Moore et al., Annu Rev Immunol. 2001; 19:683-765). Provided herein are antibody cytokine engrafted proteins comprising monomeric IL10 engrafted into the complementarity determining region (CDR) of an antibody. The antibody cytokine engrafted proteins show suitable properties to be used in human patients, for example, they retain immunosuppressive activity similar to that of native or recombinant human IL10, however, the pro-inflammatory effects are reduced.

Accordingly, the present disclosure provides antibody cytokine engrafted proteins that are agonists of the IL10 receptor, with selective activity profiles. Provided antibody cytokine engrafted proteins comprise an immunoglobulin heavy chain sequence and an immunoglobulin light chain sequence. Each immunoglobulin heavy chain sequence comprises a heavy chain variable region (VH) and a heavy chain constant region (CH), wherein the heavy chain constant region consists of CH1, CH2, and CH3 constant regions. Each immunoglobulin light chain sequence comprises a light chain variable region (VL) and a light chain constant region (CL). In each antibody cytokine engrafted protein a monomeric IL10 molecule is engrafted into a complementarity determining region (CDR) of the VH or VL region.

In some embodiments, the antibody cytokine engrafted protein comprises a monomeric IL10 engrafted into a heavy chain CDR. In certain embodiments monomeric IL10 is engrafted into heavy chain complementarity determining region 1 (HCDR1). In certain embodiments monomeric IL10 is engrafted into heavy chain complementarity determining region 2 (HCDR2). In certain embodiments monomeric IL10 is engrafted into heavy chain complementarity determining region 3 (HCDR3).

In some embodiments, the antibody cytokine engrafted protein comprises a monomeric IL10 engrafted into a light chain CDR. In certain embodiments monomeric IL10 is engrafted into light chain complementarity determining region 1 (LCDR1). In certain embodiments monomeric IL10 is engrafted into light chain complementarity determining region 2 (LCDR2). In certain embodiments monomeric IL10 is engrafted into light chain complementarity determining region 3 (LCDR3). In a preferred embodiment, monomeric IL10 is engrafted into light chain complementarity determining region 1 (LCDR1).

In some embodiments, the antibody cytokine engrafted protein comprises a monomeric IL10 engrafted into a CDR, whereby the IL10 sequence is inserted into the CDR sequence. The engrafted IL10 can be at or near the N-terminal portion of the CDR, in the center region of the CDR or at or near the C-terminal portion of the CDR. In other embodiments, the antibody cytokine engrafted protein comprises a monomeric IL10 incorporated into a CDR, wherein the IL10 sequence replaces all or part of a CDR sequence. A replacement can be at or near the beginning of the CDR, in the middle region of the CDR or at or near the end of the CDR. A replacement can be as few as one or two amino acids of a CDR sequence, or as many as an entire CDR sequence.

In some embodiments monomeric IL10 is engrafted directly into a CDR without a peptide linker.

In some embodiments the antibody cytokine engrafted protein comprises immunoglobulin heavy chains of an IgG class antibody heavy chain. In certain embodiments an IgG heavy chain is any one of an IgG1, an IgG2 or an IgG4 subclass.

In some embodiments antibody cytokine engrafted proteins comprise heavy and light chain immunoglobulin sequences selected from a known, clinically utilized immunoglobulin sequence. In certain embodiments antibody cytokine engrafted proteins comprise heavy and light chain immunoglobulin sequences which are humanized sequences. In other certain embodiments antibody cytokine engrafted proteins comprise heavy and light chain immunoglobulin sequences which are human sequences.

In some embodiments antibody cytokine engrafted proteins comprise heavy and light chain immunoglobulin sequences selected from germline immunoglobulin sequences.

In some embodiments antibody cytokine engrafted proteins comprise heavy and light chain immunoglobulin sequences having binding specificity of the immunoglobulin variable domains to a target distinct from the cytokine receptor binding specificity of the IL10 monomer. In some embodiments the binding specificity of the immunoglobulin variable domain is retained in the presence of the engrafted cytokine. In certain embodiments the antibody binding specificity is to a non-human antigen. In other embodiments the binding specificity is to a target having therapeutic utility in conjunction with IL10 therapy. In certain embodiments modulating the binding specificity of the immunoglobulin conveys additional therapeutic benefit to the IL10 component. In certain embodiments the binding specificity of the immunoglobulin conveys synergistic activity with IL10 monomer.

In still other embodiments, the binding specificity of the immunoglobulin is reduced in the presence of the IL10 engrafted cytokine.

In some embodiments, the antibody cytokine engrafted protein confers anti-inflammatory properties similar to human IL10 or recombinant human IL10, and the engrafted protein confers reduced proportional pro-inflammatory activity as compared to human IL10 or recombinant human IL10. In some embodiments the proportional pro-inflammatory activity is reduced by at least twenty five percent (25%) as compared with IL10. In some embodiments the proportional pro-inflammatory activity is reduced by at least thirty five percent (35%) as compared with IL10. In some embodiments the proportional pro-inflammatory activity is reduced by at least about fifty percent (50%) as compared with IL10. In some embodiments the proportional pro-inflammatory activity is reduced by at least about sixty five percent (65%) as compared with IL10. In some embodiments the proportional pro-inflammatory activity is reduced by at least about seventy five percent (75%) as compared with IL10. In some embodiments the proportional pro-inflammatory activity is reduced by at least about eighty percent (80%) as compared with IL10. In some embodiments the proportional pro-inflammatory activity is reduced by more than eighty percent (80%) as compared with IL10.

In some embodiments, the antibody cytokine engrafted proteins comprise a modified immunoglobulin IgG having a modified Fc conferring modified effector function. In certain embodiments the modified Fc region comprises a mutation selected from one or more of D265A, P329A, P329G, N297A, L234A, and L235A. In particular embodiments the immunoglobulin heavy chain may comprise a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:13 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:14. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:29 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:30. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:45 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:46. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:61 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:62. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:77 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:78. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:93 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:94. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises each comprising (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:109 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:110. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:125 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:126. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:141 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:142. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:157 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:158. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:173 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:174. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:189 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:190. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:205 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:206. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:222 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:223. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:238 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:239. The immunoglobulin chain is an IgG class selected from IgG1, IgG2, or IgG4. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:15 and (ii) a light chain having at least 85%, 89%, 90%, 91%, 92%, 93%, 94%, 95%, 96%, 97%, 98%, 99%, or 100% amino acid sequence identity to SEQ ID NO:16. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:31 and (ii) a light chain having at least 85%, 89%, 90%, 91%, 92%, 93%, 94%, 95%, 96%, 97%, 98%, 99%, or 100% amino acid sequence identity to SEQ ID NO:32. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:47 and (ii) a light chain having at least 85%, 89%, 90%, 91%, 92%, 93%, 94%, 95%, 96%, 97%, 98%, 99%, or 100% amino acid sequence identity to SEQ ID NO:48. In certain embodiments the immunoglobulin heavy chain optionally comprises a mutation or combination of mutations confer- In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:63 and (ii) a light chain having at least 85%, 89%, 90%, 91%, 92%, 93%, 94%, 95%, 96%, 97%, 98%, 99%, or 100% amino acid sequence identity to SEQ ID NO:64. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:79 and (ii) a light chain having at least 85%, 89%, 90%, 91%, 92%, 93%, 94%, 95%, 96%, 97%, 98%, 99%, or 100% amino acid sequence identity to SEQ ID NO:80. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:95 and (ii) a light chain having at least 85%, 89%, 90%, 91%, 92%, 93%, 94%, 95%, 96%, 97%, 98%, 99%, or 100% amino acid sequence identity to SEQ ID NO:96. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:111 and (ii) a light chain having at least 85%, 89%, 90%, 91%, 92%, 93%, 94%, 95%, 96%, 97%, 98%, 99%, or 100% amino acid sequence identity to SEQ ID NO:112. In certain embodiments the immunoglobulin heavy chain optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:127 and (ii) a light chain having at least 85%, 89%, 90%, 91%, 92%, 93%, 94%, 95%, 96%, 97%, 98%, 99%, or 100% amino acid sequence identity to SEQ ID NO:128. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:143 and (ii) a light chain having at least 85%, 89%, 90%, 91%, 92%, 93%, 94%, 95%, 96%, 97%, 98%, 99%, or 100% amino acid sequence identity to SEQ ID NO:144. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:159 and (ii) a light chain having at least 85%, 89%, 90%, 91%, 92%, 93%, 94%, 95%, 96%, 97%, 98%, 99%, or 100% amino acid sequence identity to SEQ ID NO:160. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:175 and (ii) a light chain having at least 85%, 89%, 90%, 91%, 92%, 93%, 94%, 95%, 96%, 97%, 98%, 99%, or 100% amino acid sequence identity to SEQ ID NO:176. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:191 and (ii) a light chain having at least 85%, 89%, 90%, 91%, 92%, 93%, 94%, 95%, 96%, 97%, 98%, 99%, or 100% amino acid sequence identity to SEQ ID NO:192. In certain embodiments the immunoglobulin heavy chain optionally comprises a mutation or combination of mutations conferring reduced effector function selected from any of D265A, P329A, P329G, N297A, D265A/P329A, D265A/N297A, L234A/L235A, P329A/L234A/L235A, and P329G/L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:207 and (ii) a light chain having at least 85%, 89%, 90%, 91%, 92%, 93%, 94%, 95%, 96%, 97%, 98%, 99%, or 100% amino acid sequence identity to SEQ ID NO:208. In certain embodiments the immunoglobulin heavy chain optionally comprises a mutation or combination of mutations conferring reduced effector function selected from any of D265A, P329A, P329G, N297A, D265A/P329A, D265A/ N297A, L234A/L235A, P329A/L234A/L235A, and P329G/ L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:224 and (ii) a light chain having at least 85%, 89%, 90%, 91%, 92%, 93%, 94%, 95%, 96%, 97%, 98%, 99%, or 100% amino acid sequence identity to SEQ ID NO:225. In certain embodiments the immunoglobulin heavy chain optionally comprises a mutation or combination of mutations conferring reduced effector function selected from any of D265A, P329A, P329G, N297A, D265A/P329A, D265A/ N297A, L234A/L235A, P329A/L234A/L235A, and P329G/ L234A/L235A.

In some embodiments, the antibody cytokine engrafted protein comprises (i) a heavy chain having at least 85%, 89%, 90%, 91%, 92%, 93%, 94%, 95%, 96%, 97%, 98%, 99%, or 100% amino acid sequence identity to SEQ ID NO:240 and (ii) a light chain having at least 85%, 89%, 90%, 91%, 92%, 93%, 94%, 95%, 96%, 97%, 98%, 99%, or 100% amino acid sequence identity to SEQ ID NO:241. In certain embodiments the immunoglobulin heavy chain optionally comprises a mutation or combination of mutations conferring reduced effector function selected from any of D265A, P329A, P329G, N297A, D265A/P329A, D265A/ N297A, L234A/L235A, P329A/L234A/L235A, and P329G/ L234A/L235A.

Engineered and Modified Antibody Cytokine Engrafted Proteins

Figure 2:
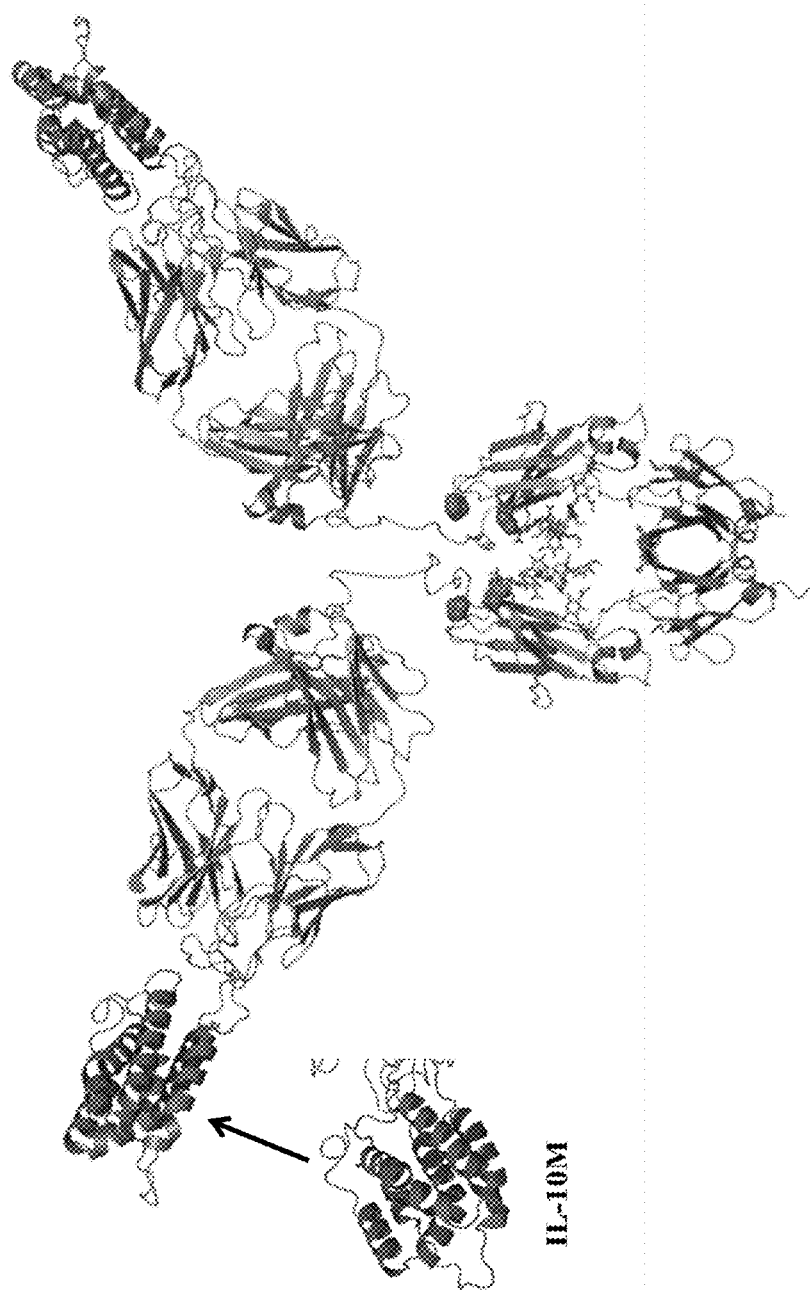
FIG. 2 illustrates the structure of an IL10 antibody cytokine engrafted protein. The insert panel depicts monomeric IL10 inserted into the LCDR1 of an antibody. Dark residues depict exemplary Fc modifications optionally incorporated in the antibody cytokine engrafted protein.

Antibody cytokine engrafted proteins are generated by engrafting a monomeric IL10 sequence into a CDR region of an immunoglobulin scaffold. Both heavy and light chain immunoglobulin chains are produced to generate final antibody engrafted proteins. Antibody cytokine engrafted proteins confer preferred therapeutic anti-inflammatory properties of IL10; however, antibody cytokine engrafted proteins have reduced proportional pro-inflammatory activity as compared with native or recombinant human IL10 (rhIL10).

To engineer engrafted constructs, monomeric IL10 (IL10M, SEQ ID NO: 209), comprising residues 19-178 of full length IL10 and a six amino acid sequence between residues 134 and 135 was engrafted into a CDR loop of an immunoglobulin scaffold. Engrafted constructs can be prepared using any of a variety of known immunoglobulin sequences which have been utilized in clinical settings, known immunoglobulin sequences which are in current discovery and/or clinical development, human germline antibody sequences, as well as sequences of novel antibody immunoglobulin chains. Antibody cytokine engrafted proteins are produced using standard molecular biology methodology utilizing recombinant DNA encoding relevant sequences. Sequences of IL10M in two exemplary scaffolds, referred to as GFTX1 and GFTX3, and are depicted in TABLE 1. Insertion points for IL10 monomer were selected to be the mid-point of the loop based on available structural or homology model data, however, insertion points may be adjusted toward one or another end of a CDR loop.

Thus the present disclosure provides antibody cytokine engrafted proteins or fragments thereof that cytokine-receptor specifically bind to an IL10R protein, comprising an IL10M protein recombinantly inserted into to a heterologous antibody protein or polypeptide to generate antibody cytokine engrafted proteins. In particular, the disclosure provides engrafted proteins comprising an antibody or antigen-binding fragment of an antibody described herein or any other relevant scaffold antibody polypeptide (e.g., a full antibody immunoglobulin protein, a Fab fragment, Fd fragment, Fv fragment, F(ab)2 fragment, a VH domain, a VH CDR, a VL domain, a VL CDR, etc.) and a heterologous cytokine protein, polypeptide, or peptide, e.g., IL10M. Methods for conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341. Additionally, antibody cytokine engrafted proteins may be generated through the techniques of gene-shuffling, motif-shuffling, exon-shuffling, and/or codon-shuffling (collectively referred to as "DNA shuffling"). DNA shuffling may be employed to prepare antibody cytokine engrafted proteins and/or to alter the activities of antibodies or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen protein of interest may be recombined with one or more components, motifs, sections, parts, domains, fragments, etc. of one or more heterologous cytokine molecules, e.g., IL10M, for preparation of antibody cytokine engrafted proteins as provided herein.

An antibody Fab contains six CDR loops, 3 in the light chain (CDRL1, CDRL2, CDRL3) and 3 in the heavy chain (CDRH1, CDRH2, CDRH3) which can serve as potential insertion sites for a cytokine protein. Structural and functional considerations are taken into account in order to determine which CDR loop(s) to insert the cytokine. As a CDR loop size and conformation vary greatly across different antibodies, the optimal CDR for insertion may be determined empirically for each particular antibody/protein combination. Additionally, since a cytokine protein will be inserted into a CDR loop, this can put additional constraints on the structure of the cytokine protein. For example, the amino and carboxy terminal of the cytokine protein should allow for possibility to be constrained relatively close in space (~25 Å). Additionally, an antibody cytokine engrafted protein should not rely on oligomerization for biological activity.

IL10 is a homodimeric cytokine that employs a domain swapped architecture. In native form, IL10 would not be suitable for antibody grafting since the domain swapped structure would not be able to form (i.e. both N and C termini are constrained in the loop). However, an engineered monomeric IL10 (IL10M), created by inserting a six residue sequence ((GGGSGG) (SEQ ID NO.251)) between helices D and E allows helices E and F (which swap into the other IL10 monomer in the native dimeric structure) to fold back into the same monomer (Josephson et al J. Biol. Chem. 2000; 275(18) 13552-7) and create the structure present in the antibody cytokine engrafted protein as shown in FIG. 2 and FIG. 13. Josephson et al., demonstrated that the IL10 monomer with the six amino acid insertion is more thermostable than the wild-type dimer and is also able to form a 1:1 interaction with the IL10 receptor chain (IL10R1). IL10M also has in vitro activity, though it is nine to eighteen-fold less active than wild-type IL10. Another feature of IL10M is that the N and C-termini are close to each other in space, which makes the modified cytokine protein suitable for antibody grafting.

An antibody cytokine engrafted protein of the disclosure further can be prepared using an antibody having one or more of the CDRs and/or VH and/or VL sequences shown herein (e.g., TABLE 1) as starting material to engineer a modified antibody cytokine engrafted protein, which may have altered properties from the starting antibody. Alternatively, any known antibody sequences may be utilized as a scaffold to engineer modified antibody cytokine engrafted proteins. For example, any known, clinically utilized antibody may be utilized as a starting materials scaffold for preparation of antibody cytokine engrafted protein. Known antibodies and corresponding immunoglobulin sequences include, e.g., palivizumab, alirocumab, mepolizumab, necitumumab, nivolumab, dinutuximab, secukinumab, evolocumab, blinatumomab, pembrolizumab, ramucirumab vedolizumab, siltuximab, obinutuzumab, trastuzumab, raxibacumab, pertuzumab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab tiuxetan, adalimumab, alemtuzumab, gemtuzumab, infliximab, basiliximab, daclizumab, rituximab, abciximab, muromonab, or modifications thereof. Known antibodies and immunoglobulin sequences also include germline antibody sequences. Framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836. In still other examples, antibody and corresponding immunoglobulin sequences from other known entities which may be in early discovery and/or drug development may be similarly adapted as starting material to engineer a modified antibody cytokine engrafted protein.

A wide variety of antibody/immunoglobulin frameworks or scaffolds can be employed so long as the resulting polypeptide includes at least one binding region which accommodates incorporation of a cytokine (e.g., IL10M). Such frameworks or scaffolds include the 5 main idiotypes of human immunoglobulins, or fragments thereof, and include immunoglobulins of other animal species, preferably having humanized and/or human aspects. Novel antibodies, frameworks, scaffolds and fragments continue to be discovered and developed by those skilled in the art.

Antibodies can be generated using methods that are known in the art. For preparation of monoclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies for use in antibody cytokine engrafted proteins of this disclosure. Also, transgenic mice, or other organisms such as other mammals, may be used to express and identify primatized or humanized or human antibodies. Alternatively, phage display technology can be used to identify antibodies and heteromeric Fab fragments that specifically bind to selected antigens for use in antibody cytokine engrafted proteins. (see, e.g., McCafferty et al., supra; Marks et al., Biotechnology, 10:779-783, (1992)).

Methods for primatizing or humanizing non-human antibodies are well known in the art. Generally, a primatized or humanized antibody has one or more amino acid residues introduced into it from a source which is non-primate or non-human. Such non-primate or non-human amino acid residues are often referred to as import residues, which are typically taken from an import variable domain. Humanization can be essentially performed following the method of Winter and co-workers (see, e.g., Jones et al., Nature 321: 522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, primatized or humanized antibodies are typically primate or human antibodies in which some complementary determining region ("CDR") residues and possibly some framework ("FR") residues are substituted by residues from analogous sites in an originating species (e.g., rodent antibodies) to confer binding specificity.

Alternatively or additionally, an in vivo method for replacing a nonhuman antibody variable region with a human variable region in an antibody while maintaining the same or providing better binding characteristics relative to that of the nonhuman antibody can be utilized to convert non-human antibodies into engineered human antibodies. See, e.g., U.S. Patent Publication No. 20050008625, U.S. Patent Publication No. 2005/0255552. Alternatively, human V segment libraries can be generated by sequential cassette replacement in which only part of the reference antibody V segment is initially replaced by a library of human sequences; and identified human "cassettes" supporting binding in the context of residual reference antibody amino acid sequences are then recombined in a second library screen to generate completely human V segments (see, U.S. Patent Publication No. 2006/0134098).

Various antibodies or antigen-binding fragments for use in preparation of antibody cytokine engrafted proteins can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including engrafted of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources. Selected immunoglobulin sequences may thus be utilized in preparation of antibody cytokine engrafted proteins as provided herein.

Antibodies or antigen-binding molecules of use in the present disclosure further include bispecific antibodies. A bispecific or bifunctional antibody is an artificial hybrid antibody having two different heavy/light chain pairs and two different binding sites. Other antigen-binding fragments or antibody portions include bivalent scFv (diabody), bispecific scFv antibodies where the antibody molecule recognizes two different epitopes, single binding domains (dAbs), and minibodies. Selected immunoglobulin sequences can be utilized in preparation of antibody cytokine engrafted proteins as provided herein.

Antigen-binding fragments of antibodies e.g., a Fab fragment, scFv, can be used as building blocks to construct antibody cytokine engrafted proteins, and optionally include multivalent formats. In some embodiments, such multivalent molecules comprise a constant region of an antibody (e.g., Fc).

Antibody cytokine engrafted proteins can be engineered by modifying one or more residues within one or both variable regions (i.e., VH and/or VL) of an antibody, for example within one or more CDR regions, and such adapted VH and/or VL region sequences utilized for incorporation of a cytokine for preparation of antibody cytokine engrafted protein. One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. CDR sequences are responsible for most antibody-antigen interactions, it is possible to express recombinant antibodies that mimic the properties of a specific antibody by constructing expression vectors that include CDR sequences from a specific antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.). In certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

In some aspects mutation of amino acid residues within the VH and/or VL CDR1, CDR2, and/or CDR3 regions to thereby improve one or more binding properties (e.g., affinity) of the antibody of interest, known as "affinity maturation," can be beneficial, e.g., to optimize antigen binding of an antibody in conjunction with the context of the cytokine engrafted protein. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples and/or alternative or additional assays known in the art. Conservative modifications can be introduced. The mutations may be amino acid substitutions, additions or deletions. Moreover, typically no more than one, two, three, four or five residues within a CDR region are altered.

Engineered antibodies or antibody fragments include those in which modifications have been made to framework residues within VH and/or VL, e.g. to improve the properties of the antibody. In some embodiments such framework modifications are made to decrease immunogenicity of the antibody. For example, one approach is to "backmutate" one or more framework residues to the corresponding germline sequence. More specifically, an antibody that has undergone somatic mutation contains framework residues that differ from germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the disclosure. Additional framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 2003/0153043 by Carr et al.

Constant regions of the antibodies or antibody fragments utilized for preparation of the antibody cytokine engrafted proteins can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments antibodies utilized in antibody cytokine engrafted proteins are engineered to generate humanized or Humaneered® antibodies. In some embodiments antibodies utilized in antibody cytokine engrafted proteins are human antibodies. In some embodiments, antibody constant region isotype is IgG, for example, IgG1, IgG2, IgG3, IgG4. In certain embodiments the constant region isotype is $IgG_1$. In some embodiments, antibody cytokine engrafted proteins comprise an IgG. In some embodiments, antibody cytokine engrafted proteins comprise an IgG1 Fc. In some embodiments, antibody cytokine engrafted proteins comprise an IgG2 Fc.

In addition or alternative to modifications made within framework or CDR regions, antibodies or antibody fragments utilized in preparation of antibody cytokine engrafted proteins can be engineered to include modifications within an Fc region, typically to alter one or more functional properties of the antibody, such as, e.g., serum half-life, complement fixation, Fc receptor binding, and/or antigen-dependent cellular cytotoxicity. Furthermore, an antibody or antibody fragment can be chemically modified (e.g., one or more chemical moieties can be attached to the antibody) or be modified to alter its glycosylation, again to alter one or more functional properties of the antibody cytokine engrafted protein.

In one embodiment, a hinge region of CH1 is modified such that the number of cysteine residues in the hinge region is altered, e.g., increased or decreased. For example, by the approach is described further in U.S. Pat. No. 5,677,425 by Bodmer et al. wherein the number of cysteine residues in the hinge region of CH1 is altered to, for example, facilitate assembly of the light and heavy chains or to increase or decrease the stability of the antibody cytokine engrafted protein. In another embodiment, an Fc hinge region of an antibody is mutated to alter the biological half-life of the antibody cytokine engrafted protein. More specifically, one or more amino acid mutations are introduced into the CH2-CH3 domain interface region of the Fc-hinge fragment such that the antibody cytokine engrafted protein has impaired Staphylococcyl protein A (SpA) binding relative to native Fc-hinge domain SpA binding. This approach is described in further detail in U.S. Pat. No. 6,165,745 by Ward et al.

The present disclosure provides for antibody cytokine engrafted proteins that specifically bind to IL10R protein which have an extended half-life in vivo. In another embodiment, an antibody cytokine engrafted protein is modified to increase its biological half-life. Various approaches are possible. Antibody cytokine engrafted proteins having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). For example, one or more of the following mutations can be introduced: T252L, T254S, T256F, as described in U.S. Pat. No. 6,277,375 to Ward. See, e.g., International Publication No. WO 98/23289; International Publication No. WO 97/34631; and U.S. Pat. No. 6,277,375. Alternatively, to increase the biological half-life, the antibody cytokine engrafted protein is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effector functions of the antibody cytokine engrafted protein. For example, one or more amino acids can be replaced with a different amino acid residue such that the antibody cytokine engrafted protein has an altered affinity for an effector ligand but retains antigen-binding ability of the parent antibody. The effector ligand to which affinity is altered can be, for example, an Fc receptor (FcR) or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody cytokine engrafted protein has altered C1q binding and/or reduced or abolished complement dependent cytotoxicity (CDC). This approach is described in further detail in U.S. Pat. No. 6,194,551 by Idusogie et al.

Antibody cytokine engrafted proteins containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235. In some embodiments, amino acid residue N267 of the IgG1 constant region is substituted to Ala267.

In another embodiment, one or more amino acid residues are altered to thereby alter the ability of the antibody cytokine engrafted protein to fix complement. This approach is described further in PCT Publication WO 94/29351 by Bodmer et al.

In yet another embodiment, an Fc region is modified to increase the ability of the antibody to mediate antibody dependent cellular cytotoxicity (ADCC) and/or to increase the affinity of the antibody cytokine engrafted protein for an Fcγ receptor by modifying one or more amino acids. This approach is described further in PCT Publication WO00/42072 by Presta. Moreover, binding sites on human IgG1 for FcγR1, FcγRII, FcγRIII and FcRn have been mapped and variants with improved binding have been described (see Shields, R. L. et al., 2001 J. Biol. Chem. 276:6591-6604).

In still another embodiment, glycosylation of an antibody cytokine engrafted protein is modified. For example, an aglycoslated antibody cytokine engrafted protein can be made (i.e., the antibody cytokine engrafted protein lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody cytokine engrafted protein can be made that has an altered type of glycosylation, such as a hypofucosylated antibody cytokine engrafted protein having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody cytokine engrafted protein in a host cell with altered glycosylation machinery. Cells with altered glycosylation machinery have been described in the art and can be used as host cells in which to express recombinant antibody cytokine engrafted proteins to thereby produce an antibody cytokine engrafted protein with altered glycosylation. For example, EP 1,176,195 by Hang et al. describes a cell line with a functionally disrupted FUT8 gene, which encodes a fucosyl transferase, such that antibody cytokine engrafted proteins expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibody cytokine engrafted proteins expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibody cytokine engrafted proteins expressed in the engineered cell lines exhibit increased bisecting GlcNac structures which results in increased ADCC activity of the antibodies (see also Umana et al., 1999 Nat. Biotech. 17:176-180).

In some embodiments, one or more domains, or regions, of an antibody cytokine engrafted protein are connected via a linker, for example, a peptide linker, such as those that are well known in the art (see e.g., Holliger, P., et al. (1993) Proc. Natl. Acad. Sci. USA 90:6444-6448; Poljak, R J., et al. (1994) Structure 2:1121-1123). A peptide linker may vary in length, e.g., a linker can be 1-100 amino acids in length, typically a linker is from five to 50 amino acids in length, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, monomeric IL10 is incorporated into the CDR sequence optionally with one or more peptide linker sequences. In certain embodiments one or more peptide linkers is independently selected from a $(Gly_n\text{-}Ser)_m$ sequence, a $(Gly_n\text{-}Ala)_m$ sequence, or any combination of a $(Gly_n\text{-}Ser)_m/(Gly_n\text{-}Ala)_m$ sequence, wherein each n is independently an integer from 1 to 5 and each m is independently an integer from 0 to 10. In some embodiments a peptide linker is $(Gly4\text{-}Ser)_m$ wherein m is an integer from 0 to 10. In some embodiments a peptide linker is $(Gly4\text{-}Ala)_m$ wherein m is an integer from 0 to 10. Examples of linkers include, but are not limited to, certain embodiments one or more linkers include $G_4S$ repeats, e.g., the Gly-Ser linker GGGGS (SEQ ID NO:252), or $(GGGGS)_m$ wherein m is a positive integer equal to or greater than 1. For example, m=1, m=2, m=3. m=4, m=5 and m=6, m=7, m=8, m=9 and m=10. In some embodiments, the linker includes multiple repeats of GGGGS (SEQ ID NO:252), including, but is not limited to $(GGGGS)_3$ or $(GGGGS)_4$. In some embodiments, Ser can be replaced with Ala e.g., linkers G/A such as (GGGGA) (SEQ ID NO: 253), or $(GGGGA)_m$ wherein m is a positive integer equal to or greater than 1. In some embodiments, the linker includes multiple repeats of GGGGA (SEQ ID NO:253). In other embodiments, a linker includes combinations and multiples of GGGGS (SEQ ID NO:252) and GGGGA (SEQ ID NO:253).

Moreover, the antibody cytokine engrafted proteins can be linked to marker sequences, such as a peptide to facilitate purification of antibody cytokine engrafted proteins. In preferred embodiments, a marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the engrafted protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Assays for Antibody Cytokine Engrafted Protein Activity

Assays for identifying antibody cytokine engrafted proteins are known in the art and are described herein. The antibody cytokine engrafted proteins bind to IL10 receptor (IL10R), and promote, induce and stimulate intracellular signaling resulting in anti-inflammatory effects as well as immunostimulatory effects.

Binding of the antibody cytokine engrafted proteins to IL-10R can be determined using any method known in the art. For example, binding to IL-10R can be determined using known techniques, including without limitation ELISA, Western blots, surface plasmon resonance (e.g., BIAcore), and flow cytometry.

Intracellular signaling through IL-10R can be measured using any method known in the art. For example, activation through IL-10R promotes STAT3 phosphorylation and signaling. Methods for measuring STAT3 activation are standard in the art (e.g., phosphorylation status of STAT3 protein, reporter gene assays, downstream signaling assays, etc.). Activation through IL-10R has anti-inflammatory effects, including suppression of pro-inflammatory cytokines as well as differentiation and proliferation of macrophages. Additionally, activation through IL-10R has immunostimulatory effects including stimulation of B cell proliferation, mast cell proliferation (e.g., MC/9), and natural killer (NK) cell proliferation and proliferation of activated $CD8^+$ T cells, as well as induction of certain pro-inflammatory cytokines. Methods for measuring proliferation of cells are standard in the art (e.g., $^3$H-thymidine incorporation assays, CFSE labeling). Methods for measuring cytokine production are well known in the art (e.g., ELISA assays, ELISpot assays). In performing in vitro assays, test cells or culture supernatant from test cells contacted with an agonist antibody cytokine engrafted proteins can be compared to control cells or culture supernatants from control cells that have not been contacted with an agonist antibody cytokine engrafted proteins and/or those that have been contacted with recombinant human IL10 (rhIL10).

IL10 receptor agonist activity of the antibody cytokine engrafted proteins can also be measured ex vivo and/or in vivo. In some aspects, methods for measuring STAT3 activation across various cell types ex vivo from animals treated with antibody cytokine engrafted proteins as compared to untreated control animals and/or animals similarly treated with rhIL10 may be used to show differential activity of the antibody engrafted proteins across cell types. Preferred antibody cytokine engrafted proteins have the ability to activate and expand monocytes. For example, in vivo activation and expansion of monocytes can be measured using any method known in the art, e.g., by flow cytometry. Antibody cytokine engrafted proteins can be therapeutically useful in suppressing levels of pro-inflammatory response following stimulation. Levels of pro-inflammatory cytokines can be measured using any method known in the art in samples isolated from animals treated with an antibody cytokine engrafted protein before, during and/or after treatment with a stimulatory agent (eg., LPS), and results may be compared to non-treated control animals and/or animals similarly treated with recombinant human IL10 (rhIL10) therapy. Preferred agonist antibody cytokine engrafted proteins can be therapeutically useful in preventing, reducing, inhibiting or eliminating inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD). The efficacy of the agonist antibody cytokine engrafted proteins can be determined by administering a therapeutically effective amount of the antibody cytokine engrafted protein to a subject and comparing the subject before and after administration of the antibody cytokine engrafted protein. Efficacy of the agonist antibody cytokine engrafted protein in therapy for inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD) also can be determined by administering a therapeutically effective amount of an antibody cytokine engrafted protein to a test subject and comparing the test subject to a control subject who has not been administered the antibody cytokine engrafted protein and/or comparison to a subject similarly treated with rhIL10.

Polynucleotides Encoding Antibody Cytokine Engrafted Proteins

In another aspect, isolated nucleic acids encoding heavy and light chain proteins of the antibody cytokine engrafted proteins are provided. Antibody cytokine engrafted proteins can be produced by any means known in the art, including but not limited to, recombinant expression, chemical synthesis, and enzymatic digestion of antibody tetramers. Recombinant expression can be from any appropriate host cells known in the art, for example, mammalian host cells, bacterial host cells, yeast host cells, insect host cells, etc.

Provided herein are polynucleotides that encode the variable regions exemplified in any one of SEQ ID NO:109, SEQ ID NO:110, SEQ ID NO:205, and SEQ ID NO:206; the variable regions exemplified in any one of SEQ ID NO:111, SEQ ID NO:112, SEQ ID NO:207, SEQ ID NO:208, the CDRs exemplified in any one of SEQ ID NO:109, SEQ ID NO:110, SEQ ID NO:205, and SEQ ID NO:206; the heavy and light chains exemplified in any one of SEQ ID NO:111, SEQ ID NO:112, SEQ ID NO:207 and SEQ ID NO:208.

The disclosure thus provides polynucleotides encoding the heavy and/or light chain polypeptides of the antibody cytokine engrafted proteins described herein, e.g., polynucleotides encoding heavy or light chain variable regions or segments comprising the complementary determining regions as described herein. In some embodiments, the polynucleotide encoding the heavy chain variable regions comprises a sequence having at least 85%, 89%, 90%, 91%, 92%, 93%, 94%, 95%, 96%, 97%, 98%, 99%, or 100% nucleic acid sequence identity with a polynucleotide of SEQ ID NO:242. In some embodiments, the polynucleotide encoding the light chain variable regions comprises a sequence having at least 85%, 89%, 90%, 91%, 92%, 93%, 94%, 95%, 96%, 97%, 98%, 99%, or 100% nucleic acid sequence identity with a polynucleotide of SEQ ID NO:243.

In some embodiments, the polynucleotide encoding the heavy chain variable regions comprises a sequence having at least 85%, 89%, 90%, 91%, 92%, 93%, 94%, 95%, 96%, 97%, 98%, 99%, or 100% nucleic acid sequence identity with a polynucleotide of SEQ ID NO:246. In some embodiments, the polynucleotide encoding the light chain variable regions comprises a sequence having at least 85%, 89%, 90%, 91%, 92%, 93%, 94%, 95%, 96%, 97%, 98%, 99%, or 100% nucleic acid sequence identity with a polynucleotide of SEQ ID NO:247.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:244. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:245.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:248. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide selected of SEQ ID NO:249.

Polynucleotides can encode the variable region sequence of an antibody cytokine engrafted protein. They can also encode both a variable region and a constant region of the antibody cytokine engrafted protein. Some of the polynucleotide sequences encode a polypeptide that comprises variable regions of both the heavy chain and the light chain of one of the antibody cytokine engrafted proteins. Some other polynucleotides encode two polypeptide segments that respectively are substantially identical to the variable regions of the heavy chain and the light chain of one of the antibody protein engrafted proteins.

In certain embodiments polynucleotides or nucleic acids comprise DNA. In other embodiments polynucleotides or nucleic acids comprise RNA, which may be single stranded or double stranded.

In some embodiments a recombinant host cell comprising the nucleic acids encoding one or more cytokine engrafted protein or fragment thereof, and optionally, secretion signals are provided. In certain embodiments a recombinant host cell comprises a vector encoding an antibody cytokine engrafted protein or fragment thereof and secretion signals. In other certain embodiments a recombinant host cell comprises one or more vectors encoding two immunoglobulin protein chains of the antibody cytokine engrafted protein and secretion signals. In some embodiments a recombinant host cell comprises a single vector encoding two immunoglobulin protein chains of the antibody cytokine engrafted protein and secretion signals. In some embodiments a recombinant host cell comprises two vectors, one encoding a heavy chain immunoglobulin protein chain, and another encoding a light chain immunoglobulin protein chain of the heterodimer of the antibody cytokine engrafted protein, with each including secretion signals. A recombinant host cell may be a prokaryotic or eukaryotic cell. In some embodiments a host cell is a eukaryotic cell line. In some embodiments a host cell is a mammalian cell line.

Additionally provided are methods for producing the antibody cytokine engrafted proteins. In some embodiments the method comprises the steps of (i) culturing a host cell comprising one or more vectors encoding immunoglobulin protein chains of an antibody cytokine engrafted protein under conditions suitable for expression, formation, and secretion of the antibody cytokine engrafted protein and (ii) recovering the antibody cytokine engrafted protein.

The polynucleotide sequences can be produced by de novo solid-phase DNA synthesis or by PCR mutagenesis of an existing sequence (e.g., sequences as described herein) encoding a polypeptide chain of an antibody cytokine engrafted protein. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the disclosure are expression vectors and host cells for producing the antibody cytokine engrafted proteins described above. Various expression vectors can be employed to express polynucleotides encoding the immunoglobulin polypeptide chains, or fragments, of the antibody cytokine engrafted proteins. Both viral-based and nonviral expression vectors can be used to produce the immunoglobulin proteins in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the antibody cytokine engrafted protein polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding the antibody cytokine engrafted protein. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an immunoglobulin chain or fragment of the antibody cytokine engrafted proteins. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

Expression vectors can also provide a secretion signal sequence to form a heterologous protein in addition to sequences encoded by the antibody cytokine engrafted protein sequences. More often, the inserted immunoglobulin sequences of the antibody cytokine engrafted proteins are operably linked to a signal sequence before inclusion in the vector. Vectors to be used to receive sequences encoding immunoglobulin light and heavy chain variable domains sometimes also encode constant regions or parts thereof. Such vectors allow expression of the variable regions as antibody cytokine engrafted proteins with the constant regions, thereby leading to production of intact antibody cytokine engrafted proteins or fragments thereof. Typically, such constant regions are human.

Host cells for harboring and expressing the antibody cytokine engrafted protein chains can be either prokaryotic or eukaryotic. *E. coli* is one prokaryotic host useful for cloning and expressing the polynucleotides of the present disclosure. Other microbial hosts suitable for use include bacilli, such as Bacillus subtilis, and other enterobacteriaceae, such as Salmonella, Serratia, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express antibody cytokine engrafted proteins. Insect cells in combination with baculovirus vectors can also be used.

In some preferred embodiments, mammalian host cells are used to express and produce the antibody cytokine engrafted proteins of the present disclosure. For example, they can be a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, engrafted to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express antibody cytokine engrafted protein immunoglobulin chains can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Compositions Comprising Antibody Cytokine Engrafted Proteins

Provided are pharmaceutical compositions comprising an antibody cytokine engrafted protein formulated together with a pharmaceutically acceptable carrier. Optionally, pharmaceutical compositions additionally contain other therapeutic agents that are suitable for treating or preventing a given disorder. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. Route and/or mode of administration vary depending upon the desired results. It is preferred that administration be by parenteral administration (e.g., selected from any of intravenous, intramuscular, intraperitoneal, intrathecal, intraarterial, or subcutaneous), or administered proximal to the site of the target. A pharmaceutically acceptable carrier is suitable for administration by any one or more of intravenous, intramuscular, intraperitoneal, intrathecal, intraarterial, subcutaneous, intranasal, inhalational, spinal or epidermal administration (e.g., by injection or infusion). Depending on the route of administration, active compound, e.g., antibody cytokine engrafted protein, may be coated in a material to protect the compound from the action of acids and other natural conditions that may inactivate the compound. In some embodiments the pharmaceutical composition is formulated for intravenous administration. In some embodiments the pharmaceutical composition is formulation for subcutaneous administration.

An antibody cytokine engrafted protein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, a pharmaceutical composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. In certain embodiments compositions can be prepared for storage in a lyophilized form using appropriate excipients (e.g., sucrose).

Pharmaceutical compositions can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present disclosure. Applicable methods for formulating an antibody cytokine engrafted protein and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of an antibody cytokine engrafted protein is employed in the pharmaceutical compositions. An antibody cytokine engrafted protein is formulated into pharmaceutically acceptable dosage form by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Co-Formulation with Second Agent

In some embodiments, the pharmacological compositions comprise a mixture of an antibody cytokine engrafted protein and one or more additional pharmacological agent(s). Exemplary second agents for inclusion in mixtures with the present antibody cytokine engrafted protein include without limitation anti-inflammatory agents, immunomodulatory agents, aminosalicylates, and antibiotics. Appropriate selection may depend on preferred formulation, dosage and/or delivery method.

In some embodiments an antibody cytokine engrafted protein is co-formulated (i.e., provided as a mixture or prepared in a mixture) with an anti-inflammatory agent. In particular embodiments, corticosteroid anti-inflammatory agents can be used in conjunction with the antibody cytokine engrafted protein. Corticosteroids for use can be selected from any of methylprednisolone, hydrocortisone, prednisone, budenisonide, mesalamine, and dexamethasone. Appropriate selection will depend on formulation and delivery preferences.

In some embodiments, an antibody cytokine engrafted protein is co-formulated with an immunomodulatory agent. In particular embodiments, the immunomodulatory agent is selected from any of 6-mercaptopurine, azathioprine, cyclosporine A, tacrolimus, and methotrexate. In a particular embodiment, the immunomodulatory agent is selected from an anti-TNF agent (e.g., infliximab, adalimumab, certolizumab, golimumab), natalizumab, and vedolizumab.

In some embodiments an antibody cytokine engrafted protein is co-formulated with an aminosalicylate agent. In particular embodiments, an aminosalicylate is selected from sulfasalazine, mesalamine, balsalazide, olsalazine or other derivatives of 5-aminosalicylic acid.

In some embodiments an antibody cytokine engrafted protein is co-formulated with an antibacterial agent. Exemplary antibacterial agents include without limitation sulfonamides (e.g., sulfanilamide, sulfadiazine, sulfamethoxazole, sulfisoxazole, sulfacetamide), trimethoprim, quinolones (e.g., nalidixic acid, cinoxacin, norfloxacin, ciprofloxacin, ofloxacin, sparfloxacin, fleroxacin, perloxacin, levofloxacin, garenoxacin and gemifloxacin), methenamine, nitrofurantoin, penicillins (e.g., penicillin G, penicillin V, methicilin oxacillin, cloxacillin, dicloxacillin, nafcilin, ampicillin, amoxicillin, carbenicillin, ticarcillin, mezlocillin, and piperacillin), cephalosporins (e.g., cefazolin, cephalexin, cefadroxil, cefoxitin, cefaclor, cefprozil, cefuroxime, cefuroxime acetil, loracarbef, cefotetan, ceforanide, cefotaxime, cefpodoxime proxetil, cefibuten, cefdinir, cefditoren pivorxil, ceftizoxime, ceftriaxone, cefoperazone, ceftazidime, and cefepine), carbapenems (e.g., imipenem, aztreonam), and aminoglycosides (e.g., neomycin, kanamycin, streptomycin, gentamicin, toramycin, netilmicin, and amikacin).

Articles of Manufacture/Kits

In some aspects, an antibody cytokine engrafted protein is provided in an article of manufacture (i.e., a kit). The antibody cytokine engrafted protein is generally in a vial or a container. Thus, an article of manufacture comprises a container and a label or package insert, on or associated with the container. Suitable containers include, for example, a bottle, vial, syringe, solution bag, etc. As appropriate, the antibody cytokine engrafted protein can be in liquid or dried (e.g., lyophilized) form. The container holds a composition which, by itself or combined with another composition, is effective for preparing a composition for treating, preventing and/or ameliorating an immune related disorder. The label or package insert indicates the composition is used for treating, preventing and/or ameliorating an immune related disorder. Articles of manufacture (kits) comprising an antibody cytokine engrafted protein, as described herein, optionally contain one or more additional agent. In some embodiments, an article of manufacture (kit) contains antibody cytokine engrafted protein and a pharmaceutically acceptable diluent. In some embodiments an antibody cytokine engrafted protein is provided in an article of manufacture (kit) with one or more additional active agent in the same formulation (e.g., as mixtures). In some embodiments an antibody cytokine engrafted protein is provided in an article of manufacture (kit) with a second or third agent in separate formulations (e.g., in separate containers). In certain embodiments an article of manufacture (kit) contains aliquots of the antibody cytokine engrafted protein, wherein the aliquot provides for one or more doses. In some embodiments aliquots for multiple administrations are provided, wherein doses are uniform or varied. In particular embodiments varied dosing regimens are escalating or decreasing, as appropriate. In some embodiments dosages of an antibody cytokine engrafted protein and a second agent are independently uniform or independently varying. In certain embodiments, an article of manufacture (kit) comprises an additional agent selected from any of an anti-inflammatory agent, immunomodulatory agent, aminosalicylate, and antibiotic. Selection of one or more additional agent will depend on the dosage, delivery, and disease condition to be treated.

Methods of Treatment of and Use of Antibody Cytokine Engrafted Proteins in Immune Related Disorders Conditions Subject to Treatment or Prevention Antibody cytokine engrafted proteins find use in the treatment, amelioration or prophylaxis of immune related disorders. In one aspect, the disclosure provides methods of treatment of immune related disorders in an individual in need thereof, comprising administering to the individual a therapeutically effective amount of an antibody cytokine engrafted protein as described herein. The disclosure also provides in one aspect, an antibody cytokine engrafted protein for use as a therapeutic agent. In some embodiment an antibody cytokine engrafted protein is provided for use as a therapeutic agent in the treatment or prophylaxis of an immune related disorder in an individual. In some embodiments use of an antibody cytokine engrafted protein is provided for manufacture of a medicament for treatment of an immune related disorder in an individual in need thereof. In a further aspect, the disclosure provides a composition comprising such an antibody cytokine engrafted protein for use in treating or ameliorating an immune related disorder in an individual in need thereof.

For therapeutic purposes, an individual can have an immune related disorder. For preventative or prophylactic purposes, an individual may be in remission from an active state of immune related disorder or may anticipate future onset. In some embodiments, the patient has an immune related disorder, is suspected of having an immune related disorder, or is in remission from an immune related disorder. Immune related disorders subject to treatment with the antibody cytokine engrafted protein usually derive benefit from activation of IL10 receptor signaling, as described herein. Immune related disorders subject to treatment include without limitation: inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD).

Administration of Antibody Cytokine Engrafted Proteins

A physician or veterinarian can start doses of an antibody cytokine engrafted protein employed in a pharmaceutical composition at levels lower than that required to achieve the desired therapeutic effect and gradually increase the dosage until the desired effect is achieved. In general, effective doses of the compositions of the present disclosure vary depending upon many different factors, including the specific disease or condition to be treated, means of administration, target site, physiological state of the patient, whether a patient is human or an animal, other medications administered, and whether treatment is prophylactic or therapeutic. Treatment dosages typically require titration to optimize safety and efficacy. For administration with an antibody cytokine engrafted protein, dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

The antibody cytokine engrafted protein can be administered in single or divided doses. An antibody cytokine engrafted protein is usually administered on multiple occasions. Intervals between single dosages can be weekly, bi-weekly, monthly or yearly, as needed or desired. Intervals can also be irregular as indicated by measuring blood levels of antibody cytokine engrafted protein in the patient. In some methods, dosage is adjusted to achieve a plasma antibody cytokine engrafted protein concentration of 1-1000 µg/ml and in some methods 25-300 µg/ml. Alternatively, antibody cytokine engrafted protein can be administered as a sustained release formulation, in which case less frequent administration is required. Dosage and frequency vary depending on the half-life of the antibody cytokine engrafted protein in the patient. In general, antibody cytokine engrafted proteins show longer half-life than that of native cytokines (e.g. IL10). Dosage and frequency of administration can vary depending on whether treatment is prophylactic or therapeutic. In general for prophylactic applications, a relatively low dosage is administered at relatively infrequent intervals over a long period of time. Some patients continue to receive treatment for the duration of their lives. In general for therapeutic applications, a relatively high dosage in relatively short intervals is sometimes required until progression of the disease is reduced or terminated, and preferably until the patient shows partial or complete amelioration of symptoms of disease. Thereafter, a patient can be administered a prophylactic regime.

Co-Administration with a Second Agent

In some embodiments, an antibody cytokine engrafted protein is co-administered with one or more additional pharmacological agent(s). In some embodiments, an antibody cytokine engrafted protein and an additional one or more agent(s) are administered as a mixture. In some embodiments, an antibody cytokine engrafted protein and an additional one or more agent(s) are administered as separate formulations. In certain embodiments where separate formulations are utilized, administration is concurrent. In certain embodiments where separate formulations are utilized, administration is sequential. In certain embodiments where separate formulations are utilized, administration is via the same route. In certain embodiments where separate formulations are utilized, administration is via different routes. Exemplary additional agents for co-administration with an antibody cytokine engrafted protein include without limitation anti-inflammatory agents, immunomodulatory agents, aminosalicylates, and antibiotics. Appropriate selection may depend on preferred formulation, dosage and/or delivery method. The antibody cytokine engrafted proteins also find use in combination therapies with additional established procedures for treating immune related disorder conditions, e.g., surgery.

In some embodiments, an antibody cytokine engrafted protein is co-administered with an anti-inflammatory agent. In particular embodiments corticosteroid anti-inflammatory agents may be used in conjunction with the antibody cytokine engrafted protein. Corticosteroids for use may be selected from any of methylprednisolone, hydrocortisone, prednisone, budenisonide, mesalamine, and dexamethasone. Appropriate selection will depend on formulation and delivery preferences.

In some embodiments, an antibody cytokine engrafted protein is co-administered with an immunomodulatory agent. In certain embodiments, the immunomodulatory agent is selected from any of 6-mercaptopurine, azathioprine, cyclosporine A, tacrolimus, and methotrexate. In particular embodiments, an immunomodulatory agent is selected from an anti-TNF agent (e.g., infliximab, adalimumab, certolizumab, golimumab), natalizumab, and vedolizumab.

In some embodiments an antibody cytokine engrafted protein is co-administered with an aminosalicylate agent. In particular embodiments the aminosalicylate agent is selected from sulfasalazine, mesalamine, balsalazide, olsalazine or other derivatives of 5-aminosalicylic acid.

In some embodiments an antibody cytokine engrafted protein is co-administered with an antibacterial agent. Exemplary antibacterial agents include without limitation sulfonamides (e.g., sulfanilamide, sulfadiazine, sulfamethoxazole, sulfisoxazole, sulfacetamide), trimethoprim, quinolones (e.g., nalidixic acid, cinoxacin, norfloxacin, ciprofloxacin, ofloxacin, sparfloxacin, fleroxacin, perloxacin, levofloxacin, garenoxacin and gemifloxacin), methenamine, nitrofurantoin, penicillins (e.g., penicillin G, penicillin V, methicilin oxacillin, cloxacillin, dicloxacillin, nafcilin, ampicillin, amoxicillin, carbenicillin, ticarcillin, mezlocillin, and piperacillin), cephalosporins (e.g., cefazolin, cephalexin, cefadroxil, cefoxitin, cefaclor, cefprozil, cefuroxime, cefuroxime acetil, loracarbef, cefotetan, ceforanide, cefotaxime, cefpodoxime proxetil, cefibuten, cefdinir, cefditoren pivorxil, ceftizoxime, ceftriaxone, cefoperazone, ceftazidime, and cefepine), carbapenems (e.g., imipenem, aztreonam), and aminoglycosides (e.g., neomycin, kanamycin, streptomycin, gentamicin, toramycin, netilmicin, and amikacin).

EXAMPLES

Example 1: Creation of Immunoglobulin-IL10 Engrafted Constructs

Engrafted constructs IgGIL10M1, IgGIL10M2, IgGIL10M3, IgGIL10M4, IgGIL10M5, IgGIL10M6, IgGIL10M7, IgGIL10M8, IgGIL10M9, IgGIL10M10, IgGIL10M11, IgGIL10M12, IgGIL10M13, IgGIL10M14, and IgGIL10M15 were generated by engineering a monomeric IL10 sequence into CDR regions of various immunoglobulin scaffolds, then both heavy and light chain immunoglobulin chains were produced to generate final protein constructs. IgGIL10M engrafted constructs confer preferred therapeutic anti-inflammatory properties of IL10; however, IgGIL10M engrafted constructs have reduced proportional pro-inflammatory activity as compared with rhIL10.

To create antibody cytokine engrafted proteins, monomeric IL10 (IL10M), comprising residues 19-178 of full length IL10 with a six amino acid linker between residues 134 and 135 (SEQ ID NO: 209) was inserted into various CDR loops of immunoglobulin chain scaffold. Engrafted constructs were prepared using a variety of known immunoglobulin sequences which have been utilized in clinical settings as well as germline antibody sequences. Sequences of IL10M in two exemplary scaffolds, referred to as GFTX1 and GFTX3, are depicted in TABLE 1. Insertion points were selected to be the mid-point of the CDR loop based on available structural or homology model data. Antibody cytokine engrafted proteins were produced using standard molecular biology methodology utilizing recombinant DNA encoding the relevant sequences.

For example, a variable region of each antibody containing IL10M inserted into one of the six CDRs was synthesized. DNA encoding variable region was amplified via PCR and the resulting fragment was sub-cloned into vector containing either the light chain constant region or the heavy chain constant and Fc regions. In this manner IL10M antibody cytokine engrafted proteins were made corresponding to insertion of IL10M into each of the 6 CDRs (L1, L2, L3, H1, H2, H3). Resulting constructs are shown in TABLE 1. Transfections of the appropriate combination of heavy and light chain vectors results in the expression of a recombinant antibody with two grafted IL10M molecules (one IL10 monomer in each Fab arm). See FIG. 2.

The selection of which CDR is chosen for cytokine engraftment is chosen on the parameters of: the required biology, the biophysical properties and a favorable development profile. At this time, modeling software is only partially useful in predicting which CDR and which location within the CDR will provide the desired parameters, so therefore all six possible antibody cytokine grafts are made and then evaluated in biological assays. If the required biological activity was achieved, then the biophysical properties such as structural resolution of the antibody cytokine engrafted molecule was resolved.

By virtue of the grafting of IL10 into a CDR, the antibody portion of the antibody cytokine engrafted protein presents the IL10 monomer with a unique structure which influences the binding to the IL10 receptor as discussed below. There are no off-target effects due to the antibody portion. In addition, the Fc portion of the antibody cytokine engrafted protein has been modified to be fully silent regarding ADCC (Antibody Dependent Cell-mediated Cytotoxicity) and CDC (Complement-Dependent Cytotoxicity).

In summary, the insertion point in each CDR was chosen on a structural basis, with the hypothesis that grafting into the CDR would provide some level of steric hindrance to individual subunits of the IL10 receptor. The final selection of which CDR graft is best for a particular cytokine is based on desired biology and biophysical properties. The nature of the cytokine receptor, the cytokine/receptor interactions and the mechanism of signaling also played a role and this was resolved by comparing each individual antibody cytokine engrafted molecule for their respective properties. For example, engrafting of IL10 into the light chain CDR1 (CDRL1) produced the desired biological activity of activating monocytes but not other cells such as NK cells. This was seen in the exemplary antibody cytokine engrafted proteins IgGIL10M7 and IgGIL10M13.

TABLE 1

| SEQ ID NO: | Description | | Comments |
|---|---|---|---|
| 1 | CDRH1 of IgGIL10M1 (Chothia) | GFTFSSY | GFTX1 |
| 2 | CDRH2 of IgGIL10M1 (Chothia) | SGSGGS | GFTX1 |
| 3 | CDRH3 of IgGIL10M1 (Chothia) | TRTKRF | GFTX1 |
| 4 | CDRL 1 of IgGIL10M1 (Chothia) | SQSVSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNSSSY | GFTX1 Monomeric IL10 grafted into CDRL1. IL10 is bolded, underlined |
| 5 | CDRL2 of IgGIL10M1 (Chothia) | GAS | GFTX1 |
| 6 | CDRL3 of IgGIL10M1 (Chothia) | YGSSPL | GFTX1 |
| 7 | CDRH1 of IgGIL10M1 (Kabat) | SYAMS | GFTX1 |
| 8 | CDRH2 of IgGIL10M1 (Kabat) | AISGSGGSTYYGDSVKG | GFTX1 |
| 9 | CDRH3 of IgGIL10M1 (Kabat) | TRTKRF | GFTX1 |
| 10 | CDRL1 of IgGIL10M1 (Kabat) | RASQSVSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCEGGGSGGNKSKAVEQVKNAFNKLQEKGIYKAMSEFDIFINYIEAYMTMKIRNSSSYLA | GFTX1 Monomeric IL10 grafted into CDRL1. IL10 is bolded, underlined |
| 11 | CDRL2 of IgGIL10M1 (Kabat) | GASSRAT | GFTX1 |
| 12 | CDRL3 of IgGIL10M1 (Kabat) | QQYGSSPLT | GFTX1 |

TABLE 1-continued

| SEQ ID NO: | Description | | Comments |
|---|---|---|---|
| 13 | VH of IgGIL10M1 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSS | GFTX1 |
| 14 | VL of IgGIL10M1 | EIVLTQSPGTLSLSPGERATLSCRASQSVS PGQGTQSENSCTHFPGNLPNMLRDLRD AFSRVKTFFQMKDQLDNLLLKESLLED FKGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIE AYMTMKIRNSSSYLAWYQQKPGQAPRL LIYGASSRATGIPDRFSGSGSGTDFTLTISR LEPEDFAVYYCQQYGSSPLTFGGGTKVEI K | GFTX1 Monomeric IL10 grafted into CDRL1. |
| 15 | Heavy chain of IgGIL10M1 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSSASTKGPSVFPLAPSSKSTSGGTAALGC LVKDYFPEPVTVSWNSGALTSGVHTFPA VLQSSGLYSLSSVVTVPSSSLGTQTYICNV NHKPSNTKVDKRVEPKSCDKTHTCPPCP APELLGGPSVFLFPPKPKDTLMISRTPEVT CVVVDVSHEDPEVKFNWYVDGVEVHNA KTKPREEQYNSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK | GFTX1 |
| 16 | Light chain of IgGIL10M1 | EIVLTQSPGTLSLSPGERATLSCRASQSVS PGQGTQSENSCTHFPGNLPNMLRDLRD AFSRVKTFFQMKDQLDNLLLKESLLED FKGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNSSSYLAWYQQKPGQAPRLLIYGASS RATGIPDRFSGSGSGTDFTLTISRLEPEDFA VYYCQQYGSSPLTFGGGTKVEIKRTVAAP SVFIFPPSDEQLKSGTASVVCLLNNFYPRE AKVQWKVDNALQSGNSQESVTEQDSKD STYSLSSTLTLSKADYEKHKVYACEVTHQ GLSSPVTKSFNRGEC | GFTX1 Monomeric IL10 grafted into CDRL1. |
| 17 | CDRH1 of IgGIL10M2 (Chothia) | GFTFSSY | GFTX1 |
| 18 | CDRH2 of IgGIL10M2 (Chothia) | SGSGGS | GFTX1 |
| 19 | CDRH3 of IgGIL10M2 (Chothia) | TRTKRF | GFTX1 |
| 20 | CDRL1 of IgGIL10M2 (Chothia) | SQSVSSSY | GFTX1 |
| 21 | CDRL2 of IgGIL10M2 (Chothia) | GASSSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRN | GFTX1 Monomeric IL10 grafted into CDRL2. IL10 is bolded, underlined |

TABLE 1-continued

| SEQ ID NO: | Description | | Comments |
|---|---|---|---|
| 22 | CDRL3 of IgGIL10M2 (Chothia) | YGSSPL | GFTX1 |
| 23 | CDRH1 of IgGIL10M2 (Kabat) | SYAMS | GFTX1 |
| 24 | CDRH2 of IgGIL10M2 (Kabat) | AISGSGGSTYYGDSVKG | GFTX1 |
| 25 | CDRH3 of IgGIL10M2 (Kabat) | TRTKRF | GFTX1 |
| 26 | CDRL1 of IgGIL10M2 (Kabat) | RASQSVSSSYLA | GFTX1 |
| 27 | CDRL2 of IgGIL10M2 (Kabat) | GASSSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRNRAT | GFTX1 Monomeric IL10 grafted into CDRL2. IL10 is bolded, underlined |
| 28 | CDRL3 of IgGIL10M2 (Kabat) | QQYGSSPLT | GFTX1 |
| 29 | VH of IgGIL10M2 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSS | GFTX1 |
| 30 | VL of IgGIL10M2 | EIVLTQSPGTLSLSPGERATLSCRASQSVS SSYLAWYQQKPGQAPRLLIYGASSSPGQ GTQSENSCTHFPGNLPNMLRDLRDAFS RVKTFFQMKDQLDNLLLKESLLEDFK GYLGCQALSEMIQFYLEEVMPQAENQ DPDIKAHVNSLGENLKTLRLRLRRCHR FLPCENGGGSGGKSKAVEQVKNAFNK LQEKGIYKAMSEFDIFINYIEAYMTMKI RNRATGIPDRFSGSGSGTDFTLTISRLEPE DFAVYYCQQYGSSPLTFGGGTKVEIK | GFTX1 Monomeric IL10 grafted into CDRL2. |
| 31 | Heavy chain of IgGIL10M2 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSSASTKGPSVFPLAPSSKSTSGGTAALGC LVKDYFPEPVTVSWNSGALTSGVHTFPA VLQSSGLYSLSSVVTVPSSSLGTQTYICNV NHKPSNTKVDKRVEPKSCDKTHTCPPCP APELLGGPSVFLFPPKPKDTLMISRTPEVT CVVVDVSHEDPEVKFNWYVDGVEVHNA KTKPREEQYNSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK | GFTX1 |
| 32 | Light chain of IgGIL10M2 | EIVLTQSPGTLSLSPGERATLSCRASQSVS SSYLAWYQQKPGQAPRLLIYGASSSPGQ GTQSENSCTHFPGNLPNMLRDLRDAFS RVKTFFQMKDQLDNLLLKESLLEDFK GYLGCQALSEMIQFYLEEVMPQAENQ DPDIKAHVNSLGENLKTLRLRLRRCHR FLPCENGGGSGGKSKAVEQVKNAFNK LQEKGIYKAMSEFDIFINYIEAYMTMKI RNRATGIPDRFSGSGSGTDFTLTISRLEPE DFAVYYCQQYGSSPLTFGGGTKVEIKRTV AAPSVFIFPPSDEQLKSGTASVVCLLNNFY PREAKVQWKVDNALQSGNSQESVTEQDS KDSTYSLSSTLTLSKADYEKHKVYACEVT HQGLSSPVTKSFNRGEC | GFTX1 Monomeric IL10 grafted into CDRL2. IL10 is bolded, underlined |

TABLE 1-continued

| SEQ ID NO: | Description | | Comments |
|---|---|---|---|
| 33 | CDRH1 of IgGIL10M3 (Chothia) | GFTFSSY | GFTX1 |
| 34 | CDRH2 of IgGIL10M3 (Chothia) | SGSGGS | GFTX1 |
| 35 | CDRH3 of IgGIL10M3 (Chothia) | TRTKRF | GFTX1 |
| 36 | CDRL1 of IgGIL10M3 (Chothia) | SQSVSSSY | GFTX1 |
| 37 | CDRL2 of IgGIL10M3 (Chothia) | GAS | GFTX1 |
| 38 | CDRL3 of IgGIL10M3 (Chothia) | YGSSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNSPL | GFTX1 Monomeric IL10 grafted into CDRL3. IL10 is bolded, underlined |
| 39 | CDRH1 of IgGIL10M3 (Kabat) | SYAMS | GFTX1 |
| 40 | CDRH2 of IgGIL10M3 (Kabat) | AISGSGGSTYYGDSVKG | GFTX1 |
| 41 | CDRH3 of IgGIL10M3 (Kabat) | TRTKRF | GFTX1 |
| 42 | CDRL1 of IgGIL10M3 (Kabat) | RASQSVSSSYLA | GFTX1 |
| 43 | CDRL2 of IgGIL10M3 (Kabat) | GASSRAT | GFTX1 |
| 44 | CDRL3 of IgGIL10M3 (Kabat) | QQYGSSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNSPLT | GFTX1 Monomeric IL10 grafted into CDRL3. IL10 is bolded, underlined |
| 45 | VH of IgGIL10M3 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSS | GFTX1 |
| 46 | VL of IgGIL10M3 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNSPLTFGGGTKVEIK | GFTX1 Monomeric IL10 grafted into CDRL3. IL10 is bolded, underlined |
| 47 | Heavy chain of IgGIL10M3 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTKRFWGQGTLVT VSSASTKGPSVFPLAPSSKSTSGGTAALGC | GFTX1 |

TABLE 1-continued

| SEQ ID NO: | Description | | Comments |
|---|---|---|---|
| | | LVKDYFPEPVTVSWNSGALTSGVHTFPA VLQSSGLYSLSSVVTVPSSSLGTQTYICNV NHKPSNTKVDKRVEPKSCDKTHTCPPCP APELLGGPSVFLFPPKPKDTLMISRTPEVT CVVVDVSHEDPEVKFNWYVDGVEVHNA KTKPREEQYNSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK | |
| 48 | Light chain of IgGIL10M3 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSGGKSKAVE QVKNAFNKLQEKGIYKAMSEFDIFINYI EAYMTMKIRNSPLTFGGGTKVEIKRTVA APSVFIFPPSDEQLKSGTASVVCLLNNFYP REAKVQWKVDNALQSGNSQESVTEQDS KDSTYSLSSTLTLSKADYEKHKVYACEVT HQGLSSPVTKSFNRGEC | GFTX1 Monomeric IL10 grafted into CDRL3. |
| 49 | CDRH1 of IgGIL10M4 (Chothia) | GFTFSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRNSSY | GFTX1 Monomeric IL10 grafted into CDRH1. IL10 is bolded, underlined |
| 50 | CDRH2 of IgGIL10M4 (Chothia) | SGSGGS | GFTX1 |
| 51 | CDRH3 of IgGIL10M4 (Chothia) | TRTKRF | GFTX1 |
| 52 | CDRL1 of IgGIL10M4 (Chothia) | SQSVSSSY | GFTX1 |
| 53 | CDRL2 of IgGIL10M4 (Chothia) | GAS | GFTX1 |
| 54 | CDRL3 of IgGIL10M4 (Chothia) | YGSSPL | GFTX1 |
| 55 | CDRH1 of IgGIL10M4 (Kabat) | SPGQGTQSENSCTHFPGNLPNMLRDLR DAFSRVKTFFQMKDQLDNLLLKESLLE DFKGYLGCQALSEMIQFYLEEVMPQAE NQDPDIKAHVNSLGENLKTLRLRLRRC HRFLPCENGGGSGGKSKAVEQVKNAF NKLQEKGIYKAMSEFDIFINYIEAYMT MKIRNSSYAMS | GFTX1 Monomeric IL10 grafted into CDRH1. IL10 is bolded, underlined |
| 56 | CDRH2 of IgGIL10M4 (Kabat) | AISGSGGSTYYGDSVKG | GFTX1 |
| 57 | CDRH3 of IgGIL10M4 (Kabat) | TRTKRF | GFTX1 |
| 58 | CDRL1 of IgGIL10M4 (Kabat) | RASQSVSSSYLA | GFTX1 |
| 59 | CDRL2 of IgGIL10M4 (Kabat) | GASSRAT | GFTX1 |

TABLE 1-continued

| SEQ ID NO: | Description | | Comments |
|---|---|---|---|
| 60 | CDRL3 of IgGIL10M4 (Kabat) | QQYGSSPLT | GFTX1 |
| 61 | VH of IgGIL10M4 | EVQLLESGGGLVQPGGSLRLSCAASGFTF SPGQGTQSENSCTHFPGNLPNMLRDLR DAFSRVKTFFQMKDQLDNLLLKESLLE DFKGYLGCQALSEMIQFYLEEVMPQAE NQDPDIKAHVNSLGENLKTLRLRLRRC HRFLPCENGGGSGGKSKAVEQVKNAF NKLQEKGIYKAMSEFDIFINYIEAYMT MKIRNSSYAMSWVRQAPGKGLEWVSAI SGSGGSTYYGDSVKGRFTISRDNSKNTLY LQMNSLRAEDTAVYYCARTRTKRFWGQ GTLVTVSS | GFTX1 Monomeric IL10 grafted into CDRH1 |
| 62 | VL of IgGIL10M4 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIK | GFTX1 |
| 63 | Heavy chain of IgGIL10M4 | EVQLLESGGGLVQPGGSLRLSCAASGFTF SPGQGTQSENSCTHFPGNLPNMLRDLR DAFSRVKTFFQMKDQLDNLLLKESLLE DFKGYLGCQALSEMIQFYLEEVMPQAE NQDPDIKAHVNSLGENLKTLRLRLRRC HRFLPCENGGGSGGKSKAVEQVKNAF NKLQEKGIYKAMSEFDIFINYIEAYMT MKIRNSSYAMSWVRQAPGKGLEWVSAI SGSGGSTYYGDSVKGRFTISRDNSKNTLY LQMNSLRAEDTAVYYCARTRTKRFWGQ GTLVTVSSASTKGPSVFPLAPSSKSTSGGT AALGCLVKDYFPEPVTVSWNSGALTSGV HTFPAVLQSSGLYSLSSVVTVPSSSLGTQT YICNVNHKPSNTKVDKRVEPKSCDKTHT CPPCPAPELLGGPSVFLFPPKPKDTLMISR TPEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPPV LDSDGSFFLYSKLTVDKSRWQQGNVFSC SVMHEALHNHYTQKSLSLSPGK | GFTX1 Monomeric IL10 grafted into CDRH1 |
| 64 | Light chain of IgGIL10M4 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIKRTVAAPSVFIF PPSDEQLKSGTASVVCLLNNFYPREAKVQ WKVDNALQSGNSQESVTEQDSKDSTYSL SSTLTLSKADYEKHKVYACEVTHQGLSSP VTKSFNRGEC | GFTX1 |
| 65 | CDRH1 of IgGIL10M5 (Chothia) | GFTFSSY | GFTX1 |
| 66 | CDRH2 of IgGIL10M5 (Chothia) | SGSGSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRNGS | GFTX1 Monomeric IL10 grafted into CDRH2. IL10 is bolded, underlined |
| 67 | CDRH3 of IgGIL10M5 (Chothia) | TRTKRF | GFTX1 |
| 68 | CDRL1 of IgGIL10M5 (Chothia) | SQSVSSSY | GFTX1 |
| 69 | CDRL2 of IgGIL10M5 (Chothia) | GAS | GFTX1 |

TABLE 1-continued

| SEQ ID NO: | Description | | Comments |
|---|---|---|---|
| 70 | CDRL3 of IgGIL10M5 (Chothia) | YGSSPL | GFTX1 |
| 71 | CDRH1 of IgGIL10M5 (Kabat) | SYAMS | GFTX1 |
| 72 | CDRH2 of IgGIL10M5 (Kabat) | AISGSGSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNGSTYYGDSVKG | GFTX1 Monomeric IL10 grafted into CDRH2. IL10 is bolded, underlined |
| 73 | CDRH3 of IgGIL10M5 (Kabat) | TRTKRF | GFTX1 |
| 74 | CDRL1 of IgGIL10M5 (Kabat) | RASQSVSSSYLA | GFTX1 |
| 75 | CDRL2 of IgGIL10M5 (Kabat) | GASSRAT | GFTX1 |
| 76 | CDRL3 of IgGIL10M5 (Kabat) | QQYGSSPLT | GFTX1 |
| 77 | VH of IgGIL10M5 | EVQLLESGGGLVQPGGSLRLSCAASGFTF SSYAMSWVRQAPGKGLEWVSAISGSGSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNGSTYYGDSVKGRFTISRDNSKNTLY LQMNSLRAEDTAVYYCARTRTKRFWGQ GTLVTVSS | GFTX1 Monomeric IL10 grafted into CDRH2 |
| 78 | VL of IgGIL10M5 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIK | GFTX1 |
| 79 | Heavy chain of IgGIL10M5 | EVQLLESGGGLVQPGGSLRLSCAASGFTF SSYAMSWVRQAPGKGLEWVSAISGSGSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNGSTYYGDSVKGRFTISRDNSKNTLY LQMNSLRAEDTAVYYCARTRTKRFWGQ GTLVTVSSASTKGPSVFPLAPSSKSTSGGT AALGCLVKDYFPEPVTVSWNSGALTSGV HTFPAVLQSSGLYSLSSVVTVPSSSLGTQT YICNVNHKPSNTKVDKRVEPKSCDKTHT CPPCPAPELLGGPSVFLFPPKPKDTLMISR TPEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPPV LDSDGSFFLYSKLTVDKSRWQQGNVFSC SVMHEALHNHYTQKSLSLSPGK | GFTX1 Monomeric IL10 grafted into CDRH2 |
| 80 | Light chain of IgGIL10M5 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIKRTVAAPSVFIF PPSDEQLKSGTASVVCLLNNFYPREAKVQ WKVDNALQSGNSQESVTEQDSKDSTYSL SSTLTLSKADYEKHKVYACEVTHQGLSSP VTKSFNRGEC | GFTX1 |

TABLE 1-continued

| SEQ ID NO: | Description | | Comments |
|---|---|---|---|
| 81 | CDRH1 of IgGIL10M6 (Chothia) | GFTFSSY | GFTX1 |
| 82 | CDRH2 of IgGIL10M6 (Chothia) | SGSGGS | GFTX1 |
| 83 | CDRH3 of IgGIL10M6 (Chothia) | TRTSPGQGTQSENSCTHFPGNLPNMR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNKRF | GFTX1 Monomeric IL10 grafted into CDRH3. IL10 is bolded, underlined |
| 84 | CDRL1 of IgGIL10M6 (Chothia) | SQSVSSSY | GFTX1 |
| 85 | CDRL2 of IgGIL10M6 (Chothia) | GAS | GFTX1 |
| 86 | CDRL3 of IgGIL10M6 (Chothia) | YGSSPL | GFTX1 |
| 87 | CDRH1 of IgGIL10M6 (Kabat) | SYAMS | GFTX1 |
| 88 | CDRH2 of IgGIL10M6 (Kabat) | AISGSGGSTYYGDSVKG | GFTX1 |
| 89 | CDRH3 of IgGIL10M6 (Kabat) | TRTSPGQGTQSENSCTHFPGNLPNMR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNKRF | GFTX1 Monomeric IL10 grafted into CDRH3. IL10 is bolded, underlined |
| 90 | CDRL1 of IgGIL10M6 (Kabat) | RASQSVSSSYLA | GFTX1 |
| 91 | CDRL2 of IgGIL10M6 (Kabat) | GASSRAT | GFTX1 |
| 92 | CDRL3 of IgGIL10M6 (Kabat) | QQYGSSPLT | GFTX1 |
| 93 | VH of IgGIL10M6 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTSPGQGTQSENSC THFPGNLPNMLRDLRDAFSRVKTFFQM KDQLDNLLLKESLLEDFKGYLGCQALS EMIQFYLEEVMPQAENQDPDIKAHVNS LGENLKTLRLRRCHRFLPCENGGGS GGKSKAVEQVKNAFNKLQEKGIYKAM SEFDIFINYIEAYMTMKIRNKRFWGQGT LVTVSS | GFTX1 Monomeric IL10 grafted into CDRH3 |
| 94 | VL of IgGIL10M6 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIK | GFTX1 |
| 95 | Heavy chain of IgGIL10M6 | EVQLLESGGGLVQPGGSLRLSCAASGFTF SSYAMSWVRQAPGKGLEWVSAISGSGGS TYYGDSVKGRFTISRDNSKNTLYLQMNS LRAEDTAVYYCARTRTSPGQGTQSENSC THFPGNLPNMLRDLRDAFSRVKTFFQM KDQLDNLLLKESLLEDFKGYLGCQALS EMIQFYLEEVMPQAENQDPDIKAHVNS | GFTX1 Monomeric IL10 grafted into CDRH3 |

TABLE 1-continued

| SEQ ID NO: | Description | | Comments |
|---|---|---|---|
| | | LGENLKTLRLRLRRCHRFLPCENGGGS GGKSKAVEQVKNAFNKLQEKGIYKAM SEFDIFINYIEAYMTMKIRNKRFWGQGT LVTVSSASTKGPSVFPLAPSSKSTSGGTAA LGCLVKDYFPEPVTVSWNSGALTSGVHT FPAVLQSSGLYSLSSVVTVPSSSLGTQTYI CNVNHKPSNTKVDKRVEPKSCDKTHTCP PCPAPELLGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | |
| 96 | Light chain of IgGIL10M6 | EIVLTQSPGTLSLSPGERATLSCRASQSVS SSYLAWYQQKPGQAPRLLIYGASSRATGI PDRFSGSGSGTDFTLTISRLEPEDFAVYYC QQYGSSPLTFGGGTKVEIKRTVAAPSVFIF PPSDEQLKSGTASVVCLLNNFYPREAKVQ WKVDNALQSGNSQESVTEQDSKDSTYSL SSTLTLSKADYEKHKVYACEVTHQGLSSP VTKSFNRGEC | GFTX1 |
| 97 | CDRH1 of IgGIL10M7 (Chothia) | GFSLSTSGM | GFTX3 |
| 98 | CDRH2 of IgGIL10M7 (Chothia) | WWDDK | GFTX3 |
| 99 | CDRH3 of IgGIL10M7 (Chothia) | SMITNWYFDV | GFTX3 |
| 100 | CDRL1 of IgGIL10M7 (Chothia) | QLSSPGQGTQSENSCTHFPGNLPNMLR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNVGY | Monomeric IL10 grafted into CDRL1. IL10 is bolded, underlined |
| 101 | CDRL2 of IgGIL10M7 (Chothia) | DTS | GFTX3 |
| 102 | CDRL3 of IgGIL10M7 (Chothia) | GSGYPF | GFTX3 |
| 103 | CDRH1 of IgGIL10M7 (Kabat) | TSGMSVG | GFTX3 |
| 104 | CDRH2 of IgGIL10M7 (Kabat) | DIWWDDKKDYNPSLKS | GFTX3 |
| 105 | CDRH3 of IgGIL10M7 (Kabat) | SMITNWYFDV | GFTX3 |
| 106 | CDRL1 of IgGIL10M7 (Kabat) | KAQLSSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSGGKSKAVE QVKNAFNKLQEKGIYKAMSEFDIFINYI EAYMTMKIRNVGYMH | Monomeric IL10 grafted into CDRL1. IL10 is bolded, underlined |
| 107 | CDRL2 of IgGIL10M7 (Kabat) | DTSKLAS | GFTX3 |
| 108 | CDRL3 of IgGIL10M7 (Kabat) | FQGSGYPFT | GFTX3 |

TABLE 1-continued

| SEQ ID NO: | Description | | Comments |
|---|---|---|---|
| 109 | VH of IgGIL10M7 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 110 | VL of IgGIL10M7 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIK | Monomeric IL10 grafted into CDRL1. |
| 111 | Heavy chain of IgGIL10M7 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTCP PCPAPELLGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | GFTX3 |
| 112 | Light chain of IgGIL10M7 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIKRTVA APSVFIFPPSDEQLKSGTASVVCLLNNFYP REAKVQWKVDNALQSGNSQESVTEQDS KDSTYSLSSTLTLSKADYEKHKVYACEVT HQGLSSPVTKSFNRGEC | Monomeric IL10 grafted into CDRL1. |
| 113 | CDRH1 of IgGIL10M8 (Chothia) | GFSLSTSGM | GFTX3 |
| 114 | CDRH2 of IgGIL10M8 (Chothia) | WWDDK | GFTX3 |
| 115 | CDRH3 of IgGIL10M8 (Chothia) | SMITNWYFDV | GFTX3 |
| 116 | CDRL1 of IgGIL10M8 (Chothia) | QLSVGY | GFTX3 |
| 117 | CDRL2 of IgGIL10M8 (Chothia) | DTSPGQGTQSENSCTHFPGNLPNMLRD LRDAFSRVKTFFQMKDQLDNLLLKESL LEDFKGYLGCQALSEMIQFYLEEVMPQ AENQDPDIKAHVNSLGENLKTLRLRLR RCHRFLPCENGGGSGGKSKAVEQVKN AFNKLQEKGIYKAMSEFDIFINYIEAYM TMKIRNS | GFTX3 Monomeric IL10 grafted into CDRL2. IL10 is bolded, underlined |

TABLE 1-continued

| SEQ ID NO: | Description | | Comments |
|---|---|---|---|
| 118 | CDRL3 of IgGIL10M8 (Chothia) | GSGYPF | GFTX3 |
| 119 | CDRH1 of IgGIL10M8 (Kabat) | TSGMSVG | GFTX3 |
| 120 | CDRH2 of IgGIL10M8 (Kabat) | DIWWDDKKDYNPSLKS | GFTX3 |
| 121 | CDRH3 of IgGIL10M8 (Kabat) | SMITNWYFDV | GFTX3 |
| 122 | CDRL1 of IgGIL10M8 (Kabat) | KAQLSVGYMH | GFTX3 |
| 123 | CDRL2 of IgGIL10M8 (Kabat) | DTSPGQGTQSENSCTHFPGNLPNMLRD LRDAFSRVKTFFQMKDQLDNLLLKESL LEDFKGYLGCQALSEMIQFYLEEVMPQ AENQDPDIKAHVNSLGENLKTLRLRLR RCHRFLPCENGGGSGGKSKAVEQVKN AFNKLQEKGIYKAMSEFDIFINYIEAYM TMKIRNSKLAS | GFTX3 Monomeric IL10 grafted into CDRL2. IL10 is bolded, underlined |
| 124 | CDRL3 of IgGIL10M8 (Kabat) | FQGSGYPFT | GFTX3 |
| 125 | VH of IgGIL10M8 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 126 | VL of IgGIL10M8 | DIQMTQSPSTLSASVGDRVTITCKAQLSV GYMHWYQQKPGKAPKWYDTSPGQGT QSENSCTHFPGNLPNMLRDLRDAFSRV KTFFQMKDQLDNLLLKESLLEDFKGYL GCQALSEMIQFYLEEVMPQAENQDPDI KAHVNSLGENLKTLRLRLRRCHRFLPC ENGGGSGGKSKAVEQVKNAFNKLQEK GIYKAMSEFDIFINYIEAYMTMKIRNSK LASGVPSRFSGSGSGTAFTLTISSLQPDDF ATYYCFQGSGYPFTFGGGTKLEIK | GFTX3 Monomeric IL10 grafted into CDRL2. |
| 127 | Heavy chain of IgGIL10M8 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTCP PCPAPELLGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | GFTX3 |
| 128 | Light chain of IgGIL10M8 | DIQMTQSPSTLSASVGDRVTITCKAQLSV GYMHWYQQKPGKAPKLLIYDTSPGQGT QSENSCTHFPGNLPNMLRDLRDAFSRV KTFFQMKDQLDNLLLKESLLEDFKGYL GCQALSEMIQFYLEEVMPQAENQDPDI KAHVNSLGENLKTLRLRLRRCHRFLPC ENGGGSGGKSKAVEQVKNAFNKLQEK GIYKAMSEFDIFINYIEAYMTMKIRNSK LASGVPSRFSGSGSGTAFTLTISSLQPDDF ATYYCFQGSGYPFTFGGGTKLEIKRTVAA PSVFIFPPSDEQLKSGTASVVCLLNNFYPR EAKVQWKVDNALQSGNSQESVTEQDSK DSTYSLSSTLTLSKADYEKHKVYACE VTHQGLSSPVTKSFNRGEC | GFTX3 Monomeric IL10 grafted into CDRL2. |

TABLE 1-continued

| SEQ ID NO: | Description | | Comments |
|---|---|---|---|
| 129 | CDRH1 of IgGIL10M9 (Chothia) | GFSLSTSGM | GFTX3 |
| 130 | CDRH2 of IgGIL10M9 (Chothia) | WWDDK | GFTX3 |
| 131 | CDRH3 of IgGIL10M9 (Chothia) | SMITNWYFDV | GFTX3 |
| 132 | CDRL1 of IgGIL10M9 (Chothia) | QLSVGY | GFTX3 |
| 133 | CDRL2 of IgGIL10M9 (Chothia) | DTS | GFTX3 |
| 134 | CDRL3 of IgGIL10M9 (Chothia) | GSGSPGQGTQSENSCTHFPGNLPNMLR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNYPF | GFTX3 Monomeric IL10 grafted into CDRL3. IL10 is bolded, underlined |
| 135 | CDRH1 of IgGIL10M9 (Kabat) | TSGMSVG | GFTX3 |
| 136 | CDRH2 of IgGIL10M9 (Kabat) | DIWWDDKKDYNPSLKS | GFTX3 |
| 137 | CDRH3 of IgGIL10M9 (Kabat) | SMITNWYFDV | GFTX3 |
| 138 | CDRL1 of IgGIL10M9 (Kabat) | KAQLSVGYMH | GFTX3 |
| 139 | CDRL2 of IgGIL10M9 (Kabat) | DTSKLAS | GFTX3 |
| 140 | CDRL3 of IgGIL10M9 (Kabat) | FQGSGSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSGGKSKAVE QVKNAFNKLQEKGIYKAMSEFDIFINYI EAYMTMKIRNYPFT | GFTX3 Monomeric IL10 grafted into CDRL3. IL10 is bolded, underlined |
| 141 | VH of IgGIL10M9 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 142 | VL of IgGIL10M9 | DIQMTQSPSTLSASVGDRVTITCKAQLSV GYMHWYQQKPGKAPKLLIYDTSKLASG VPSRFSGSGSGTAFTLTISSLQPDDFATYY CFQGSGSPGQGTQSENSCTHFPGNLPN MLRDLRDAFSRVKTFFQMKDQLDNLL LKESLLEDFKGYLGCQALSEMIQFYLE EVMPQAENQDPDIKAHVNSLGENLKTL RLRLRRCHRFLPCENGGGSGGKSKAV EQVKNAFNKLQEKGIYKAMSEFDIFIN YIEAYMTMKIRNYPFTFGGGTKLEIK | GFTX3 Monomeric IL10 grafted into CDRL3. |
| 143 | Heavy chain of IgGIL10M9 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA ALGCLVKDYFPEPVTVSWNSGALTSGVH | GFTX3 |

TABLE 1-continued

| SEQ ID NO: | Description | | Comments |
|---|---|---|---|
| | | TFPAVLQSSGLYSLSSVVTVPSSSLGTQTY ICNVNHKPSNTKVDKRVEPKSCDKTHTCP PCPAPELLGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | |
| 144 | Light chain of IgGIL10M9 | DIQMTQSPSTLSASVGDRVTITCKAQLSV GYMHWYQQKPGKAPKLLIYDTSKLASG VPSRFSGSGSGTAFTLTISSLQPDDFATYY CFQGSGSPGQGTQSENSCTHFPGNLPN MLRDLRDAFSRVKTFFQMKDQLDNLL LKESLLEDFKGYLGCQALSEMIQFYLE EVMPQAENQDPDIKAHVNSLGENLKTL RLRLRRCHRFLPCENGGGSGGKSKAV EQVKNAFNKLQEKGIYKAMSEFDIFIN YIEAYMTMKIRNYPFTFGGGTKLEIKRT VAAPSVFIFPPSDEQLKSGTASVVCLLNNF YPREAKVQWKVDNALQSGNSQESVTEQ DSKDSTYSLSSTLTLSKADYEKHKVYACE VTHQGLSSPVTKSFNRGEC | GFTX3 Monomeric IL10 grafted into CDRL3. |
| 145 | CDRH1 of IgGIL10M10 (Chothia) | GFSLSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRNSTSGM | GFTX3 Monomeric IL10 grafted into CDRH1. IL10 is bolded, underlined |
| 146 | CDRH2 of IgGIL10M10 (Chothia) | WWDDK | GFTX3 |
| 147 | CDRH3 of IgGIL10M10 (Chothia) | SMITNWYFDV | GFTX3 |
| 148 | CDRL1 of IgGIL10M10 (Chothia) | QLSVGY | GFTX3 |
| 149 | CDRL2 of IgGIL10M10 (Chothia) | DTS | GFTX3 |
| 150 | CDRL3 of IgGIL10M10 (Chothia) | GSGYPF | GFTX3 |
| 151 | CDRH1 of IgGIL10M10 (Kabat) | SPGQGTQSENSCTHFPGNLPNMLRDLR DAFSRVKTFFQMKDQLDNLLLKESLLE DFKGYLGCQALSEMIQFYLEEVMPQAE NQDPDIKAHVNSLGENLKTLRLRLRRC HRFLPCENGGGSGGKSKAVEQVKNAF NKLQEKGIYKAMSEFDIFINYIEAYMT MKIRNSTSGMSVG | GFTX3 Monomeric IL10 grafted into CDRH1. IL10 is bolded, underlined |
| 152 | CDRH2 of IgGIL10M10 (Kabat) | DIWWDDKKDYNPSLKS | GFTX3 |
| 153 | CDRH3 of IgGIL10M10 (Kabat) | SMITNWYFDV | GFTX3 |
| 154 | CDRL1 of IgGIL10M10 (Kabat) | KAQLSVGYMH | GFTX3 |
| 155 | CDRL2 of IgGIL10M10 (Kabat) | DTSKLAS | GFTX3 |

TABLE 1-continued

| SEQ ID NO: | Description | | Comments |
|---|---|---|---|
| 156 | CDRL3 of IgGIL10M10 (Kabat) | FQGSGYPFT | GFTX3 |
| 157 | VH of IgGIL10M10 | QVTLRESGPALVKPTQTLTLTCTFSGFSLS PGQGTQSENSCTHFPGNLPNMLRDLRD AFSRVKTFFQMKDQLDNLLLKESLLED FKGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNSTSGMSVGWIRQPPGKALEWLADI WWDDKKDYNPSLKSRLTISKDTSANQVV LKVTNMDPADTATYYCARSMITNWYFD VWGAGTTVTVSS | GFTX3 Monomeric IL10 grafted into CDRH1 |
| 158 | VL of IgGIL10M10 | DIQMTQSPSTLSASVGDRVTITCKAQLSV GYMHWYQQKPGKAPKLLIYDTSKLASG VPSRFSGSGSGTAFTLTISSLQPDDFATYY CFQGSGYPFTFGGGTKLEIK | GFTX3 |
| 159 | Heavy chain of IgGIL10M10 | QVTLRESGPALVKPTQTLTLTCTFSGFSLS PGQGTQSENSCTHFPGNLPNMLRDLRD AFSRVKTFFQMKDQLDNLLLKESLLED FKGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNSTSGMSVGWIRQPPGKALEWLADI WWDDKKDYNPSLKSRLTISKDTSANQVV LKVTNMDPADTATYYCARSMITNWYFD VWGAGTTVTVSSASTKGPSVFPLAPSSKS TSGGTAALGCLVKDYFPEPVTVSWNSGA LTSGVHTFPAVLQSSGLYSLSSVVTVPSSS LGTQTYICNVNHKPSNTKVDKRVEPKSC DKTHTCPPCPAPELLGGPSVFLFPPKPKDT LMISRTPEVTCVVVDVSHEDPEVKFNWY VDGVEVHNAKTKPREEQYNSTYRVVSVL TVLHQDWLNGKEYKCKVSNKALPAPIEK TISKAKGQPREPQVYTLPPSREEMTKNQV SLTCLVKGFYPSDIAVEWESNGQPENNY K TTPPVLDSDGSFFLYSKLTVDKSRWQQG NVFSCSVMHEALHNHYTQKSLSLSPGK | GFTX3 Monomeric IL10 grafted into CDRH1 |
| 160 | Light chain of IgGIL10M10 | DIQMTQSPSTLSASVGDRVTITCKAQLSV GYMHWYQQKPGKAPKLLIYDTSKLASG VPSRFSGSGSGTAFTLTISSLQPDDFATYY CFQGSGYPFTFGGGTKLEIKRTVAAPSVFI FPPSDEQLKSGTASVVCLLNNFYPREAKV QWKVDNALQSGNSQESVTEQDSKDSTYS LSSTLTLSKADYEKHKVYACEVTHQGLSS PVTKSFNRGEC | GFTX3 |
| 161 | CDRH1 of IgGIL10M11 (Chothia) | GFSLSTSGM | GFTX3 |
| 162 | CDRH2 of IgGIL10M11 (Chothia) | WWDSPGQGTQSENSCTHFPGNLPNML RDLRDAFSRVKTFFQMKDQLDNLLLK ESLLEDFKGYLGCQALSEMIQFYLEEV MPQAENQDPDIKAHVNSLGENLKTLRL RLRRCHRFLPCENGGGSGGKSKAVEQ VKNAFNKLQEKGIYKAMSEFDIFINYIE AYMTMKIRNDK | GFTX3 Monomeric IL10 grafted into CDRH2. IL10 is bolded, underlined |
| 163 | CDRH3 of IgGIL10M11 (Chothia) | SMITNWYFDV | GFTX3 |
| 164 | CDRL1 of IgGIL10M11 (Chothia) | QLSVGY | GFTX3 |
| 165 | CDRL2 of IgGIL10M11 (Chothia) | DTS | GFTX3 |

TABLE 1-continued

| SEQ ID NO: | Description | | Comments |
|---|---|---|---|
| 166 | CDRL3 of IgGIL10M11 (Chothia) | GSGYPF | GFTX3 |
| 167 | CDRH1 of IgGIL10M11 (Kabat) | TSGMSVG | GFTX3 |
| 168 | CDRH2 of IgGIL10M11 (Kabat) | DIWWDSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSGGKSKAVE QVKNAFNKLQEKGIYKAMSEFDIFINYI EAYMTMKIRNDKKDYNPSLKS | GFTX3 Monomeric IL10 grafted into CDRH2. IL10 is bolded, underlined |
| 169 | CDRH3 of IgGIL10M11 (Kabat) | SMITNWYFDV | GFTX3 |
| 170 | CDRL1 of IgGIL10M11 (Kabat) | KAQLSVGYMH | GFTX3 |
| 171 | CDRL2 of IgGIL10M11 (Kabat) | DTSKLAS | GFTX3 |
| 172 | CDRL3 of IgGIL10M11 (Kabat) | FQGSGYPFT | GFTX3 |
| 173 | VH of IgGIL10M11 | QVTLRESGPALVKPTQTLTLTCTFSGFSLS TSGMSVGWIRQPPGKALEWLADIWWDSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNDKKDYNPSLKSRLTISKDTSANQVV LKVTNMDPADTATYYCARSMITNWYFD VWGAGTTVTVSS | GFTX3 Monomeric IL10 grafted into CDRH2 |
| 174 | VL of IgGIL10M11 | DIQMTQSPSTLSASVGDRVTITCKAQLSV GYMHWYQQKPGKAPKLLIYDTSKLASG VPSRFSGSGSGTAFTLTISSLQPDDFATYY CFQGSGYPFTFGGGTKLEIK | GFTX3 |
| 175 | Heavy chain of IgGIL10M11 | QVTLRESGPALVKPTQTLTLTCTFSGFSLS TSGMSVGWIRQPPGKALEWLADIWWDSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNDKKDYNPSLKSRLTISKDTSANQVV LKVTNMDPADTATYYCARSMITNWYFD VWGAGTTVTVSSASTKGPSVFPLAPSSKS TSGGTAALGCLVKDYFPEPVTVSWNSGA LTSGVHTFPAVLQSSGLYSLSSVVTVPSSS LGTQTYICNVNHKPSNTKVDKRVEPKSC DKTHTCPPCPAPELLGGPSVFLFPPKPKDT LMISRTPEVTCVVVDVSHEDPEVKFNWY VDGVEVHNAKTKPREEQYNSTYRVVSVL TVLHQDWLNGKEYKCKVSNKALPAPIEK TISKAKGQPREPQVYTLPPSREEMTKNQV SLTCLVKGFYPSDIAVEWESNGQPENNYK TTPPVLDSDGSFFLYSKLTVDKSRWQQG NVFSCSVMHEALHNHYTQKSLSLSPGK | GFTX3 Monomeric IL10 grafted into CDRH2 |
| 176 | Light chain of IgGIL10M11 | DIQMTQSPSTLSASVGDRVTITCKAQLSV GYMHWYQQKPGKA TABLE 1-continued

| SEQ ID NO: | Description | | Comments |
|---|---|---|---|
| 177 | CDRH1 of IgGIL10M12 (Chothia) | GFSLSTSGM | GFTX3 |
| 178 | CDRH2 of IgGIL10M12 (Chothia) | WWDDK | GFTX3 |
| 179 | CDRH3 of IgGIL10M12 (Chothia) | SMITSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNNWYFDV | GFTX3 Monomeric IL10 grafted into CDRH3. IL10 is bolded, underlined |
| 180 | CDRL1 of IgGIL10M12 (Chothia) | QLSVGY | GFTX3 |
| 181 | CDRL2 of IgGIL10M12 (Chothia) | DTS | GFTX3 |
| 182 | CDRL3 of IgGIL10M12 (Chothia) | GSGYPF | GFTX3 |
| 183 | CDRH1 of IgGIL10M12 (Kabat) | TSGMSVG | GFTX3 |
| 184 | CDRH2 of IgGIL10M12 (Kabat) | DIWWDDKKDYNPSLKS | GFTX3 |
| 185 | CDRH3 of IgGIL10M12 (Kabat) | SMITSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNNWYFDV | GFTX3 Monomeric IL10 grafted into CDRH3. IL10 is bolded, underlined |
| 186 | CDRL1 of IgGIL10M12 (Kabat) | KAQLSVGYMH | GFTX3 |
| 187 | CDRL2 of IgGIL10M12 (Kabat) | DTSKLAS | GFTX3 |
| 188 | CDRL3 of IgGIL10M12 (Kabat) | FQGSGYPFT | GFTX3 |
| 189 | VH of IgGIL10M12 | QVTLRESGPALVKPTQTLTLTCTFSGFSLSTSGMSVGWIRQPPGKALEWLADIWWDDKKDYNPSLKSRLTISKDTSANQVVLKVTNMDPADTATYYCARSMITSPGQGTQSENSCTHFPGNLPNMLRDLRDAFSRVKTFFQMKDQLDNLLLKESLLEDFKGYLGCQALSEMIQFYLEEVMPQAENQDPDIKAHVNSLGENLKTLRLRLRRCHRFLPCENGGGSGGKSKAVEQVKNAFNKLQEKGIYKAMSEFDIFINYIEAYMTMKIRNNWYFDVWGAGTTVTVSS | GFTX3 Monomeric IL10 grafted into CDRH3 |
| 190 | VL of IgGIL10M12 | DIQMTQSPSTLSASVGDRVTITCKAQLSVGYMHWYQQKPGKAPKLLIYDTSKLASGVPSRFSGSGSGTAFTLTISSLQPDDFATYYCFQGSGYPFTFGGGTKLEIK | GFTX3 |
| 191 | Heavy chain of IgGIL10M12 | QVTLRESGPALVKPTQTLTLTCTFSGFSLSTSGMSVGWIRQPPGKALEWLADIWWDDKKDYNPSLKSRLTISKDTSANQVVLKVTNMDPADTATYYCARSMITSPGQGTQSENSCTHFPGNLPNMLRDLRDAFSRVKTFFQMKDQLDNLLLKESLLEDFKGYLGCQA | GFTX3 Monomeric IL10 grafted into CDRH3 |

TABLE 1-continued

| SEQ ID NO: | Description | | Comments |
|---|---|---|---|
| | | LSEMIQFYLEEVMPQAENQDPDIKAHV NSLGENLKTLRLRLRRCHRFLPCENGG GSSGGKSKAVEQVKNAFNKLQEKGIYK AMSEFDIFINYIEAYMTMKIRNNWYFD VWGAGTTVTVSSASTKGPSVFPLAPSSKS TSGGTAALGCLVKDYFPEPVTVSWNSGA LTSGVHTFPAVLQSSGLYSLSSVVTVPSSS LGTQTYICNVNHKPSNTKVDKRVEPKSC DKTHTCPPCPAPELLGGPSVFLFPPKPKDT LMISRTPEVTCVVVDVSHEDPEVKFNWY VDGVEVHNAKTKPREEQYNSTYRVVSVL TVLHQDWLNGKEYKCKVSNKALPAPIEK TISKAKGQPREPQVYTLPPSREEMTKNQV SLTCLVKGFYPSDIAVEWESNGQPENNYK TTPPVLDSDGSFFLYSKLTVDKSRWQQG NVFSCSVMHEALHNHYTQKSLSLSPGK | |
| 192 | Light chain of IgGIL10M12 | DIQMTQSPSTLSASVGDRVTITCKAQLSV GYMHWYQQKPGKAPKLLIYDTSKLASG VPSRFSGSGSGTAFTLTISSLQPDDFATYY CFQGSGYPFTFGGGTKLEIKRTVAAPSVFI FPPSDEQLKSGTASVVCLLNNFYPREAKV QWKVDNALQSGNSQESVTEQDSKDSTYS LSSTLTLSKADYEKHKVYACEVTHQGLSS PVTKSFNRGEC | GFTX3 |
| 193 | CDRH1 of IgGIL10M13 (Chothia) | GFSLSTSGM | GFTX3 |
| 194 | CDRH2 of IgGIL10M13 (Chothia) | WWDDK | GFTX3 |
| 195 | CDRH3 of IgGIL10M13 (Chothia) | SMITNWYFDV | GFTX3 |
| 196 | CDRL1 of IgGIL10M13 (Chothia) | QLSSPGQGTQSENSCTHFPGNLPNMLR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSAVEQVK NAFNKLQEKGIYKAMSEFDIFINYIEAY MTMKIRNVGY | Monomeric IL10 grafted into CDRL1. IL10 is bolded, underlined |
| 197 | CDRL2 of IgGIL10M13 (Chothia) | DTS | GFTX3 |
| 198 | CDRL3 of IgGIL10M13 (Chothia) | GSGYPF | GFTX3 |
| 199 | CDRH1 of IgGIL10M13 (Kabat) | TSGMSVG | GFTX3 |
| 200 | CDRH2 of IgGIL10M13 (Kabat) | DIWWDDKKDYNPSLKS | GFTX3 |
| 201 | CDRH3 of IgGIL10M13 (Kabat) | SMITNWYFDV | GFTX3 |
| 202 | CDRL1 of IgGIL10M13 (Kabat) | KAQLSSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGSGGKSAVE QVKNAFNKLQEKGIYKAMSEFDIFINYI EAYMTMKIRNVGYMH | Monomeric IL10 grafted into CDRL1 IL10 is bolded, underlined GFTX3 |
| 203 | CDRL2 of IgGIL10M13 (Kabat) | DTSKLAS | GFTX3 |
| 204 | CDRL3 of IgGIL10M13 (Kabat) | FQGSGYPFT | GFTX3 |

TABLE 1-continued

| SEQ ID NO: | Description | | Comments |
|---|---|---|---|
| 205 | VH of IgGIL10M13 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 206 | VL of IgGIL10M13 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSYPFTFGGGTKLEIK | Monomeric IL10 grafted into CDRL1 GFTX3 |
| 207 | Heavy chain of IgGIL10M13 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTCP PCPAPELLGGPSVFLFPPKPKDTLMISRTP EVTCVVVAVSHEDPEVKFNWYVDGVEV HNAKTKPREEQYNSTYRVVSVLTVLHQD WLNGKEYKCKVSNKALAAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | GFTX3 |
| 208 | Light chain of IgGIL10M13 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSYPFTFGGGTKLEIKRTVA APSVFIFPPSDEQLKSGTASVVCLLNNFYP REAKVQWKVDNALQSGNSQESVTEQDS KDSTYSLSSTLTLSKADYEKHKVYACEVT HQGLSSPVTKSFNRGEC | Monomeric IL10 grafted into CDRL1 GFTX3 |
| 209 | Monomeric IL10 (IL10M) | SPGQGTQSENSCTHFPGNLPNMLRDLRD AFSRVKTFFQMKDQLDNLLLKESLLEDFK GYLGCQALSEMIQFYLEEVMPQAENQDP DIKAHVNSLGENLKTLRLRLRRCHRFLPC ENGGGSGGKSKAVEQVKNAFNKLQEKGI YKAMSEFDIFINYIEAYMTMKIRN | Mature form of IL10, with an internal G3SG2 spacer |
| 210 | CDRH1 of IgGIL10M14 (Chothia) | GFSLSTSGM | GFTX3 |
| 211 | CDRH2 of IgGIL10M14 (Chothia) | WWDDK | GFTX3 |
| 212 | CDRH3 of IgGIL10M14 (Chothia) | SMITNWYFDV | GFTX3 |
| 213 | CDRL1 of IgGIL10M14 (Chothia) | QLSSPGQGTQSENSCTHFPGNLPNMLR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNVGY | Monomeric IL10 grafted into CDRL1. IL10 is bolded, underlined GFTX3 |

TABLE 1-continued

| SEQ ID NO: | Description | | Comments |
|---|---|---|---|
| 214 | CDRL2 of IgGIL10M14 (Chothia) | DTS | GFTX3 |
| 215 | CDRL3 of IgGIL10M14 (Chothia) | GSGYPF | GFTX3 |
| 216 | CDRH1 of IgGIL10M14 (Kabat) | TSGMSVG | GFTX3 |
| 217 | CDRH2 of IgGIL10M14 (Kabat) | DIWWDDKKDYNPSLKS | GFTX3 |
| 218 | CDRH3 of IgGIL10M14 (Kabat) | SMITNWYFDV | GFTX3 |
| 219 | CDRL1 of IgGIL10M14 (Kabat) | KAQLSSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSSGGKSKAVE QVKNAFNKLQEKGIYKAMSEFDIFINYI EAYMTMKIRNVGYMH | Monomeric IL10 grafted into CDRL1. IL10 is bolded, underlined GFTX3 |
| 220 | CDRL2 of IgGIL10M14 (Kabat) | DTSKLAS | GFTX3 |
| 221 | CDRL3 of IgGIL10M14 (Kabat) | FQGSGYPFT | GFTX3 |
| 222 | VH of IgGIL10M14 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 223 | VL of IgGIL10M14 | DIQMTQSPSTLSASVGDRVTITCKAQLSSP GQGT0SENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIK | Monomeric IL10 grafted into CDRL1 GFTX3 |
| 224 | Heavy chain of IgGIL10M14 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTCP PCPAPEAAGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK | GFTX3 LALA |
| 225 | Light chain of IgGIL10M14 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIKRTVA APSVFIFPPSDEQLKSGTASVVCLLNNFYP | GFTX3 LALA Monomeric IL10 grafted into CDRL1. |

TABLE 1-continued

| SEQ ID NO: | Description | | Comments |
|---|---|---|---|
| | | REAKVQWKVDNALQSGNSQESVTEQDS KDSTYSLSSTLTLSKADYEKHKVYACEVT HQGLSSPVTKSFNRGEC | |
| 226 | CDRH1 of IgGIL10M15 (Chothia) | GFSLSTSGM | GFTX3 |
| 227 | CDRH2 of IgGIL10M15 (Chothia) | WWDDK | GFTX3 |
| 228 | CDRH3 of IgGIL10M15 (Chothia) | SMITNWYFDV | GFTX3 |
| 229 | CDRL1 of IgGIL10M15 (Chothia) | QLSSPGQGTQSENSCTHFPGNLPNMR DLRDAFSRVKTFFQMKDQLDNLLLKES LLEDFKGYLGCQALSEMIQFYLEEVMP QAENQDPDIKAHVNSLGENLKTLRLRL RRCHRFLPCENGGGSGGKSKAVEQVK NAFNKLQEKGIYKAMSEFDIFINYIEAY MTMKIRNVGY | Monomeric IL10 grafted into CDRL1. IL10 is bolded, underlined |
| 230 | CDRL2 of IgGIL10M15 (Chothia) | DTS | GFTX3 |
| 231 | CDRL3 of IgGIL10M15 (Chothia) | GSGYPF | GFTX3 |
| 232 | CDRH1 of IgGIL10M15 (Kabat) | TSGMSVG | GFTX3 |
| 233 | CDRH2 of IgGIL10M15 (Kabat) | DIWWDDKKDYNPSLKS | GFTX3 |
| 234 | CDRH3 of IgGIL10M15 (Kabat) | SMITNWYFDV | GFTX3 |
| 235 | CDRL1 of IgGIL10M15 (Kabat) | KAQLSSPGQGTQSENSCTHFPGNLPNM LRDLRDAFSRVKTFFQMKDQLDNLLL KESLLEDFKGYLGCQALSEMIQFYLEE VMPQAENQDPDIKAHVNSLGENLKTLR LRLRRCHRFLPCENGGGSGGKSKAVE QVKNAFNKLQEKGIYKAMSEFDIFINYI EAYMTMKIRNVGYMH | Monomeric IL10 grafted into CDRL1 IL10 is bolded, underlined GFTX3 |
| 236 | CDRL2 of IgGIL10M15 (Kabat) | DTSKLAS | GFTX3 |
| 237 | CDRL3 of IgGIL10M15 (Kabat) | FQGSGYPFT | GFTX3 |
| 238 | VH of IgGIL10M15 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSS | GFTX3 |
| 239 | VL of IgGIL10M15 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIK | Monomeric IL10 grafted into CDRL1 IL10 is bolded, underlined GFTX3 |
| 240 | Heavy chain of IgGIL10M15 | QVTLRESGPALVKPTQTLTLTCTFSGFSLS TSGMSVGWIRQPPGKALEWLADIWWDD KKDYNPSLKSRLTISKDTSANQVVLKVTN MDPADTATYYCARSMITNWYFDVWGAG TTVTVSSASTKGPSVFPLAPSSKSTSGGTA | GFTX3 NEM |

TABLE 1-continued

| SEQ ID NO: | Description | | Comments |
|---|---|---|---|
| | | ALGCLVKDYFPEPVTVSWNSGALTSGVH TFPAVLQSSGLYSLSSVVTVPSSSLGTQTY ICNVNHKPSNTKVDKRVEPKSCDKTHTCP PCPAPELLGGPSVFLFPPKPKDTLMISRTP EVTCVVVDVSHEDPEVKFNWYVDGVEV HNAKTKPREEQYASTYRVVSVLTVLHQD WLNGKEYKCKVSNKALPAPIEKTISKAK GQPREPQVYTLPPSREEMTKNQVSLTCLV KGFYPSDIAVEWVSNGQPENNYKTTPPVL DSDGSFFLYSKLTVDKSRWQQGNVFSCS VIHEALHNHYTQKSLSLSPGK | |
| 241 | Light chain of IgGIL10M15 | DIQMTQSPSTLSASVGDRVTITCKAQLSSP GQGTQSENSCTHFPGNLPNMLRDLRDA FSRVKTFFQMKDQLDNLLLKESLLEDF KGYLGCQALSEMIQFYLEEVMPQAEN QDPDIKAHVNSLGENLKTLRLRLRRCH RFLPCENGGGSGGKSKAVEQVKNAFN KLQEKGIYKAMSEFDIFINYIEAYMTM KIRNVGYMHWYQQKPGKAPKLLIYDTS KLASGVPSRFSGSGSGTAFTLTISSLQPDD FATYYCFQGSGYPFTFGGGTKLEIKRTVA APSVFIFPPSDEQLKSGTASVVCLLNNFYP REAKVQWKVDNALQSGNSQESVTEQDS KDSTYSLSSTLTLSKADYEKHKVYACEVT HQGLSSPVTKSFNRGEC | GFTX3 NEM Monomeric IL10 grafted into CDRL1. IL10 is bolded, underlined |
| 242 | VH of IgGIL10M7 | CAGGTCACACTGAGAGAGTCAGGCCCT GCCCTGGTCAAGCCTACTCAGACCCTGA CCCTGACCTGCACCTTTAGCGGCTTTAG CCTGAGCACTAGCGGAATGAGCGTGGG CTGGATTAGACAGCCCCCTGGTAAAGC CCTGGAGTGGCTGGCCGATATTTGGTGG GACGATAAGAAGGACTATAACCCTAGC CTGAAGTCTAGGCTGACTATCTCTAAGG ACACTAGCGCTAATCAGGTGGTGCTGA AAGTGACTAATATGGACCCCGCCGACA CCGCTACCTACTACTGCGCTAGATCTAT GATCACTAACTGGTACTTCGACGTGTGG GGCGCTGGCACTACCGTGACCGTGTCTA GC | |
| 243 | VL of IgGIL10M7 | GATATTCAGATGACTCAGTCACCTAGCA CCCTGAGCGCTAGTGTGGGCGATAGAG TGACTATCACCTGTAAAGCTCAGCTGTC TAGCCCAGGTCAGGGAACTCAGTCAGA GAATAGCTGCACTCACTTCCCCGGTAAC CTGCCTAATATGCTGAGAGATCTGAGG GACGCCTTCTCTAGGGTCAAGACCTTCT TTCAGATGAAGGATCAGCTGGATAACC TGCTGCTGAAAGAGTCACTGCTGGAGG ACTTTAAGGGCTACCTGGGCTGTCAGGC CCTGAGCGAGATGATTCAGTTCTACCTG GAAGAAGTGATGCCCCAGGCCGAGAAT CAGGACCCCGATATTAAGGCTCACGTG AACTCACTGGGCGAGAACCTGAAAACC CTGAGACTGAGGCTGAGGCGGTGTCAC CGGTTTCTGCCCTGCGAGAACGGCGGA GGTAGCGGCGGTAAATCTAAGGCCGTG GAACAGGTCAAAAACGCCTTTAACAAG CTGCAGGAAAAGGGAATCTATAAGGCT ATGAGCGAGTTCGACATCTTTATTAACT ATATCGAGGCCTATATGACTATGAAGA TTAGGAACGTGGGCTATATGCACTGGT ATCAGCAGAAGCCCGGTAAAGCCCCTA AGCTGCTGATCTACGACACCTCTAAGCT GGCTAGTGGCGTGCCCTCTAGGTTTAGC GGTAGCGGTAGTGGCACCGCCTTCACC CTGACTATCTCTAGCCTGCAGCCCGACG ACTTCGCTACCTACTACTGTTTTCAGGG TAGCGGCTACCCCTTCACCTTCGGCGGA GGCACTAAGCTGGAGATTAAG | |
| 244 | Heavy Chain of IgGIL10M7 | CAGGTCACACTGAGAGAGTCAGGCCCT GCCCTGGTCAAGCCTACTCAGACCCTGA CCCTGACCTGCACCTTTAGCGGCTTTAG CCTGAGCACTAGCGGAATGAGCGTGGG | |

TABLE 1-continued

| SEQ ID NO: | Description | | Comments |
|---|---|---|---|
| | | CTGGATTAGACAGCCCCCTGGTAAAGC CCTGGAGTGGCTGGCCGATATTTGGTGG GACGATAAGAAGGACTATAACCCTAGC CTGAAGTCTAGGCTGACTATCTCTAAGG ACACTAGCGCTAATCAGGTGGTGCTGA AAGTGACTAATATGGACCCCGCCGACA CCGCTACCTACTACTGCGCTAGATCTAT GATCACTAACTGGTACTTCGACGTGTGG GGCGCTGGCACTACCGTGACCGTGTCTA GCGCTAGCACTAAGGGCCCAAGTGTGT TTCCCCTGGCCCCCAGCAGCAAGTCTAC TTCCGGCGGAACTGCTGCCCTGGGTTGC CTGGTGAAGGACTACTTCCCCGAGCCC GTGACAGTGTCCTGGAACTCTGGGGCTC TGACTTCCGGCGTGCACACCTTCCCCGC CGTGCTGCAGAGCAGCGGCCTGTACAG CCTGAGCAGCGTGGTGACAGTGCCCTC CAGCTCTCTGGGAACCCAGACCTATATC TGCAACGTGAACCACAAGCCCAGCAAC ACCAAGGTGGACAAGAGAGTGGAGCCC AAGAGCTGCGACAAGACCCACACCTGC CCCCCCTGCCCAGCTCCAGAACTGCTGG GAGGGCCTTCCGTGTTCCTGTTCCCCCC CAAGCCCAAGGACACCCTGATGATCAG CAGGACCCCCGAGGTGACCTGCGTGGT GGTGGACGTGTCCCACGAGGACCCAGA GGTGAAGTTCAACTGGTACGTGGACGG CGTGGAGGTGCACAACGCCAAGACCAA GCCCAGAGAGGAGCAGTACAACAGCAC CTACAGGGTGGTGTCCGTGCTGACCGTG CTGCACCAGGACTGGCTGAACGGCAAA GAATACAAGTGCAAAGTCTCCAACAAG GCCCTGCCAGCCCCAATCGAAAAGACA ATCAGCAAGGCCAAGGGCCAGCCACGG GAGCCCCAGGTGTACACCCTGCCCCCC AGCCGGGAGGAGATGACCAAGAACCAG GTGTCCCTGACCTGTCTGGTGAAGGGCT TCTACCCCAGCGATATCGCCGTGGAGTG GGAGAGCAACGGCCAGCCCGAGAACAA CTACAAGACCACCCCCCCAGTGCTGGA CAGCGACGGCAGCTTCTTCCTGTACAGC AAGCTGACCGTGGACAAGTCCAGGTGG CAGCAGGGCAACGTGTTCAGCTGCAGC GTGATGCACGAGGCCCTGCACAACCAC TACACCCAGAAGTCCCTGAGCCTGAGC CCCGGCAAG | |
| 245 | Light Chain of IgGIL10M7 | GATATTCAGATGACTCAGTCACCTAGCA CCCTGAGCGCTAGTGTGGGCGATAGAG TGACTATCACCTGTAAAGCTCAGCTGTC TAGCCCAGGTCAGGGAACTCAGTCAGA GAATAGCTGCACTCACTTCCCCGGTAAC CTGCCTAATATGCTGAGAGATCTGAGG GACGCCTTCTCTAGGGTCAAGACCTTCT TTCAGATGAAGGATCAGCTGGATAACC TGCTGCTGAAAGAGTCACTGCTGGAGG ACTTTAAGGGCTACCTGGGCTGTCAGGC CCTGAGCGAGATGATTCAGTTCTACCTG GAAGAAGTGATGCCCCAGGCCGAGAAT CAGGACCCCGATATTAAGGCTCACGTG AACTCACTGGGCGAGAACCTGAAAACC CTGAGACTGAGGCTGAGGCGGTGTCAC CGGTTTCTGCCCTGCGAGAACGGCGGA GGTAGCGGCGGTAAATCTAAGGCCGTG GAACAGGTCAAAAACGCCTTTAACAAG CTGCAGGAAAAGGGAATCTATAAGGCT ATGAGCGAGTTCGACATCTTTATTAACT ATATCGAGGCCTATATGACTATGAAGA TTAGGAACGTGGGCTATATGCACTGGT ATCAGCAGAAGCCCGGTAAAGCCCCTA AGCTGCTGATCTACGACACCTCTAAGCT GGCTAGTGGCGTGCCCTCTAGGTTTAGC GGTAGCGGTAGTGGCACCGCCTTCACC CTGACTATCTCTAGCCTGCAGCCCGACG ACTTCGCTACCTACTACTGTTTTCAGGG TAGCGGCTACCCCTTCACCTTCGGCGGA GGCACTAAGCTGGAGATTAAGCGTACG | |

TABLE 1-continued

| SEQ ID NO: | Description | | Comments |
|---|---|---|---|
| | | GTGGCCGCTCCCAGCGTGTTCATCTTCC<br>CCCCCAGCGACGAGCAGCTGAAGAGCG<br>GCACCGCCAGCGTGGTGTGCCTGCTGA<br>ACAACTTCTACCCCGGGAGGCCAAGG<br>TGCAGTGGAAGGTGGACAACGCCCTGC<br>AGAGCGGCAACAGCCAGGAGAGCGTCA<br>CCGAGCAGGACAGCAAGGACTCCACCT<br>ACAGCCTGAGCAGCACCCTGACCCTGA<br>GCAAGGCCGACTACGAGAAGCATAAGG<br>TGTACGCCTGCGAGGTGACCCACCAGG<br>GCCTGTCCAGCCCCGTGACCAAGAGCTT<br>CAACAGGGGCGAGTGC | |
| 246 | VH of IgGIL10M13 | CAGGTCACACTGAGAGAGTCAGGCCCT<br>GCCCTGGTCAAGCCTACTCAGACCCTGA<br>CCCTGACCTGCACCTTTAGCGGCTTTAG<br>CCTGAGCACTAGCGGAATGAGCGTGGG<br>CTGGATTAGACAGCCCCCTGGTAAAGC<br>CCTGGAGTGGCTGGCCGATATTTGGTGG<br>GACGATAAGAAGGACTATAACCCTAGC<br>CTGAAGTCTAGGCTGACTATCTCTAAGG<br>ACACTAGCGCTAATCAGGTGGTGCTGA<br>AAGTGACTAATATGGACCCCGCCGACA<br>CCGCTACCTACTACTGCGCTAGATCTAT<br>GATCACTAACTGGTACTTCGACGTGTGG<br>GGCGCTGGCACTACCGTGACCGTGTCTA<br>GC | |
| 247 | VL of IgGIL10M13 | GATATTCAGATGACTCAGTCACCTAGCA<br>CCCTGAGCGCTAGTGTGGGCGATAGAG<br>TGACTATCACCTGTAAAGCTCAGCTGTC<br>TAGCCCAGGTCAGGGAACTCAGTCAGA<br>GAATAGCTGCACTCACTTCCCCGGTAAC<br>CTGCCTAATATGCTGAGAGATCTGAGG<br>GACGCCTTCTCTAGGGTCAAGACCTTCT<br>TTCAGATGAAGGATCAGCTGGATAACC<br>TGCTGCTGAAAGAGTCACTGCTGGAGG<br>ACTTTAAGGGCTACCTGGGCTGTCAGGC<br>CCTGAGCGAGATGATTCAGTTCTACCTG<br>GAAGAAGTGATGCCCCAGGCCGAGAAT<br>CAGGACCCCGATATTAAGGCTCACGTG<br>AACTCACTGGGCGAGAACCTGAAAACC<br>CTGAGACTGAGGCTGAGGCGGTGTCAC<br>CGGTTTCTGCCCTGCGAGAACGGCGGA<br>GGTAGCGGCGGTAAATCTAAGGCCGTG<br>GAACAGGTCAAAAACGCCTTTAACAAG<br>CTGCAGGAAAAGGGAATCTATAAGGCT<br>ATGAGCGAGTTCGACATCTTTATTAACT<br>ATATCGAGGCCTATATGACTATGAAGA<br>TTAGGAACGTGGGCTATATGCACTGGT<br>ATCAGCAGAAGCCCGGTAAAGCCCCTA<br>AGCTGCTGATCTACGACACCTCTAAGCT<br>GGCTAGTGGCGTGCCCTCTAGGTTTAGC<br>GGTAGCGGTAGTGGCACCGCCTTCACC<br>CTGACTATCTCTAGCCTGCAGCCCGACG<br>ACTTCGCTACCTACTACTGTTTTCAGGG<br>TAGCGGCTACCCCTTCACCTTCGGCGGA<br>GGCACTAAGCTGGAGATTAAG | |
| 248 | Heavy Chain of IgGIL10M13 | CAGGTCACACTGAGAGAGTCAGGCCCT<br>GCCCTGGTCAAGCCTACTCAGACCCTGA<br>CCCTGACCTGCACCTTTAGCGGCTTTAG<br>CCTGAGCACTAGCGGAATGAGCGTGGG<br>CTGGATTAGACAGCCCCCTGGTAAAGC<br>CCTGGAGTGGCTGGCCGATATTTGGTGG<br>GACGATAAGAAGGACTATAACCCTAGC<br>CTGAAGTCTAGGCTGACTATCTCTAAGG<br>ACACTAGCGCTAATCAGGTGGTGCTGA<br>AAGTGACTAATATGGACCCCGCCGACA<br>CCGCTACCTACTACTGCGCTAGATCTAT<br>GATCACTAACTGGTACTTCGACGTGTGG<br>GGCGCTGGCACTACCGTGACCGTGTCTA<br>GCGCTAGCACTAAGGGCCCCTCCGTGTT<br>CCCTCTGGCCCCTTCCAGCAAGTCTACC<br>TCCGGCGGCACAGCTGCTCTGGGCTGCC<br>TGGTCAAGGACTACTTCCCTGAGCCTGT<br>GACAGTGTCCTGGAACTCTGGCGCCCTG | |

TABLE 1-continued

| SEQ ID NO: | Description | | Comments |
|---|---|---|---|
| | | ACCTCTGGCGTGCACACCTTCCCTGCCG TGCTGCAGTCCTCCGGCCTGTACTCCCT GTCCTCCGTGGTCACAGTGCCTTCAAGC AGCCTGGGCACCCAGACCTATATCTGC AACGTGAACCACAAGCCTTCCAACACC AAGGTGGACAAGCGGGTGGAGCCTAAG TCCTGCGACAAGACCCACACCTGTCCTC CCTGCCCTGCTCCTGAACTGCTGGGCGG CCCTTCTGTGTTCCTGTTCCCTCCAAAG CCCAAGGACACCCTGATGATCTCCCGG ACCCCTGAAGTGACCTGCGTGGTGGTG GCCGTGTCCCACGAGGATCCTGAAGTG AAGTTCAATTGGTACGTGGACGGCGTG GAGGTGCACAACGCCAAGACCAAGCCT CGGGAGGAACAGTACAACTCCACCTAC CGGGTGGTGTCCGTGCTGACCGTGCTGC ACCAGGACTGGCTGAACGGCAAAGAGT ACAAGTGCAAAGTCTCCAACAAGGCCC TGGCCGCCCCTATCGAAAAGACAATCT CCAAGGCCAAGGGCCAGCCTAGGGAAC CCCAGGTGTACACCCTGCCACCCAGCC GGGAGGAAATGACCAAGAACCAGGTGT CCCTGACCTGTCTGGTCAAGGGCTTCTA CCCTTCCGATATCGCCGTGGAGTGGGA GTCTAACGGCCAGCCTGAGAACAACTA CAAGACCACCCCTCCTGTGCTGGACTCC GACGGCTCCTTCTTCCTGTACTCCAAAC TGACCGTGGACAAGTCCCGGTGGCAGC AGGGCAACGTGTTCTCCTGCTCCGTGAT GCACGAGGCCCTGCACAACCACTACAC CCAGAAGTCCCTGTCCCTGTCTCCCGGC AAG | |
| 249 | Light Chain of IgGIL10M13 | GATATTCAGATGACTCAGTCACCTAGCA CCCTGAGCGCTAGTGTGGGCGATAGAG TGACTATCACCTGTAAAGCTCAGCTGTC TAGCCCAGGTCAGGGAACTCAGTCAGA GAATAGCTGCACTCACTTCCCCGGTAAC CTGCCTAATATGCTGAGAGATCTGAGG GACGCCTTCTCTAGGGTCAAGACCTTCT TTCAGATGAAGGATCAGCTGGATAACC TGCTGCTGAAAGAGTCACTGCTGGAGG ACTTTAAGGGCTACCTGGGCTGTCAGGC CCTGAGCGAGATGATTCAGTTCTACCTG GAAGAAGTGATGCCCCAGGCCGAGAAT CAGGACCCCGATATTAAGGCTCACGTG AACTCACTGGGCGAGAACCTGAAAACC CTGAGACTGAGGCTGAGGCGGTGTCAC CGGTTTCTGCCCTGCGAGAACGGCGGA GGTAGCGGCGGTAAATCTAAGGCCGTG GAACAGGTCAAAAACGCCTTTAACAAG CTGCAGGAAAAGGGAATCTATAAGGCT ATGAGCGAGTTCGACATCTTTATTAACT ATATCGAGGCCTATATGACTATGAAGA TTAGGAACGTGGGCTATATGCACTGGT ATCAGCAGAAGCCCGGTAAAGCCCCTA AGCTGCTGATCTACGACACCTCTAAGCT GGCTAGTGGCGTGCCCTCTAGGTTTAGC GGTAGCGGTAGTGGCACCGCCTTCACC CTGACTATCTCTAGCCTGCAGCCCGACG ACTTCGCTACCTACTACTGTTTTCAGGG TAGCGGCTACCCCTTCACCTTCGGCGGA GGCACTAAGCTGGAGATTAAGCGTACG GTGGCCGCTCCCAGCGTGTTCATCTTCC CCCCAGCGACGAGCAGCTGAAGAGCG GCACCGCCAGCGTGGTGTGCCTGCTGA ACAACTTCTACCCCCGGGAGGCCAAGG TGCAGTGGAAGGTGGACAACGCCCTGC AGAGCGGCAACAGCCAGGAGAGCGTCA CCGAGCAGGACAGCAAGGACTCCACCT ACAGCCTGAGCAGCACCCTGACCCTGA GCAAGGCCGACTACGAGAAGCATAAGG TGTACGCCTGCGAGGTGACCCACCAGG GCCTGTCCAGCCCCGTGACCAAGAGCTT CAACAGGGGCGAGTGC |

TABLE 1-continued

| SEQ ID NO: | Description | | Comments |
|---|---|---|---|
| 250 | Monomeric IL10 | AGTCCCGGTCAGGGAACTCAGTCAGAG AATAGCTGCACTCACTTCCCCGGTAACC TGCCTAATATGCTGAGAGATCTGAGGG ACGCCTTCTCTAGGGTCAAGACCTTCTT TCAGATGAAGGATCAGCTGGATAACCT GCTGCTGAAAGAGTCACTGCTGGAGGA CTTTAAGGGCTACCTGGGCTGTCAGGCC CTGAGCGAGATGATTCAGTTCTACCTGG AAGAAGTGATGCCCCAGGCCGAGAATC AGGACCCCGATATTAAGGCTCACGTCA ACTCACTGGGCGAGAACCTGAAAACCC TGAGACTGAGGCTGAGGCGGTGTCACC GGTTTCTGCCCTGCGAGAACGGCGGAG GTAGCGGCGGTAAATCTAAGGCCGTGG AACAGGTCAAAAACGCCTTTAACAAGC TGCAGGAAAAGGGAATCTATAAGGCTA TGAGCGAGTTCGACATCTTTATTAACTA TATCGAGGCCTATATGACTATGAAGATT AGGAAC | |
| 251 | linker | GGGSGG | |
| 252 | linker | GGGGS | |
| 253 | linker | GGGGA | |

Example 2: Antibody Cytokine Engrafted Proteins Have Anti-Inflammatory Activity Using an assay developed in support of rhIL10's pro-inflammatory activity in the clinic (Lauw et al., J Immunol. 2000; 165(5):2783-9), the pro-inflammatory activity of IgGIL10M13 in human whole blood was assessed. In order to assess pro-inflammatory activity, antibody cytokine engrafted proteins were profiled for their ability to induce interferon gamma (IFNγ) or granzyme B in activated primary human CD8 T cells. It was found that antibody cytokine engrafted proteins such as IgGIL10M13 demonstrated significantly less pro-inflammatory activity than recombinant human IL10 (rhIL10) as measured by IFNγ production. This data is shown in FIG. 3A. Similar results were found in assays measuring granzyme B (data not shown), as well as with other exemplary antibody cytokine engrafted proteins (IgGIL10M7). The significantly decreased pro-inflammatory activity demonstrated by IgGIL10M13 as compared to rhIL10 indicates it would be superior to rhIL10 for treating immune related disorders, as IgGIL10M13 could be administered over a broader dose range.

To examine anti-inflammatory activity, antibody cytokine engrafted proteins and rhIL10 were tested for their ability to inhibit LPS-induced TNFα in human whole blood. This data is shown in FIG. 3B, wherein increasing concentrations of either rhIL10 or IgGIL10M13 reduced TNFα production. Note that the rhIL10 and IgGIL10M13 curves are similar, indicating that both molecules had potent anti-inflammatory activity.

In summary, these results show that antibody cytokine engrafted proteins have the desired properties of having anti-inflammatory properties similar to IL10, but without the dose limiting, and unwanted pro-inflammatory properties.

Example 3: IL10 Dependent Signaling

Figure 4:
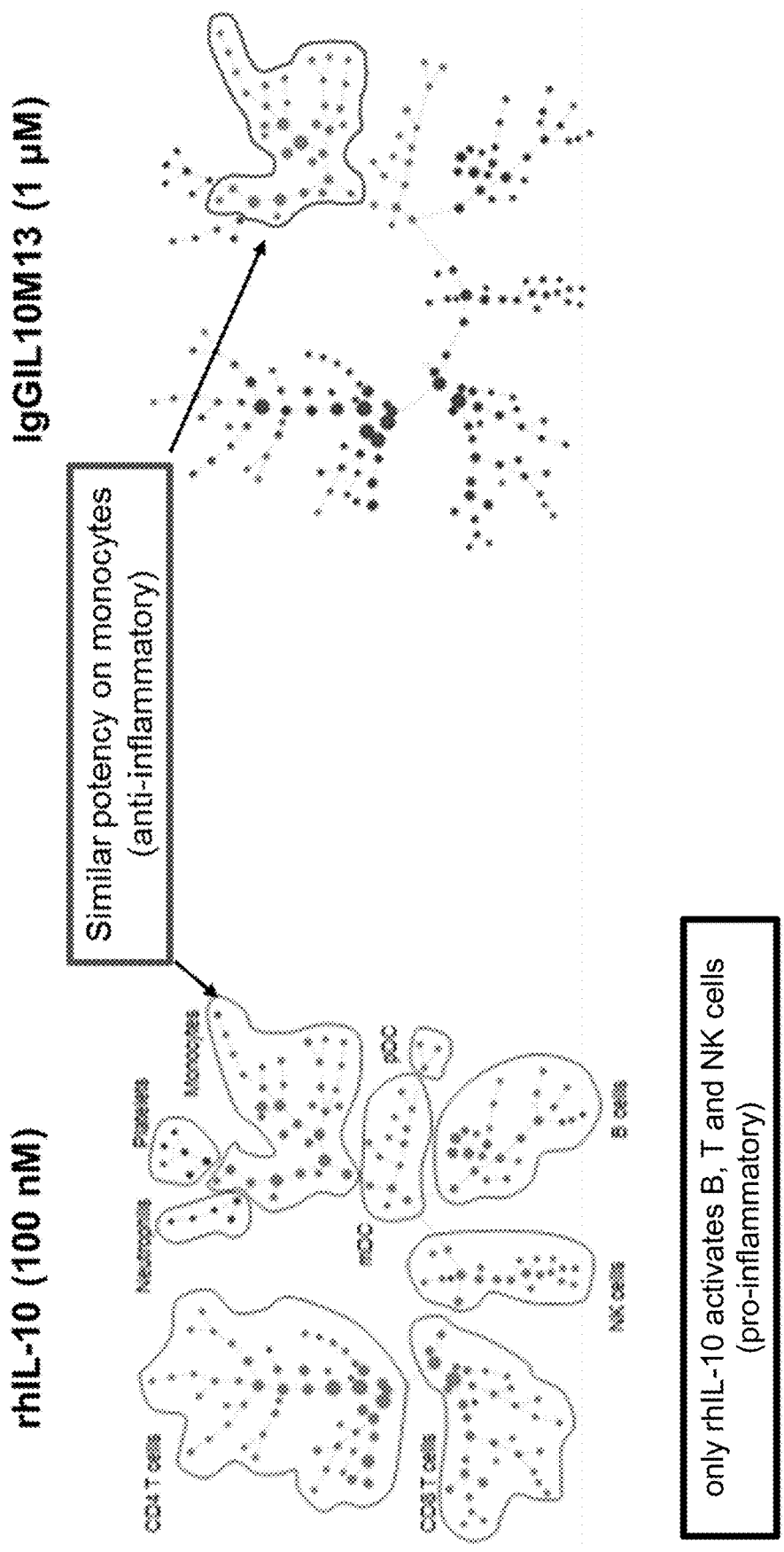
FIG. 4 depicts results of CyTOF analysis of IL10 dependent pSTAT3 signaling in human whole blood stimulated with equal molar amounts recombinant human IL10 rhIL10 (left panel) or IgGIL10M13 (right panel). IL10 induces anti-inflammatory activities in monocytes; and activation of T, B or NK cells induces pro-inflammatory cytokines. Results of fold change in activity of cells over unstimulated are depicted by heat map (changes in shading). Left panel indicates rhIL10 confers stimulation across all IL10 sensitive cell types (with outline); however, as seen in the right panel IgGIL10M13 confers less potent stimulation on T, B, and NK cells, with levels similar or slightly above unstimulated cells; while a similar potency of stimulation of monocytes (outlined) and mDC cells was demonstrated with IgG-IL10M and rhIL10. These relevant cell types (monocytes, mDC) are key cells for maintenance of gut homeostatis in inflammatory bowel disease.

In vitro signaling studies in human PBMCs and whole blood indicate that antibody cytokine engrafted proteins such as IgGIL10M13 had a more specific signaling profile when compared to rhIL10. Using CyTOF, a FACS based method that utilizes mass spectrometry, antibody cytokine engrafted protein signaling in multiple different cell populations in whole blood was assessed by pSTAT3 detection (FIG. 4). Antibody cytokine engrafted proteins such IgGIL10M13 induced a pSTAT3 signal only on monocytes, macrophages and plasmacytoid dendritic cells above μM concentrations (up to 1.8 μM). All of these cell types are known to have increased expression of IL10 receptor. rhIL10 induced a pSTAT3 signal on monocytes, but also on additional cell types such as T cells, B cells, and NK cells. This was seen even at low nM concentrations of rhIL10. In whole blood treated with rhIL10 at a concentration of 100 nM, the strongest pSTAT3 signal was seen on monocytes and myeloid dendritic cells with additional moderate activation of T, NK, B cells, and Granulocytes. The functional consequences of pSTAT3 signaling leads to increased production of IFNγ and Granzyme B from CD8 T cells and NK cells. There is also proliferation of B cells in response to rhIL10 signaling. This pro-inflammatory activity of rhIL10 in human whole blood is observed at exposures less than 5-fold above the anti-inflammatory IC90. The more selective cellular profile of antibody cytokine engrafted proteins such as IgGIL10M13 resulted in reduced pro-inflammatory activity leading to better anti-inflammatory efficacy.

Example 4: Antibody Cytokine Engrafted Protein Signaling in Various Species rhIL10 potently inhibits LPS-induced pro-inflammatory cytokine production in human monocytes, PBMCs, and whole blood. The antibody cytokine engrafted protein IgGIL10M13 exhibits pM potency on target cells, although 10-fold less potent than rhIL10. Table 2 is a potency comparison for IL10 or IgGIL10M13 activity in human whole blood as well as whole blood of selected toxicity species.

Potency calculations are based on ex vivo whole blood assays from either mouse, cynomolgus monkey or human. For each species tested, IgGIL10M13 or rhIL10 were titrated and assessed for ability to inhibit LPS-induced TNFα production. IC50s were calculated as the level of molecule that gave rise to 50% inhibition of total TNFα signal. IC90s and IC30s were calculated taking into account Hill slope value for each assay with the following equation: log EC50=log ECF−(1/HillSlope)*lob(F/100−F)), where ECF is the concentration that gives a response of F percent of total TNFα signal.

TABLE 2

|  |  | IgGIL10M13 (CV %) | IL10 (CV %) |
|---|---|---|---|
| Mouse | IC30 | 2.2 pM (pooled blood) | 0.57 pM (pooled blood) |
|  | IC50 | 12 pM | 1.7 pM |
|  | IC90 | 108 pM | 15 pM |
| Cyno | IC30 | 4.13 pM (48% n = 3) | 0.44 pM (28% n = 3) |
|  | IC50 | 6.67 pM (53%) | 0.65 pM (31%) |
|  | IC90 | 24 pM (73%) | 1.9 pM (43%) |
| Human | IC30 | 10.8 pM (76% n = 48) | 1.3 pM (96% n = 48) |
|  | IC50 | 25.2 pM (76%) | 2.8 pM (98%) |
|  | IC90 | 262 pM (94%) | 22.8 pM (79%) |

Example 5: Evaluation of Antibody Cytokine Engrafted Protein Pharmacokinetics rhIL10 has a short half-life, limiting its target tissue exposure and requiring the patient to undergo multiple dosing. The half-life of antibody cytokine engrafted proteins was assessed in C57Bl/6 mice. Antibody cytokine engrafted proteins (e.g. IgGIL10M13) were injected at 0.2 mg/kg subcutaneously and blood was sampled beginning at 5 minutes post-injection up to 144 hours post-injection. IgGIL10M13 had a significant half-life extension of approximately 4.4 days (FIG. 5B) compared to rhIL10 which had a half-life of approximately 1 hr (FIG. 5A).

Example 6: Evaluation of Antibody Cytokine Engrafted Protein Pharmacodynamics

Consistent with extended half-life, antibody cytokine engrafted proteins also demonstrated improved pharmacodynamics. Phospho-STAT3 (pSTAT3), a marker of IL10 receptor activation and signaling was monitored in mouse colon after subcutaneous dosing of IgGIL10M13. Enhanced pSTAT3 signal was detected in colon at least up to 72 hours post-dose, and absent by 144 hours post-dose. See FIG. 5C. This profile is a dramatic improvement over rhIL10, whose signal is absent by 24 hours post-dose. FIG. 5D depicts improved duration of in vivo response of IgGIL10M13 as compared to rhIL10 as measured by inhibition of TNFα in blood in response to LPS challenge following antibody cytokine engrafted protein dosing.

Example 7: Efficacy of Antibody Cytokine Engrafted Proteins in a Mouse Model

Figure 6:
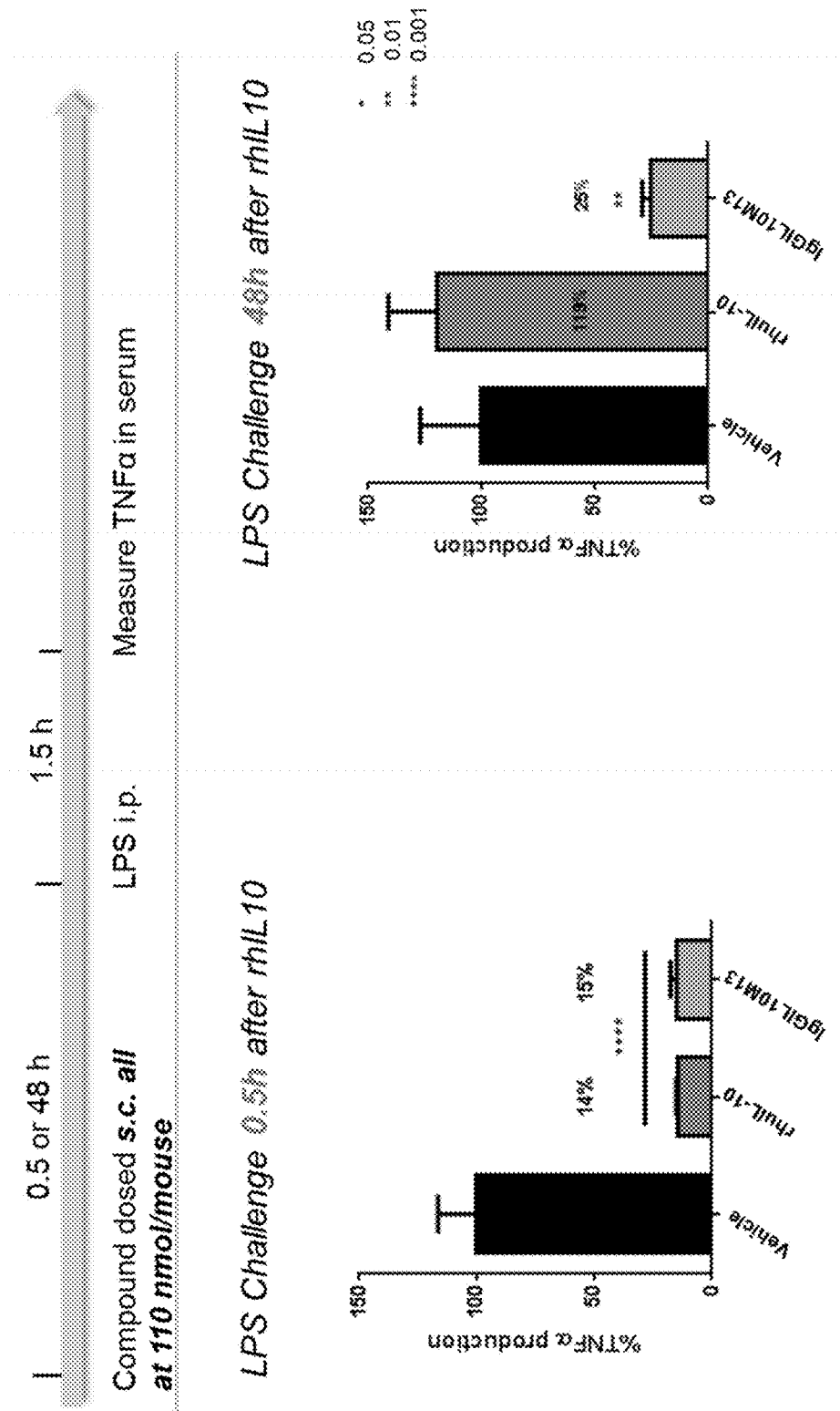
FIG. 6 is the results of an LPS challenge model, demonstrating IgGIL10M13 reduces TNFα induction 48 hours after LPS challenge.

A direct comparison of efficacy for TNFα inhibition after LPS challenge was performed. C57/BL6 mice were dosed subcutaneously with vehicle, or equimolar levels of IL10 at 110 nmol/mouse, calculated for both recombinant IL10 and IgGIL10M13. Mice were then challenged with LPS delivered intraperitoneally to assess IL10 dependent inhibition of TNFα levels. IgGIL10M13 demonstrated comparable efficacy to rhIL10 at the initial assessment time period of 0.5 hour, however, up to at least forty-eight hours post dosing, IgGIL10M13 sustained superior efficacy to rhIL10 as measured by TNFα production. This data is shown in FIG. 6.

Example 8: Antibody Cytokine Engrafted Proteins Have Improved Exposure

Figure 7:
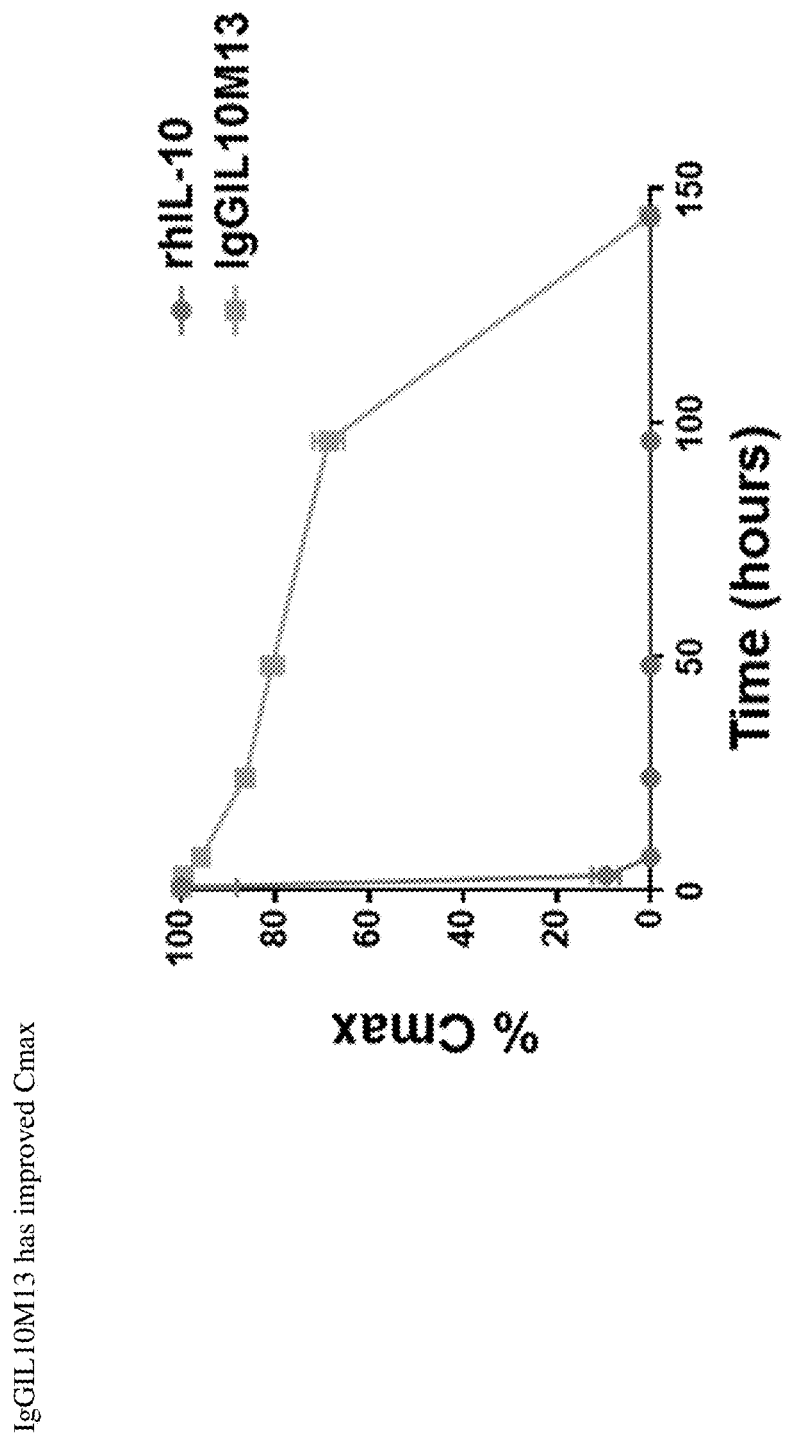
FIG. 7 is a graph representing the improved % CMAX of IL10 antibody cytokine engrafted proteins.

The peak serum concentration (Cmax) of antibody cytokine engrafted proteins was assessed in C57Bl/6 mice. Antibody cytokine engrafted proteins were injected at 0.2 mg/kg (10 ml/kg dose volume) in 0.9% saline subcutaneously and blood was sampled beginning at 1 hour post-injection and up to 144 hours post-injection. Whole blood was collected into heparin-treated tubes at each time point and centrifuged at 12,500 rpm for 10 minutes at 4° C. Plasma supernatant was collected and stored at −80° C. until all time points were collected. Antibody cytokine engrafted proteins levels in plasma were measured using two different immunoassay methods to enable detection of both the IL10 and antibody domains of the antibody cytokine engrafted protein. As shown in FIG. 7, the antibody cytokine engrafted protein (e.g. IgGIL10M13) maintained greater than 60% Cmax past 100 hours. In contrast, rhIL10 levels dropped below 20% Cmax within 3.5 hours.

Figure 8:
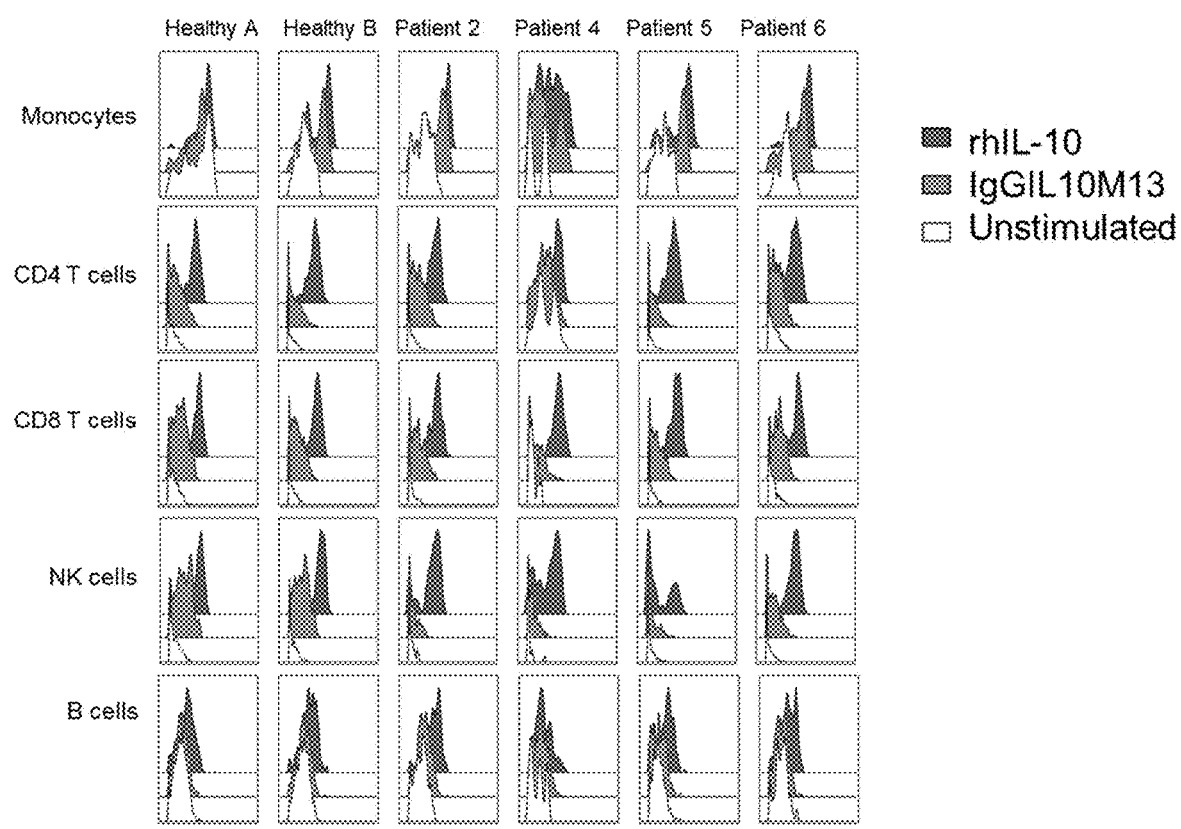
FIG. 8 depicts CyTOF data of pSTAT3 activity in various immune cells from healthy subjects and patients when stimulated with rhIL10 or with IgGIL10M13.

Example 9: Antibody Cytokine Engrafted Proteins Act Only on Certain Cell Types in Human Patients CyTOF was run as previously described (see Example 3 and Materials and Methods below) on immune cells from human healthy donors and patients with Crohn's disease. As shown in the graphs in FIG. 8, IgGIL10M13 stimulated only monocytes, and the stimulation as measured by pSTAT3 levels is comparable to rhIL10. Monocytes are the target cells for inflammatory related disorders such as Crohn's disease and Ulcerative Colitis and express very high levels of IL10 receptor. However, FIG. 9 also shows the unwanted pro-inflammatory effects of rhIL10, for example, the increased pSTAT3 signaling on CD4 T cells, CD8 T cells and NK cells. It is noteworthy that IgGIL10M13, does not display this unwanted pro-inflammatory effect either on normal human cells or in cells taken Crohn's disease patients. This demonstrates that IgGIL10M13 has a larger, safer therapeutic index as administration of the antibody cytokine engrafted protein will act only on the desired cell type and not on other cell types such as CD8 T cells which would only worsen immune related disorders such as Crohn's disease and Ulcerative Colitis.

Example 10: IgGIL10M13 Has Reduced Pro-Inflammatory Activity in PHA Stimulated Human Whole Blood Compared to rhIL10

Despite extensive clinical data linking genetic IL10 deficiency to IBD susceptibility, rhIL10 showed only mild efficacy in IBD clinical trials (Herfarth et al., Gut 2002: 50(2):146-147). Retrospective analyses of trial data suggest that rhIL10's efficacy was limited by its intrinsic pro-inflammatory activity such as enhanced production of IFNγ. As discussed previously, in human functional cell-based assays, rhIL10 signaling leads to production of IFNγ and Granzyme B from T cells and NK cells.

Figure 9A:
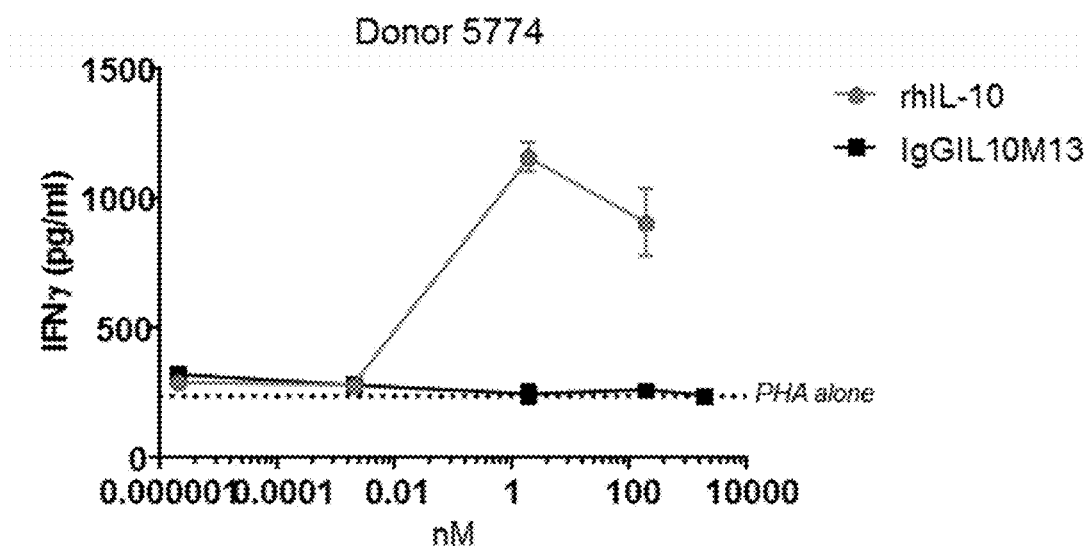
FIGS. 9A-9C are graphical representations demonstrating IgGIL10M13 has reduced pro-inflammatory activity in PHA stimulated human whole blood compared to rhIL10.
Figure 9A:
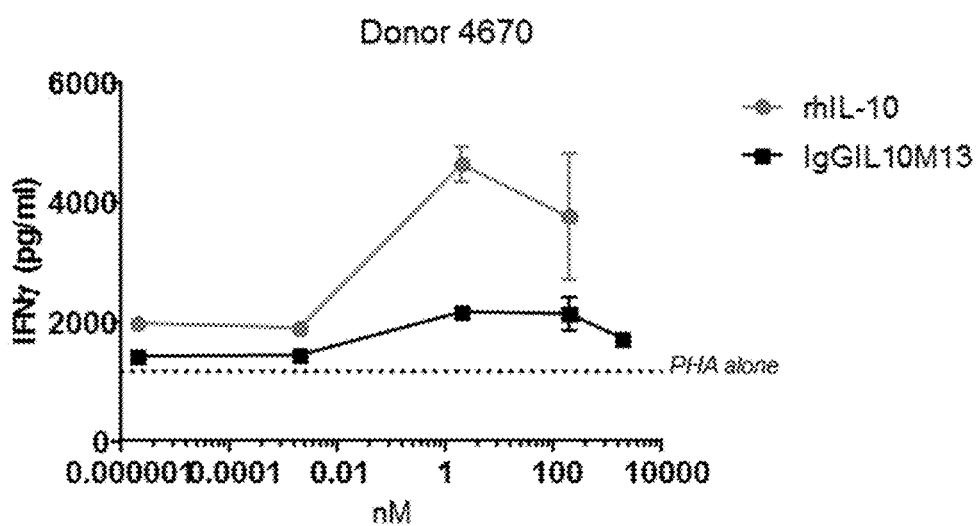
Figure 9B:
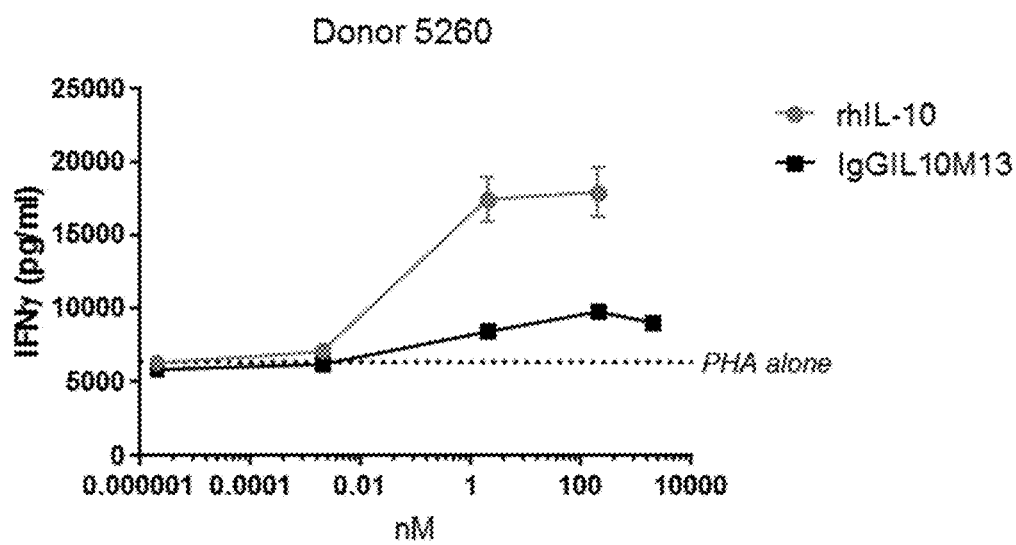
Figure 9B:
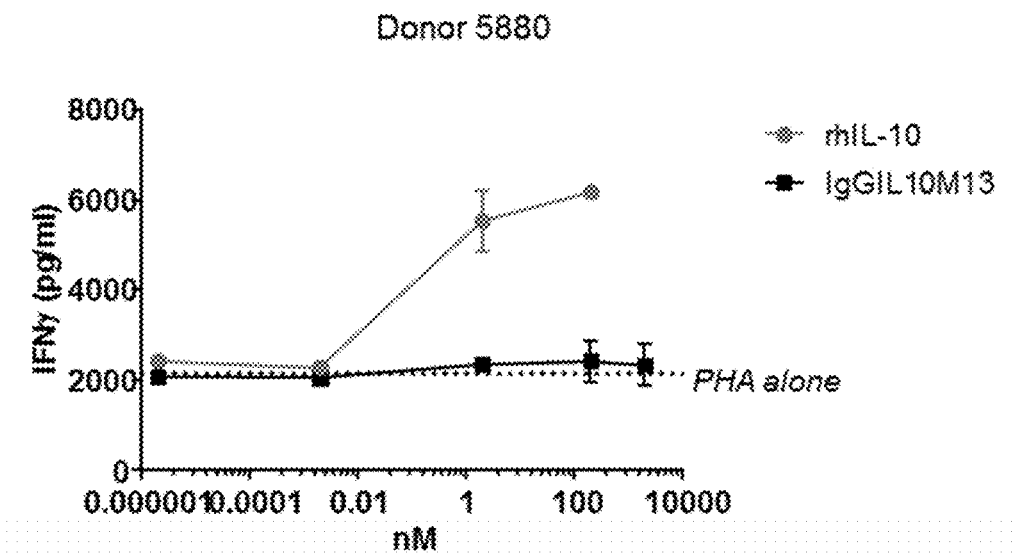
Figure 9C:
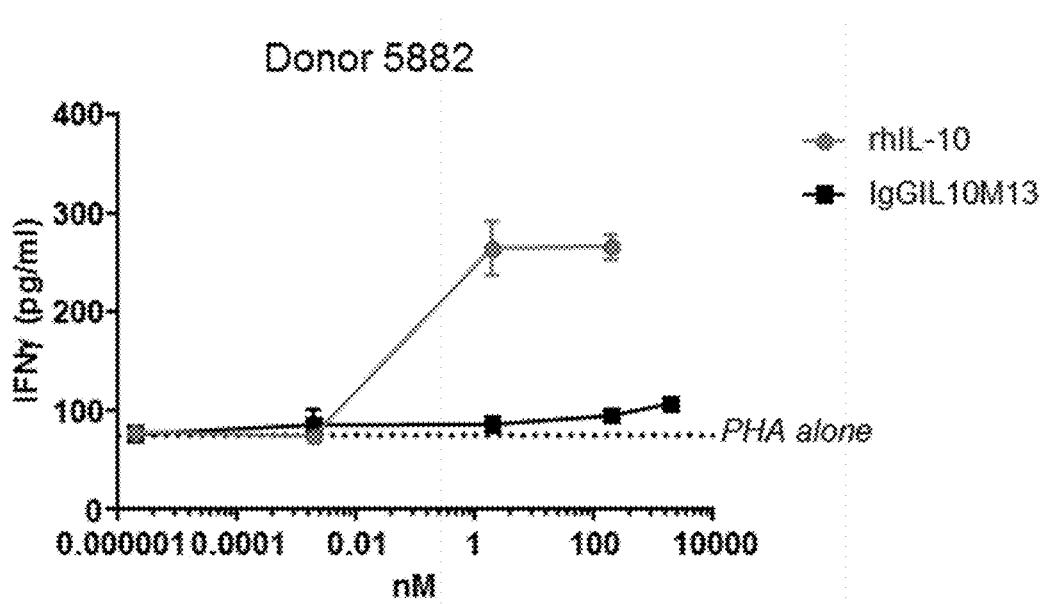

Whole blood was taken from patients with Crohn's Disease and the levels of IFNγ were measured after stimulation with rhIL10, IgGIL10M13 and PHA alone. This data is shown in FIGS. 9A-9C. Increasing doses of rhIL10 causes a sharp increase in IFNγ production, which then plateaus. In contrast, in treatment of these cells with IgGIL10M13 little to no production of IFNγ was seen, indicating that IgGIL10M13 did not induce, or induced only very low levels of IFNγ production from T cells or NK cells.

Figure 9D:
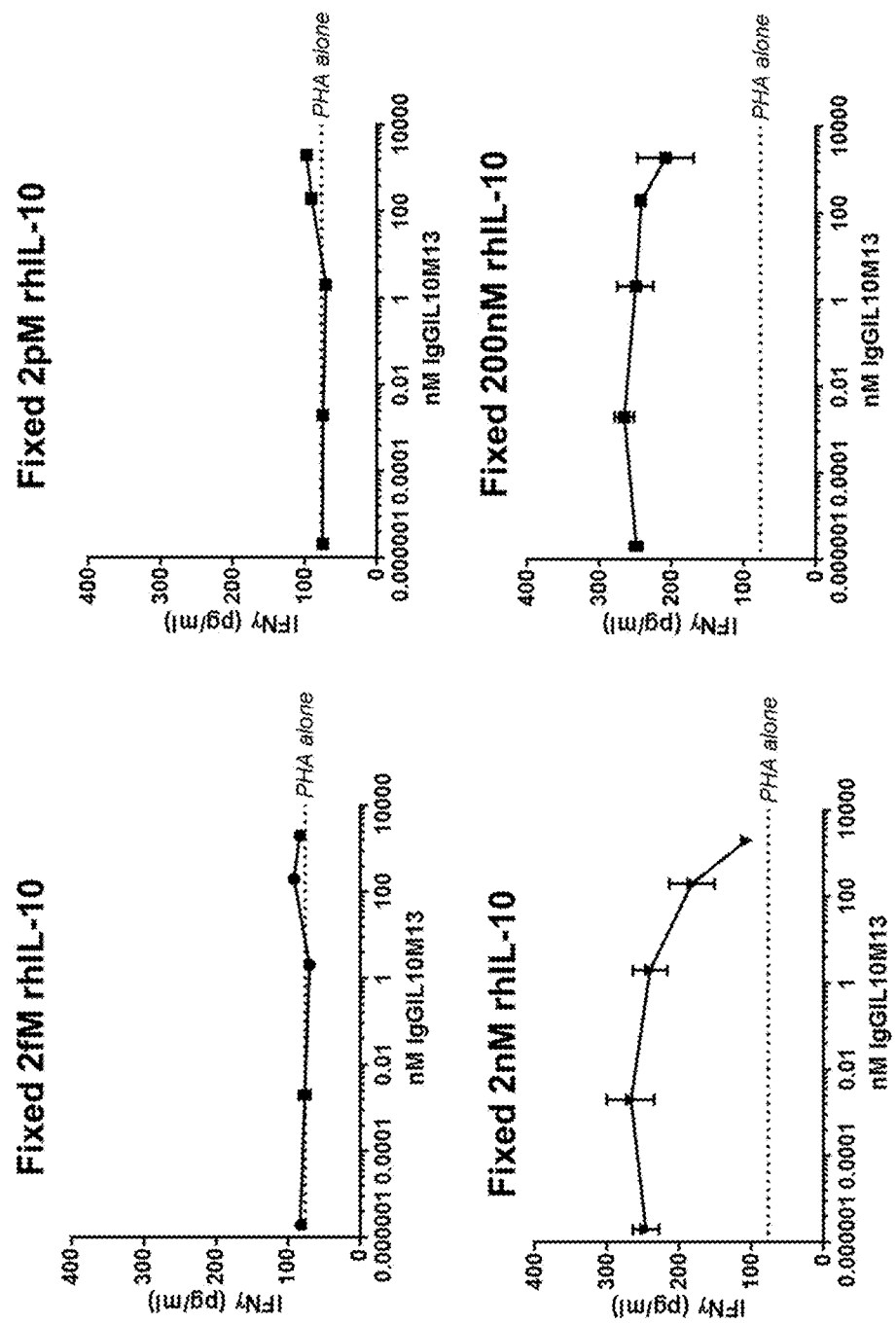
FIG. 9D shows the graphs of a titration experiment with rhIL10 and IgGIL10M13.

An additional titration experiment was performed with these patient donor samples. In this experiment, IL10 levels from the donor patient sera was measured and found to be in the range of 1.5 to 5 femtomolar (fM), although the scientific literature has reported that patient IL10 levels could be as high as 20 fM (Szkaradkiewicz et al., Arch. Immunol. Ther Exp 2009: 57(4):291-294). rhIL10 was administered to the donor patient cells at the fixed concentrations of 2 femtomolar (fM), 2 pM, 2 nM and 200 nM. To these fixed concentrations of rhIL10, increasing concentrations of the antibody cytokine engrafted protein IgGIL10M13 was administered, and IFNγ production assayed. The data is shown in FIG. 9D. At the fixed concentrations of 2 fM and 2 pM, IgGIL10M13 competes with rhIL10 and reduced the production of IFNγ to baseline levels. At the fixed concentration of 2 nM, IFNγ production was reduced by nanomolar concentrations of IgGIL10M13. Finally, at the fixed excess concentration of 200 nM rhIL10, only very little reduction of IFNγ production by IgGIL10M13 was seen. This indicates that at physiological levels of IL10, IgGIL10M13 competed out IL10, reducing the production of IFNγ, and the unwanted pro-inflammatory effects.

Example 11: Aggregation Properties of Antibody Cytokine Engrafted Proteins

Figure 10A:
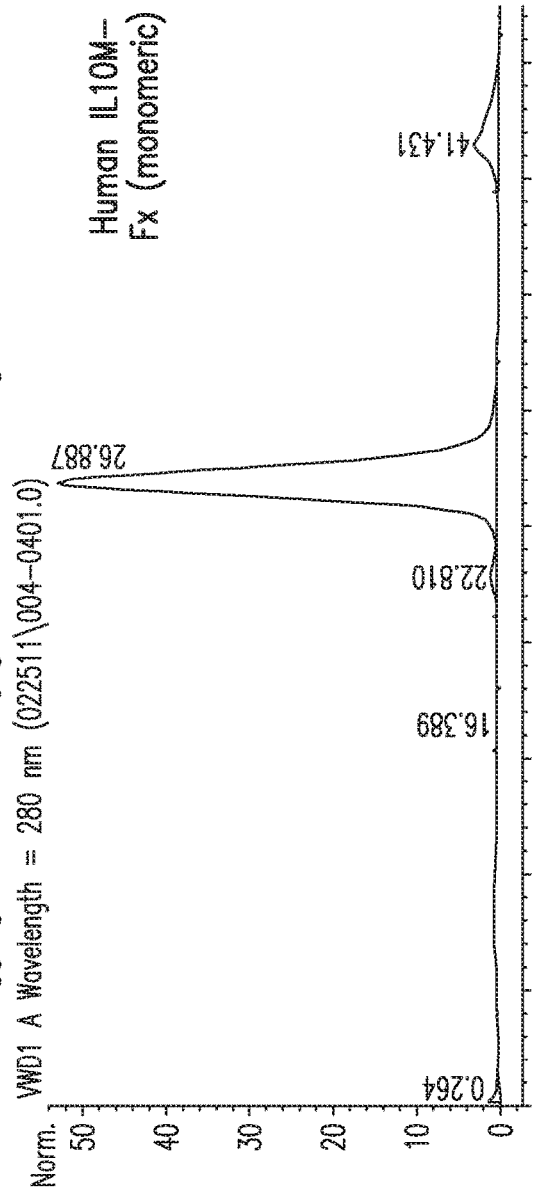
FIGS. 10A-10B depict the aggregation properties of IL10 wild type or monomeric when conjugated via a linker to an Fc, compared to the aggregation properties of an antibody cytokine engrafted protein.
Figure 10A:
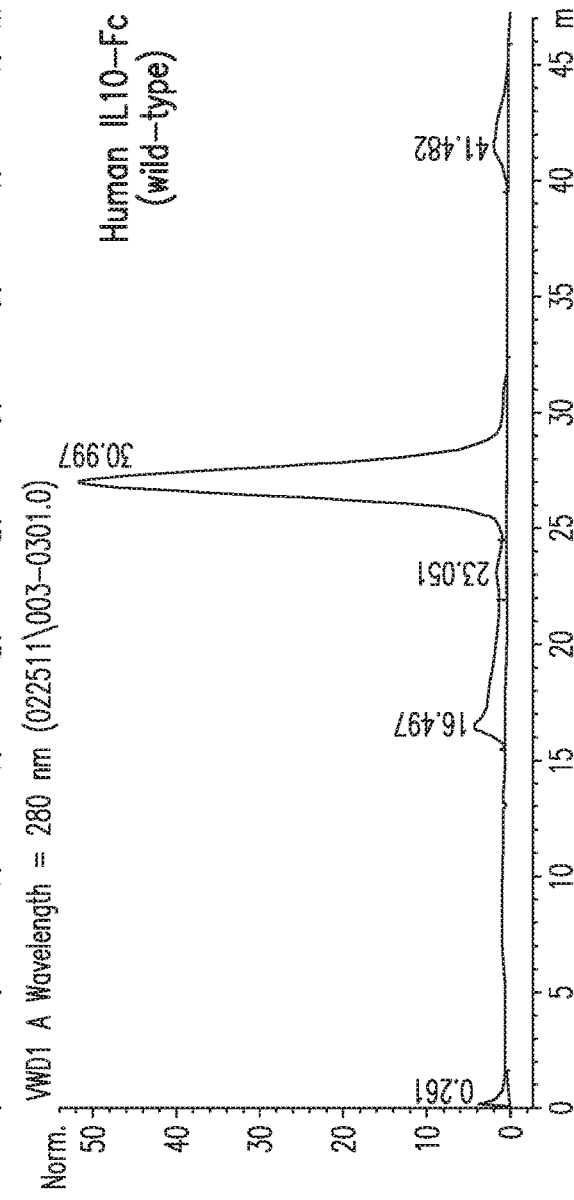
Figure 10B:
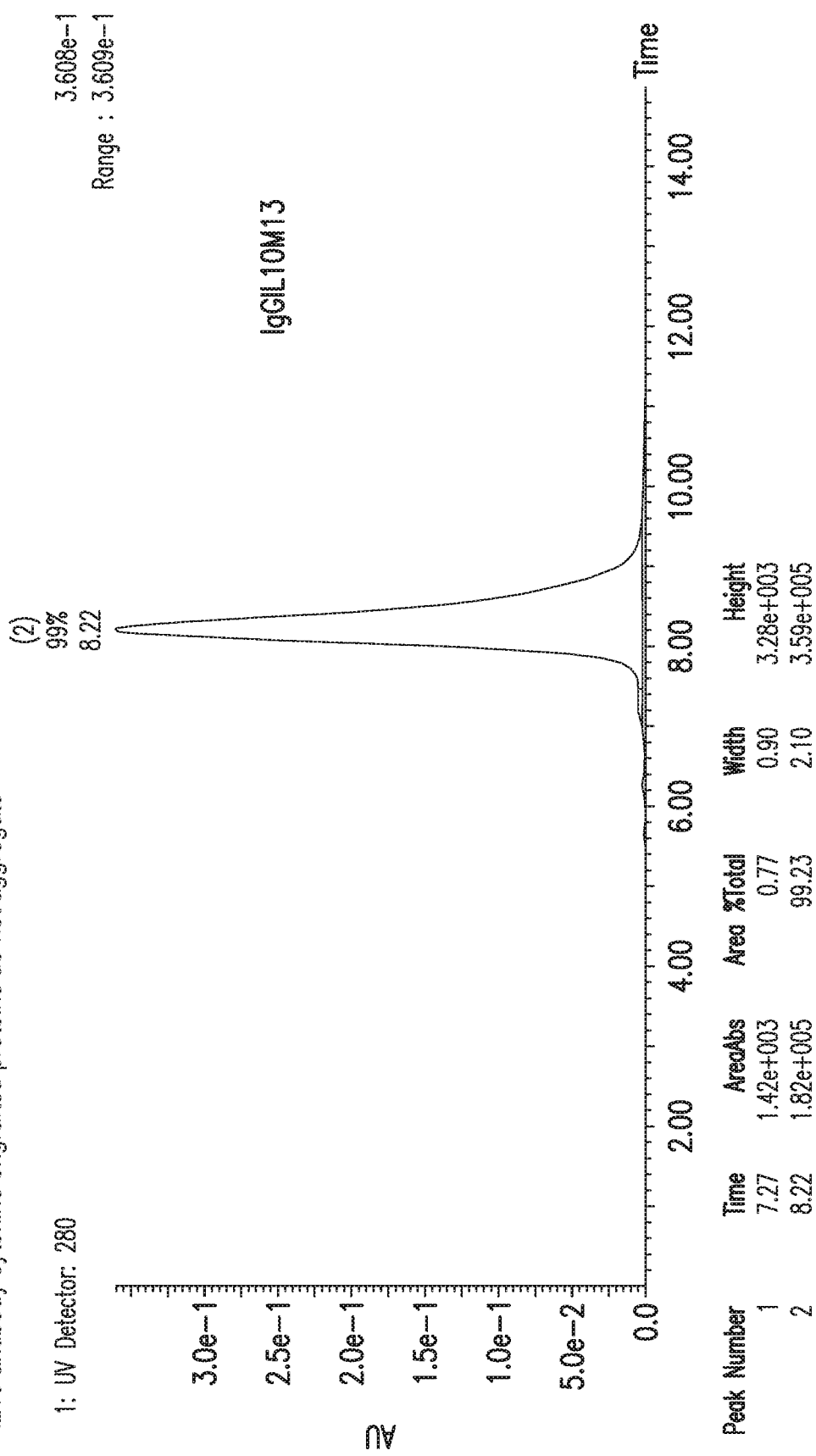
Figure 12:
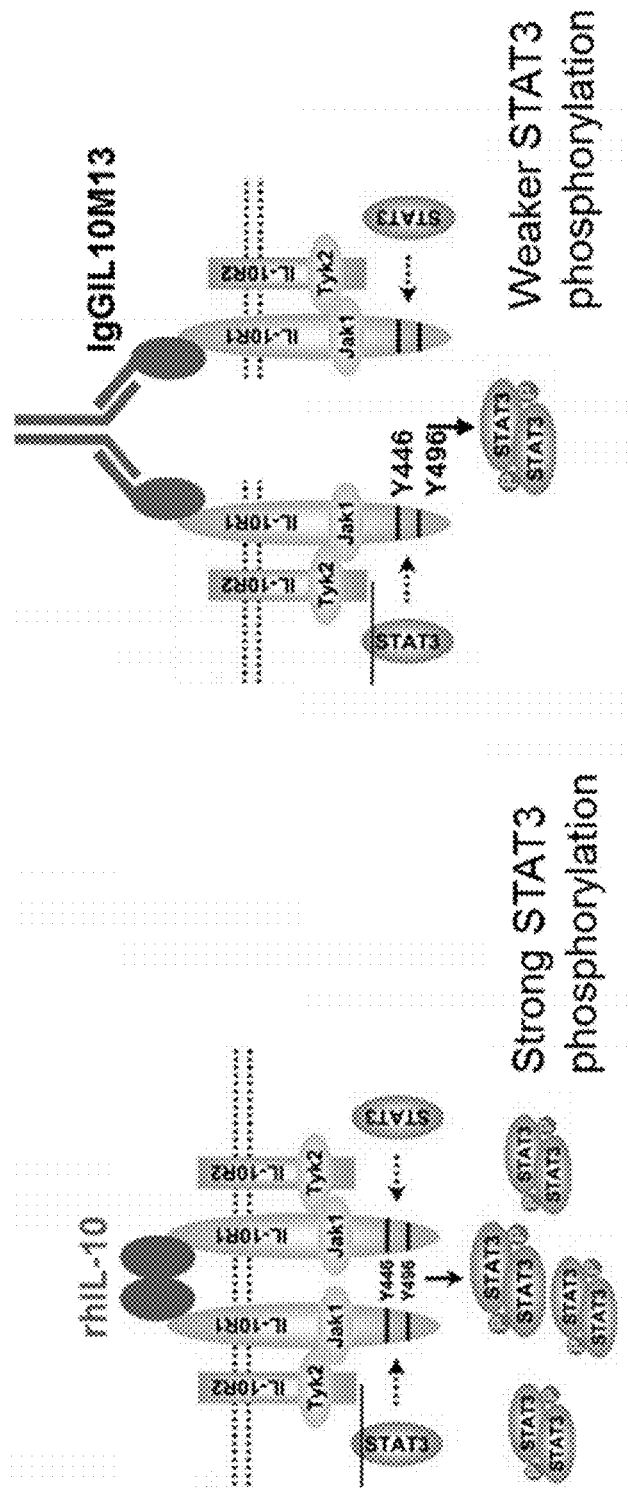
FIG. 12 is a representation of the mechanism of action of an IL10 antibody cytokine engrafted protein. The left panel shows how a normal rhIL10 dimer binds IL-10R1, and initiates strong pSTAT3 signaling. The right panel depicts how an IL10 monomer engrafted into a CDR of an antibody is constrained to have less efficient binding to IL-10R1 and thus produces a weaker pSTAT3 signal.

In clinical trials for IBD, rhIL10 was observed to have a very short half-life; however simple Fc fusions to the IL10 dimer to extend half-life were not pursued given aggregation properties of such a molecule. FIG. 10A shows aggregation of both an IL10 wild type linked to an Fc and IL10 monomer linked to an Fc. However, as shown in FIG. 10B, the antibody structure of the antibody cytokine engrafted protein prevents IL10 aggregation, thus promoting ease of administration. In addition, reducing aggregation has the benefit of reducing an immune reaction to the therapeutic, and the generation of anti-drug antibodies.

Example 12: Retained Binding of Antibody Cytokine Engrafted Proteins

Figures 13A, 13B, 13C, 13D:
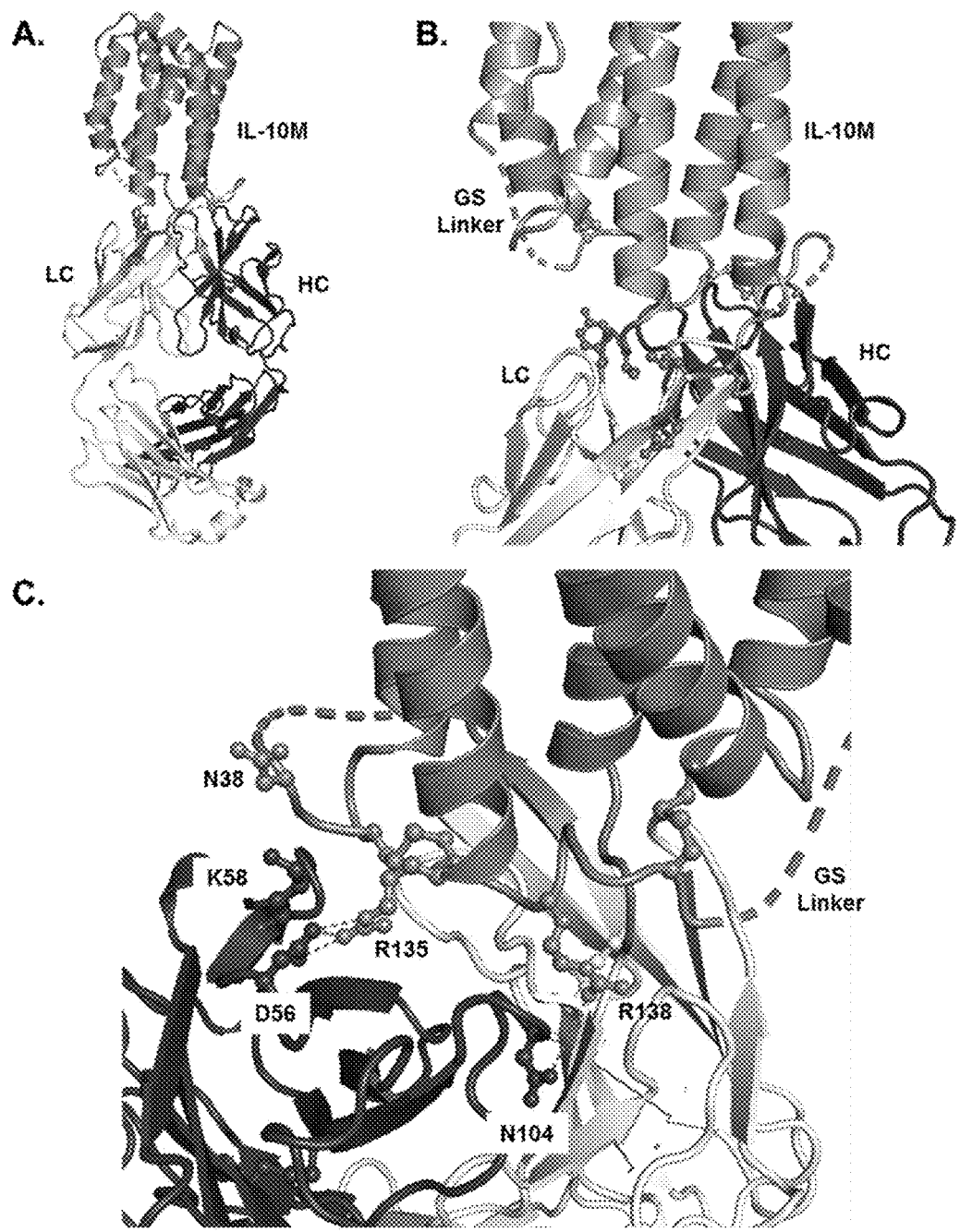
FIGS. 13A-C is the crystal structure resolution of IL10 monomer engrafted into LCDR1 of palivizumab.

Palivizumab is an anti-RSV antibody, and was chosen as the antibody structure for cytokine engrafting. This antibody had the advantages of a known structure, and as its target was RSV, a non-human target. The choice of a non-human target was to insure that there would be no toxicity associated with the antibody cytokine engrafted protein binding to an off target human antigen. It was uncertain after engrafting IL10M into palivizumab, whether the final IL10 antibody cytokine engrafted protein would still bind the RSV target protein. As assayed by ELISA, the IL10 antibody cytokine engrafted protein still bound to RSV target protein, despite the presence of the IL10M. This data is shown in FIG. 11.

Example 13: Structural Conformation of the Antibody Cytokine Engrafted Protein Results in Differential Activity Across Cell Types Antibody cytokine engrafted proteins (e.g. IgGIL10M13) incorporates monomeric IL10 (SEQ ID NO:209) into the Light Chain CDR 1 of an antibody (FIG. 2). Insertion of a 6 amino acid glycine-serine linker between helices D and E of IL10 renders the normally heterodimeric molecule incapable of domain swapping dimerization. As such, engrafting IL10M into an antibody results in an antibody cytokine engrafted protein with 2 monomeric IL10 molecules. However, due to flexibility of the antibody Fab arms, the angle and distance between the IL10 monomers is not fixed, as in the wild-type IL10 dimer, thus affecting its interaction with the IL10R1/R2 receptor complex. This is shown graphically in FIG. 12. Specifically, due to antibody engraftment, the angle of the engrafted IL10 dimer is larger and variable, rendering signal transduction less efficient on cells with lower expression levels of IL10R1 and R2 as found on the pro-inflammatory cell types such as CD4 and CD8 T cells, B cells and NK cells. In contrast, antibody cytokine engrafted proteins signal more efficiently on cells with high IL-10R1 and R2 expression such as monocytes. A class average negative stain EM study of IgGIL10M13 highlighted the additional flexibility and wider angle between monomers, confirming that the geometry is altered compared to rhIL10. The less restricted geometry of the IL10 dimer in IgGIL10M13 alters its interaction with IL10R complex. As a consequence, the structure of the IgGIL10M13 antibody cytokine engrafted protein results in the biological effect of only producing a productive signal on cell types with high levels of IL10R1 and R2 expression.

Example 14: Crystal Structure of IgGIL10M13

The IgGIL10M13 Fab was concentrated to 16.2 mg/ml in 20 mM HEPES pH 8.0, 150 mM NaCl and used directly in hanging drop vapor diffusion crystallization trials. Crystallization screens were setup by mixing 0.2 μl of protein solution with 0.2 μl of reservoir solution and equilibrated against 50 μl of the same reservoir solutions. Crystals for data collection appeared after 3-4 weeks at 20° C. from a reservoir solution of 20% PEG3350, 200 mM magnesium acetate, pH 7.9. Prior to data collection, the crystals were soaked in reservoir solution supplemented with 20% ethylene glycol and flash cooled in liquid nitrogen. Diffraction data were collected at the ALS beamline 5.0.3 with an ADSC Quantum 315R detector. Data was indexed and scaled using the HKL2000 software package (Otwinowski and Minor. (1997) Methods in Enzymology, Volume 276: Macromolecular Crystallography, part A, p. 307-326). The data for the IgGIL10M13 Fab was processed to 2.40 Å in space group $P2_1$ with cell dimensions a=80.6 Å, b=104.7 Å, c=82.8 Å, alpha=90°, beta=115.3°, gamma=90°. The structure was solved by molecular replacement using PHASER (McCoy et al., (2007) J. Appl. Cryst. 40:658-674) with the palivizumab Fab structure (PDB code: 2HWZ) and monomeric IL10 structure (PDB Code: 1LK3 chain A) as search models. The top molecular replacement solution contained 2 molecules of the IgGIL10M13 Fab in the asymmetric unit. The final model was built in COOT (Emsley & Cowtan (2004) Acta Cryst. D60:2126-2132) and refined with PHENIX (Adams et al., (2010) Acta Cryst. D66, 213-221). The $R_{work}$ and $R_{free}$ values are 18.8% and 23.9% respectively with root-mean-square (r.m.s) deviation values from ideal bond lengths and bond angles were 0.005 Å and 0.882° respectively.

Overall Structure

The IgGIL10M13 Fab crystallized with 2 molecules in the asymmetric unit, both with similar conformations. The electron density maps were similar for both molecules. The overall structure (FIG. 13A) shows that the Fab and grafted monomeric IL10 (IL10M) can adopt a collinear arrangement (Fab light chain in white, Fab heavy chain in black, IL10M in dark grey). FIG. 13B shows a closer view of the grafting point in CDR-L1. The three flanking CDR residues are show with dark grey sticks. Dashed lines illustrate portions of the structure which could not be fit in the model due to missing electron density, presumably due to structural flexibility in these areas. The two areas include 6 residues at N-terminus of IL10M just after the grafting point and 8 residues between helices 4 and 5 in IL10M which encompass the inserted 6 residue linker (GGGSGG) (SEQ ID NO:251). There are also 3 pairs of hydrogen bonding interactions between the grafted IL10M molecule and portions of the Fab heavy chain (FIG. 13C). These include R138 and N104 (sidechain), R135 and D56 (sidechain), and N38 and K58 (backbone/sidechain).

Materials and Methods

Anti-Inflammatory Assays (LPS-Challenge Human Whole Blood)

IL10 antibody cytokine engrafted proteins were prepared at 10× at 1000 ng/ml in assay medium (RPMI 1640 with glutamine (Hyclone), 10% heat inactivated FBS (Omega Scientific), 1% Penicillin/Streptomycin (Gibco), 50 uM 2-mercaptoethonal (Gibco), 10 mM Hepes ph 7.4 (Hyclone), 0.1 mM Non-essential Amino Acids (Hyclone), 1 mM Sodium Pyruvate (Hyclone) and 1× human insulin/transferrin/selenium (Gibco). Each 10× stock of IL10 antibody cytokine engrafted protein in assay medium was serially diluted 1:3 to create an 11-point dose titration.

Human whole blood was diluted to 90% in assay medium and gently mixed. Unstimulated diluted whole blood was plated in n=3 wells (45 µl/well), and assay medium added (5 ul/well) to bring final well volume to 50 µl. Lipopolysaccharide (LPS, Invivogen stock 100 µg/ml) was spiked into diluted whole blood at 220 ng/ml and gently mixed. LPS spiked whole blood was then plated, IL10 proteins added to each respective well, then gently mixed and incubated for ~20 hours in a 37 C incubator, 5% CO2. Plates were then gently mixed and centrifuged at 1400 rpm for 5 minutes at room temperature and supernatant harvested by transferring 10 µl/well from assay plate to a proxy plate for TNFα detection using the Human TNF-alpha HTRF kit (Cisbio®) according to manufacturer's instructions, and results compared to a standard curve generated using manufacturer provided control.

Pro-Inflammatory Assays (Human Primary CD8 T-Cell Activation)

Peripheral blood mononuclear cells (PBMCs) were isolated from buffy coats from the Blutspende Zentrum Basel. Eight Leucosep tubes (Greiner, 227290) per buffy coat were each filled with 15 ml Ficoll-Paque PLUS® (GE Healthcare, 17-1440-03) and centrifuged (1 minute, 1000 g, 20° C.). Buffy coats were diluted 1:4 in phosphate buffered saline (PBS) pH 7.4 (Gibco, 10010-015) and 35 ml were overlaid onto each Ficoll gradient. After centrifugation (800 g, 20 min, 20° C.) the lymphocytes separate into a white cell layer. This cell layer was transferred to fresh tubes and washed with PBS. Erythrocytes were lysed by resuspending cell pellets in 2 ml Gey's red blood lysing buffer (155 mM $NH_4Cl$, 10 mM $KHCO_3$, 0.1 mM EDTA) per tube. After incubation for 5 min, the cells were washed twice with PBS. After the last wash, the PBMCs were resuspended in T cell medium (TCM). TCM contains RPMI 1640 (Gibco, 21875-034), 10% fetal bovine serum (Gibco, 10082147), 1% Penicillin-Streptomycin (Gibco, 15070063) 2 mM GlutaMax (Gibco, 35050-038) and 50 U/ml penicillin, 50 µg/ml streptomycin. PBMCs were filtered through 40 µm cell strainers (BD Falcon, 734-0002) to obtain single cell suspensions, and counted. $CD8^+$ T cells were purified from PBMCs using the human $CD8^+$ T cell enrichment kit (StemCell, 19053) according to the manufacturer's protocol for the Big Easy Magnet® (StemCell, 18001). After isolation, the cells were washed, counted and resuspended in TCM at a concentration of $1.8 \times 10^6$ cells/ml. The anti-CD3/CD28 coated plate (see section 2.1.1) was washed once with 2 ml TCM per well followed by the addition of $1.8 \times 10^6$ $CD8^+$ T cells in 1 ml per well. Plates were centrifuged (5 min, 520 g, 20° C.) and incubated for 3 days in a cell incubator (Binder) at 37° C., 5% $CO_2$, 95% humidity Stimulation with IL10 Antibody Cytokine Engrafted Proteins After three days of incubation, activated CD8+ T cells were pooled from the 24 well plates and washed once with TCM. The cells were counted, resuspended in TCM at $3 \times 10^6$ cells per ml and 300,000 cells per well in 100 µl were added into Nunclon Delta Surface® 96 well round bottom plate (Thermo Scientific, 163320). IL10 antibody cytokine engrafted protein pre-dilutions at double the final concentration were prepared in TCM in a separate plate at the following concentrations: 40, 4, 0.4, 0.04, 0.004 and 0 nM. 100 µl of these pre-dilutions were added in duplicates to the 100 µl cell suspension resulting in the final concentration of the antibody cytokine engrafted proteins of 20, 2, 0.2, 0.02, 0.002 and 0 nM. Plates were incubated at 37° C. for 48 h PMA and Anti-CD3 Stimulation and Golgistop After the incubation period, the plates were centrifuged (2 min, 970 g, 20° C.) and the supernatant was discarded. Cell pellets were resuspended in 200 µl TCM containing 2 ng/ml Phorbol-myristate-acetate (PMA, Sigma Aldrich, 79346), 2.5 µg/ml anti-CD3 (BD, 555336) and 1:1500 GolgiStop (BD, 554724). Plates were incubated for 5 h at 37° C. to restimulate the cells. Afterwards, plates were centrifuged (2 minutes, 970 g, 20° C.), supernatants discarded and 200 µl ice cold PBS was added to wash the cell pellet. After centrifugation (2 minutes, 970 g, 20° C.), PBS was removed and the cells were resuspended in 200 µl ice cold 200 mM Tris-HCl buffer (pH 8.1) containing 2% Triton X-100 (Serva, 39795) to lyse the cells. The plates were left for 15 min on ice and centrifuged (10 min, 970 g, 4° C.) to eliminate debris. The supernatant was carefully transferred into a new 96 well plate and frozen for storage. To detect interferon-γ (IFN-γ in the supernatant, the human IFN-γ DuoSet® ELISA (R&D systems, DY285) was used according to the manufacturer's protocol. The supernatants obtained as described in section 2.1.5 were diluted 1:2 in the recommended assay diluent. To detect Granzyme B (GrzB) in the supernatant, the human Granzyme B® ELISA (Mabtech, 3485-1H-20) was used according to the manufacturer's protocol. The supernatants were diluted 1:50 in the recommended assay diluent. The optical density (OD) of the ELISA plates were acquired by SpectraMax® 340PC plate reader (Molecular Devices) and converted to concentrations by SoftMax® Pro software according to the automatically generated standard curve. The data were exported to Microsoft Excel where the concentrations were back calculated regarding their dilution factor.

IL10 Dependent Signaling

CyTOF is a FACS/Mass spectrometry technique to assess the activation of multiple cell populations by a single agent simultaneously. Antibody cytokine engrafted protein was incubated with human whole blood 20 minutes. Post-stimulation, PBMCs were treated with metal-conjugated antibodies against cell specific surface receptors CD14, HLA-DR, CD4, CD8, CD19, CD56 and the signaling marker pSTAT3 and analyzed by CyTOF. Results indicate that IgGIL10M13 at all doses primarily activated monocyte and macrophage cell populations with little activation of T cell, B cell, NK cell and dendritic cell populations. Conversely, rhIL10 activated all cell populations tested to some extent.

Pharmacokinetics Evaluation

Half-life of the antibody cytokine engrafted proteins was assessed in C57Bl/6 mice. Antibody cytokine engrafted proteins were injected at 0.2 mg/kg (10 ml/kg dose volume) in 0.9% saline subcutaneously and blood was sampled beginning at 1 hour post-injection and up to 144 hours post-injection. Whole blood was collected into heparin-treated tubes at each time point and centrifuged at 12,500 rpm for 10 minutes at 4° C. Plasma supernatant was collected and stored at −80° C. until all time points were collected. Antibody cytokine engrafted proteins levels in plasma were measured using two different immunoassay methods to enable detection of both the IL10 and antibody domains of the antibody cytokine engrafted protein. The first method utilized a commercially available IL-10 ELISA kit employed as recommended (BD OptEIA® Human IL10 ELISA Set, Capture: rhIL10/Detection: biotin-rhIL10). The second consisted of an IL10 based capture and Fc-based detect immunoassay run on a GyroLab® xP Workstation (Gyros AB Uppsala, Sweden). Specifically, the reagents employed consisted of Biotinylated Human IL10 capture (R&D Systems BAF217) and Alexafluor 647 goat anti-human IgG, Fcγ specific detection (Jackson ImmunoResearch #109-605-098). The assay was run on 200 nL CDs (Gyros #P0004180) using a Gyros-approved wizard method. The buffers used were Rexxip A® (Gyros #P0004820) for standard and sample dilution and Rexxip F® (Gyros #P0004825) for detection preparation. Analysis of results was done using the Gyrolab® data analysis software.

Pharmacodynamics Evaluation

Consistent with the extended half-life, antibody cytokine engrafted proteins also demonstrated improved pharmacodynamics. Phospho-stat3 (pSTAT3), a marker of IL10R activation was monitored in target tissues (blood and colon) after subcutaneous dosing. Antibody cytokine engrafted proteins were injected at 0.2 mg/kg (10 ml/kg dose volume) in 0.9% saline subcutaneously. Terminal whole blood and colon tissue (2 cm at ileo-cecal junction) were harvested beginning at 1 hour post-injection and up to 144 hours post-injection. Whole blood was collected into heparin-treated tubes containing 1× phosphatase inhibitors (Pierce Halt Phosphatase Inhibitor Cocktail) and kept on ice until phospho-Stat3 assay. Colon tissue was collected in tubes containing cold PBS and 1× phosphatase inhibitors. Once all tissue was collected for the time point, colon tissue was transferred into tubes containing a steel bead and 700 µl of Complete Cell Lysis Buffer containing PBS with 10 µM DTT, 1× protease inhibitor cocktail, 10× phosphatase inhibitor cocktail and 10× cell lysis buffer (Active Motif Nuclear Extraction Kit). Colon tissue was homogenized by tissue-lyser at 30 rps for 5 minutes at room temperature. Lysed tissue was centrifuged for 10 minutes at 14,000×g at 4° C. Supernatant was collected and stored on ice until phospho-STAT3 assay.

A phospho-Stat3 assay plate (Meso Scale Discovery® pSTAT3(Tyr705) Assay) was run on the same day as whole blood and colon tissue collection and processing. Ice-cold whole blood was lysed using the provided 1×MSD Lysis Buffer containing 1× Phosphatase Inhibitor 2, 1× Phosphatase Inhibitor 3 and 1× Protease Inhibitor. Each tube of whole blood was centrifuged at 12,500 rpm for 10 minutes at 4° C. Plasma was collected and discarded. Pelleted whole blood was resuspended in 220 µl of MSD Lysis Buffer+ Inhibitors and vortexed thoroughly. Lysed whole blood was plated into respective wells of the phospho-STAT3 assay plate at 50 µl/well. Colon tissue supernatant protein detection was performed using the Bradford Assay (Pierce). Colon protein was then plated on the phospho-STAT3 assay plate at 50 µl/well. Plates were incubated at room temperature for 2 hours, washed, and treated with phospho-STAT3 or Total STAT3 antibody (Meso Scale Discovery). Plates were analyzed for relative fluorescence units (RFU) on the MSD Sector Imager 2400 (Meso Scale Discovery). Whole blood phospho-STAT3 RFU was normalized to total STAT3 RFU. Colon protein phospho-STAT3 RFU was normalized to loaded protein concentration. Enhanced pSTAT3 signal is detected in both tissues at least up to 72 hours post-dose, and absent by 144 hours post-dose. See FIG. 5, not shown. This profile is a dramatic improvement over rhIL10, whose signal is absent by 24 hours post-dose.

Ex Vivo Efficacy

A direct comparison of efficacy for TNFα inhibition after LPS challenge was performed. In the assay, C57/B16 mice were dosed subcutaneously with vehicle, 0.2 mg/kg of IgGIL10M13 (10 ml/kg dose volume), or equimolar levels of rhIL10. Whole blood was collected prior to, at 1.5 hrs post-dose and up to 144 hrs post-dose. Whole blood was collected into heparin-treated tubes. Prior to blood collection, assay medium was prepared. Assay medium contained RPMI 1640 with glutamine (Hyclone) with 10% heat inactivated FBS (Omega Scientific), 1% Penicillin/Streptomycin (Gibco), 50 µM 2-mercaptoethonal (Gibco), 10 mM Hepes ph 7.4 (Hyclone), 0.1 mM Non-essential Amino Acids (Hyclone) and 1 mM Sodium Pyruvate (Hyclone). Mouse whole blood was plated in 25 µl/well/replicate/mouse on a 384 well plate. Assay medium was added to unstimulated control wells (25 µl/well) to bring final well volume to 50 µl. For LPS challenge, LPS (Invivogen, stock 100 µg/ml) was spiked into assay medium at 200 ng/ml [100 ng/ml final in assay] and gently mixed. LPS spiked BCM was then plated at 25 µl/well for each required well containing mouse whole blood. The plate was gently mixed and incubated for 21 hours in a 37° C. incubator, 5% CO2. The next day, the assay plate was centrifuged at 1400 rpm for 5 minutes at room temperature. Supernatants from each well were collected and frozen at −80° C. until all time points had been assayed. Once all time points could be analysed, supernatants were plated onto an MSD V-plex® Mouse Pro-Inflammatory Cytokine Assay Plate (Meso Scale Discovery). Plates were analysed for TNFα (pg/ml) on the MSD Sector Imager 2400® (Meso Scale Discovery)

Immunostimulatory Assays

MC/9 Cell Proliferation

The immunostimulatory activity of IL10 antibody cytokine engrafted proteins were assessed by examining the ability to stimulate MC/9 (a mast cell line derived from mouse fetal liver) cell proliferation. First, IL10 antibody cytokine engrafted proteins were diluted in a separate 384 well plate at 7× in growth media with no T-STIM (7×=700 ng/ml). IL-4 was included as a positive control (7×=1,000 ng/ml, [final]=143 ng/ml). Second, 30 µl of $1.67×10^4$ cells/ml MC/9 cells were plated in a white 384-well TC treated plate (500 cells/well) in media with no T-STIM (washing cells prior to assay was not necessary). Third, 5 µl of diluted IL10 antibody cytokine engrafted protein was added to the cells. Plate was briefly mixed using a plate mixer, and then pulse spun at 1,000 rpm. Plate was covered with custom porous lid to aerate cells. Fourth, plate was incubated at 37° C. for 72 hours. Fifth, 30 µl of Promega Cell Titer Glo® was added to the cells, incubated for 10 min at room temp and read on Envision® (0.1 sec read).

B Cell Proliferation

PBMCs were isolated from human buffy coats as described above. For the isolation of B cells, the human B cell enrichment Kit® (Stemcell, 19054) was used according to manufacturer's protocol for the Big Easy Magnet® (Stemcell, 18001). After isolation, the B cells were washed with B cell medium (BCM), counted and resuspended at a concentration of $4\times10^5$ cells/ml. BCM contains RPMI 1640, 10% fetal bovine serum (Gibco, 10082147), 1% Penicillin-Streptomycin (Gibco, 15070063) and 2 mM GlutaMax (Gibco, 35050-038), 1% Non-essential amino acids (Gibco, 11140035) and 1 mM sodium pyruvate (Gibco, 11360-039), 50 U/ml penicillin and 50 µg/ml streptomycin. Isolated B cells were counted and resuspended at a concentration of $4\times10^5$ cells/ml in BCM. To stimulate the B cells, 8.4 µg/ml anti-CD40 and 40 U/ml recombinant human IL-2 (R&D systems, 202-IL-50) were added to the suspension. B cells were then added at a concentration of $4\times10^4$ cells in 100 µl into wells of Nunclon Delta Surface® 96 well round bottom plates (Thermo Scientific, 163320). IL10 antibody engrafted protein pre-dilutions at the double the final concentration were prepared in a separate plate. A titration of the compounds was performed obtaining the following concentrations: 40, 4, 0.4, 0.04, 0.004 and 0 nM. 100 µl of these pre-dilutions were added in duplicates to the 100 µl cell suspension resulting in the final concentration of the compounds of 20, 2, 0.2, 0.02, 0.002 and 0 nM and a final concentration of 4.2 mg/ml anti-CD40 and 20 U/ml recombinant IL-2. The plate was incubated for 5 days in a cell culture incubator (37° C., 5% $CO_2$, 95% humidity). After 5 days of incubation, proliferation of B cells was determined by the thymidine incorporation assay. Cells were pulsed with 0.5 µCi 3H-thymidine (ANAWA, ART-178) per well in 20 µl BCM for the final 16 h of the culture period at 37° C. Using the TomTec 9600® harvester, cells were harvested onto a membrane according to manufacturer's protocol. Membranes were sealed in a bag, scintillation liquid was added and radioactivity was measured on scintillation counter. For each of the antibody engrafted proteins, the percentage of proliferation at 20 nM ("top") was calculated relative to the proliferation at an equimolar concentration of rhIL10, in relation to the respective background cytokine production ("bottom"). The resulting % of max values were calculated using the following formula:

$$\% \text{ of max} = (\text{top}_{compound} - \text{bottom}_{compound})/(\text{top}_{rhIL-10} - \text{bottom}_{rhIL-10}) * 100$$

Means of different experimental series were determined, and the standard error of the mean (SEM) was calculated if the compound was measured on more than two donors.

It is understood that the examples and embodiments described herein are for illustrative purposes and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method of treatment of an immune related disorder in an individual in need thereof, comprising administering to the individual a therapeutically effective amount of an antibody cytokine engrafted protein comprising
a heavy chain variable region that comprises (a) a HCDR1 of SEQ ID NO: 193, (b) a HCDR2 of SEQ ID NO:194, (c) a HCDR3 of SEQ ID NO:195 and a light chain variable region that comprises: (d) a LCDR1 of SEQ ID NO:196, (e) a LCDR2 of SEQ ID NO:197, and (f) a LCDR3 of SEQ ID NO:198,
wherein the immune related disorder is selected from the group consisting of:
inflammatory bowel disease, Crohn's disease, ulcerative colitis, rheumatoid arthritis, psoriasis, type I diabetes, acute pancreatitis, uveitis, Sjogren's disease, Behcet's disease, sarcoidosis, and graft versus host disease (GVHD).

2. The method of claim 1, wherein the antibody cytokine engrafted protein is administered in combination with another therapeutic agent.

3. The method of claim 2, wherein the therapeutic agent is an anti-TNF agent selected from the group consisting of: infliximab, adalimumab, certolizumab, golimumab, natalizumab, and vedolizumab.

4. The method of claim 2, wherein the therapeutic agent is an aminosalicylate agent selected from the group consisting of: sulfasalazine, mesalamine, balsalazide, olsalazine and other derivatives of 5-aminosalicylic acid.

5. The method of claim 2, wherein the therapeutic agent is a corticosteroid selected from the group consisting of: methylprednisolone, hydrocortisone, prednisone, budenisonide, mesalamine, and dexamethasone.

6. The method of claim 2, wherein the therapeutic agent is an antibacterial agent.

7. The method of claim 1, wherein the antibody cytokine engrafted protein is capable of less activation of T cells or NK cells when compared to recombinant human IL10.

8. The method of claim 1, wherein the antibody cytokine engrafted protein has a longer half-life than rhIL10.

9. The method of claim 1, wherein the antibody cytokine engrafted protein comprises a heavy chain variable region (VH) that comprises SEQ ID NO:205, and a light chain variable region (VL) that comprises SEQ ID NO:206.

10. The method of claim 1, further comprising a modified Fc region corresponding with reduced effector function.

11. The method of claim 10, wherein the modified Fc region comprises a mutation selected from one or more of D265A, P329A, P329G, N297A, L234A, and L235A.

12. The method of claim 1, wherein the antibody cytokine engrafted protein comprises: HCDR1 of SEQ ID NO: 193, HCDR2 of SEQ ID NO:194, HCDR3 of SEQ ID NO:195, LCDR1 of SEQ ID NO:196, LCDR2 of SEQ ID NO:197, LCDR3 of SEQ ID NO:198, a modified Fc region containing the mutation D265A/P329A, and wherein the antibody cytokine engrafted protein has less activation of T cells or NK cells when compared to rhIL10.

* * * * *